US 6,673,804 B1
(12) United States Patent
Kimura et al.

(10) Patent No.: US 6,673,804 B1
(45) Date of Patent: Jan. 6, 2004

(54) SULFONAMIDE DERIVATIVES

(75) Inventors: Tomio Kimura, Tokyo (JP); Shoujiro Miyazaki, Tokyo (JP); Keiji Ueda, Tokyo (JP); Kazuhiko Tanzawa, Koganei (JP); Shigeru Ushiyama, Tokyo (JP); Wataru Takasaki, Koshigaya (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/678,294

(22) Filed: Oct. 2, 2000

Related U.S. Application Data

(63) Continuation of application No. PCT/JP99/01751, filed on Apr. 2, 1999.

(30) Foreign Application Priority Data

| Apr. 3, 1998 | (JP) | ............................................. 10-91819 |
| Mar. 1, 1999 | (JP) | ............................................. 11-53164 |

(51) Int. Cl.[7] ................... C07D 209/46; C07D 217/24; C07D 231/56; C07C 311/29; A61K 31/00
(52) U.S. Cl. ......................... 514/274; 544/54; 544/88; 544/242; 546/290
(58) Field of Search ................... 544/54, 88, 242; 546/290; 514/274

(56) References Cited

U.S. PATENT DOCUMENTS

| 5,455,258 A | * | 10/1995 | MacPherson et al. | ........ 514/357 |
| 5,929,097 A | | 7/1999 | Levin et al. | ................. 514/351 |
| 5,962,481 A | | 10/1999 | Levin et al. | ................. 514/352 |
| 5,977,408 A | | 11/1999 | Levin et al. | ................. 562/622 |
| 6,159,995 A | | 12/2000 | Thorwart et al. | |
| 6,277,987 B1 | * | 8/2001 | Kukkola et al. | ............. 544/285 |
| 6,355,673 B1 | | 3/2002 | Thorwart et al. | |

FOREIGN PATENT DOCUMENTS

| EP | 0757984 A | 2/1997 | |
| EP | 0877019 A | 11/1998 | |
| EP | 877019 A1 | * 11/1998 | ......... C07C/311/19 |
| EP | 0950656 A | 10/1999 | |
| JP | 9-104672 A | 4/1997 | |
| WO | WO 97/27174 | 7/1997 | |
| WO | WO 99/06340 A | 2/1999 | |

OTHER PUBLICATIONS

CAS printout for MacPherson et al.*
P.G. Mitchell et al, "Cloning, Expression, and Type II Collagenolytic Activity of Matrix Metalloproteinase–13 from Human Osteoarthritic Cartilage", *J. of Clinical Investigation*, vol. 97, No. 3, pp. 761–768 (1996).
P. Reboul et al, "The New Collagenase, Collagenase–3, Is Expressed and Synthesized by Human Chondrocytes But Not by Synoviocytes", *J. of Clinical Investigation*, vol. 97, No. 9, pp. 2011–2019 (1996).

(List continued on next page.)

*Primary Examiner*—Mukund J. Shah
*Assistant Examiner*—Hong Liu
(74) *Attorney, Agent, or Firm*—Frishauf, Holtz, Goodman & Chick, P.C.

(57) ABSTRACT

A compound of the formula (I) or a pharmacologically acceptable salt, ester or other derivative thereof:

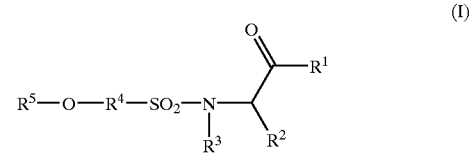

$R^1$ is H or NHOH. $R^2$ is H, optionally substituted alkyl, cycloalkyl or a group —$AR^6$.

A is an alkylene which may be optionally interrupted by O, —S(O)m— or —$N(R^9)$. $R^6$ is a group (II), (III), (IV)

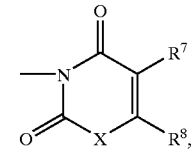

(II)

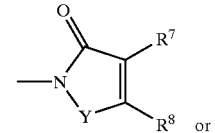

(III)

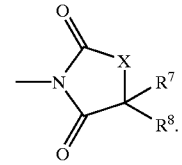

(IV)

X is O, S, —$N(R^{10})$—, —$C(R^{11})(R^{12})$—. Y is O, CO, —S(O)n—, —$N(R^{10})$—, —$C(R^{11})(R^{12})$—. Each of $R^7$ and $R^8$ is H, alkyl, COOH, optionally substituted alkyl, etc. Each of $R^9$, $R^{10}$, $R^{11}$, and $R^{12}$ is H, alkyl, etc. Each of m and n is 0 to 2. $R^3$ is H, optionally substituted alkyl, optionally substituted cycloalkyl, optionally substituted alkenyl, optionally substituted alkynyl. $R^4$ is optionally substituted (hetero)arylene. $R^5$ is optionally substituted alkyl, optionally substituted (hetero)aryl. These compounds have matrixmetalloproteinase—13 inhibitory activity and aglycanase inhibitory activity.

44 Claims, No Drawings

OTHER PUBLICATIONS

D. Wernicke et al, "Cloning of Collagenase 3 from the Synovial Membrane and Its Expression in Rheumatoid Arthritis and Osteoarthritis", *J. of Rheumatology*, vol. 23, pp. 590–595 (1996).

J.D. Sandy et al, "Catabolism of Aggrecan in Cartilage Explants", *J. of Biological Chemistry*, vol. 266, No. 14, pp. 8683–8685 (1991).

M.W. Lark et al, "Cell–mediated Catabolism of Aggrecan", *J. of Biological Chemistry*, vol. 270, No. 6, pp. 2550–2556 (1995).

J.M.P. Freije et al, "Molecular Cloning and Expression of Collagenase–3, a Novel Human Matrix Metalloproteinase Produced by Breast Carcinomas", *J. of Biological Chemistry*, vol. 269, No. 24, 16766–16773 (1994).

\* cited by examiner

SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: PCR primer
      to amplify a cDNA encoding human pro-MMP13

<400> SEQUENCE: 1
gctgagctca tgcatccagg ggtcctggct gcc                               33

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: PCR primer
      to amplify a cDNA encoding human pro-MMP13

<400> SEQUENCE: 2
cgaggtacca ttaccccaaa tgctcttcag ga                                32

SULFONAMIDE DERIVATIVES

This application is a continuation application of International Application PCT/JP99/01751 filed Apr. 2, 1999.

TECHNICAL FIELD

The present invention relates to novel sulfonamide derivatives having excellent matrix metalloproteinase 13 inhibitory action and aglycanase inhibitory action, and to pharmaceutical compositions containing the same.

BACKGROUND ART

A nonsteroidal anti-inflammatory drug (NSAID) is conventionally used for the treatment of osteoarthritis and chronic rheumatoid arthritis. However, such therapeutic methods are only symptomatic therapies, and there are still no medicaments for etiotropic therapy that inhibits the progress of these diseases.

In addition, in the field of antitumor drugs, since drugs currently used in the clinical setting are generally associated with strong adverse side effects, there is a need for drugs that are effective for not only the treatment of cancer, but also for both the prevention of the disease and the prevention of relapse and that cause only mild adverse side effects, if any.

Matrix metalloproteinase (hereinafter referred to as "MMP") is known to be an enzyme that decomposes protein components of connective tissue. MMP-13 (collagenase-3), which is one of several subtypes of MMP, has strong decomposition activity against type II collagen, one of the main components of joint cartilage. MMP-13 is an enzyme that is found locally in joints, and its expression has been reported to be elevated in the joints of patients with osteoarthritis and chronic rheumatoid arthritis as compared with that in the joints of healthy people (P. G. Mitchell et al., Journal of Clinical Investigation, vol. 97, 761–768, 1996; P. Reboul et al., Journal of Clinical Investigation, vol. 97, 2011–2019, 1996; D. Wernicke et al., Journal of Rheumatology, vol. 23, 590–595, 1996). Based on these reports, MMP-13 is considered to play an important role in the destruction of joint cartilage matrix in the course of development of arthritis.

In addition, aglycan, another main component of joint cartilage, is reported to be decomposed by an enzyme referred to as aglycanase in osteoarthritis. Although the actual form of aglycanase has not been identified, this enzyme is known to cleave aglycan at an extremely characteristic sequence of Glu373-Ala374 (J. D. Sandy et al., Journal of Biological Chemistry, vol. 266, 8683–8685, 1990; J. D. Sandy et al., Journal of Biological Chemistry, vol. 270, 2550–2556, 1995).

Thus, on the basis of the above findings, compounds that strongly inhibit both MMP, particularly MMP-13, and aglycanase are considered to be useful as therapeutic and preventive agents against osteoarthritis and other forms of arthritis.

On the other hand, MMP-13 is known to be expressed at a high level in breast carcinoma and several other cancerous tissues, and it has been indicated that it has a strong possibility of playing an important role in the growth and metastasis of these cancers (J. M. P. Freije et al., Journal of Biological Chemistry, vol. 269, 16766–16773, 1994). Thus, compounds that have inhibitory action against this enzyme are considered to be useful inhibitors of metastasis, invasion and growth of various cancer cells.

Compounds having MMP inhibitory activity, for example, those shown below, are disclosed in WO 97/27174.

However, the inhibitory action of these compounds against MMP-13 is not disclosed, and there is no disclosure or suggestion of aglycanase inhibitory action.

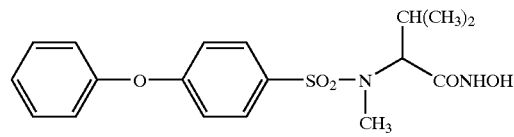

WO97/27174. Example 235

As a result of earnest research on the synthesis and pharmacological action of compounds that strongly inhibit both MMP-13 and aglycanase, the inventors of the present invention found that novel sulfonamide derivatives have potent MMP-13 inhibitory activity and aglycanase inhibitory activity, thereby leading to completion of the present invention.

Disclosure of the Invention

The present invention relates to (1) a compound of the following formula (I) or a pharmacologically acceptable salt, ester or other derivative thereof:

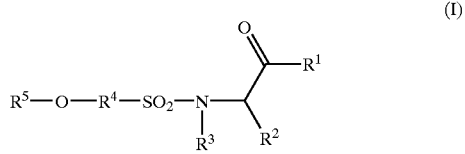

{wherein $R^1$ represents a hydroxyl group or a hydroxyamino group;

$R^2$ represents a hydrogen atom, a lower alkyl group, a lower alkyl group substituted with at least one group selected from Substituent group α, a cycloalkyl group having from 3 to 7 carbon atoms or a group of the formula: —A—$R^6$

[wherein

A represents a lower alkylene group or a lower alkylene group interrupted by an oxygen atom, —S(O)$_m$— or —N($R^9$)—;

$R^6$ represents a group of the following formula (II), (III) or (IV):

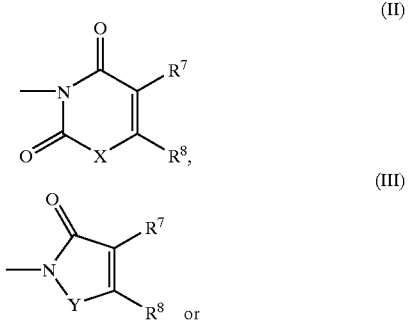

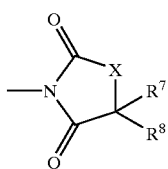

(wherein
X represents an oxygen atom, a sulfur atom, —N(R$^{10}$)— or —C(R$^{11}$)(R$^{12}$);

Y represents an oxygen atom, a carbonyl group, —S(O)$_n$—, —N(R$^{10}$)— or —C(R$^{11}$)(R$^{12}$);

R$^7$ and R$^8$ may be the same or different from each other and each represents a hydrogen atom, a lower alkyl group, a carboxyl group, one group selected from Substituent group α, a lower alkyl group substituted with at least one group selected from Substituent group α, a lower alkoxy group substituted with at least one group selected from Substituent group α, a lower alkylthio group substituted with at least one group selected from Substituent group α, a lower alkylsulfinyl group substituted with at least one group selected from Substituent group α or a lower alkylsulfonyl group substituted with at least one group selected from Substituent group α, or R$^7$ and R$^8$ may form, together with the carbon atom(s) to which they are attached, a non-aromatic hydrocarbon ring, a non-aromatic heterocycle, a non-aromatic hydrocarbon ring substituted with at least one group selected from Substituent group α and Substituent group β, a non-aromatic heterocycle substituted with at least one group selected from Substituent group α and Substituent group β, an aryl ring, a heteroaryl ring, an aryl ring substituted with at least one group selected from Substituent group α and Substituent group β or a heteroaryl ring substituted with at least one group selected from Substituent group α and Substituent group β; and R$^9$, R$^{10}$, R$^{11}$ and R$^{12}$ may be the same or different from one another and each represents a hydrogen atom or a lower alkyl group, and further R$^{11}$ and R$^{12}$ may form, together with the carbon atom(s) to which they are attached, a non-aromatic hydrocarbon ring, a non-aromatic heterocycle, a non-aromatic hydrocarbon ring substituted with at least one group selected from Substituent group α and Substituent group β or a non-aromatic heterocycle substituted with at least one group selected from Substituent group α and Substituent group β, with the proviso that when R$^7$ and R$^8$ are attached to the same carbon atom, R$^7$ and R$^8$ do not form, together with the carbon atom to which they are attached, an aryl ring, a heteroaryl ring, an aryl ring substituted with at least one group selected from Substituent group α and Substituent group β or a heteroaryl ring substituted with at least one group selected from Substituent group α and Substituent group β), and m and n may be the same or different from each other and each represents 0, 1 or 2], R$^3$ represents a hydrogen atom, a lower alkyl group, a cycloalkyl group having from 3 to 7 carbon atoms, an alkenyl group, an alkynyl group, a lower alkyl group substituted with at least one group selected from Substituent group α, a cycloalkyl group having from 3 to 7 carbon atoms substituted with at least one group selected from Substituent group α and Substituent group β, an alkenyl group substituted with at least one group selected from Substituent group α or an alkynyl group substituted with at least one group selected from Substituent group α;

R$^4$ represents an arylene group, a heteroarylene group, an arylene group substituted with at least one group selected from Substituent group α and Substituent group β or a heteroarylene group substituted with at least one group selected from Substituent group α and Substituent group β; and R$^5$ represents a lower alkyl group, a lower alkyl group substituted with at least one group selected from Substituent group α, an aryl group, a heteroaryl group, an aryl group substituted with at least one group selected from Substituent group α and Substituent group β or a heteroaryl group substituted with at least one group selected from Substituent group α and Substituent group β;

with the proviso that when R$^2$ represents a hydrogen atom, a lower alkyl group, a lower alkyl group substituted with at least one group selected from Substituent group α or a cycloalkyl group having from 3 to 7 carbon atoms, R$^3$ represents alkynyl or an alkynyl group substituted with at least one group selected from Substituent group α.

[Substituent Group α]

halogen atoms, cycloalkyl groups having from 3 to 7 carbon atoms, lower alkoxy groups, halogeno lower alkoxy groups, lower alkanoyl groups, lower alkylthio groups, halogeno lower alkylthio groups, lower alkylsulfinyl groups, lower alkylsulfonyl groups, amino groups, mono-lower alkylamino groups, di-(lower alkyl)amino groups, cyano groups, nitro groups, aryl groups, heteroaryl groups, aryloxy groups, heteroaryloxy groups, arylthio groups, heteroarylthio groups, aryl groups substituted with at least one group selected from Substituent group γ, heteroaryl groups substituted with at least one group selected from Substituent group γ, aryloxy groups substituted with at least one group selected from Substituent group γ, heteroaryloxy groups substituted with at least one group selected from Substituent group γ, arylthio groups substituted with at least one group selected from Substituent group γ, heteroarylthio groups substituted with at least one group selected from Substituent group γ,

[Substituent Group β]

lower alkyl groups, halogeno lower alkyl groups,

[Substituent Group γ]

halogen atoms, lower alkyl groups, halogeno lower alkyl groups, lower alkoxy groups, halogeno lower alkoxy groups, lower alkylthio groups, halogeno lower alkylthio groups, nitro groups, cyano groups.

Of these compounds, preferred are:

(2) a compound in which R$^1$ is a hydroxyamino group;

(3) a compound in which R$^2$ is an alkyl group having from 1 to 4 carbon atoms or an alkyl group having from 1 to 4 carbon atoms substituted with at least one group selected from Substituent group α;

(4) a compound in which R$^2$ is an alkyl group having from 1 to 4 carbon atoms or an alkyl group having from 1 to 4 carbon atoms substituted with at least one group selected from the following Substituent group α$^1$;

(5) a compound in which R$^2$ is an alkyl group having from 1 to 4 carbon atoms or an alkyl group having from 1 to 4 carbon atoms substituted with at least one group selected from the following Substituent group α$^2$;

(6) a compound in which R² is a methyl, ethyl, propyl, isopropyl, 2-methoxyethyl, 2-methylthiophenyl, 3,3,3-trifluoropropyl, benzyl, 2-phenylethyl, benzyloxymethyl, benzylthiomethyl or 2-thienylthiomethyl group;

(7) a compound in which A is an alkylene group having from 1 to 4 carbon atoms or a lower alkylene group interrupted by an oxygen atom or —S(O)$_m$—;

(8) a compound in which A is a methylene, ethylene, 1,1-dimethylethylene, trimethylene, tetramethylene, —CH$_2$O(CH$_2$)$_2$— or —CH$_2$S(CH$_2$)$_2$— group;

(9) a compound in which A is a methylene, ethylene or trimethylene group;

(10) a compound in which R⁶ is

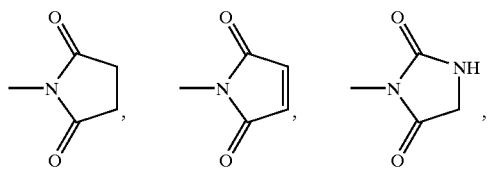

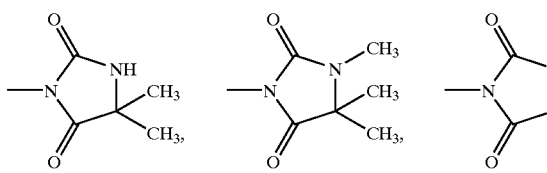

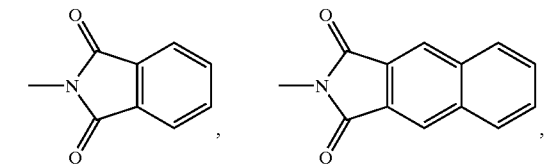

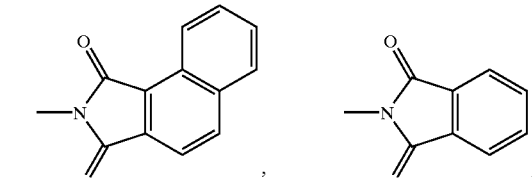

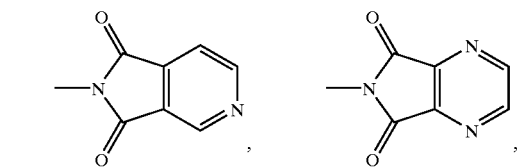

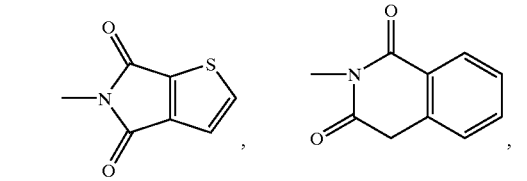

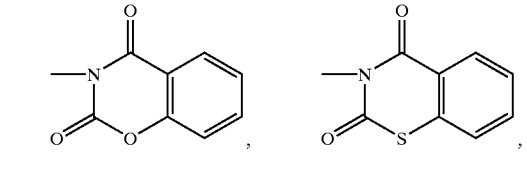

-continued

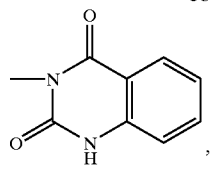
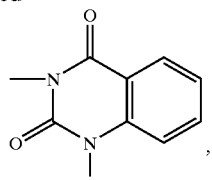

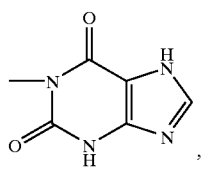
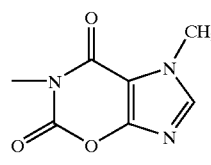

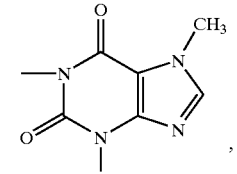
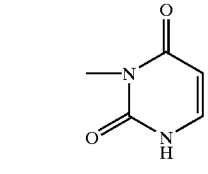

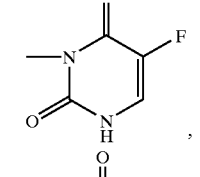
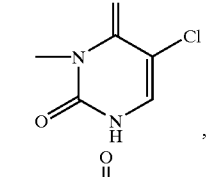

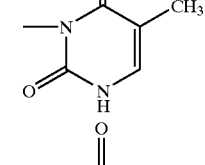
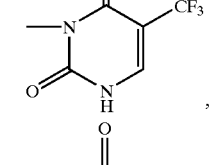

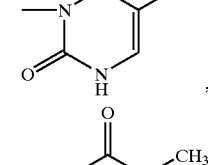
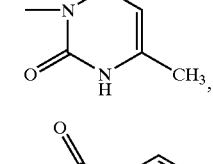

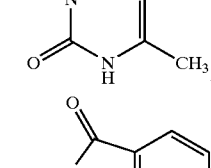
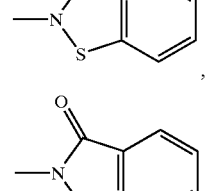

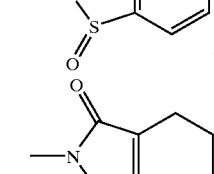
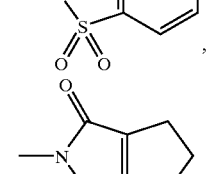

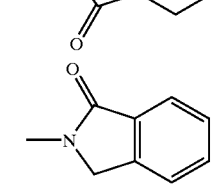
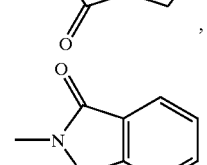

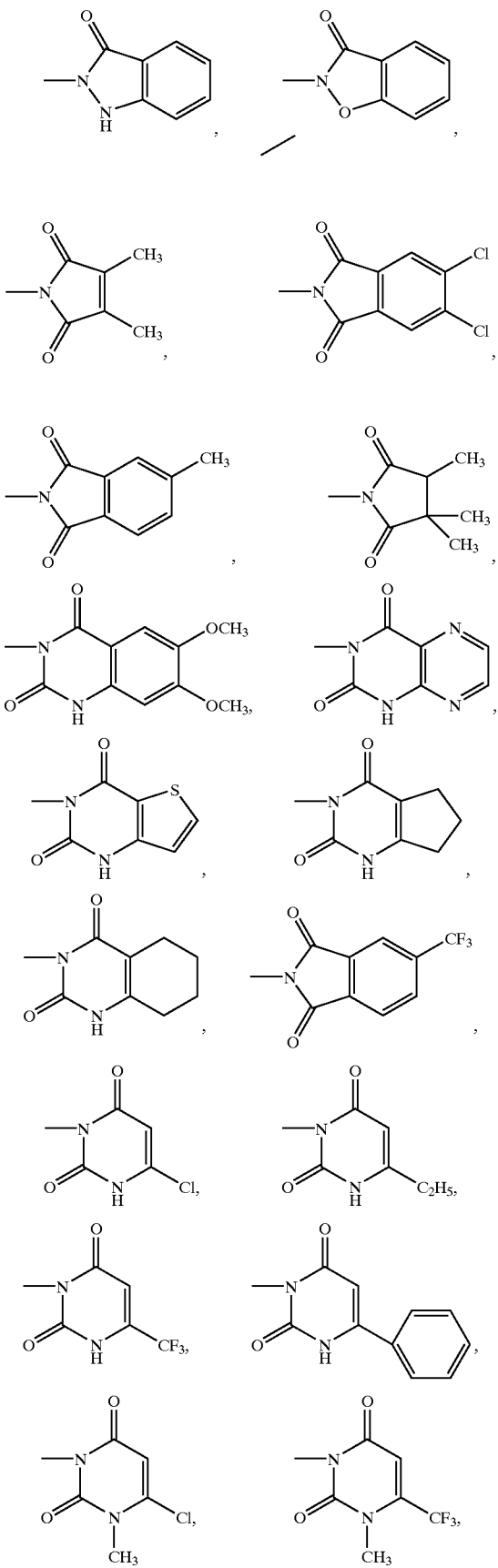

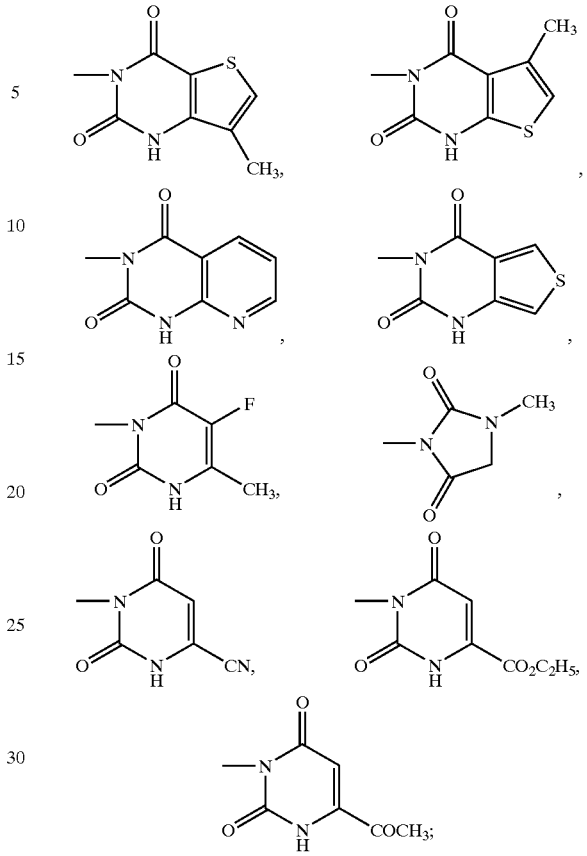

(11) a compound in which $R^3$ is a hydrogen atom, a lower alkyl group, a cycloalkyl group having from 3 to 7 carbon atoms, an alkenyl group, an alkynyl group, a lower alkyl group substituted with an aryl group, a lower alkyl group substituted with a heteroaryl group, an alkenyl group substituted with an aryl group, an alkenyl group substituted with a heteroaryl group, an alkynyl group substituted with an aryl group or an alkynyl group substituted with a heteroaryl group (here, the "aryl group" and the "heteroaryl group" are unsubstituted or substituted with at least one group selected from Substituent group α and Substituent group β, described above);

(12) a compound in which $R^3$ is an alkyl group having from 1 to 6 carbon atoms, a cycloalkyl group having from 3 to 7 carbon atoms, an alkenyl group having from 3 to 6 carbon atoms, an alkynyl group having from 3 to 6 carbon atoms, an alkyl group having from 1 to 3 carbon atoms substituted with an aryl group, an alkyl group having from 1 to 3 carbon atoms substituted with a heteroaryl group, an alkenyl group having 3 carbon atoms substituted with an aryl group, an alkenyl group having 3 carbon atoms substituted with a heteroaryl group, an alkynyl group having 3 carbon atoms substituted with an aryl group or an alkynyl group having 3 carbon atoms substituted with a heteroaryl group;

(13) a compound in which $R^3$ is a methyl, ethyl, propyl, cyclopropyl, allyl, 2-butenyl, propargyl, 2-butynyl, benzyl, 2-phenylethyl, 3-phenylpropyl, 3-(4-chlorophenyl)-propyl, 3-phenylpropargyl or 3-(4-chlorophenyl)propargyl group;

(14) a compound in which $R^4$ is a phenylene, naphthylene or thienylene group;

(15) a compound in which $R^4$ is a p-phenylene group;

(16) a compound in which $R^5$ is an alkyl group having from 1 to 6 carbon atoms, a halogenoalkyl group having from 1 to 4 carbon atoms, an aryl group, a heteroaryl group, an aryl group substituted with at least one group selected from Substituent group α and Substituent group β or a heteroaryl group substituted with at least one group selected from Substituent group α and Substituent group β;

(17) a compound in which $R^5$ is a methyl, ethyl, propyl, butyl, trifluoromethyl, phenyl, 3-fluorophenyl, 4-fluorophenyl, 3-chlorophenyl, 4-chlorophenyl, 3-methylphenyl, 4-methylphenyl, 3-methoxyphenyl, 4-methoxyphenyl, 3-cyanophenyl, 4-cyanophenyl, 2,4-difluorophenyl, 2,4-dichlorophenyl, 3,4-difluorophenyl, 3,4-dichlorophenyl, 3-pyridyl, 4-pyridyl, 2-thienyl or 3-thienyl group;

(18) a compound in which $R^7$ and $R^8$ may be the same or different from each other and each represents a hydrogen atom, a nitro group, an amino group, a mono-lower alkylamino group, a di(lower alkyl)amino group, a cyano group, a carboxyl group, a halogen atom, an aryl group, a heteroaryl group, a lower alkyl group, a lower alkanoyl group, a lower alkyl group substituted with at least one group selected from Substituent group α, a lower alkoxy group substituted with at least one group selected from Substituent group α, a lower alkylthio group substituted with at least one group selected from Substituent group α, a lower alkylsulfinyl group substituted with at least one group selected from Substituent group α or a lower alkylsulfonyl group substituted with at least one group selected from Substituent group α, or $R^7$ and $R^8$ form, together with the carbon atom(s) to which they are attached, a non-aromatic hydrocarbon ring, a non-aromatic heterocycle, a non-aromatic hydrocarbon ring substituted with at least one group selected from Substituent group α and Substituent group β, a non-aromatic heterocycle substituted with at least one group selected from Substituent group α and Substituent group β, an aryl ring, a heteroaryl ring, an aryl ring substituted with at least one group selected from Substituent group α and Substituent group β or a heteroaryl ring substituted with at least one group selected from Substituent group α and Substituent group β;

(19) a compound in which $R^7$ and $R^8$ may be the same or different from each other and each represents a hydrogen atom, a nitro group, a cyano group, a carboxyl group, a halogen atom, an aryl group, a heteroaryl group, a lower alkyl group, a lower alkanoyl group or a lower alkyl group substituted with at least one group selected from Substituent group α, or $R^7$ and $R^8$ form, together with the carbon atom(s) to which they are attached, a non-aromatic hydrocarbon ring, a non-aromatic heterocycle, a non-aromatic hydrocarbon ring substituted with at least one group selected from Substituent group α and Substituent group β, a non-aromatic heterocycle substituted with at least one group selected from Substituent group α and Substituent group β, an aryl ring, a heteroaryl ring, an aryl ring substituted with at least one group selected from Substituent group α and Substituent group β or a heteroaryl ring substituted with at least one group selected from Substituent group α and Substituent group β;

or a pharmacologically acceptable salt, ester or other derivative thereof.

[Substituent Group $α^1$]
halogen atoms, cycloalkyl groups having from 3 to 7 carbon atoms, lower alkoxy groups, lower alkylthio groups, amino groups, mono-lower alkylamino groups, di-(lower alkyl)amino groups, cyano groups, aryl groups, heteroaryl groups, aryloxy groups, heteroaryloxy groups, arylthio groups, heteroarylthio groups.

[Substituent Group $α^2$]
lower alkoxy groups, lower alkylthio groups, aryl groups, heteroaryl groups, aryloxy groups, heteroaryloxy groups, arylthio groups, heteroarylthio groups.

In the above compounds, particularly preferred are:

(20) a compound selected from the following compounds or a pharmacologically acceptable salt, ester or other derivative thereof:

(±)-N-hydroxy-Nα-methyl-Nα-(4-phenoxybenzenesulfonyl)-2-(2-phthalimidoethyl)glycinamide, (±)-N-hydroxy-Nα-methyl-Nα-(4-phenoxybenzenesulfonyl)-2-[2-(thiazolidin-2,4-dione-3-yl)ethyl]glycinamide, (±)-N-hydroxy-Nα-methyl-Nα-(4-phenoxybenzenesulfonyl)-2-[2-(quinazolin-2,4-dione-3-yl)ethyl]glycinamide, (±)-2-[2-(5-fluoropyrimidin-2,4-dione-3-yl)ethyl]-N-hydroxy-Nα-methyl-Nα-(4-phenoxybenzenesulfonyl)glycinamide, (±)-N-hydroxy-Nα-methyl-Nα-(4-phenoxybenzenesulfonyl)-2-[2-(thieno[3,2-d]pyrimidin-2,4-dione-3-yl)ethyl]glycinamide, (±)-N-hydroxy-Nα-methyl-2-[2-(7-methylxanthin-1-yl)ethyl]-Nα-(4-phenoxybenzenesulfonyl)glycinamide, (±)-N-hydroxy-Nα-methyl-Nα-(4-phenoxybenzenesulfonyl)-2-[2-pteridin-2,4-dione-3-yl)ethyl]glycinamide, (±)-2-[2-(1,1-dioxo-1,2-benzisothiazol-3-one-2-yl)ethyl]-N-hydroxy-Nα-methyl-Nα-(4-phenoxybenzenesulfonyl)glycinamide, (±)-N-hydroxy-Nα-methyl-2-[2-(6-methylpyrimidin-2,4-dione-3-yl)ethyl]-Nα-(4-phenoxybenzenesulfonyl)glycinamide, (±)-N-hydroxy-Nα-methyl-Nα-(4-phenoxybenzenesulfonyl)-2-[2-(5-trifluoromethylpyrimidin-2,4-dione-3-yl)ethyl]glycinamide, N-hydroxy-Nα-methyl-Nα-(4-phenoxybenzenesulfonyl)-2(R)-(2-phthalimidoethyl)glycinamide, (±)-Nα-[4-(4-fluorophenoxy)benzenesulfonyl]-N-hydroxy-Nα-methyl-2-(2-phthalimidoethyl)glycinamide, (±)-2-[2-(6-chloropyrimidin-2,4-dione-3-yl)ethyl]-N-hydroxy-Nα-methyl-Nα-(4-phenoxybenzenesulfonyl)glycinamide, (±)-N-hydroxy-Nα-methyl-Nα-(4-phenoxybenzenesulfonyl)-2-[2-(6-trifluoromethylpyrimidin-2,4-dione-3-yl)ethyl]glycinamide, (±)-N-hydroxy-Nα-methyl-Nα-[4-(pyridin-4-yl)oxybenzenesulfonyl]-2-[2-thieno[3,2-d]pyrimidin-2,4-dione-3-yl)ethyl]glycinamide, (±)-2-[2-(6-chloro-1-methylpyrimidin-2,4-dione-3-yl)ethyl]-N-hydroxy-Nα-methyl-Nα-(4-phenoxybenzenesulfonyl)glycinamide, (±)-Nα-[4-(4-chlorophenoxy)benzenesulfonyl]-2-[2-(6-chloropyrimidin-2,4-dione-3-yl)ethyl]-N-hydroxy-Nα-methylglycinamide, (±)-2-[2-(6-chloropyrimidin-2,4-dione-3-yl)ethyl-Nα-[4-(4-fluorophenoxy)-benzenesulfonyl]-N-hydroxy-Nα-methylglycinamide, (±)-Nα-[4-(4-chlorophenoxy)benzenesulfonyl]-N-hydroxy-Nα-methyl-2-[2-(6-trifluoromethylpyrimidin-2,4-dione-3-yl)ethyl]glycinamide, (±)-Nα-[4-(4-fluorophenoxy)benzenesulfonyl]-N-hydroxy-Nα-methyl-2-[2-(6-trifluoromethylpyrimidin-2,4-dione-3-yl)ethyl]glycinamide, (±)-Nα-[4-(3-chlorophenoxy)benzenesulfonyl]-N-hydroxy-Nα-methyl-2-[2-(6-trifluoromethylpyrimidin-2,4-dione-3-yl)ethyl]glycinamide, (±)-Nα-[4-(3-chlorophenoxy)benzenesulfonyl]-2-[2-(6-chloropyrimidin-2,4-dione-3-yl)ethyl]-N-hydroxy-Nα-methylglycinamide, (±)-2-[2-(6-chloropyrimidin-2,4-dione-3-yl)ethyl]-Nα-ethyl-N-hydroxy-Nα-(4-phenoxybenzenesulfonyl)glycinamide, (±)-2-[2-(6-chloropyrimidin-2,4-dione-3-yl)ethyl]-Nα-[4-(3-fluorophenoxy)-benzenesulfonyl]-N-hydroxy-Nα-methylglycinamide, (±)-2-[2-(6-chloropyrimidin-2,4-dione-3-yl)ethyl]-N-hydroxy-Nα-methyl-Nα-[4-(pyridin-4-yl)oxybenzenesulfonyl]glycinamide, (±)-Nα-[4-(3-fluorophenoxy)benzenesulfonyl]-N-hydroxy-Nα-methyl-2-[2-(6-trifluoromethylpyrimidin-2,4-dione-3-yl)ethyl]glycinamide, (±)-N-hydroxy-Nα-methyl-Nα-[4-(pyridin-4-yl)oxybenzenesulfonyl]-2-[2-(6-trifluoromethylpyrimidin-2,4-dione-3-yl)ethyl]glycinamide, (±)-Nα-ethyl-N-hydroxy-Nα-(4-phenoxybenzenesulfonyl)-2-[2-(6-trifluoromethylpyrimidin-2,4-dione-3-yl)ethyl]glycinamide, (±)-N-hydroxy-Nα-methyl-2-[2-(1-methyl-6-trifluoromethylpyrimidin-2,4-dione-3-yl)ethyl]-Nα-(4-phenoxybenzenesulfonyl)glycinamide, (±)-2-[2-(5-chloropyrimidin-2,4-dione-3-yl)ethyl]-N-hydroxy-Nα-methyl-Nα-(4-phenoxybenzenesulfonyl)glycinamide, Nα-[4-(3-chlorophenoxy)benzenesulfonyl]-N-hydroxy-Nα-methyl-2-[2-quinazolin-2,4-dione-3-yl)ethyl]glycinamide, Nα-[4-(3-chlorophenoxy)benzenesulfonyl]-N-hydroxy-Nα-methyl-2-[2-(thieno[3,2-d]pyrimidin-2,4-dione-3-yl)ethyl]glycinamide, and Nα-[4-(3-chlorophenoxy)benzenesulfonyl]-N-hydroxy-Nα-methyl-2-(2-phthalimidoethyl)glycinamide.

Another object of the present invention is to provide:

(21) a medicament (particularly a MMP-13 inhibitory agent and an aglycanase inhibitory agent) containing the compound described in any one selected from the above (1) to (20) or a pharmacologically acceptable salt, ester or other derivative thereof as an active ingredient, more specifically

(22) the medicament described in (21) for the prevention or treatment of arthritis (particularly osteoarthritis), or

(23) the medicament described in (21) for inhibiting metastasis, invasion or growth of cancer (particularly breast cancer).

Furthermore, the present invention also provides

(24) a method for preventing or treating arthritis (particularly osteoarthritis) or a method for inhibiting metastasis, invasion or growth of cancer (particularly breast cancer), comprising administering the compound or a pharmacologically acceptable salt, ester or other derivative thereof described in any one of the above-mentiond (1) to (20), and

(25) a use of the compound or a pharmacologically acceptable salt, ester or other derivative thereof described in any one of the above-mentiond (1) to (20) for manufacturing a medicament for the prevention or treatment of arthritis (particularly osteoarthritis) or a medicament for inhibiting metastasis, invasion or growth of cancer (particularly breast cancer).

In the above formula (I):

the "lower alkyl group" in the definition of $R^2$, $R^3$, $R^5$, $R^7$, $R^8$, $R^9$, $R^{10}$, $R^{11}$, $R^{12}$, "Substituent group β" and "Substituent group γ"; the "lower alkyl group" of the "lower alkyl group substituted with at least one group selected from Substituent group α" in the definition of $R^2$, $R^3$, $R^5$, $R^7$ and $R^8$; the "lower alkyl" moiety of the "lower alkoxy group substituted with at least one group selected from Substituent group α", the "lower alkylthio group substituted with at least one group selected from Substituent group α", the "lower alkylsulfinyl group substituted with at least one group selected from Substituent group α" and the "lower alkylsulfonyl group substituted with at least one group selected from Substituent group α" in the definition of $R^7$ and $R^8$; the "lower alkyl" moiety of the "lower alkoxy group", the "halogeno lower alkoxy group", the "lower alkylthio group", the "halogeno lower alkylthio group", the "lower alkylsulfinyl group", the "lower alkylsulfonyl group", the "mono-lower alkylamino group" and the "di-(lower alkyl)amino group" in the definition of "Substituent group α"; the "lower alkyl" moiety of the "halogeno lower alkyl group" in the definition of the "Substituent group β"; and the "lower alkyl" moiety of the "halogeno lower alkyl group", the "lower alkoxy group", the "halogeno lower alkoxy group", the "lower alkylthio group" and the "halogeno lower alkylthio group" in the definition of "Substituent group γ" represent a straight or branched chain alkyl group having from 1 to 6 carbon atoms such as methyl, ethyl, propyl, isopropyl, butyl, isobutyl, s-butyl, t-butyl, pentyl, 2-pentyl, 3-pentyl, 2-methylbutyl, 3-methylbutyl, 1,1-dimethylpropyl, 1,2-dimethylpropyl, 2,2-dimethylpropyl, hexyl, 2-hexyl, 3-hexyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl and 1,2,2-trimethylpropyl groups, preferably a straight or branched chain alkyl group having from 1 to 4 carbon atoms, particularly preferably a methyl, ethyl, propyl, isopropyl or butyl group.

The "cycloalkyl group having from 3 to 7 carbon atoms" in the definition of $R^2$, $R^3$ and the "substituent group α"; and the "cycloalkyl group having from 3 to 7 carbon atoms" of the "cycloalkyl group having from 3 to 7 carbon atoms substituted with a group selected from the substituent group α and the substituent group β" in the definition of $R^3$ include cyclopropyl, cyclobutyl, cyclopentyl, cyclohexyl and cycloheptyl groups.

The "lower alkylene group" in the definition of A represents a straight or branched alkylene group having from 1 to 6 carbon atoms such as methylene, ethylene, trimethylene, propylene, tetramethylene, 1,1-dimethylethylene, 1,1-dimethyltrimethylene and 1,1-dimethyltetramethylene, preferably a straight or branched alkylene group having from 1 to 4 carbon atoms, more preferably a straight alkylene group having from 1 to 4 carbon atoms, particularly preferably a methylene, ethylene or trimethylene group.

The "lower alkylene group interrupted by an oxygen atom, —S(O)$_m$— "or —N(R$^9$)—" in the definition of A represents a group in which an oxygen atom, —S(O)$_m$— or —N(R$^9$)— is present between two carbon atoms of the above "lower alkylene group", and preferred examples of such a group include —CH$_2$OCH$_2$—, —CH$_2$SCH$_2$—, —CH$_2$NHCH$_2$—, —CH$_2$N(CH$_3$)CH$_2$—, —CH$_2$OCH$_2$CH$_2$—, —CH$_2$SCH$_2$CH$_2$—, —CH$_2$NHCH$_2$CH$_2$—, —CH$_2$N(CH$_3$)CH$_2$CH$_2$—, —CH$_2$SOCH$_2$CH$_2$— and —CH$_2$SO$_2$CH$_2$—.

The "lower alkoxy group" in the definition of "Substituent group α" and "Substituent group γ"; and the "lower alkoxy group" of the "lower alkoxy group substituted with at least one group selected from Substituent group α" in the definition of R$^7$ and R$^8$ represent a group in which an oxygen atom is attached to the above "lower alkyl" group, preferably a straight or branched alkoxy group having from 1 to 4 carbon atoms, more preferably a methoxy, ethoxy, propoxy, isopropoxy or butoxy group, particularly preferably a methoxy, ethoxy or propoxy group.

The "lower alkylthio group" in the definition of "Substituent group α" and "Substituent group γ"; and the "lower alkylthio group" of the "lower alkylthio group substituted with at least one group selected from Substituent group α" in the definition of R$^7$ and R$^8$ represent a group in which a sulfur atom is attached to the above "lower alkyl" group, preferably a straight or branched alkylthio group having from 1 to 4 carbon atoms, more preferably a methylthio, ethylthio, propylthio, isopropylthio or butylthio group, particularly preferably a methylthio, ethylthio or propylthio group.

The "lower alkylsulfinyl group" in the definition of "Substituent group α"; and the "lower alkylsulfinyl group" of the "lower alkylsulfinyl group substituted with at least one group selected from Substituent group α" in the definition of R$^7$ and R$^8$ represent a group in which a sulfinyl moiety (—SO—) is attached to the above "lower alkyl" group, preferably a straight or branched alkylsulfinyl group having from 1 to 4 carbon atoms, more preferably a methylsulfinyl, ethylsulfinyl, propylsulfinyl, isopropylsulfinyl or butylsulfinyl group, particularly preferably a methylsulfinyl, ethylsulfinyl or propylsulfinyl group.

The "lower alkylsulfonyl group" in the definition of "Substituent group α"; and the "lower alkylsulfonyl group" of the "lower alkylsulfonyl group substituted with at least one group selected from Substituent group α" in the definition of R$^7$ and R$^8$ represent a group in which a sulfonyl (—SO$_2$—) moiety is attached to the above "lower alkyl" group, preferably a straight or branched alkylsulfonyl group having from 1 to 4 carbon atoms, more preferably a methylsulfonyl, ethylsulfonyl, propylsulfonyl, isopropylsulfonyl or butylsulfonyl group, particularly preferably a methylsulfonyl, ethylsulfonyl or propylsulfonyl group.

The "non-aromatic hydrocarbon ring" which is formed by R$^7$ and R$^8$, together with the carbon atom(s) to which they are attached; the "non-aromatic hydrocarbon ring" of the "non-aromatic hydrocarbon ring substituted with at least one group selected from Substituent group α and Substituent group β" which is formed by R$^7$ and R$^8$, together with the carbon atom(s) to which they are attached; the "non-aromatic hydrocarbon ring" which is formed by R$^{11}$ and R$^{12}$, together with the carbon atom(s) to which they are attached; and the "non-aromatic hydrocarbon ring" of the "non-aromatic hydrocarbon ring substituted with at least one group selected from Substituent group α and Substituent group β" which is formed by R$^{11}$ and R$^{12}$, together with the carbon atom(s) to which they are attached, represent a saturated hydrocarbon ring having from 3 to 7 carbon atoms such as a cyclopropane ring, cyclobutane ring, cyclopentane ring, cyclohexane ring and cycloheptane ring or an unsaturated hydrocarbon ring having from 3 to 7 carbon atoms such as a cyclopropene ring, cyclobutene ring, cyclopentene ring, cyclohexene ring and cycloheptene ring, preferably a saturated hydrocarbon ring having 5 or 6 carbon atoms or an unsaturated hydrocarbon ring having 5 or 6 carbon atoms, more preferably an unsaturated hydrocarbon ring having 5 or 6 carbon atoms.

In the above formulae (II) and (III), since a double bond exists between the carbon atom to which R$^7$ is attached and the carbon atom to which R$^8$ is attached, R$^7$ and R$^8$, together with a carbon atom to which are attached, do not form a saturated hydrocarbon ring.

The "non-aromatic heterocycle" which is formed by R$^7$ and R$^8$, together with the carbon atom(s) to which they are attached; the "non-aromatic heterocycle" of the "non-aromatic heterocycle substituted with at least one group selected from Substituent group α and Substituent group β" which is formed by R$^7$ and R$^8$, together with the carbon atom(s) to which they are attached; the "non-aromatic heterocycle" which is formed by R$^{11}$ and R$^{12}$, together with the carbon atom(s) to which they are attached; and the "non-aromatic heterocycle" of the "non-aromatic heterocycle substituted with at least one group selected from Substituent group α and Substituent group β" which is formed by R$^{11}$ and R$^{12}$, together with the carbon atom(s) to which they are attached, represent a 5- to 7-membered saturated heterocycle or partially saturated heterocycle containing from 1 to 3 sulfur atoms, oxygen atoms and/or nitrogen atoms, preferably a 5- or 6-membered saturated heterocycle or partially saturated heterocycle containing one or two sulfur atoms, oxygen atoms and/or nitrogen atoms, and examples of such a ring include for example a dithiolane ring, dioxane ring and pyrrolidine ring.

The "aryl ring" which is formed by R$^7$ and R$^8$, together with the carbon atom(s) to which they are attached; and the "aryl ring" of the "aryl ring substituted with at least one group selected from Substituent group α and Substituent group β" which is formed by R$^7$ and R$^8$, together with the carbon atom(s) to which they are attached, represent an aromatic hydrocarbon ring having from 6 to 10 carbon atoms such as a benzene ring and a naphthalene ring, preferably a benzene ring or a naphthalene ring, particularly preferably the benzene ring.

The above "aryl ring" may be fused with a cycloalkyl group having from 3 to 10 carbon atoms and such fused rings include an indane ring.

The "heteroaryl ring" which is formed by R$^7$ and R$^8$, together with the carbon atom(s) atom to which they are attached; and the "heteroaryl ring" of the "heteroaryl ring substituted with at least one group selected from Substituent group α and Substituent group β" which is formed by R$^7$ and R$^8$, together with the carbon atom(s) to which they are attached represent a 5- to 7-membered aromatic heterocycle containing from 1 to 3 sulfur atoms, oxygen atoms and/or nitrogen atoms, and examples of such a ring include a furan ring, a thiophene ring, a pyrrole ring, an azepine ring, a pyrazole ring, an imidazole ring, an oxazole ring, an isoxazole ring, a thiazole ring, an isothiazole ring, a 1,2,3-oxadiazole ring, a triazole ring, a thiadiazole ring, a pyridine ring, a pyridazine ring, a pyrimidine ring and a pyrazine ring, preferably a 5- or 6-membered aromatic heterocycle containing one or two sulfur atoms, oxygen atoms and/or nitrogen atoms, more preferably a thiophene ring, an imidazole ring, a pyridine ring and a pyrazine ring.

The above "heteroaryl ring" may be fused with an other cyclic group, and examples of such a fused ring include an indole ring, a benzofuran ring, a benzothiophene ring, an isoquinoline ring and a quinoline ring.

Specific examples of the "group of formula (II), (III) or (IV)" in the definition of $R^6$ preferably include:

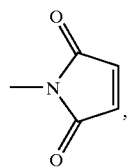 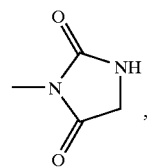

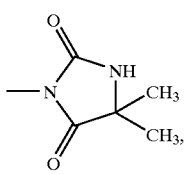 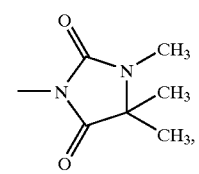 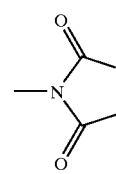

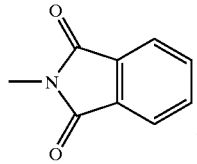 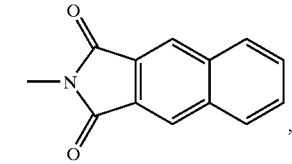

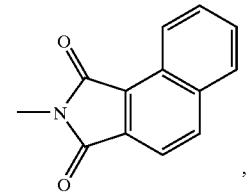 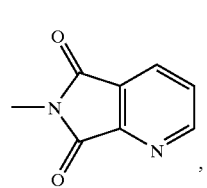

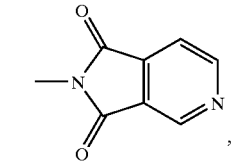 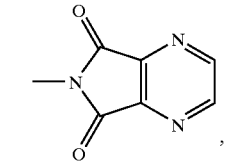

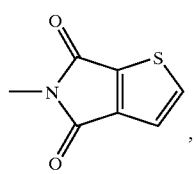 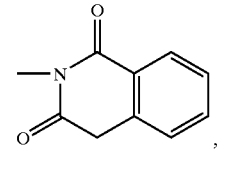

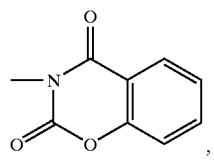 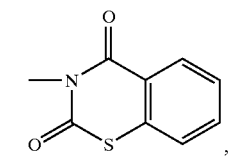

-continued

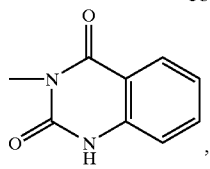 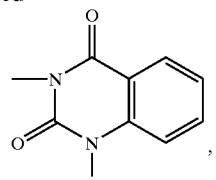

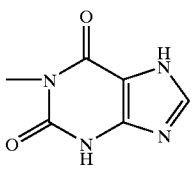 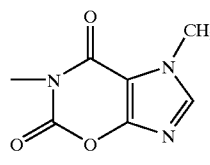

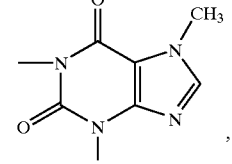 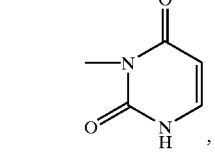

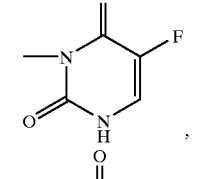 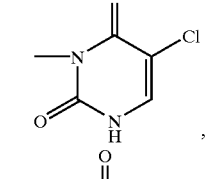

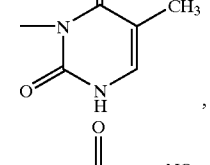 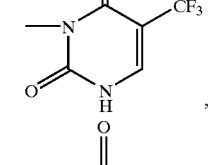

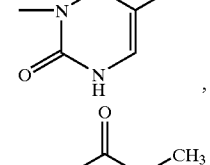 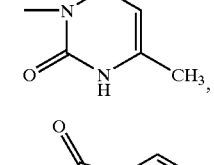

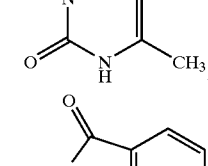 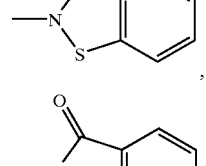

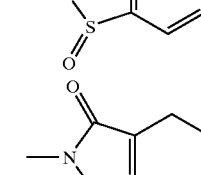 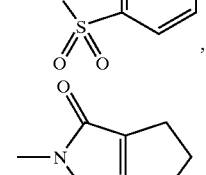

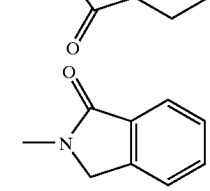 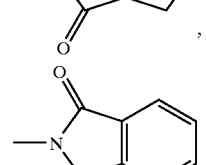

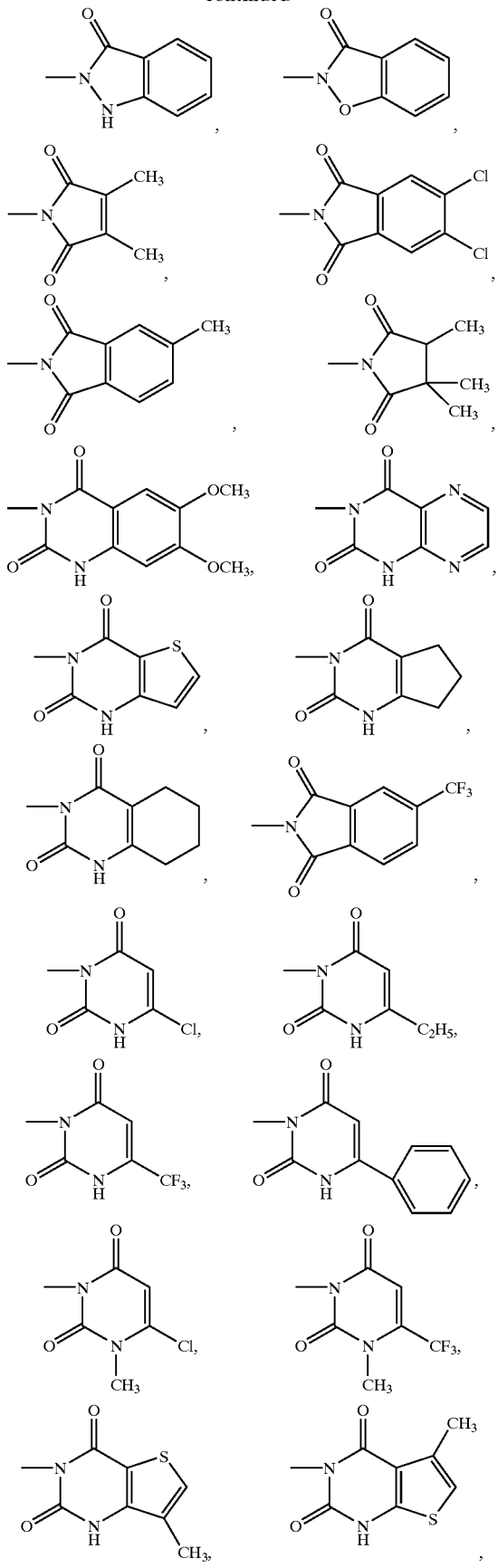
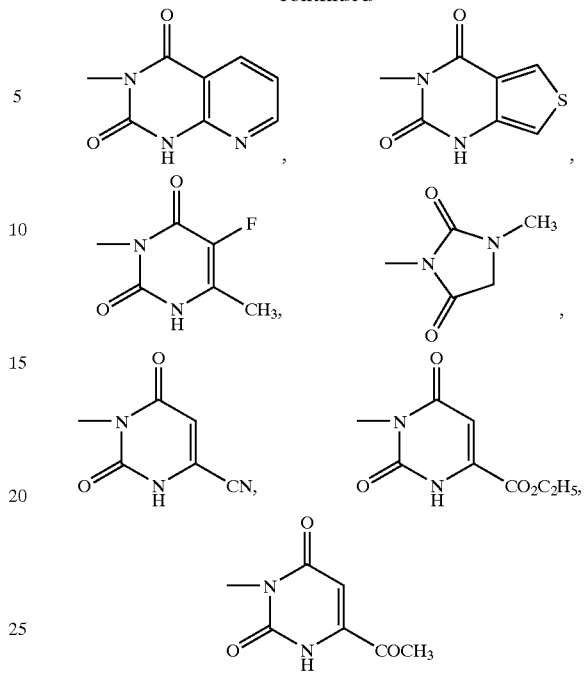

The "alkenyl group" and the "alkenyl group" of the "alkenyl group substituted with at least one group selected from Substituent group α" in the definition of $R^3$ represent a straight or branched alkenyl group having from 3 to 10 carbon atoms, preferably a straight or branched alkenyl group having from 3 to 6 carbon atoms such as allyl, 2-butenyl, 3-butenyl, 2-methylallyl, 2-pentenyl, 3-pentenyl, 4-pentenyl, 5-pentenyl, 2-hexenyl, 3-hexenyl, 4-hexenyl and 5-hexenyl groups, more preferably a straight or branched alkenyl group having 3 or 4 carbon atoms, particularly preferably an allyl or 2-butenyl group.

The "alkynyl group" and the "alkynyl group" of the "alkynyl group substituted with at least one group selected from Substituent group α" in the definition of $R^3$ represent a straight or branched alkynyl group having from 3 to 10 carbon atoms, preferably a straight or branched alkynyl group having from 3 to 6 carbon atoms such as propargyl, 2-butynyl, 3-butynyl, 2-methyl-3-butynyl, 2-pentynyl, 3-pentynyl, 4-pentynyl, 5-pentynyl, 2-hexynyl, 3-hexynyl, 4-hexynyl and 5-hexynyl groups, more preferably a straight or branched alkynyl group having 3 or 4 carbon atoms, particularly preferably a propargyl or 2-butynyl group.

The "arylene group" and the "arylene group" of the "arylene group substituted with at least one group selected from Substituent group α and Substituent group β" in the definition of $R^4$ represent a divalent aromatic hydrocarbon ring having from 6 to 10 carbon atoms such as phenylene and naphthylene, preferably a phenylene group, particularly preferably a p-phenylene group.

The above "arylene group" may be fused with a cycloalkyl group having from 3 to 10 carbon atoms, and examples of such a group include an indan-4,7-di-yl group.

The "heteroarylene group" and the "heteroarylene group" of the "heteroarylene group substituted with at least one group selected from Substituent group α and Substituent group β" in the definition of $R^4$ represent a divalent 5- to 7-membered aromatic heterocyclic ring containing from 1 to 3 sulfur atoms, oxygen atoms and/or nitrogen atoms, and examples thereof include furanylene, thienylene, pyrrolylene, azepinylene, pyrazolylene, imidazolylene, oxazolylene, isoxazolylene, thiazolylene, isothiazolylene, 1,2,3-oxadiazolylene, triazolylene, thiadiazolylene, pyridylene, pyridazinylene, pyrimidinylene and pyrazinylene groups. Preferably, it represents a 5- or 6-membered aromatic heterocycle containing one or two sulfur atoms, oxygen atoms or/and nitrogen atoms, more preferably the thienylene, imidazolylene, pyridylene or pyrazinylene group, particularly preferably a thienylene group.

The above "heteroarylene group" may be fused with other cyclic groups, and examples of such a fused ring include indole-4,7-diyl and benzothiophene-4,7-diyl.

The "aryl group" in the definition of $R^5$ and "Substituent group α"; the "aryl group" of the "aryl group substituted with at least one group selected from Substituent group α and Substituent group β" in the definition of $R^5$; and the "aryl group" of the "aryl group substituted with at least one group selected from Substituent group γ" in the definition of "Substituent group α" represent a monovalent aromatic hydrocarbon ring having from 6 to 10 carbon atoms such as phenyl and naphthyl, more preferably a phenyl group.

The above "aryl group" may be fused with a cycloalkyl group having from 3 to 10 carbon atoms, and examples of such a group include 5-indanyl.

The "heteroaryl group" in the definition of $R^5$ and "Substituent group α"; the "heteroaryl group" of the "heteroaryl group substituted with at least one group selected from Substituent group α and Substituent group β" in the definition of $R^5$; and the "heteroaryl group" of the "heteroaryl group substituted with at least one group selected from Substituent group γ" in the definition of "Substituent group α" represent a monovalent 5- to 7-membered aromatic heterocyclic group containing from 1 to 3 sulfur atoms, oxygen atoms and/or nitrogen atoms and include furanyl, thienyl, pyrrolyl, azepinyl, pyrazolyl, imidazolyl, oxazolyl, isoxazolyl, thiazolyl, isothiazolyl, 1,2,3-oxadiazolyl, triazolyl, thiadiazolyl, pyridyl, pyridazinyl, pyrimidinyl and pyrazinyl groups. Preferably, it represents a monovalent 5- or 6-membered aromatic heterocyclic group containing one or two sulfur atoms, oxygen atoms and/or nitrogen atoms, more preferably a thienyl, imidazolyl, pyridyl or pyrazinyl group, and particularly preferably a thienyl or pyridyl group.

The above heteroaryl group may be fused with an other cyclic group, and examples of such fused rings include indolyl, benzofuranyl, benzothienyl, isoquinolyl and quinolyl groups.

The "halogen atom" in the definition of "Substituent group α" and "Substituent group γ" includes a fluorine atom, a chlorine atom, a bromine atom and an iodine atom.

The "halogeno lower alkoxy group" in the definition of "Substituent group α" and "Substituent group γ" represents a group in which a "halogeno lower alkyl group" described below is attached to an oxygen atom and, particularly preferably, it is a difluoromethoxy, trifluoromethoxy or 2,2,2-trifluoroethoxy group.

The "lower alkanoyl group" in the definition of "Substituent group α" represents a formyl group or a group in which a carbonyl group is attached to the above "lower alkyl group". Preferably, it is a straight or branched alkanoyl group having from 1 to 4 carbon atoms, more preferably a formyl, acetyl, propionyl, butyryl or isobutyryl group, still more preferably a formyl, acetyl or propionyl group, and particularly preferably a formyl or acetyl group.

The "halogeno lower alkylthio group" in the definition of "Substituent group α" and "Substituent group γ" represents a group in which a "halogeno lower alkyl group" described below is attached to a sulfur atom. Particularly preferably, it is a difluoromethylthio, trifluoromethylthio or 2,2,2-trifluoroethylthio group.

The "mono-lower alkylamino group" in the definition of "Substituent group α" represents a group in which one hydrogen atom of a —NH$_2$ group is substituted with the above "lower alkyl group". Preferably, it is a straight or branched monoalkylamino group having from 1 to 4 carbon atoms, more preferably a methylamino, ethylamino, propylamino, isopropylamino or butylamino group, particularly preferably a methylamino, ethylamino or propylamino group.

The "di(lower alkyl)amino group" in the definition of "Substituent group α" represents a group in which the two hydrogen atoms of a —NH$_2$ group are substituted with the above "lower alkyl group" which may be the same or different. Preferably, it is a dialkylamino group in which any two alkyl groups are a straight or branched alkyl group having from 1 to 4 carbon atoms, more preferably a dimethylamino, ethylmethylamino, methylpropylamino, isopropylmethylamino, butylmethylamino, diethylamino or diisopropylamino group, particularly preferably a dimethylamino, ethylmethylamino or diethylamino group.

The "aryloxy group" and the "aryloxy group" of the "aryloxy group substituted with at least one group selected from Substituent group γ" in the definition of "Substituent group α" represent a group in which the above "aryl group" is attached to an oxygen atom.

The "heteroaryloxy group" and the "heteroaryloxy group" of the "heteroaryloxy group substituted with at least one group selected from Substituent group γ" in the definition of the "substituent group α" represent a group in which the above "heteroaryl group" is attached to an oxygen atom.

The "arylthio group" and the "arylthio group" of the "arylthio group substituted with at least one group selected from Substituent group γ" in the definition of "Substituent group α" represent a group in which the above "aryl group" is attached to a sulfur atom.

The "heteroarylthio group" and the "heteroarylthio group" of the "heteroarylthio group substituted with at least one group selected from "Substituent group γ" in the definition of "Substituent group α" represent a group in which the above "heteroaryl group" is attached to a sulfur atom.

The "halogeno lower alkyl group" in the definition of "Substituent group " and "Substituent group γ" represents a group in which one or two or more hydrogen atoms of the above "lower alkyl group" is substituted with the above "halogen atom". Preferably, it is a halogeno lower alkyl group having from 1 to 4 carbon atoms, more preferably a trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl or 2,2-dibromoethyl group, particularly preferably a trifluoromethyl, trichloromethyl, difluoromethyl or fluoromethyl group.

Since the compound (I) of the present invention can be converted to an ester, the "ester" means such an ester and includes an "ester of a hydroxyl group" and an "ester of a carboxyl group", and includes an ester in which each ester residue is a "general protecting group" or a "protecting group removable by a biological method such as hydrolysis in vivo".

The "general protecting group" means a protecting group removable according to a chemical method such as hydrogenolysis, hydrolysis, electrolysis and photolysis.

Preferred examples of the "general protecting group" for the "ester of the hydroxyl group" include "aliphatic acyl groups", for example, alkylcarbonyl groups such as formyl, acetyl, propionyl, butyryl, isobutyryl, pentanoyl, pivaloyl, isovaleryl, octanoyl, nonylcarbonyl, decylcarbonyl, 3-methylnonylcarbonyl, 8-methylnonylcarbonyl, 3-ethyloctylcarbonyl, 3,7-dimethyloctylcarbonyl, undecylcarbonyl, dodecylcarbonyl, tridecylcarbonyl, tetradecylcarbonyl, pentadecylcarbonyl, hexadecylcarbonyl, 1-methylpentadecylcarbonyl, 14-methylpentadecylcarbonyl, 13,13-dimethyltetradecylcarbonyl, heptadecylcarbonyl, 15-methylhexadecylcarbonyl, octadecylcarbonyl, 1-methylheptadecylcarbonyl, nonadecylcarbonyl, eicosylcarbonyl and heneicosylcarbonyl groups, halogenated alkylcarbonyl groups such as chloroacetyl, dichloroacetyl, trichloroacetyl and trifluoroacetyl groups, lower alkoxyalkylcarbonyl groups such as methoxyacetyl groups and unsaturated alkylcarbonyl groups such as acryloyl, propioloyl, methacryloyl, crotonoyl, isocrotonoyl and (E)-2-methyl-2-butenoyl groups, (of which, a lower aliphatic acyl group having 1 to 6 carbon atoms is preferred); "aromatic acyl groups", for example, arylcarbonyl groups such as benzoyl, α-naphthoyl and β-naphthoyl groups, halogenated arylcarbonyl groups such as 2-bromobenzoyl and 4-chlorobenzoyl groups, lower alkylated arylcarbonyl groups such as 2,4,6-trimethylbenzoyl and 4-toluoyl groups, lower alkoxylated arylcarbonyl groups such as 4-anisoyl groups, nitrated arylcarbonyl groups such as 4-nitrobenzoyl and 2-nitrobenzoyl groups, lower alkoxycarbonylated arylcarbonyl groups such as 2-(methoxycarbonyl)benzoyl groups and arylated arylcarbonyl groups such as 4-phenylbenzoyl groups; "alkoxycarbonyl groups" such as lower alkoxycarbonyl groups, e.g., methoxycarbonyl, ethoxycarbonyl, propoxycarbonyl, butoxycarbonyl, s-butoxycarbonyl, t-butoxycarbonyl and isobutoxycarbonyl groups, and lower alkoxycarbonyl groups substituted with halogen atoms or a tri(lower alkyl) silyl group, e.g., 2,2,2-trichloroethoxycarbonyl and 2-trimethylsilylethoxycarbonyl; the "general protecting group" for a hydroxy group also includes ethers including "tetrahydropyranyl or tetrahydrothiopyranyl groups" such as tetrahydropyran-2-yl, 3-bromotetrahydropyran-2-yl, 4-methoxytetrahydropyran-4-yl groups, tetrahydrothiopyran-2-yl and 4-methoxytetrahydrothiopyran-4-yl groups; "tetrahydrofuranyl or tetrahydrothiofuranyl groups" such as tetrahydrofuran-2-yl groups and tetrahydrothiofuran-2-yl groups; "silyl groups", for example, tri(lower alkyl)silyl groups such as trimethylsilyl, triethylsilyl, isopropyldimethylsilyl, t-butyldimethylsilyl, methyldiisopropylsilyl, methyl-di-t-butylsilyl and triisopropylsilyl groups, and tri(lower alkyl)silyl groups in which 1 or 2 alkyl groups are substituted by 1 or 2 aryl groups such as diphenylmethylsilyl, diphenylbutylsilyl, diphenylisopropylsilyl and phenyldiisopropylsilyl groups; "alkoxymethyl groups", for example, lower alkoxymethyl groups such as methoxymethyl, 1,1-dimethyl-1-methoxymethyl, ethoxymethyl, propoxymethyl, isopropoxymethyl, butoxymethyl and t-butoxymethyl groups, lower alkoxylated lower alkoxymethyl groups such as 2-methoxyethoxymethyl groups and lower halogeno alkoxymethyl groups such as 2,2,2-trichloroethoxymethyl and bis(2-chloroethoxy)methyl groups; "substituted ethyl groups", for example, lower alkoxylated ethyl groups such as 1-ethoxyethyl and 1-(isopropoxy)ethyl groups and halogenated ethyl groups such as 2,2,2-trichloroethyl groups; "aralkyl groups", for example, lower alkyl groups substituted with 1 to 3 aryl groups such as benzyl, α-naphthylmethyl, β-naphthylmethyl, diphenylmethyl, triphenylmethyl, α-naphthyldiphenylmethyl and 9-anthrylmethyl groups and lower alkyl groups substituted with 1 to 3 aryl groups each having an aryl ring substituted with a lower alkyl, lower alkoxy, nitro, halogen orcyano group, for example, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; "alkenyloxycarbonyl groups" such as vinyloxycarbonyl and allyloxycarbonyl groups; and "aralkyloxycarbonyl groups" having an aryl ring which may be substituted with one or two lower alkoxy or nitro groups such as benzyloxycarbonyl, 4-methoxybenzyloxycarbonyl, 3,4-dimethoxy-benzyloxycarbonyl, 2-nitrobenzyloxycarbonyl and 4-nitrobenzyloxycarbonyl groups.

Preferred examples of the "general protecting group" relating to an "ester of a carboxyl group" include the above-mentioned "lower alkyl groups"; lower alkenyl groups such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl groups and 5-hexenyl groups; lower alkynyl groups such as ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups; the above-mentioned "halogeno lower alkyl groups"; hydroxy "lower alkyl groups" such as 2-hydroxyethyl, 2,3-dihydroxypropyl, 3-hydroxypropyl, 3,4-dihydroxybutyl and 4-hydroxybutyl groups; "lower aliphatic acyl"–"lower alkyl groups" such as acetyl methyl; the above-mentioned "aralkyl groups"; and the above-mentioned "silyl groups".

The "protecting group removable by a biological method such as hydrolysis in vivo" means a group which is removable through a biological method such as hydrolysis in the human body to give a free acid compound or a salt thereof. Whether a compound is such a derivative or not can be determined as follows: the compound is intravenously administered to an experimental animal such as a rat or mouse and the body fluid of the animal is thereafter studied. If the original compound or a pharmacologically acceptable salt thereof can be detected from the body fluid, the compound thus studied is judged as a derivative.

Preferred examples of the "protecting group which can be cleaved through a biological method such as hydrolysis in vivo" for a hydroxy group include "carbonyloxyalkyl groups" such as 1-(acyloxy)"lower alkyl groups" including 1-("lower aliphatic acyl"oxy)"lower alkyl groups", e.g. formyloxymethyl, acetoxymethyl, dimethylaminoacetoxymethyl, propionyloxymethyl, butyryloxymethyl, pivaloyloxymethyl, valeryloxymethy, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups, 1-("cycloalkyl"carbonyloxy) "lower alkyl groups", e.g. cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl groups; 1-("aromatic acyl"oxy)"lower alkyl groups", e.g. benzoyloxymethyl goups; (lower alkoxycarbonyloxy)alkyl groups, e.g. methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxym ethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy) ethyl, 1-(butoxycarbonyloxy)ethyl, 1-(isobutoxycarbonyloxy)ethyl, 1-(tert-butoxycarbonyloxy) ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 2-(methoxycarbonyloxy) ethyl, 2-(ethoxycarbonyloxy)ethyl, 2-(propoxycarbonyloxy) ethyl, 2-(isopropoxycarbonyloxy)ethyl, 2-(butoxycarbonyloxy)ethyl, 2-(isobutoxycarbonyloxy) ethyl, 2-(pentyloxycarbonyloxy)ethyl, 2-(hexyloxycarbonyloxy)ethyl, 1-(methoxycarbonyloxy) propyl, 1-(ethoxycarbonyloxy)propyl, 1-(propoxycarbonyloxy)propyl, 1-(isopropoxycarbonyloxy) propyl, 1-(butoxycarbonyloxy)propyl, 1-(isobutoxycarbonyloxy)propyl, 1-(pentyloxycarbonyloxy) propyl, 1-(hexyloxycarbonyloxy)propyl, 1-(methoxycarbonyloxy)butyl, 1-(ethoxycarbonyloxy) butyl, 1-(propoxycarbonyloxy)butyl, 1-(isopropoxycarbonyloxy)butyl, 1-(butoxycarbonyloxy) butyl, 1-(isobutoxycarbonyloxy)butyl, 1-(methoxycarbonyloxy)pentyl, 1-(ethoxycarbonyloxy) pentyl, 1-(methoxycarbonyloxy)hexyl and 1-(ethoxycarbonyloxy)hexyl groups; oxodioxolenylmethyl groups, e.g (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl) methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl groups; and the like; "phthalidyl groups", e.g. phthalidyl, dimethylphthalidyl and dimethoxyphthalidyl groups; the above-mentioned "lower aliphatic acyl groups"; the above-mentioned "aromatic acyl groups"; "half-ester salt residues of succinic acid"; "phosphate ester salt residues"; "ester-forming residues of an amino acid or the like"; carbamoyl groups; carbamoyl groups substituted with 1 or 2 lower alkyl groups; and "1-(acyloxy) alkyloxycarbonyl groups, e.g. pivaloyloxymethyloxycarbonyl.

Preferred examples of the "protecting group removable by a biological method such as hydrolysis in vivo" for a carboxyl group include "alkoxy lower alkyl groups" such as lower alkoxy lower alkyl groups, e.g. methoxyethyl, 1-ethoxyethyl, 1-methyl-1-methoxyethyl, 1-(isopropoxy) ethyl, 2-methoxyethyl, 2-ethoxyethyl, 1,1-dimethyl-1-methoxyethyl, ethoxymethyl, n-propoxymethyl, isoproxymethyl, n-butoxymethyl or tert-butoxymethyl groups (lower alkoxy lower alkoxy)alkyl groups such as 2-methoxyethoxymethyl groups; lower alkoxylated lower alkoxy lower alkyl groups, e.g. 2-methoxyethoxymethyl groups, "aryl"oxy"lower alkyl groups", e.g. phenoxymethyl groups, and halogeno lower alkoxy lower alkyl groups, e.g. 2,2,2-trichloroethoxymethyl and bis(2-chloroethoxy)methyl groups; ""lower alkoxy"carbonyl"lower alkyl groups"", e.g. methoxycarbonyl groups; "cyano"lower alkyl groups"" e.g. cyanomethyl or 2-cyanomethyl groups; ""lower alkyl"thiomethyl groups", e.g. methylthiomethyl or ethylthiomethyl groups; ""aryl"thiomethyl groups", e.g. phenylthiomethyl or naphthylthiomethyl groups; ""lower alkyl"sulfonyl"lower alkyl groups optionally substituted with halogen atoms"", e.g. 2-methanesulfonylethyl or 2-trifluoromethanesulfonylethyl groups; ""aryl"sulfonyl-"lower alkyl groups", e.g. 2-benzenesulfonylethyl or 2-toluenesulfonylethyl groups; the above-mentioned "1-(acyloxy)"lower alkyl groups""; the above-mentioned "phthalidyl groups"; the above-mentioned "aryl groups"; the above-mentioned "lower alkyl groups"; "carboxy alkyl groups", e.g. carboxymethyl groups; and "amide-forming residues of an amino acid", e.g. phenylalanine groups.

In the case where the compound (I) of the present invention has a basic group such as an amino group, the compound can be converted to a salt by reacting it with an acid and in the case where the compound (I) has an acidic group such as a carboxyl group, the compound can be converted to the salt by reacting it with a base; the "pharmacologically acceptable salt thereof" means such salts.

Preferred examples of the salt based on the basic group include inorganic acid salts such as a hydrohalogenated acid salts, e.g., hydrofluoride, hydrochloride, hydrobromide and hydroiodide salts, nitrates, perchlorates, sulfates and phosphates; organic acid salts such as a lower alkanesulfonate, e.g., methanesulfonate, trifluoromethanesulfonate and ethanesulfonate salts, arylsulfonate, e.g., benzenesulfonate and p-toluenesulfonate salts, acetates, malates, fumarates, succinates, citrates, ascorbates, tartrates, oxalates and maleates; and amino acid salts such as glycine salts, lysine salts, arginates, omithine salts, glutamates and aspartates.

Whereas, preferred examples of the salt based on the acidic group include metal salts such as an alkali metal salt, e.g., sodium salts, potassium salts and lithium salts, an alkali earth metal salt, e.g., calcium salts and magnesium salts, aluminum salts and iron salts; amine salts such as inorganic salts, e.g., ammonium salts and organic salts, e.g., t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocain salts, procain salts, diethanolamine salts, N-benzylphenethylamine salts, piperazine salts, tetramethylammonium salts and tris(hydroxymethyl)aminomethane salts; and amino acid salts such as glycine salts, lysine salts, arginates, omithine salts, glutaminates and aspartates.

Since the compound (I) of the present invention can be converted to a derivative other than the above-mentioned "pharmaceutically acceptable salt" and the above-mentioned "ester" when it has an amino group and/or carboxy group, the "other derivative" means such a derivative. Examples of such a derivative include amide derivatives.

The compounds of formula (I) of the present invention sometimes absorb moisture when they are left to stand in the atmosphere or crystallized so that they carry adsorbed water and are thus hydrated. Such hydrates are also included in the present invention and included in the term "compound of the formula (I)" and species thereof.

Since the compound of the formula (I) has an asymmetric carbon atom in the molecule thereof, it has various isomers. In the compound of the present invention, these isomers and mixtures of these isomers are shown by a single formula, i.e., the formula (I). Accordingly, the present invention includes all of these isomers and the mixtures of these isomers.

Specific examples of the compounds of the formula (I) of the present invention include the compounds described in the following Table 1 to Table 9.

TABLE 1

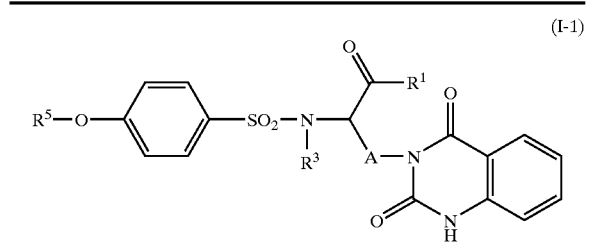

(I-1)

| Cpd. No. | A | $R^1$ | $R^3$ | $R^5$ |
|---|---|---|---|---|
| 1-1 | $CH_2$ | NHOH | H | Me |
| 1-2 | $(CH_2)_2$ | NHOH | H | Me |
| 1-3 | $(CH_2)_3$ | NHOH | H | Me |
| 1-4 | $(CH_2)_4$ | NHOH | H | Me |
| 1-5 | $CH_2O(CH_2)_2$ | NHOH | H | Me |
| 1-6 | $CH_2S(CH_2)_2$ | NHOH | H | Me |
| 1-7 | $CH_2NH(CH_2)_2$ | NHOH | H | Me |
| 1-8 | $CH_2$ | NHOH | H | Ph |
| 1-9 | $(CH_2)_2$ | NHOH | H | Ph |
| 1-10 | $(CH_2)_3$ | NHOH | H | Ph |
| 1-11 | $(CH_2)_4$ | NHOH | H | Ph |
| 1-12 | $CH(CH_3)$ | NHOH | H | Ph |
| 1-13 | $CH(CH_3)CH_2$ | NHOH | H | Ph |
| 1-14 | $CH_2CH(CH_3)$ | NHOH | H | Ph |
| 1-15 | $C(CH_3)_2CH_2$ | NHOH | H | Ph |
| 1-16 | $CH_2C(CH_3)_2$ | NHOH | H | Ph |
| 1-17 | $CH_2OCH_2$ | NHOH | H | Ph |
| 1-18 | $CH_2SCH_2$ | NHOH | H | Ph |
| 1-19 | $CH_2NHCH_2$ | NHOH | H | Ph |
| 1-20 | $CH_2O(CH_2)_2$ | NHOH | H | Ph |
| 1-21 | $CH_2S(CH_2)_2$ | NHOH | H | Ph |
| 1-22 | $CH_2NH(CH_2)_2$ | NHOH | H | Ph |
| 1-23 | $CH_2N(CH_3)(CH_2)_2$ | NHOH | H | Ph |
| 1-24 | $CH_2$ | NHOH | Me | Ph |
| 1-25 | $(CH_2)_2$ | NHOH | Me | Ph |
| 1-26 | $(CH_2)_3$ | NHOH | Me | Ph |
| 1-27 | $(CH_2)_4$ | NHOH | Me | Ph |
| 1-28 | $CH(CH_3)$ | NHOH | Me | Ph |
| 1-29 | $CH(CH_3)CH_2$ | NHOH | Me | Ph |
| 1-30 | $CH_2CH(CH_3)$ | NHOH | Me | Ph |
| 1-31 | $C(CH_3)_2CH_2$ | NHOH | Me | Ph |
| 1-32 | $CH_2C(CH_3)_2$ | NHOH | Me | Ph |
| 1-33 | $CH_2OCH_2$ | NHOH | Me | Ph |
| 1-34 | $CH_2SCH_2$ | NHOH | Me | Ph |
| 1-35 | $CH_2NHCH_2$ | NHOH | Me | Ph |
| 1-36 | $CH_2O(CH_2)_2$ | NHOH | Me | Ph |

TABLE 1-continued

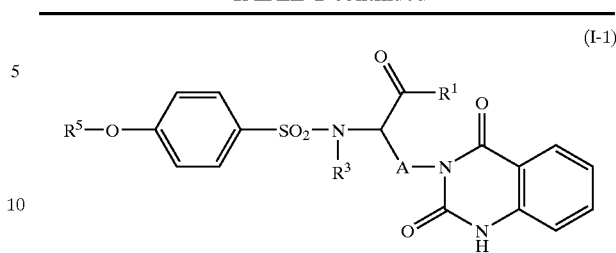

(I-1)

| Cpd. No. | A | $R^1$ | $R^3$ | $R^5$ |
|---|---|---|---|---|
| 1-37 | $CH_2S(CH_2)_2$ | NHOH | Me | Ph |
| 1-38 | $CH_2NH(CH_2)_2$ | NHOH | Me | Ph |
| 1-39 | $CH_2N(CH_3)(CH_2)_2$ | NHOH | Me | Ph |
| 1-40 | $CH_2$ | NHOH | Et | Ph |
| 1-41 | $(CH_2)_2$ | NHOH | Et | Ph |
| 1-42 | $(CH_2)_3$ | NHOH | Et | Ph |
| 1-43 | $(CH_2)_4$ | NHOH | Et | Ph |
| 1-44 | $CH(CH_3)$ | NHOH | Et | Ph |
| 1-45 | $CH(CH_3)CH_2$ | NHOH | Et | Ph |
| 1-46 | $CH_2CH(CH_3)$ | NHOH | Et | Ph |
| 1-47 | $C(CH_3)_2CH_2$ | NHOH | Et | Ph |
| 1-48 | $CH_2C(CH_3)_2$ | NHOH | Et | Ph |
| 1-49 | $CH_2OCH_2$ | NHOH | Et | Ph |
| 1-50 | $CH_2SCH_2$ | NHOH | Et | Ph |
| 1-51 | $CH_2NHCH_2$ | NHOH | Et | Ph |
| 1-52 | $CH_2O(CH_2)_2$ | NHOH | Et | Ph |
| 1-53 | $CH_2S(CH_2)_2$ | NHOH | Et | Ph |
| 1-54 | $CH_2NH(CH_2)_2$ | NHOH | Et | Ph |
| 1-55 | $CH_2N(CH_3)(CH_2)_2$ | NHOH | Et | Ph |
| 1-56 | $CH_2$ | NHOH | Pr | Ph |
| 1-57 | $(CH_2)_2$ | NHOH | Pr | Ph |
| 1-58 | $(CH_2)_3$ | NHOH | Pr | Ph |
| 1-59 | $(CH_2)_4$ | NHOH | Pr | Ph |
| 1-60 | $CH(CH_3)$ | NHOH | Pr | Ph |
| 1-61 | $CH(CH_3)CH_2$ | NHOH | Pr | Ph |
| 1-62 | $CH_2CH(CH_3)$ | NHOH | Pr | Ph |
| 1-63 | $C(CH_3)_2CH_2$ | NHOH | Pr | Ph |
| 1-64 | $CH_2C(CH_3)_2$ | NHOH | Pr | Ph |
| 1-65 | $CH_2OCH_2$ | NHOH | Pr | Ph |
| 1-66 | $CH_2SCH_2$ | NHOH | Pr | Ph |
| 1-67 | $CH_2NHCH_2$ | NHOH | Pr | Ph |
| 1-68 | $CH_2$ | NHOH | i-Pr | Ph |
| 1-69 | $(CH_2)_2$ | NHOH | i-Pr | Ph |
| 1-70 | $(CH_2)_3$ | NHOH | i-Pr | Ph |
| 1-71 | $(CH_2)_4$ | NHOH | i-Pr | Ph |
| 1-72 | $CH_2$ | NHOH | $CH_2$=$CHCH_2$ | Ph |
| 1-73 | $(CH_2)_2$ | NHOH | $CH_2$=$CHCH_2$ | Ph |
| 1-74 | $(CH_2)_3$ | NHOH | $CH_2$=$CHCH_2$ | Ph |
| 1-75 | $(CH_2)_4$ | NHOH | $CH_2$=$CHCH_2$ | Ph |
| 1-76 | $CH(CH_3)$ | NHOH | $CH_2$=$CHCH_2$ | Ph |
| 1-77 | $CH(CH_3)CH_2$ | NHOH | $CH_2$=$CHCH_2$ | Ph |
| 1-78 | $CH_2CH(CH_3)$ | NHOH | $CH_2$=$CHCH_2$ | Ph |
| 1-79 | $C(CH_3)_2CH_2$ | NHOH | $CH_2$=$CHCH_2$ | Ph |
| 1-80 | $CH_2C(CH_3)_2$ | NHOH | $CH_2$=$CHCH_2$ | Ph |
| 1-81 | $CH_2OCH_2$ | NHOH | $CH_2$=$CHCH_2$ | Ph |
| 1-82 | $CH_2SCH_2$ | NHOH | $CH_2$=$CHCH_2$ | Ph |
| 1-83 | $CH_2NHCH_2$ | NHOH | $CH_2$=$CHCH_2$ | Ph |
| 1-84 | $CH_2O(CH_2)_2$ | NHOH | $CH_2$=$CHCH_2$ | Ph |
| 1-85 | $CH_2S(CH_2)_2$ | NHOH | $CH_2$=$CHCH_2$ | Ph |
| 1-86 | $CH_2NH(CH_2)_2$ | NHOH | $CH_2$=$CHCH_2$ | Ph |
| 1-87 | $CH_2N(CH_3)(CH_2)_2$ | NHOH | $CH_2$=$CHCH_2$ | Ph |
| 1-88 | $CH_2$ | NHOH | CH≡$CCH_2$ | Ph |
| 1-89 | $(CH_2)_2$ | NHOH | CH≡$CCH_2$ | Ph |
| 1-90 | $(CH_2)_3$ | NHOH | CH≡$CCH_2$ | Ph |
| 1-91 | $(CH_2)_4$ | NHOH | CH≡$CCH_2$ | Ph |
| 1-92 | $CH(CH_3)$ | NHOH | CH≡$CCH_2$ | Ph |
| 1-93 | $CH(CH_3)CH_2$ | NHOH | CH≡$CCH_2$ | Ph |
| 1-94 | $CH_2CH(CH_3)$ | NHOH | CH≡$CCH_2$ | Ph |
| 1-95 | $C(CH_3)_2CH_2$ | NHOH | CH≡$CCH_2$ | Ph |
| 1-96 | $CH_2C(CH_3)_2$ | NHOH | CH≡$CCH_2$ | Ph |
| 1-97 | $CH_2OCH_2$ | NHOH | CH≡$CCH_2$ | Ph |
| 1-98 | $CH_2SCH_2$ | NHOH | CH≡$CCH_2$ | Ph |
| 1-99 | $CH_2NHCH_2$ | NHOH | CH≡$CCH_2$ | Ph |
| 1-100 | $CH_2O(CH_2)_2$ | NHOH | CH≡$CCH_2$ | Ph |

TABLE 1-continued

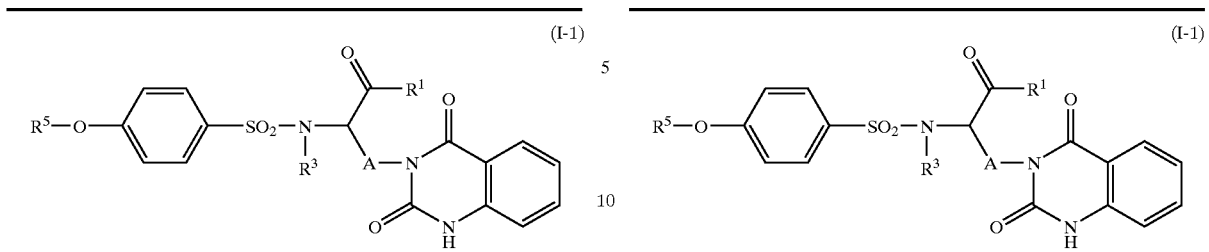

(I-1)

| Cpd. No. | A | R¹ | R³ | R⁵ |
|---|---|---|---|---|
| 1-101 | $CH_2S(CH_2)_2$ | NHOH | $CH\equiv CCH_2$ | Ph |
| 1-102 | $CH_2NH(CH_2)_2$ | NHOH | $CH\equiv CCH_2$ | Ph |
| 1-103 | $CH_2N(CH_3)(CH_2)_2$ | NHOH | $CH\equiv CCH_2$ | Ph |
| 1-104 | $CH_2$ | NHOH | $MeC\equiv CCH_2$ | Ph |
| 1-105 | $(CH_2)_2$ | NHOH | $MeC\equiv CCH_2$ | Ph |
| 1-106 | $(CH_2)_3$ | NHOH | $MeC\equiv CCH_2$ | Ph |
| 1-107 | $(CH_2)_4$ | NHOH | $MeC\equiv CCH_2$ | Ph |
| 1-108 | $CH(CH_3)$ | NHOH | $MeC\equiv CCH_2$ | Ph |
| 1-109 | $CH(CH_3)CH_2$ | NHOH | $MeC\equiv CCH_2$ | Ph |
| 1-110 | $CH_2CH(CH_3)$ | NHOH | $MeC\equiv CCH_2$ | Ph |
| 1-111 | $C(CH_3)_2CH_2$ | NHOH | $MeC\equiv CCH_2$ | Ph |
| 1-112 | $CH_2C(CH_3)_2$ | NHOH | $MeC\equiv CCH_2$ | Ph |
| 1-113 | $CH_2OCH_2$ | NHOH | $MeC\equiv CCH_2$ | Ph |
| 1-114 | $CH_2SCH_2$ | NHOH | $MeC\equiv CCH_2$ | Ph |
| 1-115 | $CH_2NHCH_2$ | NHOH | $MeC\equiv CCH_2$ | Ph |
| 1-116 | $CH_2O(CH_2)_2$ | NHOH | $MeC\equiv CCH_2$ | Ph |
| 1-117 | $CH_2S(CH_2)_2$ | NHOH | $MeC\equiv CCH_2$ | Ph |
| 1-118 | $CH_2NH(CH_2)_2$ | NHOH | $MeC\equiv CCH_2$ | Ph |
| 1-119 | $CH_2N(CH_3)(CH_2)_2$ | NHOH | $MeC\equiv CCH_2$ | Ph |
| 1-120 | $CH_2$ | NHOH | $PhC\equiv CCH_2$ | Ph |
| 1-121 | $(CH_2)_2$ | NHOH | $PhC\equiv CCH_2$ | Ph |
| 1-122 | $(CH_2)_3$ | NHOH | $PhC\equiv CCH_2$ | Ph |
| 1-123 | $(CH_2)_4$ | NHOH | $PhC\equiv CCH_2$ | Ph |
| 1-124 | $CH(CH_3)$ | NHOH | $PhC\equiv CCH_2$ | Ph |
| 1-125 | $CH(CH_3)CH_2$ | NHOH | $PhC\equiv CCH_2$ | Ph |
| 1-126 | $CH_2CH(CH_3)$ | NHOH | $PhC\equiv CCH_2$ | Ph |
| 1-127 | $C(CH_3)_2CH_2$ | NHOH | $PhC\equiv CCH_2$ | Ph |
| 1-128 | $CH_2C(CH_3)_2$ | NHOH | $PhC\equiv CCH_2$ | Ph |
| 1-129 | $CH_2OCH_2$ | NHOH | $PhC\equiv CCH_2$ | Ph |
| 1-130 | $CH_2SCH_2$ | NHOH | $PhC\equiv CCH_2$ | Ph |
| 1-131 | $CH_2NHCH_2$ | NHOH | $PhC\equiv CCH_2$ | Ph |
| 1-132 | $CH_2O(CH_2)_2$ | NHOH | $PhC\equiv CCH_2$ | Ph |
| 1-133 | $CH_2S(CH_2)_2$ | NHOH | $PhC\equiv CCH_2$ | Ph |
| 1-134 | $CH_2NH(CH_2)_2$ | NHOH | $PhC\equiv CCH_2$ | Ph |
| 1-135 | $CH_2N(CH_3)(CH_2)_2$ | NHOH | $PhC\equiv CCH_2$ | Ph |
| 1-136 | $CH_2$ | NHOH | Bn | Ph |
| 1-137 | $(CH_2)_2$ | NHOH | Bn | Ph |
| 1-138 | $(CH_2)_3$ | NHOH | Bn | Ph |
| 1-139 | $(CH_2)_4$ | NHOH | Bn | Ph |
| 1-140 | $CH(CH_3)$ | NHOH | Bn | Ph |
| 1-141 | $CH(CH_3)CH_2$ | NHOH | Bn | Ph |
| 1-142 | $CH_2CH(CH_3)$ | NHOH | Bn | Ph |
| 1-143 | $C(CH_3)_2CH_2$ | NHOH | Bn | Ph |
| 1-144 | $CH_2C(CH_3)_2$ | NHOH | Bn | Ph |
| 1-145 | $CH_2OCH_2$ | NHOH | Bn | Ph |
| 1-146 | $CH_2SCH_2$ | NHOH | Bn | Ph |
| 1-147 | $CH_2NHCH_2$ | NHOH | Bn | Ph |
| 1-148 | $CH_2O(CH_2)_2$ | NHOH | Bn | Ph |
| 1-149 | $CH_2S(CH_2)_2$ | NHOH | Bn | Ph |
| 1-150 | $CH_2NH(CH_2)_2$ | NHOH | Bn | Ph |
| 1-151 | $CH_2N(CH_3)(CH_2)_2$ | NHOH | Bn | Ph |
| 1-152 | $CH_2$ | NHOH | 3-(4-Cl-Ph)Pr | Ph |
| 1-153 | $(CH_2)_2$ | NHOH | 3-(4-Cl-Ph)Pr | Ph |
| 1-154 | $(CH_2)_3$ | NHOH | 3-(4-Cl-Ph)Pr | Ph |
| 1-155 | $(CH_2)_4$ | NHOH | 3-(4-Cl-Ph)Pr | Ph |
| 1-156 | $CH(CH_3)$ | NHOH | 3-(4-Cl-Ph)Pr | Ph |
| 1-157 | $CH(CH_3)CH_2$ | NHOH | 3-(4-Cl-Ph)Pr | Ph |
| 1-158 | $CH_2CH(CH_3)$ | NHOH | 3-(4-Cl-Ph)Pr | Ph |
| 1-159 | $C(CH_3)_2CH_2$ | NHOH | 3-(4-Cl-Ph)Pr | Ph |
| 1-160 | $CH_2C(CH_3)_2$ | NHOH | 3-(4-Cl-Ph)Pr | Ph |
| 1-161 | $CH_2OCH_2$ | NHOH | 3-(4-Cl-Ph)Pr | Ph |
| 1-162 | $CH_2SCH_2$ | NHOH | 3-(4-Cl-Ph)Pr | Ph |
| 1-163 | $CH_2NHCH_2$ | NHOH | 3-(4-Cl-Ph)Pr | Ph |
| 1-164 | $CH_2O(CH_2)_2$ | NHOH | 3-(4-Cl-Ph)Pr | Ph |
| 1-165 | $CH_2S(CH_2)_2$ | NHOH | 3-(4-Cl-Ph)Pr | Ph |
| 1-166 | $CH_2NH(CH_2)_2$ | NHOH | 3-(4-Cl-Ph)Pr | Ph |
| 1-167 | $CH_2N(CH_3)(CH_2)_2$ | NHOH | 3-(4-Cl-Ph)Pr | Ph |
| 1-168 | $(CH_2)_2$ | OH | H | Me |
| 1-169 | $(CH_2)_2$ | OH | Me | Me |
| 1-170 | $(CH_2)_2$ | OH | $CH\equiv CCH_2$ | Me |
| 1-171 | $(CH_2)_2$ | OH | H | $CF_3$ |
| 1-172 | $(CH_2)_2$ | OH | Me | $CF_3$ |
| 1-173 | $(CH_2)_2$ | OH | $CH\equiv CCH_2$ | $CF_3$ |
| 1-174 | $(CH_2)_2$ | OH | H | Bu |
| 1-175 | $(CH_2)_2$ | OH | Me | Bu |
| 1-176 | $(CH_2)_2$ | OH | $CH\equiv CCH_2$ | Bu |
| 1-177 | $(CH_2)_2$ | OH | H | Ph |
| 1-178 | $(CH_2)_2$ | OH | Me | Ph |
| 1-179 | $(CH_2)_2$ | OH | $CH\equiv CCH_2$ | Ph |
| 1-180 | $(CH_2)_2$ | NHOH | Me | 4-Cl-Ph |
| 1-181 | $(CH_2)_2$ | NHOH | Me | 4-F-Ph |
| 1-182 | $(CH_2)_2$ | NHOH | Me | 3-Cl-Ph |
| 1-183 | $(CH_2)_2$ | NHOH | Me | 2,4-diF-Ph |
| 1-184 | $(CH_2)_2$ | NHOH | Me | 4-Py |
| 1-185 | $(CH_2)_2$ | NHOH | $CH\equiv CCH_2$ | 4-Cl-Ph |
| 1-186 | $(CH_2)_2$ | NHOH | $CH\equiv CCH_2$ | 4-F-Ph |
| 1-187 | $(CH_2)_2$ | NHOH | $CH\equiv CCH_2$ | 4-MeO-Ph |
| 1-188 | $(CH_2)_2$ | NHOH | $CH\equiv CCH_2$ | 2,4-diF-Ph |
| 1-189 | $(CH_2)_2$ | NHOH | $CH\equiv CCH_2$ | 4-Py |

TABLE 2

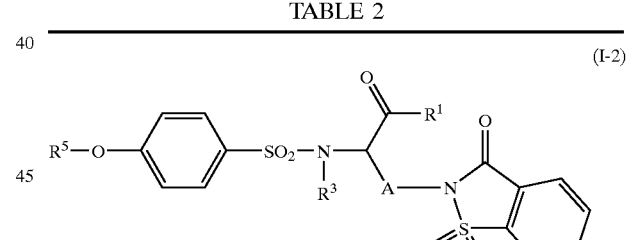

(I-2)

| Cpd. No. | A | R¹ | R³ | R⁵ |
|---|---|---|---|---|
| 2-1 | $CH_2$ | NHOH | H | Me |
| 2-2 | $(CH_2)_2$ | NHOH | H | Me |
| 2-3 | $(CH_2)_3$ | NHOH | H | Me |
| 2-4 | $(CH_2)_4$ | NHOH | H | Me |
| 2-5 | $CH_2O(CH_2)_2$ | NHOH | H | Me |
| 2-6 | $CH_2S(CH_2)_2$ | NHOH | H | Me |
| 2-7 | $CH_2NH(CH_2)_2$ | NHOH | H | Me |
| 2-8 | $CH_2$ | NHOH | H | Ph |
| 2-9 | $(CH_2)_2$ | NHOH | H | Ph |
| 2-10 | $(CH_2)_3$ | NHOH | H | Ph |
| 2-11 | $(CH_2)_4$ | NHOH | H | Ph |
| 2-12 | $CH(CH_3)$ | NHOH | H | Ph |
| 2-13 | $CH(CH_3)CH_2$ | NHOH | H | Ph |
| 2-14 | $CH_2CH(CH_3)$ | NHOH | H | Ph |
| 2-15 | $C(CH_3)_2CH_2$ | NHOH | H | Ph |
| 2-16 | $CH_2C(CH_3)_2$ | NHOH | H | Ph |
| 2-17 | $CH_2OCH_2$ | NHOH | H | Ph |
| 2-18 | $CH_2SCH_2$ | NHOH | H | Ph |

TABLE 2-continued (I-2)

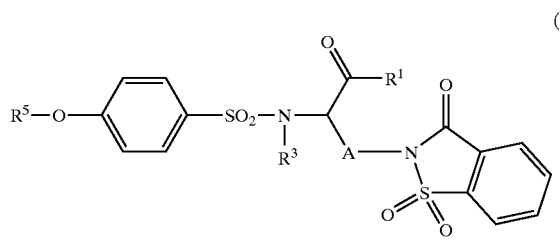

| Cpd. No. | A | R¹ | R³ | R⁵ |
|---|---|---|---|---|
| 2-19 | CH₂NHCH₂ | NHOH | H | Ph |
| 2-20 | CH₂O(CH₂)₂ | NHOH | H | Ph |
| 2-21 | CH₂S(CH₂)₂ | NHOH | H | Ph |
| 2-22 | CH₂NH(CH₂)₂ | NHOH | H | Ph |
| 2-23 | CH₂N(CH₃)(CH₂)₂ | NHOH | H | Ph |
| 2-24 | CH₂ | NHOH | Me | Ph |
| 2-25 | (CH₂)₂ | NHOH | Me | Ph |
| 2-26 | (CH₂)₃ | NHOH | Me | Ph |
| 2-27 | (CH₂)₄ | NHOH | Me | Ph |
| 2-28 | CH(CH₃) | NHOH | Me | Ph |
| 2-29 | CH(CH₃)CH₂ | NHOH | Me | Ph |
| 2-30 | CH₂CH(CH₃) | NHOH | Me | Ph |
| 2-31 | C(CH₃)₂CH₂ | NHOH | Me | Ph |
| 2-32 | CH₂C(CH₃)₂ | NHOH | Me | Ph |
| 2-33 | CH₂OCH₂ | NHOH | Me | Ph |
| 2-34 | CH₂SCH₂ | NHOH | Me | Ph |
| 2-35 | CH₂NHCH₂ | NHOH | Me | Ph |
| 2-36 | CH₂O(CH₂)₂ | NHOH | Me | Ph |
| 2-37 | CH₂S(CH₂)₂ | NHOH | Me | Ph |
| 2-38 | CH₂NH(CH₂)₂ | NHOH | Me | Ph |
| 2-39 | CH₂N(CH₃)(CH₂)₂ | NHOH | Me | Ph |
| 2-40 | CH₂ | NHOH | Et | Ph |
| 2-41 | (CH₂)₂ | NHOH | Et | Ph |
| 2-42 | (CH₂)₃ | NHOH | Et | Ph |
| 2-43 | (CH₂)₄ | NHOH | Et | Ph |
| 2-44 | CH(CH₃) | NHOH | Et | Ph |
| 2-45 | CH(CH₃)CH₂ | NHOH | Et | Ph |
| 2-46 | CH₂CH(CH₃) | NHOH | Et | Ph |
| 2-47 | C(CH₃)₂CH₂ | NHOH | Et | Ph |
| 2-48 | CH₂C(CH₃)₂ | NHOH | Et | Ph |
| 2-49 | CH₂OCH₂ | NHOH | Et | Ph |
| 2-50 | CH₂SCH₂ | NHOH | Et | Ph |
| 2-51 | CH₂NHCH₂ | NHOH | Et | Ph |
| 2-52 | CH₂O(CH₂)₂ | NHOH | Et | Ph |
| 2-53 | CH₂S(CH₂)₂ | NHOH | Et | Ph |
| 2-54 | CH₂NH(CH₂)₂ | NHOH | Et | Ph |
| 2-55 | CH₂N(CH₃)(CH₂)₂ | NHOH | Et | Ph |
| 2-56 | CH₂ | NHOH | Pr | Ph |
| 2-57 | (CH₂)₂ | NHOH | Pr | Ph |
| 2-58 | (CH₂)₃ | NHOH | Pr | Ph |
| 2-59 | (CH₂)₄ | NHOH | Pr | Ph |
| 2-60 | CH(CH₃) | NHOH | Pr | Ph |
| 2-61 | CH(CH₃)CH₂ | NHOH | Pr | Ph |
| 2-62 | CH₂CH(CH₃) | NHOH | Pr | Ph |
| 2-63 | C(CH₃)₂CH₂ | NHOH | Pr | Ph |
| 2-64 | CH₂C(CH₃)₂ | NHOH | Pr | Ph |
| 2-65 | CH₂OCH₂ | NHOH | Pr | Ph |
| 2-66 | CH₂SCH₂ | NHOH | Pr | Ph |
| 2-67 | CH₂NHCH₂ | NHOH | Pr | Ph |
| 2-68 | CH₂ | NHOH | i-Pr | Ph |
| 2-69 | (CH₂)₂ | NHOH | i-Pr | Ph |
| 2-70 | (CH₂)₃ | NHOH | i-Pr | Ph |
| 2-71 | (CH₂)₄ | NHOH | i-Pr | Ph |
| 2-72 | CH₂ | NHOH | CH₂=CHCH₂ | Ph |
| 2-73 | (CH₂)₂ | NHOH | CH₂=CHCH₂ | Ph |
| 2-74 | (CH₂)₃ | NHOH | CH₂=CHCH₂ | Ph |
| 2-75 | (CH₂)₄ | NHOH | CH₂=CHCH₂ | Ph |
| 2-76 | CH(CH₃) | NHOH | CH₂=CHCH₂ | Ph |
| 2-77 | CH(CH₃)CH₂ | NHOH | CH₂=CHCH₂ | Ph |
| 2-78 | CH₂CH(CH₃) | NHOH | CH₂=CHCH₂ | Ph |
| 2-79 | C(CH₃)₂CH₂ | NHOH | CH₂=CHCH₂ | Ph |
| 2-80 | CH₂C(CH₃)₂ | NHOH | CH₂=CHCH₂ | Ph |
| 2-81 | CH₂OCH₂ | NHOH | CH₂=CHCH₂ | Ph |
| 2-82 | CH₂SCH₂ | NHOH | CH₂=CHCH₂ | Ph |
| 2-83 | CH₂NHCH₂ | NHOH | CH₂=CHCH₂ | Ph |
| 2-84 | CH₂O(CH₂)₂ | NHOH | CH₂=CHCH₂ | Ph |
| 2-85 | CH₂S(CH₂)₂ | NHOH | CH₂=CHCH₂ | Ph |
| 2-86 | CH₂NH(CH₂)₂ | NHOH | CH₂=CHCH₂ | Ph |
| 2-87 | CH₂N(CH₃)(CH₂)₂ | NHOH | CH₂=CHCH₂ | Ph |
| 2-88 | CH₂ | NHOH | CH≡CCH₂ | Ph |
| 2-89 | (CH₂)₂ | NHOH | CH≡CCH₂ | Ph |
| 2-90 | (CH₂)₃ | NHOH | CH≡CCH₂ | Ph |
| 2-91 | (CH₂)₄ | NHOH | CH≡CCH₂ | Ph |
| 2-92 | CH(CH₃) | NHOH | CH≡CCH₂ | Ph |
| 2-93 | CH(CH₃)CH₂ | NHOH | CH≡CCH₂ | Ph |
| 2-94 | CH₂CH(CH₃) | NHOH | CH≡CCH₂ | Ph |
| 2-95 | C(CH₃)₂CH₂ | NHOH | CH≡CCH₂ | Ph |
| 2-96 | CH₂C(CH₃)₂ | NHOH | CH≡CCH₂ | Ph |
| 2-97 | CH₂OCH₂ | NHOH | CH≡CCH₂ | Ph |
| 2-98 | CH₂SCH₂ | NHOH | CH≡CCH₂ | Ph |
| 2-99 | CH₂NHCH₂ | NHOH | CH≡CCH₂ | Ph |
| 2-100 | CH₂O(CH₂)₂ | NHOH | CH≡CCH₂ | Ph |
| 2-101 | CH₂S(CH₂)₂ | NHOH | CH≡CCH₂ | Ph |
| 2-102 | CH₂NH(CH₂)₂ | NHOH | CH≡CCH₂ | Ph |
| 2-103 | CH₂N(CH₃)(CH₂)₂ | NHOH | CH≡CCH₂ | Ph |
| 2-104 | CH₂ | NHOH | MeC≡CCH₂ | Ph |
| 2-105 | (CH₂)₂ | NHOH | MeC≡CCH₂ | Ph |
| 2-106 | (CH₂)₃ | NHOH | MeC≡CCH₂ | Ph |
| 2-107 | (CH₂)₄ | NHOH | MeC≡CCH₂ | Ph |
| 2-108 | CH(CH₃) | NHOH | MeC≡CCH₂ | Ph |
| 2-109 | CH(CH₃)CH₂ | NHOH | MeC≡CCH₂ | Ph |
| 2-110 | CH₂CH(CH₃) | NHOH | MeC≡CCH₂ | Ph |
| 2-111 | C(CH₃)₂CH₂ | NHOH | MeC≡CCH₂ | Ph |
| 2-112 | CH₂C(CH₃)₂ | NHOH | MeC≡CCH₂ | Ph |
| 2-113 | CH₂OCH₂ | NHOH | MeC≡CCH₂ | Ph |
| 2-114 | CH₂SCH₂ | NHOH | MeC≡CCH₂ | Ph |
| 2-115 | CH₂NHCH₂ | NHOH | MeC≡CCH₂ | Ph |
| 2-116 | CH₂O(CH₂)₂ | NHOH | MeC≡CCH₂ | Ph |
| 2-117 | CH₂S(CH₂)₂ | NHOH | MeC≡CCH₂ | Ph |
| 2-118 | CH₂NH(CH₂)₂ | NHOH | MeC≡CCH₂ | Ph |
| 2-119 | CH₂N(CH₃)(CH₂)₂ | NHOH | MeC≡CCH₂ | Ph |
| 2-120 | CH₂ | NHOH | PhC≡CCH₂ | Ph |
| 2-121 | (CH₂)₂ | NHOH | PhC≡CCH₂ | Ph |
| 2-122 | (CH₂)₃ | NHOH | PhC≡CCH₂ | Ph |
| 2-123 | (CH₂)₄ | NHOH | PhC≡CCH₂ | Ph |
| 2-124 | CH(CH₃) | NHOH | PhC≡CCH₂ | Ph |
| 2-125 | CH(CH₃)CH₂ | NHOH | PhC≡CCH₂ | Ph |
| 2-126 | CH₂CH(CH₃) | NHOH | PhC≡CCH₂ | Ph |
| 2-127 | C(CH₃)₂CH₂ | NHOH | PhC≡CCH₂ | Ph |
| 2-128 | CH₂C(CH₃)₂ | NHOH | PhC≡CCH₂ | Ph |
| 2-129 | CH₂OCH₂ | NHOH | PhC≡CCH₂ | Ph |
| 2-130 | CH₂SCH₂ | NHOH | PhC≡CCH₂ | Ph |
| 2-131 | CH₂NHCH₂ | NHOH | PhC≡CCH₂ | Ph |
| 2-132 | CH₂O(CH₂)₂ | NHOH | PhC≡CCH₂ | Ph |
| 2-133 | CH₂S(CH₂)₂ | NHOH | PhC≡CCH₂ | Ph |
| 2-134 | CH₂NH(CH₂)₂ | NHOH | PhC≡CCH₂ | Ph |
| 2-135 | CH₂N(CH₃)(CH₂)₂ | NHOH | PhC≡CCH₂ | Ph |
| 2-136 | CH₂ | NHOH | Bn | Ph |
| 2-137 | (CH₂)₂ | NHOH | Bn | Ph |
| 2-138 | (CH₂)₃ | NHOH | Bn | Ph |
| 2-139 | (CH₂)₄ | NHOH | Bn | Ph |
| 2-140 | CH(CH₃) | NHOH | Bn | Ph |
| 2-141 | CH(CH₃)CH₂ | NHOH | Bn | Ph |
| 2-142 | CH₂CH(CH₃) | NHOH | Bn | Ph |
| 2-143 | C(CH₃)₂CH₂ | NHOH | Bn | Ph |
| 2-144 | CH₂C(CH₃)₂ | NHOH | Bn | Ph |

TABLE 2-continued (I-2)

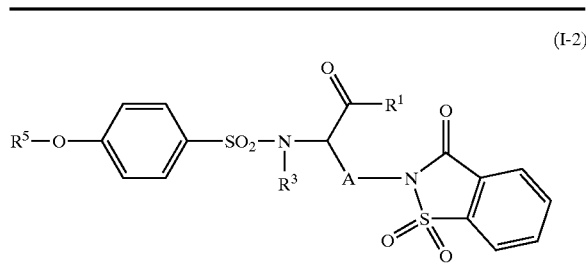

| Cpd. No. | A | R¹ | R³ | R⁵ |
|---|---|---|---|---|
| 2-145 | CH₂OCH₂ | NHOH | Bn | Ph |
| 2-146 | CH₂SCH₂ | NHOH | Bn | Ph |
| 2-147 | CH₂NHCH₂ | NHOH | Bn | Ph |
| 2-148 | CH₂O(CH₂)₂ | NHOH | Bn | Ph |
| 2-149 | CH₂S(CH₂)₂ | NHOH | Bn | Ph |
| 2-150 | CH₂NH(CH₂)₂ | NHOH | Bn | Ph |
| 2-151 | CH₂N(CH₃)(CH₂)₂ | NHOH | Bn | Ph |
| 2-152 | CH₂ | NHOH | 3-(4-Cl-Ph)Pr | Ph |
| 2-153 | (CH₂)₂ | NHOH | 3-(4-Cl-Ph)Pr | Ph |
| 2-154 | (CH₂)₃ | NHOH | 3-(4-Cl-Ph)Pr | Ph |
| 2-155 | (CH₂)₄ | NHOH | 3-(4-Cl-Ph)Pr | Ph |
| 2-156 | CH(CH₃) | NHOH | 3-(4-Cl-Ph)Pr | Ph |
| 2-157 | CH(CH₃)CH₂ | NHOH | 3-(4-Cl-Ph)Pr | Ph |
| 2-158 | CH₂CH(CH₃) | NHOH | 3-(4-Cl-Ph)Pr | Ph |
| 2-159 | C(CH₃)₂CH₂ | NHOH | 3-(4-Cl-Ph)Pr | Ph |
| 2-160 | CH₂C(CH₃)₂ | NHOH | 3-(4-Cl-Ph)Pr | Ph |
| 2-161 | CH₂OCH₂ | NHOH | 3-(4-Cl-Ph)Pr | Ph |
| 2-162 | CH₂SCH₂ | NHOH | 3-(4-Cl-Ph)Pr | Ph |
| 2-163 | CH₂NHCH₂ | NHOH | 3-(4-Cl-Ph)Pr | Ph |
| 2-164 | CH₂O(CH₂)₂ | NHOH | 3-(4-Cl-Ph)Pr | Ph |
| 2-165 | CH₂S(CH₂)₂ | NHOH | 3-(4-Cl-Ph)Pr | Ph |
| 2-166 | CH₂NH(CH₂)₂ | NHOH | 3-(4-Cl-Ph)Pr | Ph |
| 2-167 | CH₂N(CH₃)(CH₂)₂ | NHOH | 3-(4-Cl-Ph)Pr | Ph |
| 2-168 | (CH₂)₂ | OH | H | Me |
| 2-169 | (CH₂)₂ | OH | Me | Me |
| 2-170 | (CH₂)₂ | OH | CH≡CCH₂ | Me |
| 2-171 | (CH₂)₂ | OH | H | CF₃ |
| 2-172 | (CH₂)₂ | OH | Me | CF₃ |
| 2-173 | (CH₂)₂ | OH | CH≡CCH₂ | CF₃ |
| 2-174 | (CH₂)₂ | OH | H | Bu |
| 2-175 | (CH₂)₂ | OH | Me | Bu |
| 2-176 | (CH₂)₂ | OH | CH≡CCH₂ | Bu |
| 2-177 | (CH₂)₂ | OH | H | Ph |
| 2-178 | (CH₂)₂ | OH | Me | Ph |
| 2-179 | (CH₂)₂ | OH | CH≡CCH₂ | Ph |
| 2-180 | (CH₂)₂ | NHOH | Me | 4-Cl-Ph |
| 2-181 | (CH₂)₂ | NHOH | Me | 4-F-Ph |
| 2-182 | (CH₂)₂ | NHOH | Me | 4-MeO-Ph |
| 2-183 | (CH₂)₂ | NHOH | Me | 2,4-diF-Ph |
| 2-184 | (CH₂)₂ | NHOH | Me | 4-Py |
| 2-185 | (CH₂)₂ | NHOH | CH≡CCH₂ | 4-Cl-Ph |
| 2-186 | (CH₂)₂ | NHOH | CH≡CCH₂ | 4-F-Ph |
| 2-187 | (CH₂)₂ | NHOH | CH≡CCH₂ | 4-MeO-Ph |
| 2-188 | (CH₂)₂ | NHOH | CH≡CCH₂ | 2,4-diF-Ph |
| 2-189 | (CH₂)₂ | NHOH | CH≡CCH₂ | 4-Py |

TABLE 3

(I-3)

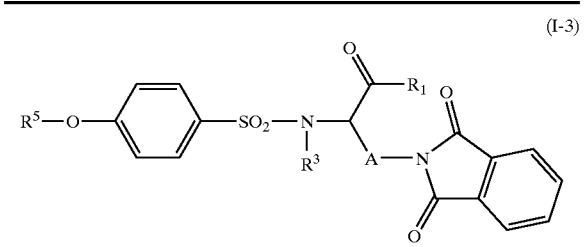

| Cpd. No. | A | R¹ | R³ | R⁵ |
|---|---|---|---|---|
| 3-1 | CH₂ | NHOH | H | Me |
| 3-2 | (CH₂)₂ | NHOH | H | Me |
| 3-3 | (CH₂)₃ | NHOH | H | Me |
| 3-4 | (CH₂)₄ | NHOH | H | Me |
| 3-5 | (CH₂)₂ | NHOH | (4-Cl-Ph)-C≡CCH₂ | Me |
| 3-6 | CH₂S(CH₂)₂ | NHOH | H | Me |
| 3-7 | (CH₂)₂ | NHOH | 3-(4-Cl-Ph)Pr | Me |
| 3-8 | (CH₂)₂ | NHOH | 3-Py-CH₂ | Me |
| 3-9 | CH₂ | NHOH | H | Ph |
| 3-10 | (CH₂)₂ | NHOH | H | Ph |
| 3-11 | (CH₂)₃ | NHOH | H | Ph |
| 3-12 | (CH₂)₄ | NHOH | H | Ph |
| 3-13 | CH(CH₃) | NHOH | H | Ph |
| 3-14 | CH(CH₃)CH₂ | NHOH | H | Ph |
| 3-15 | CH₂CH(CH₃) | NHOH | H | Ph |
| 3-16 | C(CH₃)₂CH₂ | NHOH | H | Ph |
| 3-17 | CH₂C(CH₃)₂ | NHOH | H | Ph |
| 3-18 | CH₂OCH₂ | NHOH | H | Ph |
| 3-19 | CH₂SCH₂ | NHOH | H | Ph |
| 3-20 | CH₂NHCH₂ | NHOH | H | Ph |
| 3-21 | CH₂O(CH₂)₂ | NHOH | H | Ph |
| 3-22 | CH₂S(CH₂)₂ | NHOH | H | Ph |
| 3-23 | CH₂NH(CH₂)₂ | NHOH | H | Ph |
| 3-24 | CH₂N(CH₃)(CH₂)₂ | NHOH | H | Ph |
| 3-25 | CH₂ | NHOH | Me | Ph |
| 3-26 | (CH₂)₂ | NHOH | Me | Ph |
| 3-27 | (CH₂)₃ | NHOH | Me | Ph |
| 3-28 | (CH₂)₄ | NHOH | Me | Ph |
| 3-29 | CH(CH₃) | NHOH | Me | Ph |
| 3-30 | CH(CH₃)CH₂ | NHOH | Me | Ph |
| 3-31 | CH₂CH(CH₃) | NHOH | Me | Ph |
| 3-32 | C(CH₃)₂CH₂ | NHOH | Me | Ph |
| 3-33 | CH₂C(CH₃)₂ | NHOH | Me | Ph |
| 3-34 | CH₂OCH₂ | NHOH | Me | Ph |
| 3-35 | CH₂SCH₂ | NHOH | Me | Ph |
| 3-36 | CH₂NHCH₂ | NHOH | Me | Ph |
| 3-37 | CH₂O(CH₂)₂ | NHOH | Me | Ph |
| 3-38 | CH₂S(CH₂)₂ | NHOH | Me | Ph |
| 3-39 | CH₂NH(CH₂)₂ | NHOH | Me | Ph |
| 3-40 | CH₂N(CH₃)(CH₂)₂ | NHOH | Me | Ph |
| 3-41 | CH₂ | NHOH | Et | Ph |
| 3-42 | (CH₂)₂ | NHOH | Et | Ph |
| 3-43 | (CH₂)₃ | NHOH | Et | Ph |
| 3-44 | (CH₂)₄ | NHOH | Et | Ph |
| 3-45 | CH(CH₃) | NHOH | Et | Ph |
| 3-46 | CH(CH₃)CH₂ | NHOH | Et | Ph |
| 3-47 | CH₂CH(CH₃) | NHOH | Et | Ph |
| 3-48 | C(CH₃)₂CH₂ | NHOH | Et | Ph |
| 3-49 | CH₂C(CH₃)₂ | NHOH | Et | Ph |
| 3-50 | CH₂OCH₂ | NHOH | Et | Ph |
| 3-51 | CH₂SCH₂ | NHOH | Et | Ph |
| 3-52 | CH₂NHCH₂ | NHOH | Et | Ph |
| 3-53 | CH₂O(CH₂)₂ | NHOH | Et | Ph |
| 3-54 | CH₂S(CH₂)₂ | NHOH | Et | Ph |
| 3-55 | CH₂NH(CH₂)₂ | NHOH | Et | Ph |
| 3-56 | CH₂N(CH₃)(CH₂)₂ | NHOH | Et | Ph |
| 3-57 | CH₂ | NHOH | Pr | Ph |
| 3-58 | (CH₂)₂ | NHOH | Pr | Ph |
| 3-59 | (CH₂)₃ | NHOH | Pr | Ph |
| 3-60 | (CH₂)₄ | NHOH | Pr | Ph |
| 3-61 | CH(CH₃) | NHOH | Pr | Ph |
| 3-62 | CH(CH₃)CH₂ | NHOH | Pr | Ph |
| 3-63 | CH₂CH(CH₃) | NHOH | Pr | Ph |

TABLE 3-continued (I-3)

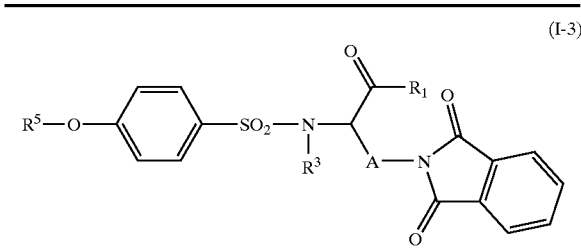 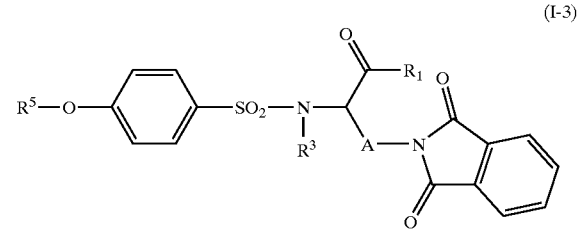

| Cpd. No. | A | R¹ | R³ | R⁵ |
|---|---|---|---|---|
| 3-64 | C(CH₃)₂CH₂ | NHOH | Pr | Ph |
| 3-65 | CH₂C(CH₃)₂ | NHOH | Pr | Ph |
| 3-66 | CH₂OCH₂ | NHOH | Pr | Ph |
| 3-67 | CH₂SCH₂ | NHOH | Pr | Ph |
| 3-68 | CH₂NHCH₂ | NHOH | Pr | Ph |
| 3-69 | CH₂ | NHOH | i-Pr | Ph |
| 3-70 | (CH₂)₂ | NHOH | i-Pr | Ph |
| 3-71 | (CH₂)₃ | NHOH | i-Pr | Ph |
| 3-72 | (CH₂)₄ | NHOH | i-Pr | Ph |
| 3-73 | CH₂ | NHOH | CH₂=CHCH₂ | Ph |
| 3-74 | (CH₂)₂ | NHOH | CH₂=CHCH₂ | Ph |
| 3-75 | (CH₂)₃ | NHOH | CH₂=CHCH₂ | Ph |
| 3-76 | (CH₂)₄ | NHOH | CH₂=CHCH₂ | Ph |
| 3-77 | CH(CH₃) | NHOH | CH₂=CHCH₂ | Ph |
| 3-78 | CH(CH₃)CH₂ | NHOH | CH₂=CHCH₂ | Ph |
| 3-79 | CH₂CH(CH₃) | NHOH | CH₂=CHCH₂ | Ph |
| 3-80 | C(CH₃)₂CH₂ | NHOH | CH₂=CHCH₂ | Ph |
| 3-81 | CH₂C(CH₃)₂ | NHOH | CH₂=CHCH₂ | Ph |
| 3-82 | CH₂OCH₂ | NHOH | CH₂=CHCH₂ | Ph |
| 3-83 | CH₂SCH₂ | NHOH | CH₂=CHCH₂ | Ph |
| 3-84 | CH₂NHCH₂ | NHOH | CH₂=CHCH₂ | Ph |
| 3-85 | CH₂O(CH₂)₂ | NHOH | CH₂=CHCH₂ | Ph |
| 3-86 | CH₂S(CH₂)₂ | NHOH | CH₂=CHCH₂ | Ph |
| 3-87 | CH₂NH(CH₂)₂ | NHOH | CH₂=CHCH₂ | Ph |
| 3-88 | CH₂N(CH₃)(CH₂)₂ | NHOH | CH₂=CHCH₂ | Ph |
| 3-89 | CH₂ | NHOH | CH≡CCH₂ | Ph |
| 3-90 | (CH₂)₂ | NHOH | CH≡CCH₂ | Ph |
| 3-91 | (CH₂)₃ | NHOH | CH≡CCH₂ | Ph |
| 3-92 | (CH₂)₄ | NHOH | CH≡CCH₂ | Ph |
| 3-93 | CH(CH₃) | NHOH | CH≡CCH₂ | Ph |
| 3-94 | CH(CH₃)CH₂ | NHOH | CH≡CCH₂ | Ph |
| 3-95 | CH₂CH(CH₃) | NHOH | CH≡CCH₂ | Ph |
| 3-96 | C(CH₃)₂CH₂ | NHOH | CH≡CCH₂ | Ph |
| 3-97 | CH₂C(CH₃)₂ | NHOH | CH≡CCH₂ | Ph |
| 3-98 | CH₂OCH₂ | NHOH | CH≡CCH₂ | Ph |
| 3-99 | CH₂SCH₂ | NHOH | CH≡CCH₂ | Ph |
| 3-100 | CH₂NHCH₂ | NHOH | CH≡CCH₂ | Ph |
| 3-101 | CH₂O(CH₂)₂ | NHOH | CH≡CCH₂ | Ph |
| 3-102 | CH₂S(CH₂)₂ | NHOH | CH≡CCH₂ | Ph |
| 3-103 | CH₂NH(CH₂)₂ | NHOH | CH≡CCH₂ | Ph |
| 3-104 | CH₂N(CH₃)(CH₂)₂ | NHOH | CH≡CCH₂ | Ph |
| 3-105 | CH₂ | NHOH | MeC≡CCH₂ | Ph |
| 3-106 | (CH₂)₂ | NHOH | MeC≡CCH₂ | Ph |
| 3-107 | (CH₂)₃ | NHOH | MeC≡CCH₂ | Ph |
| 3-108 | (CH₂)₄ | NHOH | MeC≡CCH₂ | Ph |
| 3-109 | CH(CH₃) | NHOH | MeC≡CCH₂ | Ph |
| 3-110 | CH(CH₃)CH₂ | NHOH | MeC≡CCH₂ | Ph |
| 3-111 | CH₂CH(CH₃) | NHOH | MeC≡CCH₂ | Ph |
| 3-112 | C(CH₃)₂CH₂ | NHOH | MeC≡CCH₂ | Ph |
| 3-113 | CH₂C(CH₃)₂ | NHOH | MeC≡CCH₂ | Ph |
| 3-114 | CH₂OCH₂ | NHOH | MeC≡CCH₂ | Ph |
| 3-115 | CH₂SCH₂ | NHOH | MeC≡CCH₂ | Ph |
| 3-116 | CH₂NHCH₂ | NHOH | MeC≡CCH₂ | Ph |
| 3-117 | CH₂O(CH₂)₂ | NHOH | MeC≡CCH₂ | Ph |
| 3-118 | CH₂S(CH₂)₂ | NHOH | MeC≡CCH₂ | Ph |
| 3-119 | CH₂NH(CH₂)₂ | NHOH | MeC≡CCH₂ | Ph |
| 3-120 | CH₂N(CH₃)(CH₂)₂ | NHOH | MeC≡CCH₂ | Ph |
| 3-121 | CH₂ | NHOH | PhC≡CCH₂ | Ph |
| 3-122 | (CH₂)₂ | NHOH | PhC≡CCH₂ | Ph |
| 3-123 | (CH₂)₃ | NHOH | PhC≡CCH₂ | Ph |
| 3-124 | (CH₂)₄ | NHOH | PhC≡CCH₂ | Ph |
| 3-125 | CH(CH₃) | NHOH | PhC≡CCH₂ | Ph |
| 3-126 | CH(CH₃)CH₂ | NHOH | PhC≡CCH₂ | Ph |
| 3-127 | CH₂CH(CH₃) | NHOH | PhC≡CCH₂ | Ph |
| 3-128 | C(CH₃)₂CH₂ | NHOH | PhC≡CCH₂ | Ph |
| 3-129 | CH₂C(CH₃)₂ | NHOH | PhC≡CCH₂ | Ph |
| 3-130 | CH₂OCH₂ | NHOH | PhC≡CCH₂ | Ph |
| 3-131 | CH₂SCH₂ | NHOH | PhC≡CCH₂ | Ph |
| 3-132 | CH₂NHCH₂ | NHOH | PhC≡CCH₂ | Ph |
| 3-133 | CH₂O(CH₂)₂ | NHOH | PhC≡CCH₂ | Ph |
| 3-134 | CH₂S(CH₂)₂ | NHOH | PhC≡CCH₂ | Ph |
| 3-135 | CH₂NH(CH₂)₂ | NHOH | PhC≡CCH₂ | Ph |
| 3-136 | (CH₂)₂ | NHOH | (4-Cl-Ph)-C≡CCH₂ | Ph |
| 3-137 | CH₂ | NHOH | Bn | Ph |
| 3-138 | (CH₂)₂ | NHOH | Bn | Ph |
| 3-139 | (CH₂)₃ | NHOH | Bn | Ph |
| 3-140 | (CH₂)₄ | NHOH | Bn | Ph |
| 3-141 | CH(CH₃) | NHOH | Bn | Ph |
| 3-142 | CH(CH₃)CH₂ | NHOH | Bn | Ph |
| 3-143 | CH₂CH(CH₃) | NHOH | Bn | Ph |
| 3-144 | C(CH₃)₂CH₂ | NHOH | Bn | Ph |
| 3-145 | CH₂C(CH₃)₂ | NHOH | Bn | Ph |
| 3-146 | CH₂OCH₂ | NHOH | Bn | Ph |
| 3-147 | CH₂SCH₂ | NHOH | Bn | Ph |
| 3-148 | CH₂NHCH₂ | NHOH | Bn | Ph |
| 3-149 | CH₂O(CH₂)₂ | NHOH | Bn | Ph |
| 3-150 | CH₂S(CH₂)₂ | NHOH | Bn | Ph |
| 3-151 | CH₂NH(CH₂)₂ | NHOH | Bn | Ph |
| 3-152 | CH₂N(CH₃)(CH₂)₂ | NHOH | Bn | Ph |
| 3-153 | CH₂ | NHOH | 3-(4-Cl-Ph)Pr | Ph |
| 3-154 | (CH₂)₂ | NHOH | 3-(4-Cl-Ph)Pr | Ph |
| 3-155 | (CH₂)₃ | NHOH | 3-(4-Cl-Ph)Pr | Ph |
| 3-156 | (CH₂)₄ | NHOH | 3-(4-Cl-Ph)Pr | Ph |
| 3-157 | CH(CH₃) | NHOH | 3-(4-Cl-Ph)Pr | Ph |
| 3-158 | CH(CH₃)CH₂ | NHOH | 3-(4-Cl-Ph)Pr | Ph |
| 3-159 | CH₂CH(CH₃) | NHOH | 3-(4-Cl-Ph)Pr | Ph |
| 3-160 | C(CH₃)₂CH₂ | NHOH | 3-(4-Cl-Ph)Pr | Ph |
| 3-161 | CH₂C(CH₃)₂ | NHOH | 3-(4-Cl-Ph)Pr | Ph |
| 3-162 | CH₂OCH₂ | NHOH | 3-(4-Cl-Ph)Pr | Ph |
| 3-163 | CH₂SCH₂ | NHOH | 3-(4-Cl-Ph)Pr | Ph |
| 3-164 | CH₂NHCH₂ | NHOH | 3-(4-Cl-Ph)Pr | Ph |
| 3-165 | CH₂O(CH₂)₂ | NHOH | 3-(4-Cl-Ph)Pr | Ph |
| 3-166 | CH₂S(CH₂)₂ | NHOH | 3-(4-Cl-Ph)Pr | Ph |
| 3-167 | CH₂NH(CH₂)₂ | NHOH | 3-(4-Cl-Ph)Pr | Ph |
| 3-168 | CH₂N(CH₃)(CH₂)₂ | NHOH | 3-(4-Cl-Ph)Pr | Ph |
| 3-169 | (CH₂)₂ | OH | H | Me |
| 3-170 | (CH₂)₂ | OH | Me | Me |
| 3-171 | (CH₂)₂ | OH | (4-Cl-Ph)-C≡CCH₂ | Me |
| 3-172 | (CH₂)₂ | NHOH | H | CF₃ |
| 3-173 | (CH₂)₂ | OH | Me | CF₃ |
| 3-174 | (CH₂)₂ | OH | CH≡CCH₂ | CF₃ |
| 3-175 | (CH₂)₂ | OH | H | Bu |
| 3-176 | (CH₂)₂ | OH | Me | Bu |
| 3-177 | (CH₂)₂ | OH | CH≡CCH₂ | Bu |
| 3-178 | (CH₂)₂ | OH | H | Ph |
| 3-179 | (CH₂)₂ | OH | Me | Ph |
| 3-180 | (CH₂)₂ | OH | CH≡CCH₂ | Ph |
| 3-181 | (CH₂)₂ | NHOH | Me | 4-Cl-Ph |
| 3-182 | (CH₂)₂ | NHOH | Me | 4-F-Ph |
| 3-183 | (CH₂)₂ | NHOH | Me | 3-Cl-Ph |
| 3-184 | (CH₂)₂ | NHOH | Me | 3-F-Ph |
| 3-185 | (CH₂)₂ | NHOH | H | 4-Py |
| 3-186 | (CH₂)₂ | NHOH | CH≡CCH₂ | 4-Cl-Ph |
| 3-187 | (CH₂)₂ | NHOH | CH≡CCH₂ | 4-F-Ph |
| 3-188 | (CH₂)₂ | NHOH | CH≡CCH₂ | 4-MeO-Ph |
| 3-189 | (CH₂)₂ | NHOH | CH≡CCH₂ | 2,4-diF-Ph |

TABLE 3-continued

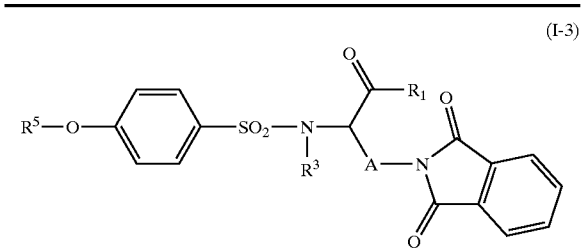

(I-3)

| Cpd. No. | A | R¹ | R³ | R⁵ |
|---|---|---|---|---|
| 3-190 | (CH₂)₂ | NHOH | CH≡CCH₂ | 4-Py |
| 3-191 | (CH₂)₂ | OH | 3-Py-CH₂ | Me |
| 3-192 | (CH₂)₂ | OH | 3-(4-Cl-Ph)Pr | Me |
| 3-193 | (CH₂)₂ | NHOH | c-Pr | Ph |

TABLE 4

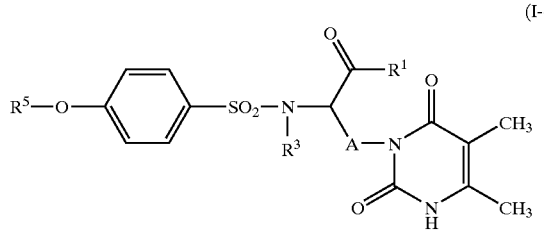

(I-4)

| Cpd. No. | A | R¹ | R³ | R⁵ |
|---|---|---|---|---|
| 4-1 | CH₂ | NHOH | H | Me |
| 4-2 | (CH₂)₂ | NHOH | H | Me |
| 4-3 | (CH₂)₃ | NHOH | H | Me |
| 4-4 | (CH₂)₄ | NHOH | H | Me |
| 4-5 | CH₂O(CH₂)₂ | NHOH | H | Me |
| 4-6 | CH₂S(CH₂)₂ | NHOH | H | Me |
| 4-7 | CH₂NH(CH₂)₂ | NHOH | H | Me |
| 4-8 | CH₂ | NHOH | H | Ph |
| 4-9 | (CH₂)₂ | NHOH | H | Ph |
| 4-10 | (CH₂)₃ | NHOH | H | Ph |
| 4-11 | (CH₂)₄ | NHOH | H | Ph |
| 4-12 | CH(CH₃) | NHOH | H | Ph |
| 4-13 | CH(CH₃)CH₂ | NHOH | H | Ph |
| 4-14 | CH₂CH(CH₃) | NHOH | H | Ph |
| 4-15 | C(CH₃)₂CH₂ | NHOH | H | Ph |
| 4-16 | CH₂C(CH₃)₂ | NHOH | H | Ph |
| 4-17 | CH₂OCH₂ | NHOH | H | Ph |
| 4-18 | CH₂SCH₂ | NHOH | H | Ph |
| 4-19 | CH₂NHCH₂ | NHOH | H | Ph |
| 4-20 | CH₂O(CH₂)₂ | NHOH | H | Ph |
| 4-21 | CH₂S(CH₂)₂ | NHOH | H | Ph |
| 4-22 | CH₂NH(CH₂)₂ | NHOH | H | Ph |
| 4-23 | CH₂N(CH₃)(CH₂)₂ | NHOH | H | Ph |
| 4-24 | CH₂ | NHOH | Me | Ph |
| 4-25 | (CH₂)₂ | NHOH | Me | Ph |
| 4-26 | (CH₂)₃ | NHOH | Me | Ph |
| 4-27 | (CH₂)₄ | NHOH | Me | Ph |
| 4-28 | CH(CH₃) | NHOH | Me | Ph |
| 4-29 | CH(CH₃)CH₂ | NHOH | Me | Ph |
| 4-30 | CH₂CH(CH₃) | NHOH | Me | Ph |
| 4-31 | C(CH₃)₂CH₂ | NHOH | Me | Ph |
| 4-32 | CH₂C(CH₃)₂ | NHOH | Me | Ph |
| 4-33 | CH₂OCH₂ | NHOH | Me | Ph |
| 4-34 | CH₂SCH₂ | NHOH | Me | Ph |
| 4-35 | CH₂NHCH₂ | NHOH | Me | Ph |
| 4-36 | CH₂O(CH₂)₂ | NHOH | Me | Ph |
| 4-37 | CH₂S(CH₂)₂ | NHOH | Me | Ph |
| 4-38 | CH₂NH(CH₂)₂ | NHOH | Me | Ph |
| 4-39 | CH₂N(CH₃)(CH₂)₂ | NHOH | Me | Ph |

TABLE 4-continued

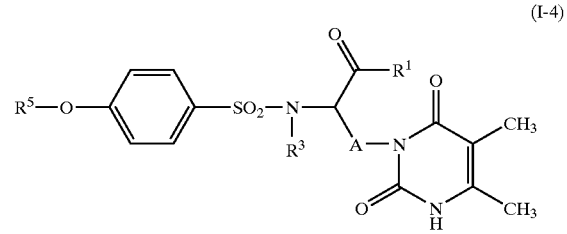

(I-4)

| Cpd. No. | A | R¹ | R³ | R⁵ |
|---|---|---|---|---|
| 4-40 | CH₂ | NHOH | Et | Ph |
| 4-41 | (CH₂)₂ | NHOH | Et | Ph |
| 4-42 | (CH₂)₃ | NHOH | Et | Ph |
| 4-43 | (CH₂)₄ | NHOH | Et | Ph |
| 4-44 | CH(CH₃) | NHOH | Et | Ph |
| 4-45 | CH(CH₃)CH₂ | NHOH | Et | Ph |
| 4-46 | CH₂CH(CH₃) | NHOH | Et | Ph |
| 4-47 | C(CH₃)₂CH₂ | NHOH | Et | Ph |
| 4-48 | CH₂C(CH₃)₂ | NHOH | Et | Ph |
| 4-49 | CH₂OCH₂ | NHOH | Et | Ph |
| 4-50 | CH₂SCH₂ | NHOH | Et | Ph |
| 4-51 | CH₂NHCH₂ | NHOH | Et | Ph |
| 4-52 | CH₂O(CH₂)₂ | NHOH | Et | Ph |
| 4-53 | CH₂S(CH₂)₂ | NHOH | Et | Ph |
| 4-54 | CH₂NH(CH₂)₂ | NHOH | Et | Ph |
| 4-55 | CH₂N(CH₃)(CH₂)₂ | NHOH | Et | Ph |
| 4-56 | CH₂ | NHOH | Pr | Ph |
| 4-57 | (CH₂)₂ | NHOH | Pr | Ph |
| 4-58 | (CH₂)₃ | NHOH | Pr | Ph |
| 4-59 | (CH₂)₄ | NHOH | Pr | Ph |
| 4-60 | CH(CH₃) | NHOH | Pr | Ph |
| 4-61 | CH(CH₃)CH₂ | NHOH | Pr | Ph |
| 4-62 | CH₂CH(CH₃) | NHOH | Pr | Ph |
| 4-63 | C(CH₃)₂CH₂ | NHOH | Pr | Ph |
| 4-64 | CH₂C(CH₃)₂ | NHOH | Pr | Ph |
| 4-65 | CH₂OCH₂ | NHOH | Pr | Ph |
| 4-66 | CH₂SCH₂ | NHOH | Pr | Ph |
| 4-67 | CH₂NHCH₂ | NHOH | Pr | Ph |
| 4-68 | CH₂ | NHOH | i-Pr | Ph |
| 4-69 | (CH₂)₂ | NHOH | i-Pr | Ph |
| 4-70 | (CH₂)₃ | NHOH | i-Pr | Ph |
| 4-71 | (CH₂)₄ | NHOH | i-Pr | Ph |
| 4-72 | CH₂ | NHOH | CH₂=CHCH₂ | Ph |
| 4-73 | (CH₂)₂ | NHOH | CH₂=CHCH₂ | Ph |
| 4-74 | (CH₂)₃ | NHOH | CH₂=CHCH₂ | Ph |
| 4-75 | (CH₂)₄ | NHOH | CH₂=CHCH₂ | Ph |
| 4-76 | CH(CH₃) | NHOH | CH₂=CHCH₂ | Ph |
| 4-77 | CH(CH₃)CH₂ | NHOH | CH₂=CHCH₂ | Ph |
| 4-78 | CH₂CH(CH₃) | NHOH | CH₂=CHCH₂ | Ph |
| 4-79 | C(CH₃)₂CH₂ | NHOH | CH₂=CHCH₂ | Ph |
| 4-80 | CH₂C(CH₃)₂ | NHOH | CH₂=CHCH₂ | Ph |
| 4-81 | CH₂OCH₂ | NHOH | CH₂=CHCH₂ | Ph |
| 4-82 | CH₂SCH₂ | NHOH | CH₂=CHCH₂ | Ph |
| 4-83 | CH₂NHCH₂ | NHOH | CH₂=CHCH₂ | Ph |
| 4-84 | CH₂O(CH₂)₂ | NHOH | CH₂=CHCH₂ | Ph |
| 4-85 | CH₂S(CH₂)₂ | NHOH | CH₂=CHCH₂ | Ph |
| 4-86 | CH₂NH(CH₂)₂ | NHOH | CH₂=CHCH₂ | Ph |
| 4-87 | CH₂N(CH₃)(CH₂)₂ | NHOH | CH₂=CHCH₂ | Ph |
| 4-88 | CH₂ | NHOH | CH≡CCH₂ | Ph |
| 4-89 | (CH₂)₂ | NHOH | CH≡CCH₂ | Ph |
| 4-90 | (CH₂)₃ | NHOH | CH≡CCH₂ | Ph |
| 4-91 | (CH₂)₄ | NHOH | CH≡CCH₂ | Ph |
| 4-92 | CH(CH₃) | NHOH | CH≡CCH₂ | Ph |
| 4-93 | CH(CH₃)CH₂ | NHOH | CH≡CCH₂ | Ph |
| 4-94 | CH₂CH(CH₃) | NHOH | CH≡CCH₂ | Ph |
| 4-95 | C(CH₃)₂CH₂ | NHOH | CH≡CCH₂ | Ph |
| 4-96 | CH₂C(CH₃)₂ | NHOH | CH≡CCH₂ | Ph |
| 4-97 | CH₂OCH₂ | NHOH | CH≡CCH₂ | Ph |
| 4-98 | CH₂SCH₂ | NHOH | CH≡CCH₂ | Ph |
| 4-99 | CH₂NHCH₂ | NHOH | CH≡CCH₂ | Ph |
| 4-100 | CH₂O(CH₂)₂ | NHOH | CH≡CCH₂ | Ph |
| 4-101 | CH₂S(CH₂)₂ | NHOH | CH≡CCH₂ | Ph |
| 4-102 | CH₂NH(CH₂)₂ | NHOH | CH≡CCH₂ | Ph |

TABLE 4-continued (I-4)

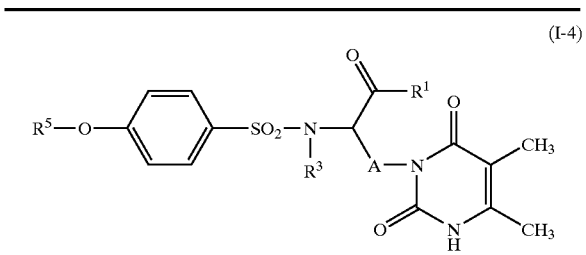

| Cpd. No. | A | R¹ | R³ | R⁵ |
|---|---|---|---|---|
| 4-103 | $CH_2N(CH_3)(CH_2)_2$ | NHOH | CH≡CCH₂ | Ph |
| 4-104 | $CH_2$ | NHOH | MeC≡CCH₂ | Ph |
| 4-105 | $(CH_2)_2$ | NHOH | MeC≡CCH₂ | Ph |
| 4-106 | $(CH_2)_3$ | NHOH | MeC≡CCH₂ | Ph |
| 4-107 | $(CH_2)_4$ | NHOH | MeC≡CCH₂ | Ph |
| 4-108 | $CH(CH_3)$ | NHOH | MeC≡CCH₂ | Ph |
| 4-109 | $CH(CH_3)CH_2$ | NHOH | MeC≡CCH₂ | Ph |
| 4-110 | $CH_2CH(CH_3)$ | NHOH | MeC≡CCH₂ | Ph |
| 4-111 | $C(CH_3)_2CH_2$ | NHOH | MeC≡CCH₂ | Ph |
| 4-112 | $CH_2C(CH_3)_2$ | NHOH | MeC≡CCH₂ | Ph |
| 4-113 | $CH_2OCH_2$ | NHOH | MeC≡CCH₂ | Ph |
| 4-114 | $CH_2SCH_2$ | NHOH | MeC≡CCH₂ | Ph |
| 4-115 | $CH_2NHCH_2$ | NHOH | MeC≡CCH₂ | Ph |
| 4-116 | $CH_2O(CH_2)_2$ | NHOH | MeC≡CCH₂ | Ph |
| 4-117 | $CH_2S(CH_2)_2$ | NHOH | MeC≡CCH₂ | Ph |
| 4-118 | $CH_2NH(CH_2)_2$ | NHOH | MeC≡CCH₂ | Ph |
| 4-119 | $CH_2N(CH_3)(CH_2)_2$ | NHOH | MeC≡CCH₂ | Ph |
| 4-120 | $CH_2$ | NHOH | PhC≡CCH₂ | Ph |
| 4-121 | $(CH_2)_2$ | NHOH | PhC≡CCH₂ | Ph |
| 4-122 | $(CH_2)_3$ | NHOH | PhC≡CCH₂ | Ph |
| 4-123 | $(CH_2)_4$ | NHOH | PhC≡CCH₂ | Ph |
| 4-124 | $CH(CH_3)$ | NHOH | PhC≡CCH₂ | Ph |
| 4-125 | $CH(CH_3)CH_2$ | NHOH | PhC≡CCH₂ | Ph |
| 4-126 | $CH_2CH(CH_3)$ | NHOH | PhC≡CCH₂ | Ph |
| 4-127 | $C(CH_3)_2CH_2$ | NHOH | PhC≡CCH₂ | Ph |
| 4-128 | $CH_2C(CH_3)_2$ | NHOH | PhC≡CCH₂ | Ph |
| 4-129 | $CH_2OCH_2$ | NHOH | PhC≡CCH₂ | Ph |
| 4-130 | $CH_2SCH_2$ | NHOH | PhC≡CCH₂ | Ph |
| 4-131 | $CH_2NHCH_2$ | NHOH | PhC≡CCH₂ | Ph |
| 4-132 | $CH_2O(CH_2)_2$ | NHOH | PhC≡CCH₂ | Ph |
| 4-133 | $CH_2S(CH_2)_2$ | NHOH | PhC≡CCH₂ | Ph |
| 4-134 | $CH_2NH(CH_2)_2$ | NHOH | PhC≡CCH₂ | Ph |
| 4-135 | $CH_2N(CH_3)(CH_2)_2$ | NHOH | PhC≡CCH₂ | Ph |
| 4-136 | $CH_2$ | NHOH | Bn | Ph |
| 4-137 | $(CH_2)_2$ | NHOH | Bn | Ph |
| 4-138 | $(CH_2)_3$ | NHOH | Bn | Ph |
| 4-139 | $(CH_2)_4$ | NHOH | Bn | Ph |
| 4-140 | $CH(CH_3)$ | NHOH | Bn | Ph |
| 4-141 | $CH(CH_3)CH_2$ | NHOH | Bn | Ph |
| 4-142 | $CH_2CH(CH_3)$ | NHOH | Bn | Ph |
| 4-143 | $C(CH_3)_2CH_2$ | NHOH | Bn | Ph |
| 4-144 | $CH_2C(CH_3)_2$ | NHOH | Bn | Ph |
| 4-145 | $CH_2OCH_2$ | NHOH | Bn | Ph |
| 4-146 | $CH_2SCH_2$ | NHOH | Bn | Ph |
| 4-147 | $CH_2NHCH_2$ | NHOH | Bn | Ph |
| 4-148 | $CH_2O(CH_2)_2$ | NHOH | Bn | Ph |
| 4-149 | $CH_2S(CH_2)_2$ | NHOH | Bn | Ph |
| 4-150 | $CH_2NH(CH_2)_2$ | NHOH | Bn | Ph |
| 4-151 | $CH_2N(CH_3)(CH_2)_2$ | NHOH | Bn | Ph |
| 4-152 | $CH_2$ | NHOH | 3-(4-Cl-Ph)Pr | Ph |
| 4-153 | $(CH_2)_2$ | NHOH | 3-(4-Cl-Ph)Pr | Ph |
| 4-154 | $(CH_2)_3$ | NHOH | 3-(4-Cl-Ph)Pr | Ph |
| 4-155 | $(CH_2)_4$ | NHOH | 3-(4-Cl-Ph)Pr | Ph |
| 4-156 | $CH(CH_3)$ | NHOH | 3-(4-Cl-Ph)Pr | Ph |
| 4-157 | $CH(CH_3)CH_2$ | NHOH | 3-(4-Cl-Ph)Pr | Ph |
| 4-158 | $CH_2CH(CH_3)$ | NHOH | 3-(4-Cl-Ph)Pr | Ph |
| 4-159 | $C(CH_3)_2CH_2$ | NHOH | 3-(4-Cl-Ph)Pr | Ph |
| 4-160 | $CH_2C(CH_3)_2$ | NHOH | 3-(4-Cl-Ph)Pr | Ph |
| 4-161 | $CH_2OCH_2$ | NHOH | 3-(4-Cl-Ph)Pr | Ph |
| 4-162 | $CH_2SCH_2$ | NHOH | 3-(4-Cl-Ph)Pr | Ph |
| 4-163 | $CH_2NHCH_2$ | NHOH | 3-(4-Cl-Ph)Pr | Ph |
| 4-164 | $CH_2O(CH_2)_2$ | NHOH | 3-(4-Cl-Ph)Pr | Ph |
| 4-165 | $CH_2S(CH_2)_2$ | NHOH | 3-(4-Cl-Ph)Pr | Ph |

TABLE 4-continued (I-4)

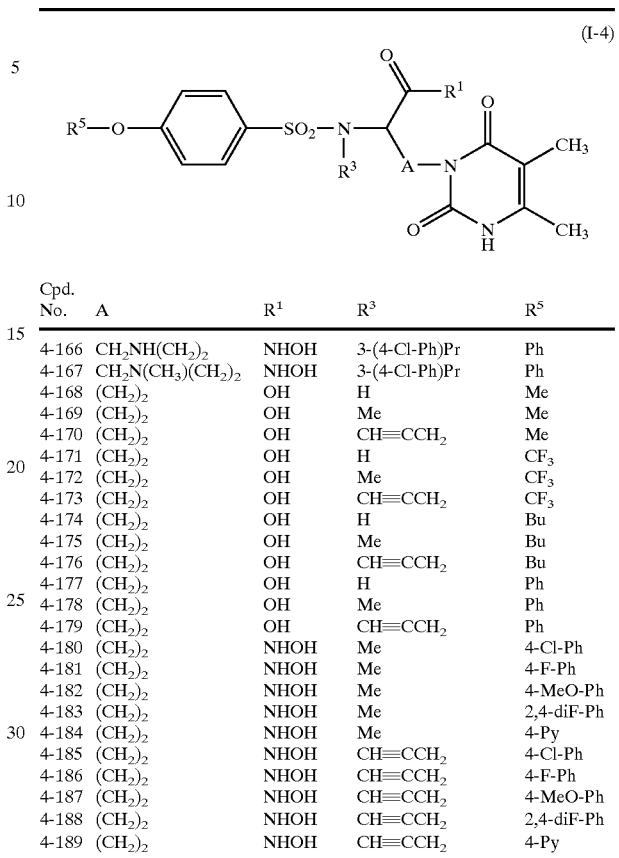

| Cpd. No. | A | R¹ | R³ | R⁵ |
|---|---|---|---|---|
| 4-166 | $CH_2NH(CH_2)_2$ | NHOH | 3-(4-Cl-Ph)Pr | Ph |
| 4-167 | $CH_2N(CH_3)(CH_2)_2$ | NHOH | 3-(4-Cl-Ph)Pr | Ph |
| 4-168 | $(CH_2)_2$ | OH | H | Me |
| 4-169 | $(CH_2)_2$ | OH | Me | Me |
| 4-170 | $(CH_2)_2$ | OH | CH≡CCH₂ | Me |
| 4-171 | $(CH_2)_2$ | OH | H | CF₃ |
| 4-172 | $(CH_2)_2$ | OH | Me | CF₃ |
| 4-173 | $(CH_2)_2$ | OH | CH≡CCH₂ | CF₃ |
| 4-174 | $(CH_2)_2$ | OH | H | Bu |
| 4-175 | $(CH_2)_2$ | OH | Me | Bu |
| 4-176 | $(CH_2)_2$ | OH | CH≡CCH₂ | Bu |
| 4-177 | $(CH_2)_2$ | OH | H | Ph |
| 4-178 | $(CH_2)_2$ | OH | Me | Ph |
| 4-179 | $(CH_2)_2$ | OH | CH≡CCH₂ | Ph |
| 4-180 | $(CH_2)_2$ | NHOH | Me | 4-Cl-Ph |
| 4-181 | $(CH_2)_2$ | NHOH | Me | 4-F-Ph |
| 4-182 | $(CH_2)_2$ | NHOH | Me | 4-MeO-Ph |
| 4-183 | $(CH_2)_2$ | NHOH | Me | 2,4-diF-Ph |
| 4-184 | $(CH_2)_2$ | NHOH | Me | 4-Py |
| 4-185 | $(CH_2)_2$ | NHOH | CH≡CCH₂ | 4-Cl-Ph |
| 4-186 | $(CH_2)_2$ | NHOH | CH≡CCH₂ | 4-F-Ph |
| 4-187 | $(CH_2)_2$ | NHOH | CH≡CCH₂ | 4-MeO-Ph |
| 4-188 | $(CH_2)_2$ | NHOH | CH≡CCH₂ | 2,4-diF-Ph |
| 4-189 | $(CH_2)_2$ | NHOH | CH≡CCH₂ | 4-Py |

TABLE 5

(I-5)

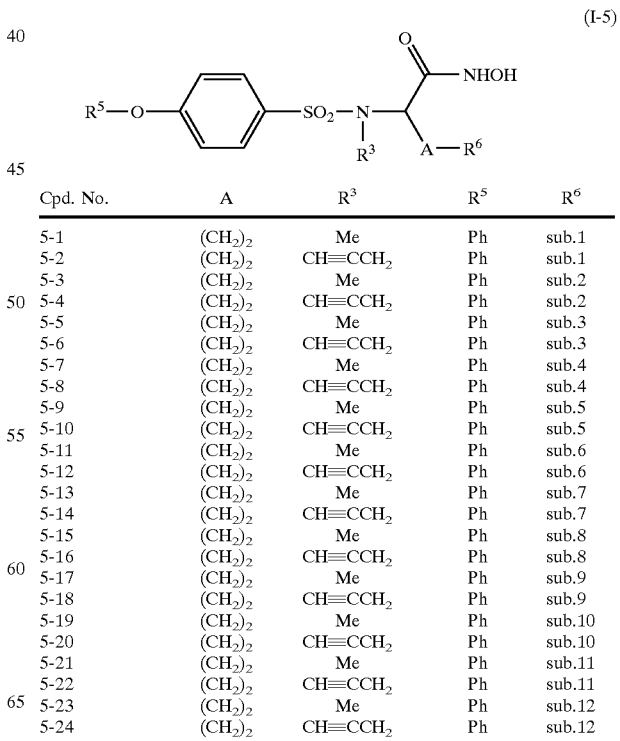

| Cpd. No. | A | R³ | R⁵ | R⁶ |
|---|---|---|---|---|
| 5-1 | $(CH_2)_2$ | Me | Ph | sub.1 |
| 5-2 | $(CH_2)_2$ | CH≡CCH₂ | Ph | sub.1 |
| 5-3 | $(CH_2)_2$ | Me | Ph | sub.2 |
| 5-4 | $(CH_2)_2$ | CH≡CCH₂ | Ph | sub.2 |
| 5-5 | $(CH_2)_2$ | Me | Ph | sub.3 |
| 5-6 | $(CH_2)_2$ | CH≡CCH₂ | Ph | sub.3 |
| 5-7 | $(CH_2)_2$ | Me | Ph | sub.4 |
| 5-8 | $(CH_2)_2$ | CH≡CCH₂ | Ph | sub.4 |
| 5-9 | $(CH_2)_2$ | Me | Ph | sub.5 |
| 5-10 | $(CH_2)_2$ | CH≡CCH₂ | Ph | sub.5 |
| 5-11 | $(CH_2)_2$ | Me | Ph | sub.6 |
| 5-12 | $(CH_2)_2$ | CH≡CCH₂ | Ph | sub.6 |
| 5-13 | $(CH_2)_2$ | Me | Ph | sub.7 |
| 5-14 | $(CH_2)_2$ | CH≡CCH₂ | Ph | sub.7 |
| 5-15 | $(CH_2)_2$ | Me | Ph | sub.8 |
| 5-16 | $(CH_2)_2$ | CH≡CCH₂ | Ph | sub.8 |
| 5-17 | $(CH_2)_2$ | Me | Ph | sub.9 |
| 5-18 | $(CH_2)_2$ | CH≡CCH₂ | Ph | sub.9 |
| 5-19 | $(CH_2)_2$ | Me | Ph | sub.10 |
| 5-20 | $(CH_2)_2$ | CH≡CCH₂ | Ph | sub.10 |
| 5-21 | $(CH_2)_2$ | Me | Ph | sub.11 |
| 5-22 | $(CH_2)_2$ | CH≡CCH₂ | Ph | sub.11 |
| 5-23 | $(CH_2)_2$ | Me | Ph | sub.12 |
| 5-24 | $(CH_2)_2$ | CH≡CCH₂ | Ph | sub.12 |

TABLE 5-continued

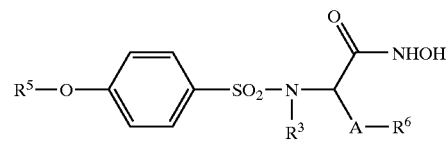

(I-5)

| Cpd. No. | A | R³ | R⁵ | R⁶ |
|---|---|---|---|---|
| 5-25 | (CH₂)₂ | Me | Ph | sub.13 |
| 5-26 | (CH₂)₂ | CH≡CCH₂ | Ph | sub.13 |
| 5-27 | (CH₂)₂ | Me | Ph | sub.14 |
| 5-28 | (CH₂)₂ | CH≡CCH₂ | Ph | sub.14 |
| 5-29 | (CH₂)₂ | Me | Ph | sub.15 |
| 5-30 | (CH₂)₂ | CH≡CCH₂ | Ph | sub.15 |
| 5-31 | (CH₂)₂ | Me | Ph | sub.16 |
| 5-32 | (CH₂)₂ | CH≡CCH₂ | Ph | sub.16 |
| 5-33 | (CH₂)₂ | Me | Ph | sub.17 |
| 5-34 | (CH₂)₂ | CH≡CCH₂ | Ph | sub.17 |
| 5-35 | (CH₂)₂ | Me | Ph | sub.18 |
| 5-36 | (CH₂)₂ | CH≡CCH₂ | Ph | sub.18 |
| 5-37 | (CH₂)₂ | Me | Ph | sub.19 |
| 5-38 | (CH₂)₂ | CH≡CCH₂ | Ph | sub.19 |
| 5-39 | (CH₂)₂ | Me | Ph | sub.20 |
| 5-40 | (CH₂)₂ | CH≡CCH₂ | Ph | sub.20 |
| 5-41 | (CH₂)₂ | Me | Ph | sub.21 |
| 5-42 | (CH₂)₂ | CH≡CCH₂ | Ph | sub.21 |
| 5-43 | (CH₂)₂ | H | Me | sub.15 |
| 5-44 | (CH₂)₂ | Me | Ph | sub.22 |
| 5-45 | (CH₂)₂ | CH≡CCH₂ | Ph | sub.22 |
| 5-46 | (CH₂)₂ | Me | Ph | sub.23 |
| 5-47 | (CH₂)₂ | CH≡CCH₂ | Ph | sub.23 |
| 5-48 | (CH₂)₂ | Me | Ph | sub.24 |
| 5-49 | (CH₂)₂ | CH≡CCH₂ | Ph | sub.24 |
| 5-50 | (CH₂)₂ | Me | Ph | sub.25 |
| 5-51 | (CH₂)₂ | CH≡CCH₂ | Ph | sub.25 |
| 5-52 | (CH₂)₂ | Me | Ph | sub.26 |
| 5-53 | (CH₂)₂ | CH≡CCH₂ | Ph | sub.26 |
| 5-54 | (CH₂)₂ | Me | Ph | sub.27 |
| 5-55 | (CH₂)₂ | CH≡CCH₂ | Ph | sub.27 |
| 5-56 | (CH₂)₂ | Me | Ph | sub.28 |
| 5-57 | (CH₂)₂ | CH≡CCH₂ | Ph | sub.28 |
| 5-58 | (CH₂)₂ | Me | Ph | sub.29 |
| 5-59 | (CH₂)₂ | CH≡CCH₂ | Ph | sub.29 |
| 5-60 | (CH₂)₂ | Me | Ph | sub.30 |
| 5-61 | (CH₂)₂ | CH≡CCH₂ | Ph | sub.30 |
| 5-62 | (CH₂)₂ | Me | Ph | sub.31 |
| 5-63 | (CH₂)₂ | CH≡CCH₂ | Ph | sub.31 |
| 5-64 | (CH₂)₂ | Me | Ph | sub.32 |
| 5-65 | (CH₂)₂ | CH≡CCH₂ | Ph | sub.32 |
| 5-66 | (CH₂)₂ | Me | Ph | sub.33 |
| 5-67 | (CH₂)₂ | CH≡CCH₂ | Ph | sub.33 |
| 5-68 | (CH₂)₂ | Me | Ph | sub.34 |
| 5-69 | (CH₂)₂ | CH≡CCH₂ | Ph | sub.34 |
| 5-70 | (CH₂)₂ | Me | Ph | sub.35 |
| 5-71 | (CH₂)₂ | CH≡CCH₂ | Ph | sub.35 |
| 5-72 | (CH₂)₂ | Me | Ph | sub.36 |
| 5-73 | (CH₂)₂ | CH≡CCH₂ | Ph | sub.36 |
| 5-74 | (CH₂)₂ | Me | Ph | sub.37 |
| 5-75 | (CH₂)₂ | CH≡CCH₂ | Ph | sub.37 |
| 5-76 | (CH₂)₂ | Me | Ph | sub.38 |
| 5-77 | (CH₂)₂ | CH≡CCH₂ | Ph | sub.38 |
| 5-78 | (CH₂)₂ | Me | Ph | sub.39 |
| 5-79 | (CH₂)₂ | CH≡CCH₂ | Ph | sub.39 |
| 5-80 | (CH₂)₂ | Me | Ph | sub.40 |
| 5-81 | (CH₂)₂ | CH≡CCH₂ | Ph | sub.40 |
| 5-82 | (CH₂)₂ | Me | Ph | sub.41 |
| 5-83 | (CH₂)₂ | CH≡CCH₂ | Ph | sub.41 |
| 5-84 | (CH₂)₂ | Me | Ph | sub.42 |
| 5-85 | (CH₂)₂ | CH≡CCH₂ | Ph | sub.42 |
| 5-86 | (CH₂)₂ | Me | Ph | sub.43 |
| 5-87 | (CH₂)₂ | CH≡CCH₂ | Ph | sub.43 |
| 5-88 | (CH₂)₂ | Me | Ph | sub.44 |
| 5-89 | (CH₂)₂ | CH≡CCH₂ | Ph | sub.44 |
| 5-90 | (CH₂)₂ | Me | Ph | sub.45 |
| 5-91 | (CH₂)₂ | CH≡CCH₂ | Ph | sub.45 |
| 5-92 | (CH₂)₂ | Me | Ph | sub.46 |
| 5-93 | (CH₂)₂ | Me | Ph | sub.47 |
| 5-94 | (CH₂)₂ | Me | Ph | sub.48 |
| 5-95 | (CH₂)₂ | Me | Ph | sub.49 |
| 5-96 | (CH₂)₂ | Me | Ph | sub.50 |
| 5-97 | (CH₂)₂ | Me | Ph | sub.51 |
| 5-98 | (CH₂)₂ | Me | 4-Py | sub.12 |
| 5-99 | (CH₂)₂ | Me | 3-Cl—Ph | sub.12 |

TABLE 6

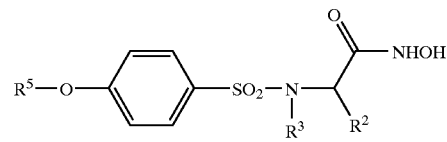

(I-6)

| Cpd. No. | R² | R³ | R⁵ |
|---|---|---|---|
| 6-1 | Me | CH≡CCH₂ | Ph |
| 6-2 | Et | CH≡CCH₂ | Ph |
| 6-3 | Pr | CH≡CCH₂ | Ph |
| 6-4 | i-Pr | CH≡CCH₂ | Ph |
| 6-5 | Bu | CH≡CCH₂ | Ph |
| 6-6 | s-Bu | CH≡CCH₂ | Ph |
| 6-7 | i-Bu | CH≡CCH₂ | Ph |
| 6-8 | t-Bu | CH≡CCH₂ | Ph |
| 6-9 | Bn | CH≡CCH₂ | Ph |
| 6-10 | PhOCH₂— | CH≡CCH₂ | Ph |
| 6-11 | PhSCH₂— | CH≡CCH₂ | Ph |
| 6-12 | (2-Thie)SCH₂— | CH≡CCH₂ | Ph |
| 6-13 | Me | MeC≡CCH₂ | Ph |
| 6-14 | Et | MeC≡CCH₂ | Ph |
| 6-15 | Pr | MeC≡CCH₂ | Ph |
| 6-16 | i-Pr | MeC≡CCH₂ | Ph |
| 6-17 | Bu | MeC≡CCH₂ | Ph |
| 6-18 | s-Bu | MeC≡CCH₂ | Ph |
| 6-19 | i-Bu | MeC≡CCH₂ | Ph |
| 6-20 | t-Bu | MeC≡CCH₂ | Ph |
| 6-21 | Bn | MeC≡CCH₂ | Ph |
| 6-22 | PhOCH₂— | MeC≡CCH₂ | Ph |
| 6-23 | PhSCH₂— | MeC≡CCH₂ | Ph |
| 6-24 | (2-Thie)SCH₂— | MeC≡CCH₂ | Ph |
| 6-25 | i-Pr | (4-Cl—Ph)—C≡CCH₂ | Me |
| 6-26 | i-Pr | (4-Cl—Ph)—C≡CCH₂ | Ph |
| 6-27 | Me | (4-Cl—Ph)—C≡CCH₂ | Me |

TABLE 7

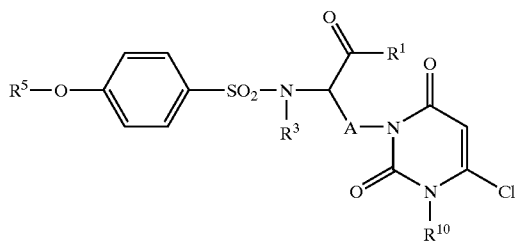
(I-7)

| Cpd. No. | A | $R^1$ | $R^3$ | $R^5$ | $R^{10}$ |
|---|---|---|---|---|---|
| 7-1 | $CH_2$ | NHOH | H | Me | H |
| 7-2 | $(CH_2)_2$ | NHOH | H | Me | H |
| 7-3 | $(CH_2)_3$ | NHOH | H | Me | H |
| 7-4 | $(CH_2)_4$ | NHOH | H | Me | H |
| 7-5 | $(CH_2)_2$ | NHOH | (4-Cl—Ph)—C≡CCH$_2$ | Me | H |
| 7-6 | $CH_2S(CH_2)_2$ | NHOH | H | Me | H |
| 7-7 | $(CH_2)_2$ | NHOH | 3-(4-Cl—Ph)Pr | Me | H |
| 7-8 | $(CH_2)_2$ | NHOH | 3-Py—CH$_2$ | Me | H |
| 7-9 | $CH_2$ | NHOH | H | Ph | H |
| 7-10 | $(CH_2)_2$ | NHOH | H | Ph | H |
| 7-11 | $(CH_2)_3$ | NHOH | H | Ph | H |
| 7-12 | $(CH_2)_4$ | NHOH | H | Ph | H |
| 7-13 | $CH(CH_3)$ | NHOH | H | Ph | H |
| 7-14 | $CH(CH_3)CH_2$ | NHOH | H | Ph | H |
| 7-15 | $CH_2CH(CH_3)$ | NHOH | H | Ph | H |
| 7-16 | $C(CH_3)_2CH_2$ | NHOH | H | Ph | H |
| 7-17 | $CH_2C(CH_3)_2$ | NHOH | H | Ph | H |
| 7-18 | $CH_2OCH_2$ | NHOH | H | Ph | H |
| 7-19 | $CH_2SCH_2$ | NHOH | H | Ph | H |
| 7-20 | $CH_2NHCH_2$ | NHOH | H | Ph | H |
| 7-21 | $CH_2O(CH_2)_2$ | NHOH | H | Ph | H |
| 7-22 | $CH_2S(CH_2)_2$ | NHOH | H | Ph | H |
| 7-23 | $CH_2NH(CH_2)_2$ | NHOH | H | Ph | H |
| 7-24 | $CH_2N(CH_3)(CH_2)$ | NHOH | H | Ph | H |
| 7-25 | $CH_2$ | NHOH | Me | Ph | H |
| 7-26 | $(CH_2)_2$ | NHOH | Me | 4-Py | H |
| 7-27 | $(CH_2)_3$ | NHOH | Me | Ph | H |
| 7-28 | $(CH_2)_4$ | NHOH | Me | Ph | H |
| 7-29 | $CH(CH_3)$ | NHOH | Me | Ph | H |
| 7-30 | $CH(CH_3)CH_2$ | NHOH | Me | Ph | H |
| 7-31 | $CH_2CH(CH_3)$ | NHOH | Me | Ph | H |
| 7-32 | $C(CH_3)_2CH_2$ | NHOH | Me | Ph | H |
| 7-33 | $CH_2C(CH_3)_2$ | NHOH | Me | Ph | H |
| 7-34 | $CH_2OCH_2$ | NHOH | Me | Ph | H |
| 7-35 | $CH_2SCH_2$ | NHOH | Me | Ph | H |
| 7-36 | $CH_2NHCH_2$ | NHOH | Me | Ph | H |
| 7-37 | $CH_2O(CH_2)_2$ | NHOH | Me | Ph | H |
| 7-38 | $CH_2S(CH_2)_2$ | NHOH | Me | Ph | H |
| 7-39 | $CH_2NH(CH_2)_2$ | NHOH | Me | Ph | H |
| 7-40 | $CH_2N(CH_3)(CH_2)$ | NHOH | Me | Ph | H |
| 7-41 | $CH_2$ | NHOH | Et | Ph | H |
| 7-42 | $(CH_2)_2$ | NHOH | Et | Ph | H |
| 7-43 | $(CH_2)_3$ | NHOH | Et | Ph | H |
| 7-44 | $(CH_2)_4$ | NHOH | Et | Ph | H |
| 7-45 | $CH(CH_3)$ | NHOH | Et | Ph | H |
| 7-46 | $CH(CH_3)CH_2$ | NHOH | Et | Ph | H |
| 7-47 | $CH_2CH(CH_3)$ | NHOH | Et | Ph | H |
| 7-48 | $C(CH_3)_2CH_2$ | NHOH | Et | Ph | H |
| 7-49 | $CH_2C(CH_3)_2$ | NHOH | Et | Ph | H |
| 7-50 | $CH_2OCH_2$ | NHOH | Et | Ph | H |
| 7-51 | $CH_2SCH_2$ | NHOH | Et | Ph | H |
| 7-52 | $CH_2NHCH_2$ | NHOH | Et | Ph | H |
| 7-53 | $CH_2O(CH_2)_2$ | NHOH | Et | Ph | H |
| 7-54 | $CH_2S(CH_2)_2$ | NHOH | Et | Ph | H |
| 7-55 | $CH_2NH(CH_2)_2$ | NHOH | Et | Ph | H |
| 7-56 | $CH_2N(CH_3)(CH_2)$ | NHOH | Et | Ph | H |
| 7-57 | $CH_2$ | NHOH | Pr | Ph | H |
| 7-58 | $(CH_2)_2$ | NHOH | Pr | Ph | H |
| 7-59 | $(CH_2)_3$ | NHOH | Pr | Ph | H |
| 7-60 | $(CH_2)_4$ | NHOH | Pr | Ph | H |
| 7-61 | $CH(CH_3)$ | NHOH | Pr | Ph | H |
| 7-62 | $CH(CH_3)CH_2$ | NHOH | Pr | Ph | H |

TABLE 7-continued (I-7)

| Cpd. No. | A | R¹ | R³ | R⁵ | R¹⁰ |
|---|---|---|---|---|---|
| 7-63 | CH₂CH(CH₃) | NHOH | Pr | Ph | H |
| 7-64 | C(CH₃)₂CH₂ | NHOH | Pr | Ph | H |
| 7-65 | CH₂C(CH₃)₂ | NHOH | Pr | Ph | H |
| 7-66 | CH₂OCH₂ | NHOH | Pr | Ph | H |
| 7-67 | CH₂SCH₂ | NHOH | Pr | Ph | H |
| 7-68 | CH₂NHCH₂ | NHOH | Pr | Ph | H |
| 7-69 | CH₂ | NHOH | i-Pr | Ph | H |
| 7-70 | (CH₂)₂ | NHOH | i-Pr | Ph | H |
| 7-71 | (CH₂)₃ | NHOH | i-Pr | Ph | H |
| 7-72 | (CH₂)₄ | NHOH | i-Pr | Ph | H |
| 7-73 | CH₂ | NHOH | CH₂=CHCH₂ | Ph | H |
| 7-74 | (CH₂)₂ | NHOH | CH₂=CHCH₂ | Ph | H |
| 7-75 | (CH₂)₃ | NHOH | CH₂=CHCH₂ | Ph | H |
| 7-76 | (CH₂)₄ | NHOH | CH₂=CHCH₂ | Ph | H |
| 7-77 | CH(CH₃) | NHOH | CH₂=CHCH₂ | Ph | H |
| 7-78 | CH(CH₃)CH₂ | NHOH | CH₂=CHCH₂ | Ph | H |
| 7-79 | CH₂CH(CH₃) | NHOH | CH₂=CHCH₂ | Ph | H |
| 7-80 | C(CH₃)₂CH₂ | NHOH | CH₂=CHCH₂ | Ph | H |
| 7-81 | CH₂C(CH₃)₂ | NHOH | CH₂=CHCH₂ | Ph | H |
| 7-82 | CH₂OCH₂ | NHOH | CH₂=CHCH₂ | Ph | H |
| 7-83 | CH₂SCH₂ | NHOH | CH₂=CHCH₂ | Ph | H |
| 7-84 | CH₂NHCH₂ | NHOH | CH₂=CHCH₂ | Ph | H |
| 7-85 | CH₂O(CH₂)₂ | NHOH | CH₂=CHCH₂ | Ph | H |
| 7-86 | CH₂S(CH₂)₂ | NHOH | CH₂=CHCH₂ | Ph | H |
| 7-87 | CH₂NH(CH₂)₂ | NHOH | CH₂=CHCH₂ | Ph | H |
| 7-88 | CH₂N(CH₃)(CH₂) | NHOH | CH₂=CHCH₂ | Ph | H |
| 7-89 | CH₂ | NHOH | CH≡CCH₂ | Ph | H |
| 7-90 | (CH₂)₂ | NHOH | CH≡CCH₂ | Ph | H |
| 7-91 | (CH₂)₃ | NHOH | CH≡CCH₂ | Ph | H |
| 7-92 | (CH₂)₄ | NHOH | CH≡CCH₂ | Ph | H |
| 7-93 | CH(CH₃) | NHOH | CH≡CCH₂ | Ph | H |
| 7-94 | CH(CH₃)CH₂ | NHOH | CH≡CCH₂ | Ph | H |
| 7-95 | CH₂CH(CH₃) | NHOH | CH≡CCH₂ | Ph | H |
| 7-96 | C(CH₃)₂CH₂ | NHOH | CH≡CCH₂ | Ph | H |
| 7-97 | CH₂C(CH₃)₂ | NHOH | CH≡CCH₂ | Ph | H |
| 7-98 | CH₂OCH₂ | NHOH | CH≡CCH₂ | Ph | H |
| 7-99 | CH₂SCH₂ | NHOH | CH≡CCH₂ | Ph | H |
| 7-100 | CH₂NHCH₂ | NHOH | CH≡CCH₂ | Ph | H |
| 7-101 | CH₂O(CH₂)₂ | NHOH | CH≡CCH₂ | Ph | H |
| 7-102 | CH₂S(CH₂)₂ | NHOH | CH≡CCH₂ | Ph | H |
| 7-103 | CH₂NH(CH₂)₂ | NHOH | CH≡CCH₂ | Ph | H |
| 7-104 | CH₂N(CH₃)(CH₂) | NHOH | CH≡CCH₂ | Ph | H |
| 7-105 | CH₂ | NHOH | MeC≡CCH₂ | Ph | H |
| 7-106 | (CH₂)₂ | NHOH | MeC≡CCH₂ | Ph | H |
| 7-107 | (CH₂)₃ | NHOH | MeC≡CCH₂ | Ph | H |
| 7-108 | (CH₂)₄ | NHOH | MeC≡CCH₂ | Ph | H |
| 7-109 | CH(CH₃) | NHOH | MeC≡CCH₂ | Ph | H |
| 7-110 | CH(CH₃)CH₂ | NHOH | MeC≡CCH₂ | Ph | H |
| 7-111 | CH₂CH(CH₃) | NHOH | MeC≡CCH₂ | Ph | H |
| 7-112 | C(CH₃)₂CH₂ | NHOH | MeC≡CCH₂ | Ph | H |
| 7-113 | CH₂C(CH₃)₂ | NHOH | MeC≡CCH₂ | Ph | H |
| 7-114 | CH₂OCH₂ | NHOH | MeC≡CCH₂ | Ph | H |
| 7-115 | CH₂SCH₂ | NHOH | MeC≡CCH₂ | Ph | H |
| 7-116 | CH₂NHCH₂ | NHOH | MeC≡CCH₂ | Ph | H |
| 7-117 | CH₂O(CH₂)₂ | NHOH | MeC≡CCH₂ | Ph | H |
| 7-118 | CH₂S(CH₂)₂ | NHOH | MeC≡CCH₂ | Ph | H |
| 7-119 | CH₂NH(CH₂)₂ | NHOH | MeC≡CCH₂ | Ph | H |
| 7-120 | CH₂N(CH₃)(CH₂) | NHOH | MeC≡CCH₂ | Ph | H |
| 7-121 | CH₂ | NHOH | PhC≡CCH₂ | Ph | H |
| 7-122 | (CH₂)₂ | NHOH | PhC≡CCH₂ | Ph | H |
| 7-123 | (CH₂)₃ | NHOH | PhC≡CCH₂ | Ph | H |
| 7-124 | (CH₂)₄ | NHOH | PhC≡CCH₂ | Ph | H |

TABLE 7-continued

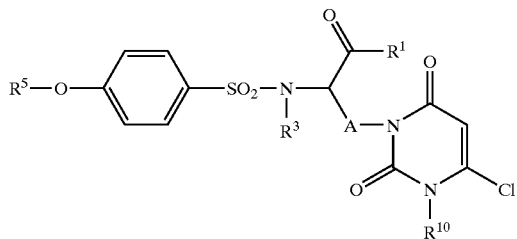

(I-7)

| Cpd. No. | A | $R^1$ | $R^3$ | $R^5$ | $R^{10}$ |
|---|---|---|---|---|---|
| 7-125 | CH(CH$_3$) | NHOH | PhC≡CCH$_2$ | Ph | H |
| 7-126 | CH(CH$_3$)CH$_2$ | NHOH | PhC≡CCH$_2$ | Ph | H |
| 7-127 | CH$_2$CH(CH$_3$) | NHOH | PhC≡CCH$_2$ | Ph | H |
| 7-128 | C(CH$_3$)$_2$CH$_2$ | NHOH | PhC≡CCH$_2$ | Ph | H |
| 7-129 | CH$_2$C(CH$_3$)$_2$ | NHOH | PhC≡CCH$_2$ | Ph | H |
| 7-130 | CH$_2$OCH$_2$ | NHOH | PhC≡CCH$_2$ | Ph | H |
| 7-131 | CH$_2$SCH$_2$ | NHOH | PhC≡CCH$_2$ | Ph | H |
| 7-132 | CH$_2$NHCH$_2$ | NHOH | PhC≡CCH$_2$ | Ph | H |
| 7-133 | CH$_2$O(CH$_2$)$_2$ | NHOH | PhC≡CCH$_2$ | Ph | H |
| 7-134 | CH$_2$S(CH$_2$)$_2$ | NHOH | PhC≡CCH$_2$ | Ph | H |
| 7-135 | CH$_2$NH(CH$_2$)$_2$ | NHOH | PhC≡CCH$_2$ | Ph | H |
| 7-136 | (CH$_2$)$_2$ | NHOH | (4-Cl—Ph)—C≡CCH$_2$ | Ph | H |
| 7-137 | CH$_2$ | NHOH | Bn | Ph | H |
| 7-138 | (CH$_2$)$_2$ | NHOH | Bn | Ph | H |
| 7-139 | (CH$_2$)$_3$ | NHOH | Bn | Ph | H |
| 7-140 | (CH$_2$)$_4$ | NHOH | Bn | Ph | H |
| 7-141 | CH(CH$_3$) | NHOH | Bn | Ph | H |
| 7-142 | CH(CH$_3$)CH$_2$ | NHOH | Bn | Ph | H |
| 7-143 | CH$_2$CH(CH$_3$) | NHOH | Bn | Ph | H |
| 7-144 | C(CH$_3$)$_2$CH$_2$ | NHOH | Bn | Ph | H |
| 7-145 | CH$_2$C(CH$_3$)$_2$ | NHOH | Bn | Ph | H |
| 7-146 | CH$_2$OCH$_2$ | NHOH | Bn | Ph | H |
| 7-147 | CH$_2$SCH$_2$ | NHOH | Bn | Ph | H |
| 7-148 | CH$_2$NHCH$_2$ | NHOH | Bn | Ph | H |
| 7-149 | CH$_2$O(CH$_2$)$_2$ | NHOH | Bn | Ph | H |
| 7-150 | CH$_2$S(CH$_2$)$_2$ | NHOH | Bn | Ph | H |
| 7-151 | CH$_2$NH(CH$_2$)$_2$ | NHOH | Bn | Ph | H |
| 7-152 | CH$_2$N(CH$_3$)(CH$_2$) | NHOH | Bn | Ph | H |
| 7-153 | CH$_2$ | NHOH | 3-(4-Cl—Ph)Pr | Ph | H |
| 7-154 | (CH$_2$)$_2$ | NHOH | 3-(4-Cl—Ph)Pr | Ph | H |
| 7-155 | (CH$_2$)$_3$ | NHOH | 3-(4-Cl—Ph)Pr | Ph | H |
| 7-156 | (CH$_2$)$_4$ | NHOH | 3-(4-Cl—Ph)Pr | Ph | H |
| 7-157 | CH(CH$_3$) | NHOH | 3-(4-Cl—Ph)Pr | Ph | H |
| 7-158 | CH(CH$_3$)CH$_2$ | NHOH | 3-(4-Cl—Ph)Pr | Ph | H |
| 7-159 | CH$_2$CH(CH$_3$) | NHOH | 3-(4-Cl—Ph)Pr | Ph | H |
| 7-160 | C(CH$_3$)$_2$CH$_2$ | NHOH | 3-(4-Cl—Ph)Pr | Ph | H |
| 7-161 | CH$_2$C(CH$_3$)$_2$ | NHOH | 3-(4-Cl—Ph)Pr | Ph | H |
| 7-162 | CH$_2$OCH$_2$ | NHOH | 3-(4-Cl—Ph)Pr | Ph | H |
| 7-163 | CH$_2$SCH$_2$ | NHOH | 3-(4-Cl—Ph)Pr | Ph | H |
| 7-164 | CH$_2$NHCH$_2$ | NHOH | 3-(4-Cl—Ph)Pr | Ph | H |
| 7-165 | CH$_2$O(CH$_2$)$_2$ | NHOH | 3-(4-Cl—Ph)Pr | Ph | H |
| 7-166 | CH$_2$S(CH$_2$)$_2$ | NHOH | 3-(4-Cl—Ph)Pr | Ph | H |
| 7-167 | CH$_2$NH(CH$_2$)$_2$ | NHOH | 3-(4-Cl—Ph)Pr | Ph | H |
| 7-168 | CH$_2$N(CH$_3$)(CH$_2$) | NHOH | 3-(4-Cl—Ph)Pr | Ph | H |
| 7-169 | (CH$_2$)$_2$ | OH | H | Me | H |
| 7-170 | (CH$_2$)$_2$ | OH | Me | Me | H |
| 7-171 | (CH$_2$)$_2$ | OH | (4-Cl—Ph)—C≡CCH$_2$ | Me | H |
| 7-172 | (CH$_2$)$_2$ | NHOH | H | CF$_3$ | H |
| 7-173 | (CH$_2$)$_2$ | OH | Me | CF$_3$ | H |
| 7-174 | (CH$_2$)$_2$ | OH | CH≡CCH$_2$ | CF$_3$ | H |
| 7-175 | (CH$_2$)$_2$ | OH | H | Bu | H |
| 7-176 | (CH$_2$)$_2$ | OH | Me | Bu | H |
| 7-177 | (CH$_2$)$_2$ | OH | CH≡CCH$_2$ | Bu | H |
| 7-178 | (CH$_2$)$_2$ | OH | H | Ph | H |
| 7-179 | (CH$_2$)$_2$ | OH | Me | Ph | H |
| 7-180 | (CH$_2$)$_2$ | OH | CH≡CCH$_2$ | Ph | H |
| 7-181 | (CH$_2$)$_2$ | NHOH | Me | 4-Cl—Ph | H |
| 7-182 | (CH$_2$)$_2$ | NHOH | Me | 4-F—Ph | H |
| 7-183 | (CH$_2$)$_2$ | NHOH | Me | 4-MeO—Ph | H |
| 7-184 | (CH$_2$)$_2$ | NHOH | Me | 2,4-diF—Ph | H |
| 7-185 | (CH$_2$)$_2$ | NHOH | H | 4-Py | H |
| 7-186 | (CH$_2$)$_2$ | NHOH | CH≡CCH$_2$ | 4-Cl—Ph | H |

TABLE 7-continued (I-7)

[Structure: R⁵—O—(phenyl)—SO₂—N(R³)—CH(A-)—C(=O)—R¹, where A connects to N of uracil ring with Cl at 6-position and R¹⁰ on other N]

| Cpd. No. | A | R¹ | R³ | R⁵ | R¹⁰ |
|---|---|---|---|---|---|
| 7-187 | (CH₂)₂ | NHOH | CH≡CCH₂ | 4-F—Ph | H |
| 7-188 | (CH₂)₂ | NHOH | CH≡CCH₂ | 4-MeO—Ph | H |
| 7-189 | (CH₂)₂ | NHOH | CH≡CCH₂ | 2,4-diF—Ph | H |
| 7-190 | (CH₂)₂ | NHOH | CH≡CCH₂ | 4-Py | H |
| 7-191 | (CH₂)₂ | OH | 3-Py—CH₂ | Me | H |
| 7-192 | (CH₂)₂ | OH | 3-(4-Cl—Ph)Pr | Me | H |
| 7-193 | (CH₂)₂ | NHOH | Et | 4-Py | H |
| 7-194 | (CH₂)₂ | NHOH | Me | 3-Cl—Ph | H |
| 7-195 | (CH₂)₂ | NHOH | Et | 3-Cl—Ph | H |
| 7-196 | (CH₂)₂ | NHOH | Me | 3-F—Ph | H |
| 7-197 | (CH₂)₂ | NHOH | Et | 3-F—Ph | H |
| 7-198 | (CH₂)₂ | NHOH | Me | 3,4-diCl—Ph | H |
| 7-199 | (CH₂)₂ | NHOH | Et | 3,4-diCl—Ph | H |
| 7-200 | (CH₂)₂ | NHOH | Me | 3,4-diF—Ph | H |
| 7-201 | (CH₂)₂ | NHOH | Et | 3,4-diF—Ph | H |
| 7-202 | (CH₂)₂ | NHOH | Me | 3-MeO—Ph | H |
| 7-203 | (CH₂)₂ | NHOH | Et | 3-MeO—Ph | H |
| 7-204 | (CH₂)₂ | NHOH | Me | 3-CN—Ph | H |
| 7-205 | (CH₂)₂ | NHOH | Et | 3-CN—Ph | H |
| 7-206 | (CH₂)₂ | NHOH | CHF₂ | Ph | H |
| 7-207 | (CH₂)₂ | NHOH | CF₃ | Ph | H |
| 7-208 | (CH₂)₂ | NHOH | c-Pr | Ph | H |
| 7-209 | (CH₂)₂ | NHOH | c-Pn | Ph | H |
| 7-210 | (CH₂)₂ | NHOH | c-Hx | Ph | H |
| 7-211 | C(CH₃)₂CH₂ | NHOH | Me | Ph | H |
| 7-212 | (CH₂)₂ | NHOH | Me | Ph | Me |
| 7-213 | (CH₂)₂ | NHOH | Me | Ph | Et |
| 7-214 | (CH₂)₂ | NHOH | Me | Ph | Pr |
| 7-215 | (CH₂)₂ | NHOH | Me | Ph | i-Pr |
| 7-216 | (CH₂)₂ | NHOH | Me | Ph | Bu |
| 7-217 | (CH₂)₂ | NHOH | Me | 3-Cl—Ph | Me |
| 7-218 | (CH₂)₂ | NHOH | Me | 3-F—Ph | Me |
| 7-219 | (CH₂)₂ | NHOH | Me | 4-Cl—Ph | Me |
| 7-220 | (CH₂)₂ | NHOH | Me | 4-F—Ph | Me |
| 7-221 | (CH₂)₂ | NHOH | Et | Ph | Me |
| 7-222 | (CH₂)₂ | OH | Me | Ph | Me |

TABLE 8

(I-8)

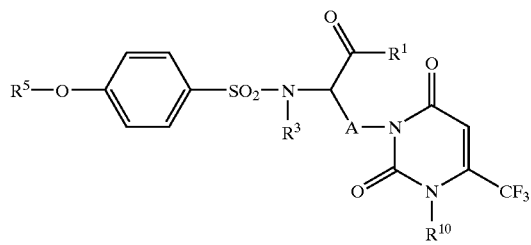

| Cpd. No. | A | R¹ | R³ | R⁵ | R¹⁰ |
|---|---|---|---|---|---|
| 8-1 | CH₂ | NHOH | H | Me | H |
| 8-2 | (CH₂)₂ | NHOH | H | Me | H |
| 8-3 | (CH₂)₃ | NHOH | H | Me | H |
| 8-4 | (CH₂)₄ | NHOH | H | Me | H |
| 8-5 | (CH₂)₂ | NHOH | (4-Cl—Ph)—C≡CCH₂ | Me | H |
| 8-6 | CH₂S(CH₂)₂ | NHOH | H | Me | H |

TABLE 8-continued (I-8)

| Cpd. No. | A | R¹ | R³ | R⁵ | R¹⁰ |
|---|---|---|---|---|---|
| 8-7 | (CH$_2$)$_2$ | NHOH | 3-(4-Cl—Ph)Pr | Me | H |
| 8-8 | (CH$_2$)$_2$ | NHOH | 3-Py—CH$_2$ | Me | H |
| 8-9 | CH$_2$ | NHOH | H | Ph | H |
| 8-10 | (CH$_2$)$_2$ | NHOH | H | Ph | H |
| 8-11 | (CH$_2$)$_3$ | NHOH | H | Ph | H |
| 8-12 | (CH$_2$)$_4$ | NHOH | H | Ph | H |
| 8-13 | CH(CH$_3$) | NHOH | H | Ph | H |
| 8-14 | CH(CH$_3$)CH$_2$ | NHOH | H | Ph | H |
| 8-15 | CH$_2$CH(CH$_3$) | NHOH | H | Ph | H |
| 8-16 | C(CH$_3$)$_2$CH$_2$ | NHOH | H | Ph | H |
| 8-17 | CH$_2$C(CH$_3$)$_2$ | NHOH | H | Ph | H |
| 8-18 | CH$_2$OCH$_2$ | NHOH | H | Ph | H |
| 8-19 | CH$_2$SCH$_2$ | NHOH | H | Ph | H |
| 8-20 | CH$_2$NHCH$_2$ | NHOH | H | Ph | H |
| 8-21 | CH$_2$O(CH$_2$)$_2$ | NHOH | H | Ph | H |
| 8-22 | CH$_2$S(CH$_2$)$_2$ | NHOH | H | Ph | H |
| 8-23 | CH$_2$NH(CH$_2$)$_2$ | NHOH | H | Ph | H |
| 8-24 | CH$_2$N(CH$_3$)(CH$_2$) | NHOH | H | Ph | H |
| 8-25 | CH$_2$ | NHOH | Me | Ph | H |
| 8-26 | (CH$_2$)$_2$ | NHOH | Me | 4-Py | H |
| 8-27 | (CH$_2$)$_3$ | NHOH | Me | Ph | H |
| 8-28 | (CH$_2$)$_4$ | NHOH | Me | Ph | H |
| 8-29 | CH(CH$_3$) | NHOH | Me | Ph | H |
| 8-30 | CH(CH$_3$)CH$_2$ | NHOH | Me | Ph | H |
| 8-31 | CH$_2$CH(CH$_3$) | NHOH | Me | Ph | H |
| 8-32 | C(CH$_3$)$_2$CH$_2$ | NHOH | Me | Ph | H |
| 8-33 | CH$_2$C(CH$_3$)$_2$ | NHOH | Me | Ph | H |
| 8-34 | CH$_2$OCH$_2$ | NHOH | Me | Ph | H |
| 8-35 | CH$_2$SCH$_2$ | NHOH | Me | Ph | H |
| 8-36 | CH$_2$NHCH$_2$ | NHOH | Me | Ph | H |
| 8-37 | CH$_2$O(CH$_2$)$_2$ | NHOH | Me | Ph | H |
| 8-38 | CH$_2$S(CH$_2$)$_2$ | NHOH | Me | Ph | H |
| 8-39 | CH$_2$NH(CH$_2$)$_2$ | NHOH | Me | Ph | H |
| 8-40 | CH$_2$N(CH$_3$)(CH$_2$) | NHOH | Me | Ph | H |
| 8-41 | CH$_2$ | NHOH | Et | Ph | H |
| 8-42 | (CH$_2$)$_2$ | NHOH | Et | Ph | H |
| 8-43 | (CH$_2$)$_3$ | NHOH | Et | Ph | H |
| 8-44 | (CH$_2$)$_4$ | NHOH | Et | Ph | H |
| 8-45 | CH(CH$_3$) | NHOH | Et | Ph | H |
| 8-46 | CH(CH$_3$)CH$_2$ | NHOH | Et | Ph | H |
| 8-47 | CH$_2$CH(CH$_3$) | NHOH | Et | Ph | H |
| 8-48 | C(CH$_3$)$_2$CH$_2$ | NHOH | Et | Ph | H |
| 8-49 | CH$_2$C(CH$_3$)$_2$ | NHOH | Et | Ph | H |
| 8-50 | CH$_2$OCH$_2$ | NHOH | Et | Ph | H |
| 8-51 | CH$_2$SCH$_2$ | NHOH | Et | Ph | H |
| 8-52 | CH$_2$NHCH$_2$ | NHOH | Et | Ph | H |
| 8-53 | CH$_2$O(CH$_2$)$_2$ | NHOH | Et | Ph | H |
| 8-54 | CH$_2$S(CH$_2$)$_2$ | NHOH | Et | Ph | H |
| 8-55 | CH$_2$NH(CH$_2$)$_2$ | NHOH | Et | Ph | H |
| 8-56 | CH$_2$N(CH$_3$)(CH$_2$) | NHOH | Et | Ph | H |
| 8-57 | CH$_2$ | NHOH | Pr | Ph | H |
| 8-58 | (CH$_2$)$_2$ | NHOH | Pr | Ph | H |
| 8-59 | (CH$_2$)$_3$ | NHOH | Pr | Ph | H |
| 8-60 | (CH$_2$)$_4$ | NHOH | Pr | Ph | H |
| 8-61 | CH(CH$_3$) | NHOH | Pr | Ph | H |
| 8-62 | CH(CH$_3$)CH$_2$ | NHOH | Pr | Ph | H |
| 8-63 | CH$_2$CH(CH$_3$) | NHOH | Pr | Ph | H |
| 8-64 | C(CH$_3$)$_2$CH$_2$ | NHOH | Pr | Ph | H |
| 8-65 | CH$_2$C(CH$_3$)$_2$ | NHOH | Pr | Ph | H |
| 8-66 | CH$_2$OCH$_2$ | NHOH | Pr | Ph | H |
| 8-67 | CH$_2$SCH$_2$ | NHOH | Pr | Ph | H |
| 8-68 | CH$_2$NHCH$_2$ | NHOH | Pr | Ph | H |
| 8-69 | CH$_2$ | NHOH | i-Pr | Ph | H |

TABLE 8-continued (I-8)

$$R^5-O-C_6H_4-SO_2-N(R^3)-CH(A-N\text{-pyrimidine})-C(=O)-R^1$$

where the pyrimidine ring has 2,4-dioxo, 6-CF$_3$, and N-R$^{10}$ substituents.

| Cpd. No. | A | R$^1$ | R$^3$ | R$^5$ | R$^{10}$ |
|---|---|---|---|---|---|
| 8-70 | (CH$_2$)$_2$ | NHOH | i-Pr | Ph | H |
| 8-71 | (CH$_2$)$_3$ | NHOH | i-Pr | Ph | H |
| 8-72 | (CH$_2$)$_4$ | NHOH | i-Pr | Ph | H |
| 8-73 | CH$_2$ | NHOH | CH$_2$=CHCH$_2$ | Ph | H |
| 8-74 | (CH$_2$)$_2$ | NHOH | CH$_2$=CHCH$_2$ | Ph | H |
| 8-75 | (CH$_2$)$_3$ | NHOH | CH$_2$=CHCH$_2$ | Ph | H |
| 8-76 | (CH$_2$)$_4$ | NHOH | CH$_2$=CHCH$_2$ | Ph | H |
| 8-77 | CH(CH$_3$) | NHOH | CH$_2$=CHCH$_2$ | Ph | H |
| 8-78 | CH(CH$_3$)CH$_2$ | NHOH | CH$_2$=CHCH$_2$ | Ph | H |
| 8-79 | CH$_2$CH(CH$_3$) | NHOH | CH$_2$=CHCH$_2$ | Ph | H |
| 8-80 | C(CH$_3$)$_2$CH$_2$ | NHOH | CH$_2$=CHCH$_2$ | Ph | H |
| 8-81 | CH$_2$C(CH$_3$)$_2$ | NHOH | CH$_2$=CHCH$_2$ | Ph | H |
| 8-82 | CH$_2$OCH$_2$ | NHOH | CH$_2$=CHCH$_2$ | Ph | H |
| 8-83 | CH$_2$SCH$_2$ | NHOH | CH$_2$=CHCH$_2$ | Ph | H |
| 8-84 | CH$_2$NHCH$_2$ | NHOH | CH$_2$=CHCH$_2$ | Ph | H |
| 8-85 | CH$_2$O(CH$_2$)$_2$ | NHOH | CH$_2$=CHCH$_2$ | Ph | H |
| 8-86 | CH$_2$S(CH$_2$)$_2$ | NHOH | CH$_2$=CHCH$_2$ | Ph | H |
| 8-87 | CH$_2$NH(CH$_2$)$_2$ | NHOH | CH$_2$=CHCH$_2$ | Ph | H |
| 8-88 | CH$_2$N(CH$_3$)(CH$_2$) | NHOH | CH$_2$=CHCH$_2$ | Ph | H |
| 8-89 | CH$_2$ | NHOH | CH≡CCH$_2$ | Ph | H |
| 8-90 | (CH$_2$)$_2$ | NHOH | CH≡CCH$_2$ | Ph | H |
| 8-91 | (CH$_2$)$_3$ | NHOH | CH≡CCH$_2$ | Ph | H |
| 8-92 | (CH$_2$)$_4$ | NHOH | CH≡CCH$_2$ | Ph | H |
| 8-93 | CH(CH$_3$) | NHOH | CH≡CCH$_2$ | Ph | H |
| 8-94 | CH(CH$_3$)CH$_2$ | NHOH | CH≡CCH$_2$ | Ph | H |
| 8-95 | CH$_2$CH(CH$_3$) | NHOH | CH≡CCH$_2$ | Ph | H |
| 8-96 | C(CH$_3$)$_2$CH$_2$ | NHOH | CH≡CCH$_2$ | Ph | H |
| 8-97 | CH$_2$C(CH$_3$)$_2$ | NHOH | CH≡CCH$_2$ | Ph | H |
| 8-98 | CH$_2$OCH$_2$ | NHOH | CH≡CCH$_2$ | Ph | H |
| 8-99 | CH$_2$SCH$_2$ | NHOH | CH≡CCH$_2$ | Ph | H |
| 8-100 | CH$_2$NHCH$_2$ | NHOH | CH≡CCH$_2$ | Ph | H |
| 8-101 | CH$_2$O(CH$_2$)$_2$ | NHOH | CH≡CCH$_2$ | Ph | H |
| 8-102 | CH$_2$S(CH$_2$)$_2$ | NHOH | CH≡CCH$_2$ | Ph | H |
| 8-103 | CH$_2$NH(CH$_2$)$_2$ | NHOH | CH≡CCH$_2$ | Ph | H |
| 8-104 | CH$_2$N(CH$_3$)(CH$_2$) | NHOH | CH≡CCH$_2$ | Ph | H |
| 8-105 | CH$_2$ | NHOH | MeC≡CCH$_2$ | Ph | H |
| 8-106 | (CH$_2$)$_2$ | NHOH | MeC≡CCH$_2$ | Ph | H |
| 8-107 | (CH$_2$)$_3$ | NHOH | MeC≡CCH$_2$ | Ph | H |
| 8-108 | (CH$_2$)$_4$ | NHOH | MeC≡CCH$_2$ | Ph | H |
| 8-109 | CH(CH$_3$) | NHOH | MeC≡CCH$_2$ | Ph | H |
| 8-110 | CH(CH$_3$)CH$_2$ | NHOH | MeC≡CCH$_2$ | Ph | H |
| 8-111 | CH$_2$CH(CH$_3$) | NHOH | MeC≡CCH$_2$ | Ph | H |
| 8-112 | C(CH$_3$)$_2$CH$_2$ | NHOH | MeC≡CCH$_2$ | Ph | H |
| 8-113 | CH$_2$C(CH$_3$)$_2$ | NHOH | MeC≡CCH$_2$ | Ph | H |
| 8-114 | CH$_2$OCH$_2$ | NHOH | MeC≡CCH$_2$ | Ph | H |
| 8-115 | CH$_2$SCH$_2$ | NHOH | MeC≡CCH$_2$ | Ph | H |
| 8-116 | CH$_2$NHCH$_2$ | NHOH | MeC≡CCH$_2$ | Ph | H |
| 8-117 | CH$_2$O(CH$_2$)$_2$ | NHOH | MeC≡CCH$_2$ | Ph | H |
| 8-118 | CH$_2$S(CH$_2$)$_2$ | NHOH | MeC≡CCH$_2$ | Ph | H |
| 8-119 | CH$_2$NH(CH$_2$)$_2$ | NHOH | MeC≡CCH$_2$ | Ph | H |
| 8-120 | CH$_2$N(CH$_3$)(CH$_2$) | NHOH | MeC≡CCH$_2$ | Ph | H |
| 8-121 | CH$_2$ | NHOH | PhC≡CCH$_2$ | Ph | H |
| 8-122 | (CH$_2$)$_2$ | NHOH | PhC≡CCH$_2$ | Ph | H |
| 8-123 | (CH$_2$)$_3$ | NHOH | PhC≡CCH$_2$ | Ph | H |
| 8-124 | (CH$_2$)$_4$ | NHOH | PhC≡CCH$_2$ | Ph | H |
| 8-125 | CH(CH$_3$) | NHOH | PhC≡CCH$_2$ | Ph | H |
| 8-126 | CH(CH$_3$)CH$_2$ | NHOH | PhC≡CCH$_2$ | Ph | H |
| 8-127 | CH$_2$CH(CH$_3$) | NHOH | PhC≡CCH$_2$ | Ph | H |
| 8-128 | C(CH$_3$)$_2$CH$_2$ | NHOH | PhC≡CCH$_2$ | Ph | H |
| 8-129 | CH$_2$C(CH$_3$)$_2$ | NHOH | PhC≡CCH$_2$ | Ph | H |
| 8-130 | CH$_2$OCH$_2$ | NHOH | PhC≡CCH$_2$ | Ph | H |
| 8-131 | CH$_2$SCH$_2$ | NHOH | PhC≡CCH$_2$ | Ph | H |
| 8-132 | CH$_2$NHCH$_2$ | NHOH | PhC≡CCH$_2$ | Ph | H |

TABLE 8-continued (I-8)

$$R^5-O-C_6H_4-SO_2-N(R^3)-CH(A-N\text{-pyrimidinedione-}CF_3,R^{10})-C(=O)-R^1$$

| Cpd. No. | A | $R^1$ | $R^3$ | $R^5$ | $R^{10}$ |
|---|---|---|---|---|---|
| 8-133 | $CH_2O(CH_2)_2$ | NHOH | $PhC\equiv CCH_2$ | Ph | H |
| 8-134 | $CH_2S(CH_2)_2$ | NHOH | $PhC\equiv CCH_2$ | Ph | H |
| 8-135 | $CH_2NH(CH_2)_2$ | NHOH | $PhC\equiv CCH_2$ | Ph | H |
| 8-136 | $(CH_2)_2$ | NHOH | $(4\text{-Cl}-Ph)-C\equiv CCH_2$ | Ph | H |
| 8-137 | $CH_2$ | NHOH | Bn | Ph | H |
| 8-138 | $(CH_2)_2$ | NHOH | Bn | Ph | H |
| 8-139 | $(CH_2)_3$ | NHOH | Bn | Ph | H |
| 8-140 | $(CH_2)_4$ | NHOH | Bn | Ph | H |
| 8-141 | $CH(CH_3)$ | NHOH | Bn | Ph | H |
| 8-142 | $CH(CH_3)CH_2$ | NHOH | Bn | Ph | H |
| 8-143 | $CH_2CH(CH_3)$ | NHOH | Bn | Ph | H |
| 8-144 | $C(CH_3)_2CH_2$ | NHOH | Bn | Ph | H |
| 8-145 | $CH_2C(CH_3)_2$ | NHOH | Bn | Ph | H |
| 8-146 | $CH_2OCH_2$ | NHOH | Bn | Ph | H |
| 8-147 | $CH_2SCH_2$ | NHOH | Bn | Ph | H |
| 8-148 | $CH_2NHCH_2$ | NHOH | Bn | Ph | H |
| 8-149 | $CH_2O(CH_2)_2$ | NHOH | Bn | Ph | H |
| 8-150 | $CH_2S(CH_2)_2$ | NHOH | Bn | Ph | H |
| 8-151 | $CH_2NH(CH_2)_2$ | NHOH | Bn | Ph | H |
| 8-152 | $CH_2N(CH_3)(CH_2)$ | NHOH | Bn | Ph | H |
| 8-153 | $CH_2$ | NHOH | 3-(4-Cl—Ph)Pr | Ph | H |
| 8-154 | $(CH_2)_2$ | NHOH | 3-(4-Cl—Ph)Pr | Ph | H |
| 8-155 | $(CH_2)_3$ | NHOH | 3-(4-Cl—Ph)Pr | Ph | H |
| 8-156 | $(CH_2)_4$ | NHOH | 3-(4-Cl—Ph)Pr | Ph | H |
| 8-157 | $CH(CH_3)$ | NHOH | 3-(4-Cl—Ph)Pr | Ph | H |
| 8-158 | $CH(CH_3)CH_2$ | NHOH | 3-(4-Cl—Ph)Pr | Ph | H |
| 8-159 | $CH_2CH(CH_3)$ | NHOH | 3-(4-Cl—Ph)Pr | Ph | H |
| 8-160 | $C(CH_3)_2CH_2$ | NHOH | 3-(4-Cl—Ph)Pr | Ph | H |
| 8-161 | $CH_2C(CH_3)_2$ | NHOH | 3-(4-Cl—Ph)Pr | Ph | H |
| 8-162 | $CH_2OCH_2$ | NHOH | 3-(4-Cl—Ph)Pr | Ph | H |
| 8-163 | $CH_2SCH_2$ | NHOH | 3-(4-Cl—Ph)Pr | Ph | H |
| 8-164 | $CH_2NHCH_2$ | NHOH | 3-(4-Cl—Ph)Pr | Ph | H |
| 8-165 | $CH_2O(CH_2)_2$ | NHOH | 3-(4-Cl—Ph)Pr | Ph | H |
| 8-166 | $CH_2S(CH_2)_2$ | NHOH | 3-(4-Cl—Ph)Pr | Ph | H |
| 8-167 | $CH_2NH(CH_2)_2$ | NHOH | 3-(4-Cl—Ph)Pr | Ph | H |
| 8-168 | $CH_2N(CH_3)(CH_2)$ | NHOH | 3-(4-Cl—Ph)Pr | Ph | H |
| 8-169 | $(CH_2)_2$ | OH | H | Me | H |
| 8-170 | $(CH_2)_2$ | OH | Me | Me | H |
| 8-171 | $(CH_2)_2$ | OH | $(4\text{-Cl}-Ph)-C\equiv CCH_2$ | Me | H |
| 8-172 | $(CH_2)_2$ | NHOH | H | $CF_3$ | H |
| 8-173 | $(CH_2)_2$ | OH | Me | $CF_3$ | H |
| 8-174 | $(CH_2)_2$ | OH | $CH\equiv CCH_2$ | $CF_3$ | H |
| 8-175 | $(CH_2)_2$ | OH | H | Bu | H |
| 8-176 | $(CH_2)_2$ | OH | Me | Bu | H |
| 8-177 | $(CH_2)_2$ | OH | $CH\equiv CCH_2$ | Bu | H |
| 8-178 | $(CH_2)_2$ | OH | H | Ph | H |
| 8-179 | $(CH_2)_2$ | OH | Me | Ph | H |
| 8-180 | $(CH_2)_2$ | OH | $CH\equiv CCH_2$ | Ph | H |
| 8-181 | $(CH_2)_2$ | NHOH | Me | 4-Cl—Ph | H |
| 8-182 | $(CH_2)_2$ | NHOH | Me | 4-F—Ph | H |
| 8-183 | $(CH_2)_2$ | NHOH | Me | 4-MeO—Ph | H |
| 8-184 | $(CH_2)_2$ | NHOH | Me | 2,4-diF—Ph | H |
| 8-185 | $(CH_2)_2$ | NHOH | H | 4-Py | H |
| 8-186 | $(CH_2)_2$ | NHOH | $CH\equiv CCH_2$ | 4-Cl—Ph | H |
| 8-187 | $(CH_2)_2$ | NHOH | $CH\equiv CCH_2$ | 4-F—Ph | H |
| 8-188 | $(CH_2)_2$ | NHOH | $CH\equiv CCH_2$ | 4-MeO—Ph | H |
| 8-189 | $(CH_2)_2$ | NHOH | $CH\equiv CCH_2$ | 2,4-diF—Ph | H |
| 8-190 | $(CH_2)_2$ | NHOH | $CH\equiv CCH_2$ | 4-Py | H |
| 8-191 | $(CH_2)_2$ | OH | 3-Py—$CH_2$ | Me | H |
| 8-192 | $(CH_2)_2$ | OH | 3-(4-Cl—Ph)Pr | Me | H |
| 8-193 | $(CH_2)_2$ | NHOH | Et | 4-Py | H |
| 8-194 | $(CH_2)_2$ | NHOH | Me | 3-Cl—Ph | H |
| 8-195 | $(CH_2)_2$ | NHOH | Et | 3-Cl—Ph | H |

TABLE 8-continued

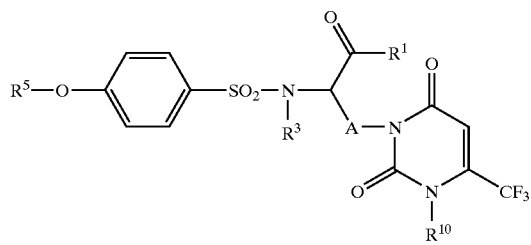

(I-8)

| Cpd. No. | A | R¹ | R³ | R⁵ | R¹⁰ |
|---|---|---|---|---|---|
| 8-196 | (CH₂)₂ | NHOH | Me | 3-F—Ph | H |
| 8-197 | (CH₂)₂ | NHOH | Et | 3-F—Ph | H |
| 8-198 | (CH₂)₂ | NHOH | Me | 3,4-diCl—Ph | H |
| 8-199 | (CH₂)₂ | NHOH | Et | 3,4-diCl—Ph | H |
| 8-200 | (CH₂)₂ | NHOH | Me | 3,4-diF—Ph | H |
| 8-201 | (CH₂)₂ | NHOH | Et | 3,4-diF—Ph | H |
| 8-202 | (CH₂)₂ | NHOH | Me | 3-MeO—Ph | H |
| 8-203 | (CH₂)₂ | NHOH | Et | 3-MeO—Ph | H |
| 8-204 | (CH₂)₂ | NHOH | Me | 3-CN—Ph | H |
| 8-205 | (CH₂)₂ | NHOH | Et | 3-CN—Ph | H |
| 8-206 | (CH₂)₂ | NHOH | CHF₂ | Ph | H |
| 8-207 | (CH₂)₂ | NHOH | CH₃ | Ph | H |
| 8-208 | (CH₂)₂ | NHOH | c-Pr | Ph | H |
| 8-209 | (CH₂)₂ | NHOH | c-Pn | Ph | H |
| 8-210 | (CH₂)₂ | NHOH | c-Hx | Ph | H |
| 8-211 | C(CH₃)₂CH₂ | NHOH | Me | Ph | H |
| 8-212 | (CH₂)₂ | NHOH | Me | Ph | Me |
| 8-213 | (CH₂)₂ | NHOH | Me | Ph | Et |
| 8-214 | (CH₂)₂ | NHOH | Me | Ph | Pr |
| 8-215 | (CH₂)₂ | NHOH | Me | Ph | i-Pr |
| 8-216 | (CH₂)₂ | NHOH | Me | Ph | Bu |
| 8-217 | (CH₂)₂ | NHOH | Me | 3-Cl—Ph | Me |
| 8-218 | (CH₂)₂ | NHOH | Me | 3-F—Ph | Me |
| 8-219 | (CH₂)₂ | NHOH | Me | 4-Cl—Ph | Me |
| 8-220 | (CH₂)₂ | NHOH | Me | 4-F—Ph | Me |
| 8-221 | (CH₂)₂ | NHOH | Et | Ph | Me |

TABLE 9

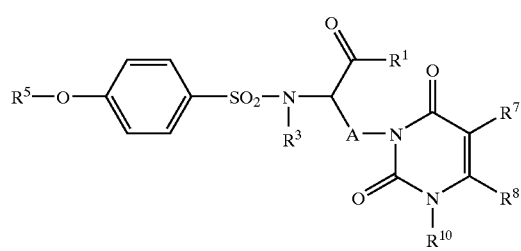

(I-9)

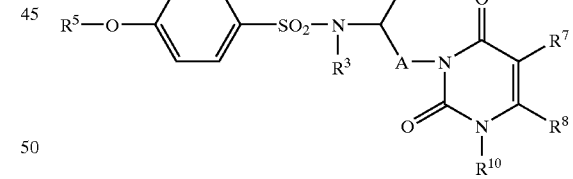

(I-9)

| Cpd. No. | A | R¹ | R³ | R⁵ | R⁷ | R⁸ | R¹⁰ | Cpd. No. | A | R¹ | R³ | R⁵ | R⁷ | R⁸ | R¹⁰ |
|---|---|---|---|---|---|---|---|---|---|---|---|---|---|---|---|
| 9-1 | (CH₂)₂ | NHOH | Me | Ph | H | NO₂ | H | 9-16 | (CH₂)₂ | NHOH | Me | Ph | Cl | CF₃ | H |
| 9-2 | (CH₂)₂ | NHOH | Me | Ph | H | CN | H | 9-17 | (CH₂)₂ | NHOH | Me | Ph | Me | F | H |
| 9-3 | (CH₂)₂ | NHOH | Me | Ph | H | CHF₂ | H | 9-18 | (CH₂)₂ | NHOH | Me | Ph | Me | Cl | H |
| 9-4 | (CH₂)₂ | NHOH | Me | Ph | H | SMe | H | 9-19 | (CH₂)₂ | NHOH | Me | Ph | Me | CF₃ | H |
| 9-5 | (CH₂)₂ | NHOH | Me | Ph | H | S(O)Me | H | 9-20 | (CH₂)₂ | NHOH | Me | 4-F—Ph | H | NO₂ | H |
| 9-6 | (CH₂)₂ | NHOH | Me | Ph | H | SO₂Me | H | 9-21 | (CH₂)₂ | NHOH | Me | 4-F—Ph | H | CN | H |
| 9-7 | (CH₂)₂ | NHOH | Me | Ph | H | OCF₃ | H | 9-22 | (CH₂)₂ | NHOH | Me | 4-F—Ph | H | CHF₂ | H |
| 9-8 | (CH₂)₂ | NHOH | Me | Ph | H | OCHF₂ | H | 9-23 | (CH₂)₂ | NHOH | Me | 4-F—Ph | H | SMe | H |
| 9-9 | (CH₂)₂ | NHOH | Me | Ph | H | F | H | 9-24 | (CH₂)₂ | NHOH | Me | 4-F—Ph | H | S(O)Me | H |
| 9-10 | (CH₂)₂ | NHOH | Me | Ph | H | CO₂Et | H | 9-25 | (CH₂)₂ | NHOH | Me | 4-F—Ph | H | SO₂Me | H |
| 9-11 | (CH₂)₂ | NHOH | Me | Ph | F | F | H | 9-26 | (CH₂)₂ | NHOH | Me | 4-F—Ph | H | OCF₃ | H |
| 9-12 | (CH₂)₂ | NHOH | Me | Ph | F | Cl | H | 9-27 | (CH₂)₂ | NHOH | Me | 4-F—Ph | H | OCHF₂ | H |
| 9-13 | (CH₂)₂ | NHOH | Me | Ph | F | CF₃ | H | 9-28 | (CH₂)₂ | NHOH | Me | 4-F—Ph | H | F | H |
| 9-14 | (CH₂)₂ | NHOH | Me | Ph | Cl | F | H | 9-29 | (CH₂)₂ | NHOH | Me | 4-F—Ph | H | CO₂Et | H |
| 9-15 | (CH₂)₂ | NHOH | Me | Ph | Cl | Cl | H | 9-30 | (CH₂)₂ | NHOH | Me | 4-F—Ph | F | F | H |

TABLE 9-continued (I-9)

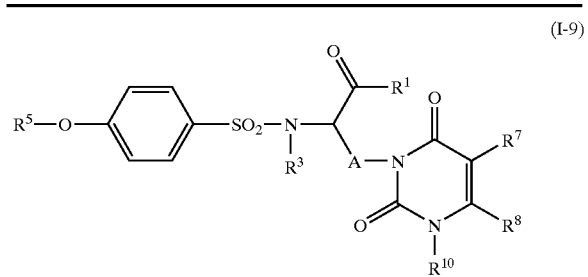

| Cpd. No. | A | $R^1$ | $R^3$ | $R^5$ | $R^7$ | $R^8$ | $R^{10}$ |
|---|---|---|---|---|---|---|---|
| 9-31 | $(CH_2)_2$ | NHOH | Me | 4-F—Ph | F | Cl | H |
| 9-32 | $(CH_2)_2$ | NHOH | Me | 4-F—Ph | F | $CF_3$ | H |
| 9-33 | $(CH_2)_2$ | NHOH | Me | 4-F—Ph | Cl | F | H |
| 9-34 | $(CH_2)_2$ | NHOH | Me | 4-F—Ph | Cl | Cl | H |
| 9-35 | $(CH_2)_2$ | NHOH | Me | 4-F—Ph | Cl | $CF_3$ | H |
| 9-36 | $(CH_2)_2$ | NHOH | Me | 4-F—Ph | Me | F | H |
| 9-37 | $(CH_2)_2$ | NHOH | Me | 4-F—Ph | Me | Cl | H |
| 9-38 | $(CH_2)_2$ | NHOH | Me | 4-F—Ph | Me | $CF_3$ | H |
| 9-39 | $(CH_2)_2$ | NHOH | Me | 4-Cl—Ph | H | $NO_2$ | H |
| 9-40 | $(CH_2)_2$ | NHOH | Me | 4-Cl—Ph | H | CN | H |
| 9-41 | $(CH_2)_2$ | NHOH | Me | 4-Cl—Ph | H | $CHF_2$ | H |
| 9-42 | $(CH_2)_2$ | NHOH | Me | 4-Cl—Ph | H | SMe | H |
| 9-43 | $(CH_2)_2$ | NHOH | Me | 4-Cl—Ph | H | S(O)Me | H |
| 9-44 | $(CH_2)_2$ | NHOH | Me | 4-Cl—Ph | H | $SO_2Me$ | H |
| 9-45 | $(CH_2)_2$ | NHOH | Me | 4-Cl—Ph | H | $OCF_3$ | H |
| 9-46 | $(CH_2)_2$ | NHOH | Me | 4-Cl—Ph | H | $OCHF_2$ | H |
| 9-47 | $(CH_2)_2$ | NHOH | Me | 4-Cl—Ph | H | F | H |
| 9-48 | $(CH_2)_2$ | NHOH | Me | 4-Cl—Ph | H | $CO_2Et$ | H |
| 9-49 | $(CH_2)_2$ | NHOH | Me | 4-Cl—Ph | F | F | H |
| 9-50 | $(CH_2)_2$ | NHOH | Me | 4-Cl—Ph | F | Cl | H |
| 9-51 | $(CH_2)_2$ | NHOH | Me | 4-Cl—Ph | F | $CF_3$ | H |
| 9-52 | $(CH_2)_2$ | NHOH | Me | 4-Cl—Ph | Cl | F | H |
| 9-53 | $(CH_2)_2$ | NHOH | Me | 4-Cl—Ph | Cl | Cl | H |
| 9-54 | $(CH_2)_2$ | NHOH | Me | 4-Cl—Ph | Cl | $CF_3$ | H |
| 9-55 | $(CH_2)_2$ | NHOH | Me | 4-Cl—Ph | Me | F | H |
| 9-56 | $(CH_2)_2$ | NHOH | Me | 4-Cl—Ph | Me | Cl | H |
| 9-57 | $(CH_2)_2$ | NHOH | Me | 4-Cl—Ph | Me | $CF_3$ | H |
| 9-58 | $(CH_2)_2$ | NHOH | Me | 3-F—Ph | H | $NO_2$ | H |
| 9-59 | $(CH_2)_2$ | NHOH | Me | 3-F—Ph | H | CN | H |
| 9-60 | $(CH_2)_2$ | NHOH | Me | 3-F—Ph | H | $CHF_2$ | H |
| 9-61 | $(CH_2)_2$ | NHOH | Me | 3-F—Ph | H | SMe | H |
| 9-62 | $(CH_2)_2$ | NHOH | Me | 3-F—Ph | H | S(O)Me | H |
| 9-63 | $(CH_2)_2$ | NHOH | Me | 3-F—Ph | H | $SO_2Me$ | H |
| 9-64 | $(CH_2)_2$ | NHOH | Me | 3-F—Ph | H | $OCF_3$ | H |
| 9-65 | $(CH_2)_2$ | NHOH | Me | 3-F—Ph | H | $OCHF_2$ | H |
| 9-66 | $(CH_2)_2$ | NHOH | Me | 3-F—Ph | H | F | H |
| 9-67 | $(CH_2)_2$ | NHOH | Me | 3-F—Ph | H | $CO_2Et$ | H |
| 9-68 | $(CH_2)_2$ | NHOH | Me | 3-F—Ph | F | F | H |
| 9-69 | $(CH_2)_2$ | NHOH | Me | 3-F—Ph | F | Cl | H |
| 9-70 | $(CH_2)_2$ | NHOH | Me | 3-F—Ph | F | $CF_3$ | H |
| 9-71 | $(CH_2)_2$ | NHOH | Me | 3-F—Ph | Cl | F | H |
| 9-72 | $(CH_2)_2$ | NHOH | Me | 3-F—Ph | Cl | Cl | H |
| 9-73 | $(CH_2)_2$ | NHOH | Me | 3-F—Ph | Cl | $CF_3$ | H |
| 9-74 | $(CH_2)_2$ | NHOH | Me | 3-F—Ph | Me | F | H |
| 9-75 | $(CH_2)_2$ | NHOH | Me | 3-F—Ph | Me | Cl | H |
| 9-76 | $(CH_2)_2$ | NHOH | Me | 3-F—Ph | Me | $CF_3$ | H |
| 9-77 | $(CH_2)_2$ | NHOH | Me | 3-Cl—Ph | H | $NO_2$ | H |
| 9-78 | $(CH_2)_2$ | NHOH | Me | 3-Cl—Ph | H | CN | H |
| 9-79 | $(CH_2)_2$ | NHOH | Me | 3-Cl—Ph | H | $CHF_2$ | H |
| 9-80 | $(CH_2)_2$ | NHOH | Me | 3-Cl—Ph | H | SMe | H |
| 9-81 | $(CH_2)_2$ | NHOH | Me | 3-Cl—Ph | H | S(O)Me | H |
| 9-82 | $(CH_2)_2$ | NHOH | Me | 3-Cl—Ph | H | $SO_2Me$ | H |
| 9-83 | $(CH_2)_2$ | NHOH | Me | 3-Cl—Ph | H | $OCF_3$ | H |
| 9-84 | $(CH_2)_2$ | NHOH | Me | 3-Cl—Ph | H | $OCHF_2$ | H |
| 9-85 | $(CH_2)_2$ | NHOH | Me | 3-Cl—Ph | H | F | H |
| 9-86 | $(CH_2)_2$ | NHOH | Me | 3-Cl—Ph | H | $CO_2Et$ | H |
| 9-87 | $(CH_2)_2$ | NHOH | Me | 3-Cl—Ph | F | F | H |
| 9-88 | $(CH_2)_2$ | NHOH | Me | 3-Cl—Ph | F | Cl | H |
| 9-89 | $(CH_2)_2$ | NHOH | Me | 3-Cl—Ph | F | $CF_3$ | H |
| 9-90 | $(CH_2)_2$ | NHOH | Me | 3-Cl—Ph | Cl | F | H |
| 9-91 | $(CH_2)_2$ | NHOH | Me | 3-Cl—Ph | Cl | Cl | H |
| 9-92 | $(CH_2)_2$ | NHOH | Me | 3-Cl—Ph | Cl | $CF_3$ | H |
| 9-93 | $(CH_2)_2$ | NHOH | Me | 3-Cl—Ph | Me | F | H |
| 9-94 | $(CH_2)_2$ | NHOH | Me | 3-Cl—Ph | Me | Cl | H |
| 9-95 | $(CH_2)_2$ | NHOH | Me | 3-Cl—Ph | Me | $CF_3$ | H |
| 9-96 | $(CH_2)_2$ | NHOH | Me | 4-Py | H | $NO_2$ | H |
| 9-97 | $(CH_2)_2$ | NHOH | Me | 4-Py | H | CN | H |
| 9-98 | $(CH_2)_2$ | NHOH | Me | 4-Py | H | $CHF_2$ | H |
| 9-99 | $(CH_2)_2$ | NHOH | Me | 4-Py | H | SMe | H |
| 9-100 | $(CH_2)_2$ | NHOH | Me | 4-Py | H | S(O)Me | H |
| 9-101 | $(CH_2)_2$ | NHOH | Me | 4-Py | H | $SO_2Me$ | H |
| 9-102 | $(CH_2)_2$ | NHOH | Me | 4-Py | H | $OCF_3$ | H |
| 9-103 | $(CH_2)_2$ | NHOH | Me | 4-Py | H | $OCHF_2$ | H |
| 9-104 | $(CH_2)_2$ | NHOH | Me | 4-Py | H | F | H |
| 9-105 | $(CH_2)_2$ | NHOH | Me | 4-Py | H | $CO_2Et$ | H |
| 9-106 | $(CH_2)_2$ | NHOH | Me | 4-Py | F | F | H |
| 9-107 | $(CH_2)_2$ | NHOH | Me | 4-Py | F | Cl | H |
| 9-108 | $(CH_2)_2$ | NHOH | Me | 4-Py | F | $CF_3$ | H |
| 9-109 | $(CH_2)_2$ | NHOH | Me | 4-Py | Cl | F | H |
| 9-110 | $(CH_2)_2$ | NHOH | Me | 4-Py | Cl | Cl | H |
| 9-111 | $(CH_2)_2$ | NHOH | Me | 4-Py | Cl | $CF_3$ | H |
| 9-112 | $(CH_2)_2$ | NHOH | Me | 4-Py | Me | F | H |
| 9-113 | $(CH_2)_2$ | NHOH | Me | 4-Py | Me | Cl | H |
| 9-114 | $(CH_2)_2$ | NHOH | Me | 4-Py | Me | $CF_3$ | H |
| 9-115 | $(CH_2)_2$ | NHOH | Et | Ph | H | $NO_2$ | H |
| 9-116 | $(CH_2)_2$ | NHOH | Et | Ph | H | CN | H |
| 9-117 | $(CH_2)_2$ | NHOH | Et | Ph | H | $CHF_2$ | H |
| 9-118 | $(CH_2)_2$ | NHOH | Et | Ph | H | SMe | H |
| 9-119 | $(CH_2)_2$ | NHOH | Et | Ph | H | S(O)Me | H |
| 9-120 | $(CH_2)_2$ | NHOH | Et | Ph | H | $SO_2Me$ | H |
| 9-121 | $(CH_2)_2$ | NHOH | Et | Ph | H | $OCF_3$ | H |
| 9-122 | $(CH_2)_2$ | NHOH | Et | Ph | H | $OCHF_2$ | H |
| 9-123 | $(CH_2)_2$ | NHOH | Et | Ph | H | F | H |
| 9-124 | $(CH_2)_2$ | NHOH | Et | Ph | H | $CO_2Et$ | H |
| 9-125 | $(CH_2)_2$ | NHOH | Et | Ph | F | F | H |
| 9-126 | $(CH_2)_2$ | NHOH | Et | Ph | F | Cl | H |
| 9-127 | $(CH_2)_2$ | NHOH | Et | Ph | F | $CF_3$ | H |
| 9-128 | $(CH_2)_2$ | NHOH | Et | Ph | Cl | F | H |
| 9-129 | $(CH_2)_2$ | NHOH | Et | Ph | Cl | Cl | H |
| 9-130 | $(CH_2)_2$ | NHOH | Et | Ph | Cl | $CF_3$ | H |
| 9-131 | $(CH_2)_2$ | NHOH | Et | Ph | Me | F | H |
| 9-132 | $(CH_2)_2$ | NHOH | Et | Ph | Me | Cl | H |
| 9-133 | $(CH_2)_2$ | NHOH | Et | Ph | Me | $CF_3$ | H |
| 9-134 | $(CH_2)_2$ | NHOH | Me | Ph | H | $NO_2$ | Me |
| 9-135 | $(CH_2)_2$ | NHOH | Me | Ph | H | CN | Me |
| 9-136 | $(CH_2)_2$ | NHOH | Me | Ph | H | $CHF_2$ | Me |
| 9-137 | $(CH_2)_2$ | NHOH | Me | Ph | H | SMe | Me |
| 9-138 | $(CH_2)_2$ | NHOH | Me | Ph | H | S(O)Me | Me |

TABLE 9-continued

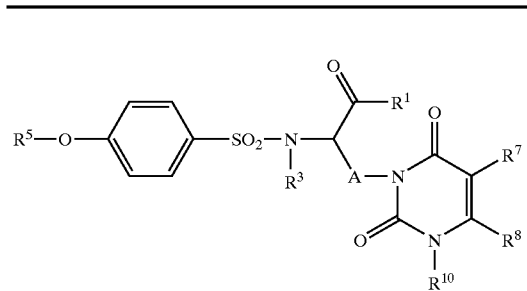
(I-9)

| Cpd. No. | A | R¹ | R³ | R⁵ | R⁷ | R⁸ | R¹⁰ |
|---|---|---|---|---|---|---|---|
| 9-139 | $(CH_2)_2$ | NHOH | Me | Ph | H | $SO_2Me$ | Me |
| 9-140 | $(CH_2)_2$ | NHOH | Me | Ph | H | $OCF_3$ | Me |
| 9-141 | $(CH_2)_2$ | NHOH | Me | Ph | H | $OCHF_2$ | Me |
| 9-142 | $(CH_2)_2$ | NHOH | Me | Ph | H | F | Me |
| 9-143 | $(CH_2)_2$ | NHOH | Me | Ph | H | $CO_2Et$ | Me |
| 9-144 | $(CH_2)_2$ | NHOH | Me | Ph | F | F | Me |
| 9-145 | $(CH_2)_2$ | NHOH | Me | Ph | F | Cl | Me |
| 9-146 | $(CH_2)_2$ | NHOH | Me | Ph | F | $CF_3$ | Me |
| 9-147 | $(CH_2)_2$ | NHOH | Me | Ph | Cl | F | Me |
| 9-148 | $(CH_2)_2$ | NHOH | Me | Ph | Cl | Cl | Me |
| 9-149 | $(CH_2)_2$ | NHOH | Me | Ph | Cl | $CF_3$ | Me |
| 9-150 | $(CH_2)_2$ | NHOH | Me | Ph | Me | F | Me |
| 9-151 | $(CH_2)_2$ | NHOH | Me | Ph | Me | Cl | Me |
| 9-152 | $(CH_2)_2$ | NHOH | Me | Ph | Me | $CF_3$ | Me |

TABLE 9-continued

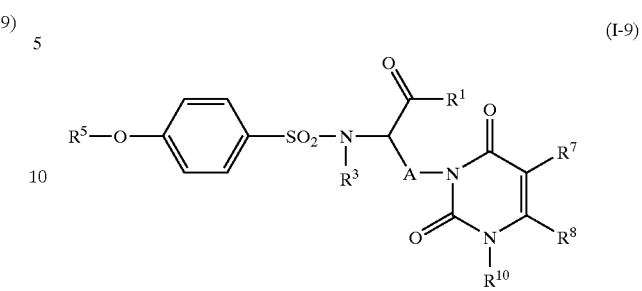
(I-9)

| Cpd. No. | A | R¹ | R³ | R⁵ | R⁷ | R⁸ | R¹⁰ |
|---|---|---|---|---|---|---|---|
| 9-153 | $(CH_2)_2$ | NHOH | Me | Ph | H | $CO_2Me$ | H |
| 9-154 | $(CH_2)_2$ | NHOH | Me | Ph | H | $CO_2NH_2$ | H |

In the above tables, "Me" means methyl, "Et" means ethyl, "Pr" means propyl, "i-Pr" means isopropyl, "c-Pr" means cyclopropyl, "Bu" means butyl, "s-Bu" means s-butyl, "i-Bu" means isobutyl, "t-Bu" means t-butyl, "c-Pn" means cyclopentyl, "c-Hx" means cyclohexyl, "Ph" means phenyl, "Py" means pyridyl, "Thie" means thienyl, and "Bn" means benzyl. In addition, "sub.1" to "sub.51" in table 5 above signify the following substituents respectively.

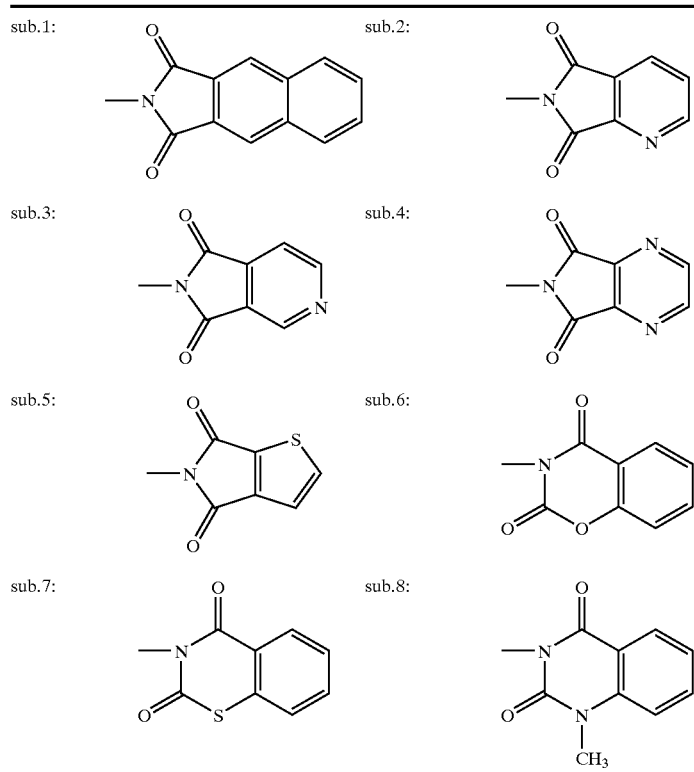

-continued
sub.9: 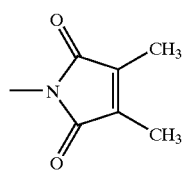 sub.10: 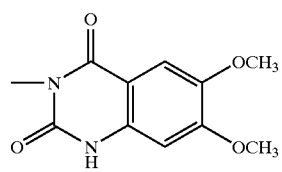
sub.11: 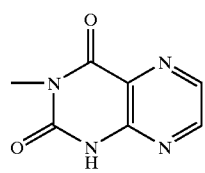 sub.12: 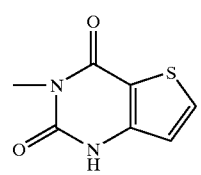
sub.13: 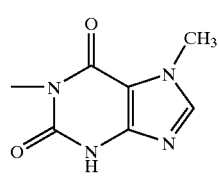 sub.14: 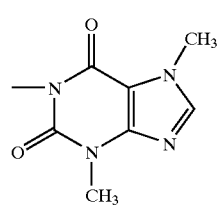
sub.15: 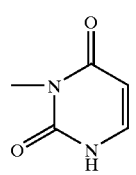 sub.16: 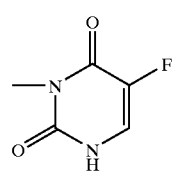
sub.17: 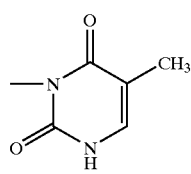 sub.18: 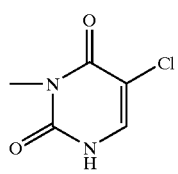
sub.19: 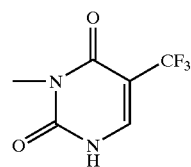 sub.20: 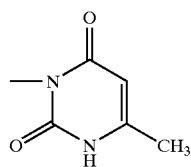
sub.21: 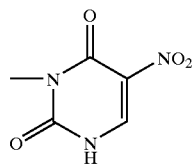 sub.22: 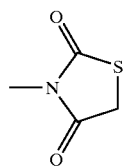
sub.23: 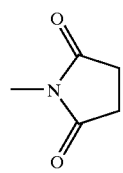 sub.24: 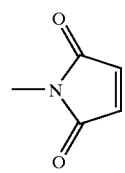

-continued
sub.25: 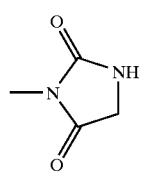
sub.26: 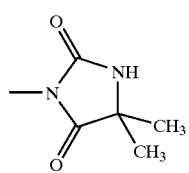
sub.27: 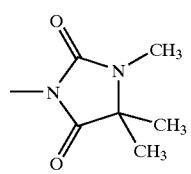
sub.28: 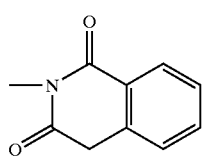
sub.29: 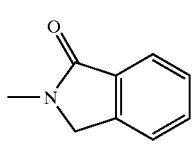
sub.30: 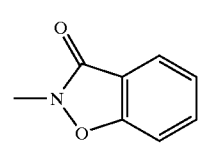
sub.31: 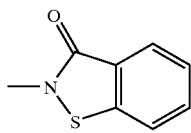
sub.32: 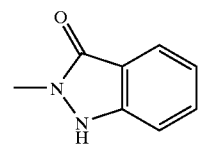
sub.33: 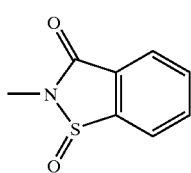
sub.34: 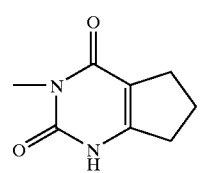
sub.35: 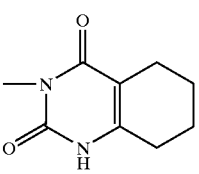
sub.36: 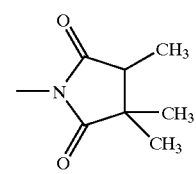
sub.37: 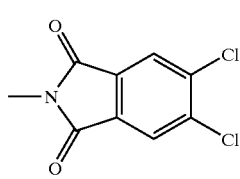
sub.38: 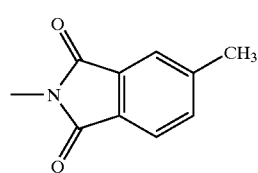
sub.39: 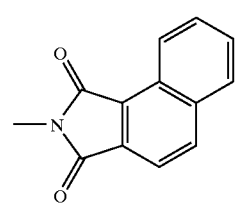
sub.40: 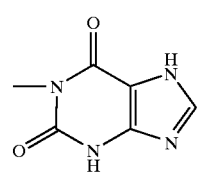
sub.41: 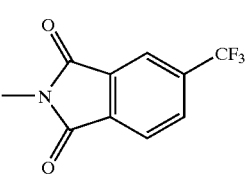
sub.42: 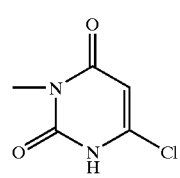

-continued sub.43: 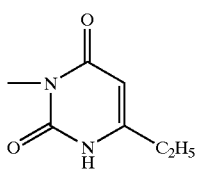  sub.44: 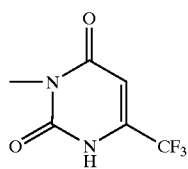

sub.45: 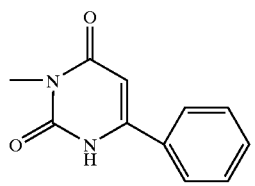  sub.46: 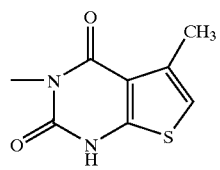

sub.47: 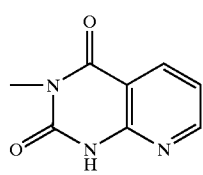  sub.48: 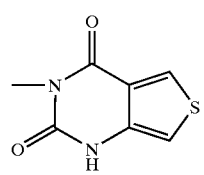

sub.49: 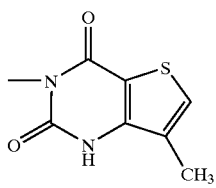  sub.50: 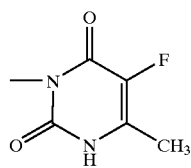

sub.51: 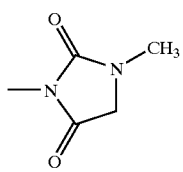

In the above tables, compounds of formula (I) in which $R^1$ is hydroxyamino group are illustrated. The present invention, however, also encompasses hydroxy derivatives [which are compounds of formula (I) wherein $R^1$ is a hydroxy group], corresponding to the above compounds as specific examples.

In the tables preferred compounds are those of compound numbers 1-1 to 1-4, 1-8 to 1-11, 1-24 to 1-27, 1-40 to 1-43, 1-56 to 1-59, 1-68 to 1-75, 1-88 to 1-91, 1-104 to 1-107, 1-1-121, 1-137, 1-153, 1-180 to 1-189, 2-1 to 2-4, 2-8 to 2-11, 2-24 to 2-27, 2-40 to 2-43, 2-56 to 2-59, 2-68 to 2-75, 2-88 to 2-91, 2-104 to 2-107, 2-121, 2-137, 2-153, 2-180 to 2-189, 3-1 to 3-5, 3-7 to 3-12, 3-25 to 3-28, 3-41 to 3-44, 3-57 to 3-60, 3-69 to 3-76, 3-89 to 3-92, 3-105 to 3-108, 3-122, 3-136, 3-138, 3-154, 3-169, 3-171, 3-172, 3-181 to 3-192, 4-1 to 4-4, 4-8 to 4-11, 4-24 to 4-27, 4-40 to 4-43, 4-56 to 4-59, 4-68 to 4-75, 4-88 to 4-91, 4-104 to 4-107, 4-121, 4-137, 4-153, 4-180 to 4-189, 5-1 to 5-91, 5-98, 5-99, 6-4, 6-10 to 6-12, 6-22 to 6-27, 7-9 to 7-12, 7-14, 7-16, 7-25 to 7-28, 7-30, 7-32, 7-41 to 7-44, 7-46, 7-48, 7-57 to 7-60, 7-62, 7-64, 7-69 to 7-76, 7-89 to 7-92, 7-94, 7-96, 7-105 to 7-108, 7-121 to 7-123, 7-136 to 7-139, 7-153 to 7-155, 7-172, 7-181 to 7-183, 7-185 to 7-187, 7-190, 7-194 to 7-197, 7-206 to 7-208, 7-211 to 7-214, 7-217 to 7-221, 8-9 to 8-12, 8-14, 8-16, 8-25 to 8-28, 8-30, 8-32, 8-41 to 8-44, 8-46, 8-48, 8-57 to 8-60, 8-62, 8-64, 8-69 to 8-76, 8-89 to 8-92, 8-94, 8-96, 8-105 to 8-108, 8-121 to 8-123, 8-136 to 8-139, 8-153 to 8-155, 8-172, 8-181 to 8-183, 8-185 to 8-187, 8-190, 8-194 to 8-197, 8-206 to 8-208, 8-211 to 8-214, 8-217 to 8-221, 9-3, 9-9, 9-11 to 9-19, 9-22, 9-28, 9-30 to 9-38, 9-41, 9-47, 9-49 to 9-57, 9-60, 9-66, 9-68 to 9-76, 9-79, 9-85, 9-87 to 9-95, 9-98, 9-104, 9-106 to 9-114, 9-117, 9-123, 9-125 to 9-133, 9-136, 9-142 and 9-144 to 9-152;

more preferred compounds are those of compound numbers 1-2, 1-9, 1-10, 1-25, 1-26, 1-41, 1-42, 1-57, 1-58, 1-69, 1-70, 1-73, 1-74, 1-89, 1-90, 1-105, 1-137, 1-153, 1-180 to 1-189, 2-2, 2-9, 2-25, 2-26, 2-41, 2-57, 2-69, 2-73, 2-89, 2-105, 2-137, 2-153, 2-180, 2-181, 2-185, 2-186, 3-2, 3-7, 3-10, 3-11, 3-25 to 3-27, 3-42, 3-43, 3-58, 3-59, 3-70, 3-71, 3-374, 3-75, 3-90, 3-91, 3-106, 3-107, 3-122, 3-136, 3-138, 3-154, 3-169, 3-171, 3-172, 3-181 to 3-192, 4-2, 4-9, 4-10, 4-25, 4-26, 4-41, 4-42, 4-57, 4-58, 4-69, 4-70, 4-73, 4-74, 4-89, 4-90, 4-105, 4-137, 4-153, 4-180 to 4-189, 5-1, 5-2, 5-9, 5-10, 5-15 to 5-35, 5-37 to 5-40, 5-43 to 5-45, 5-68 to 5-71, 5-74 to 5-79, 5-98, 5-99, 7-25 to 7-27, 7-32, 7-41 to 7-43, 7-57 to 7-59, 7-64, 7-70, 7-73 to 7-75, 7-89 to 7-91, 7-96, 7-106, 7-122, 7-138, 7-154, 7-172, 7-181, 7-182, 7-185, 7-186, 7-194 to 7-197, 7-206 to 7-208, 7-211 to 7-214, 7-217 to 7-221, 8-25 to 8-27, 8-32, 8-41 to 8-43, 8-57 to 8-59, 8-64, 8-70, 8-73 to 8-75, 8-89 to 8-91, 8-96, 8-106, 8-122, 8-138, 8-154, 8-172, 8-181, 8-182, 8-185, 8-186, 8-194 to 8-197, 8-206 to 8-208, 8-211 to 8-214, 8-217 to 8-221, 9-12, 9-13, 9-15, 9-16, 9-18, 9-19, 9-31, 9-32, 9-34, 9-35, 9-37, 9-38, 9-50, 9-51, 9-53, 9-54, 9-56, 9-57, 9-69, 9-70, 9-72, 9-73, 9-75, 9-76, 9-88, 9-89, 9-91, 9-92, 9-94, 9-95, 9-107, 9-108, 9-110, 9-111, 9-113, 9-114, 9-126, 9-127, 9-129, 9-130, 9-132, 9-133, 9-145, 9-146, 9-148, 9-149, 9-151 and 9-152;

still more preferred compounds are those of compound numbers 1-9, 1-25, 1-41, 1-57, 1-69, 1-73, 1-89, 1-180 to 1-182, 1-185, 1-186, 2-25, 2-89, 3-10, 3-26, 3-42, 3-58, 3-70, 3-74, 3-90, 3-106, 3-181 to 183, 3-186, 3-187, 4-9, 4-25, 4-41, 4-57, 4-69, 4-73, 4-89, 4-180, 4-181, 4-185, 4-186, 5-15, 5-17, 5-18, 5-21 to 5-27, 5-29 to 5-35, 5-37 to 5-40, 5-44, 5-45, 5-68 to 5-71, 5-74 to 5-77, 5-84 to 5-91, 5-98, 5-99, 7-26, 7-42, 7-58, 7-74, 7-90, 7-181, 7-182, 7-194, 7-196, 7-212, 7-213, 7-217 to 7-221, 8-26, 8-42, 8-58, 8-74, 8-90, 8-181, 8-182, 8-194, 8-196, 8-212, 8-213 and 8-217 to 8-221.

The followings can be exemplified as particularly preferable compounds:

(±)-N-hydroxy-Nα-methyl-Nα-(4-phenoxybenzenesulfonyl)-2-(2-phthalimidoethyl)glycinamide (Compound No. 3-26), (±)-N-hydroxy-Nα-methyl-Nα-(4-phenoxybenzenesulfonyl)-2-[2-(thiazolidin-2,4-dione-3-yl)ethyl]glycinamide (Compound No. 5-44), (±)-N-hydroxy-Nα-methyl-Nα-(4-phenoxybenzenesulfonyl)-2-[2-(quinazolin-2,4-dione-3-yl)ethyl]glycinamide (Compound No. 1-25), (±)-2-[2-(5-fluoropyrimidin-2,4-dione-3-yl)ethyl]-N-hydroxy-Nα-methyl-Nα-(4-phenoxybenzenesulfonyl)glycinamide (Compound No. 5-31), (±)-N-hydroxy-Nα-methyl-Nα-(4-phenoxybenzenesulfonyl)-2-[2-(thieno[3,2-d]pyrimidin-2,4-dione-3-yl)ethyl]glycinamide (Compound No. 5-23), (±)-N-hydroxy-Nα-methyl-2-[2-(7-methylxanthin-1-yl)ethyl]-Nα-(4-phenoxybenzenesulfonyl)glycinamide (Compound No. 5-25), (±)-N-hydroxy-Nα-methyl-Nα-(4-phenoxybenzenesulfonyl)-2-[2-pteridin-2,4-dione-3-yl)ethyl]glycinamide (Compound No. 5-21), (±)-2-[2-(1,1-dioxo-1,2-benzisothiazol-3-one-2-yl)ethyl]-N-hydroxy-Nα-methyl-Nα-(4-phenoxybenzenesulfonyl)glycinamide (Compound No. 2-25), (±)-N-hydroxy-Nα-methyl-2-[2-(6-methylpyrimidin-2,4-dione-3-yl)ethyl]-Nα-(4-phenoxybenzenesulfonyl)glycinamide (Compound No. 5-39), (±)-N-hydroxy-Nα-methyl-Nα-(4-phenoxybenzenesulfonyl)-2-[2-(5-trifluoromethylpyrimidin-2,4-dione-3-yl)ethyl]glycinamide (Compound No. 5-37), N-hydroxy-Nα-methyl-Nα-(4-phenoxybenzenesulfonyl)-2(R)-(2-phthalimidoethyl)glycinamide (Compound No. 3-26), (±)-Nα-[4-(4-fluorophenoxy)benzenesulfonyl]-N-hydroxy-Nα-methyl-2-(2-phthalimidoethyl)glycinamide (Compound No. 3-182), (±)-2-[2-(6-chloropyrimidin-2,4-dione-3-yl)ethyl]-N-hydroxy-Nα-methyl-Nα-(4-phenoxybenzenesulfonyl)glycinamide (Compound No. 5-84), (±)-N-hydroxy-Nα-methyl-Nα-(4-phenoxybenzenesulfonyl)-2-[2-(6-trifluoromethylpyrimidin-2,4-dione-3-yl)ethyl]glycinamide (Compound No. 5-88), (±)-N-hydroxy-Nα-methyl-Nα-[4-(pyridin-4-yl)oxybenzenesulfonyl]-2-[2-thieno[3,2-d]pyrimidin-2,4-dione-3-yl)ethyl]glycinamide (Compound No. 5-98), (±)-2-[2-(6-chloro-1-methylpyrimidin-2,4-dione-3-yl)ethyl]-N-hydroxy-Nα-methyl-Nα-(4-phenoxybenzenesulfonyl)glycinamide (Compound No. 7-212), (±)-Nα-[4-(4-chlorophenoxy)benzenesulfonyl]-2-[2-(6-chloropyrimidin-2,4-dione-3-yl)ethyl]-N-hydroxy-Nα-methylglycinamide (Compound No. 7-181), (±)-2-[2-(6-chloropyrimidin-2,4-dione-3-yl)ethyl-Nα-[4-(4-fluorophenoxy)-benzenesulfonyl]-N-hydroxy-Nα-methylglycinamide (Compound No. 7-182), (±)-Nα-[4-(4-chlorophenoxy)benzenesulfonyl]-N-hydroxy-Nα-methyl-2-[2-(6-trifluoromethylpyrimidin-2,4-dione-3-yl)ethyl]glycinamide (Compound No. 8-181), (±)-Nα-[4-(4-fluorophenoxy)benzenesulfonyl]-N-hydroxy-Nα-methyl-2-[2-(6-trifluoromethylpyrimidin-2,4-dione-3-yl)ethyl]glycinamide (Compound No. 8-182), (±)-Nα-[4-(3-chlorophenoxy)benzenesulfonyl]-N-hydroxy-Nα-methyl-2-[2-(6-trifluoromethylpyrimidin-2,4-dione-3-yl)ethyl]glycinamide (Compound No. 8-194), (±)-Nα-[4-(3-chlorophenoxy)benzenesulfonyl]-2-[2-(6-chloropyrimidin-2,4-dione-3-yl)ethyl]-N-hydroxy-Nα-methylglycinamide (Compound No. 7-194), (±)-2-[2-(6-chloropyrimidin-2,4-dione-3-yl)ethyl]-Nα-ethyl-N-hydroxy-Nα-(4-phenoxybenzenesulfonyl)glycinamide (Compound No. 7-42), (±)-2-[2-(6-chloropyrimidin-2,4-dione-3-yl)ethyl]-Nα-[4-(3-fluorophenoxy)-benzenesulfonyl]-N-hydroxy-Nα-methylglycinamide (Compound No. 7-196), (±)-2-[2-(6-chloropyrmidin-2,4-dione-3-yl)ethyl]-N-hydroxy-Nα-methyl-Nα-[4-(pyridin-4-yl)oxybenzenesulfonyl]glycinamide (Compound No. 7-26), (±)-Nα-[4-(3-fluorophenoxy)benzenesulfonyl]-N-hydroxy-Nα-methyl-2-[2-(6-trifluoromethylpyrimidin-2,4-dione-3-yl)ethyl]glycinamide (Compound No. 8-196), (±)-N-hydroxy-Nα-methyl-Nα-(4-(pyridin-4-yl)oxybenzenesulfonyl]-2-[2-(6-trifluoromethylpyrimidin-2,4-dione-3-yl)ethyl]glycinamide (Compound No. 8-26), (±)-Nα-ethyl-N-hydroxy-Nα-(4-phenoxybenzenesulfonyl)-2-[2-(6-trifluoromethylpyrimidin-2,4-dione-3-yl)ethyl]glycinamide (Compound No. 8-42), (±)-N-hydroxy-Nα-methyl-2-[2-(1-methyl-6-trifluoromethylpyrimidin-2,4-dione-3-yl)ethyl]-Nα-(4-phenoxybenzenesulfonyl)glycinamide (Compound No. 8-212), (±)-2-[2-(5-chloropyrimidin-2,4-dione-3-yl)ethyl]-N-hydroxy-Nα-methyl-Nα-(4-phenoxybenzenesulfonyl)glycinamide (Compound No. 5-35), Nα-[4-(3-chlorophenoxy)benzenesulfonyl]-N-hydroxy-Nα-methyl-2-[2-quinazolin-2,4-dione-3-yl)ethyl]glycinamide (Compound No. 1-182), Nα-[4-(3-chlorophenoxy)benzenesulfonyl]-N-hydroxy-Nα-methyl-2-[2-(thieno[3,2-d]pyrimidin-2,4-dione-3-yl)ethyl]glycinamide (Compound No. 5-99), and Nα-[4-(3-chlorophenoxy)benzenesulfonyl]-N-hydroxy-Nα-methyl-2-(2-phthalimidoethyl)glycinamide (Compound No. 3-183).

The compound of the formula (I) of the present invention can be prepared according to the following Method A to Method F.

<Method A>

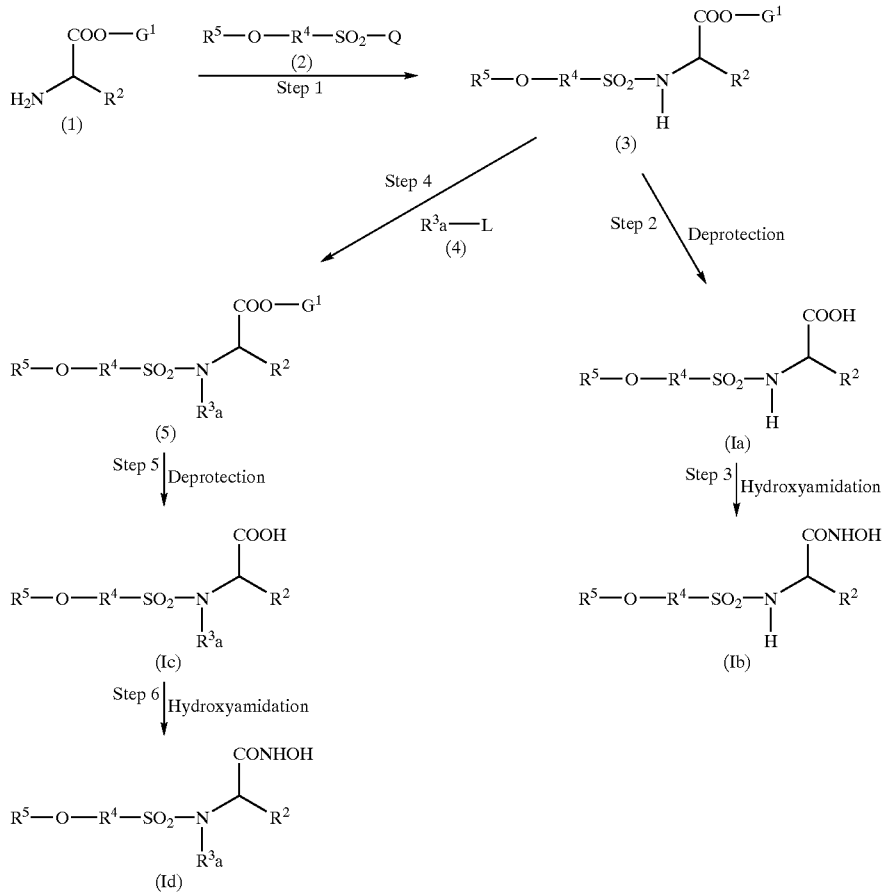

In the above formulae, $R^2$, $R^4$ and $R^5$ have the same meanings as defined above;

$R^3_a$ represents a group from the definition of $R^3$ other than the hydrogen atom;

$G^1$ represents a carboxyl protecting group;

L represents a hydroxyl group or a leaving group; and

Q represents an above-mentioned "halogen atom" (preferably a bromine atom or a chlorine atom, most preferably a chlorine atom).

The "leaving group" in the definition of L indicates a group which normally leaves as a nucleophilic residue, and examples of such a group include halogen atoms such as chlorine, bromine and iodine atoms; trihalogenomethyloxy groups such as trichloromethyloxy groups; lower alkanesulfonyloxy groups such as methanesulfonyloxy and ethanesulfonyloxy groups; halogeno lower alkanesulfonyloxy groups such as trifluoromethanesulfonyloxy and pentafluoroethanesulfonyloxy groups; and arylsulfonyloxy groups such as benzenesulfonyloxy, p-toluenesulfonyloxy and p-nitrobenzenesulfonyloxy groups, of which halogen atoms and lower alkanesulfonyloxy groups are preferred.

The "carboxyl protecting group" in the definition of $G^1$ means a protecting group which can be removed by a chemical process such as hydrogenolysis, hydrolysis, electrolysis and photolysis, and examples of such a group include similar groups to those described as the "general protecting group" relating to an "ester of a carboxyl group".

Preferably, it is a "lower alkyl group", a "lower alkenyl group", an "aryl group" or an "aralkyl group", and more preferred is a "lower alkyl group", a "lower alkenyl group" or an "aralkyl group".

Step 1 is a process to prepare the compound of formula (3) by reacting the amino group of the compound of formula (1) with the sulfonyl halide compound of formula (2), and the reaction is carried out in a solvent in the presence or absence of a base.

Examples of a solvent employable here include halogenated hydrocarbons such as dichloromethane, chloroform, carbon tetrachloride and dichloroethane; ethers such as diethyl ether, diisopropyl ether, tetrahydrofuran and dioxane; aprotic polar solvents such as N,N-dimethylformamide, N,N-dimethylacetamide and dimethyl sulfoxide; nitriles such as acetonitrile; esters such as methyl acetate and ethyl acetate; aromatic hydrocarbons such as benzene, toluene and xylene; and aliphatic hydrocarbons such as pentane, hexane and heptane.

Examples of a base employable here include alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]-7-undecene.

The reaction can be carried out at a temperature of from −20° C. to 150° C., preferably from 0° C. to 100° C.

While the reaction time varies mainly depending on the reaction temperature, the solvent used, etc., it is usually from 10 minutes to 48 hours, preferably from 30 minutes to 12 hours.

Step 2 is a process to prepare the compound of formula (Ia) of the present invention by removing the $G^1$ group from the compound of formula (3), and the removal of the protecting group, which may be varied depending on the kind thereof, can be carried out according to methods generally known in the art as follows:

In the case where a lower alkyl group or an aryl group is used as the carboxyl protecting group, it can be removed by treatment with an acid or a base.

Examples of the acid include hydrochloric acid, sulfuric acid, phosphoric acid and hydrobromic acid, and the base is not particularly limited, provided that it does not affect other parts of the compound, and preferred examples include alkali metal carbonates such as sodium carbonate and potassium carbonate, alkali metal hydroxides such as sodium hydroxide and potassium hydroxide or a conc. ammonia-methanol solution.

Incidentally, an isomerization may occur in hydrolysis with a base.

The solvent employable here is not particularly limited, provided that it is one usually used in hydrolysis reactions and does not inhibit the reaction, and preferred examples thereof include water or mixtures of water and an organic solvent such as an alcohol, e.g. methanol, ethanol or n-propanol, or an ether, e.g. tetrahydrofiran or dioxane.

While the reaction temperature and time vary depending on the starting material, the solvent, the reagent used, etc. and are not particularly limited, the reaction is usually carried out at a temperature of from 0° C. to 150° C. for the period of from 1 to 10 hours to control any side reactions.

In the case where the carboxyl protecting group is a diaryl-substituted methyl group such as diphenylmethyl, it can be usually removed by treatment with an acid in a solvent.

The solvent employable here is preferably an aromatic hydrocarbon such as anisole, and a fluorinated organic acid such as trifluoroacetic acid can be used as the acid employable here.

While the reaction temperature and time vary depending on the starting material, the solvent, the acid used, etc., the reaction is usually carried out at a room temperature for a period of from 30 minutes to 10 hours.

In the case where the carboxyl protecting group is an aralkyl group or a halogeno lower alkyl group, it can be usually removed by reduction in a solvent.

In the case where the carboxyl protecting group is a halogeno lower alkyl group, the reduction method is preferably a process of a chemical reduction such as zinc-acetic acid, and in the case where it is an aralkyl group, it can be carried out by a catalytic reduction with a catalyst such as palladium on carbon, palladium hydroxide or platinum or by a chemical reduction with an alkali metal sulfide such as potassium sulfide or sodium sulfide.

The solvent employable here is not particularly limited, provided that it does not affect the present reaction, and preferred examples thereof include alcohols such as methanol and ethanol; ethers such as tetrahydrofuran and dioxane; aliphatic acids such as acetic acid or mixtures of these organic solvents and water.

While the reaction temperature and time vary depending on the starting material, the solvent, the reduction method, etc., the reaction is usually carried out at a temperature of from 0° C. to a room temperature for a period of from 5 minutes to 12 hours.

In the case where the carboxyl protecting group is an alkoxymethyl group, it can be usually removed by treatment with an acid in a solvent.

The acid employable here is not particularly limited, provided that it is usually used as a Brønsted acid, and preferred examples include inorganic acids such as hydrochloric acid and sulfuric acid and organic acids such as acetic acid and paratoluenesulfonic acid.

The solvent employable here is not particularly limited, provided that it does not affect the present reaction, and preferred examples include alcohols such as methanol and ethanol; ethers such as tetrahydrofuran and dioxane or mixtures of these organic solvents and water.

While the reaction temperature and time vary depending on the starting material, the solvent, the kind of the acid used, etc., the reaction is usually carried out at a temperature of from 0° C. to 100° C. for a period of from 10 minutes to 18 hours.

When the removal of the carboxyl protecting group is carried out by treatment with ammonia according to a conventional method, amidation can be effected.

If desired, alkyl metal salts can be prepared according to a conventional method by dissolving the above-mentioned carboxylic acid thus produced in a mixture of water and a water-immiscible organic solvent such as ethyl acetate, adding to this solution an aqueous alkali metal carbonate or bicarbonate solution such as an aqueous sodium hydrogencarbonate solution or a potassium carbonate solution at a temperature of 0° C. to room temperature, then adjusting the pH of the mixture to approximately 7, and collecting the separated precipitates by filtering.

Further, esters re-protected with a carboxyl protecting group, which can be easily hydrolysed in vivo, can be prepared by reacting the salt thus prepared or the above-mentioned carboxylic acid with 2 equivalents of base (preferably an organic base such as triethylamine or dicyclohexylamine, a hydrogenated alkali metal salt such as sodium hydride or an alkali metal carbonate or bicarbonate such as sodium hydrogencarbonate, sodium carbonate or potassium carbonate) in a solvent (preferably an ether such as tetrahydrofuran or a polar solvent such as N,N-dimethylformamide, dimethyl sulfoxide, hexamethylphosphoric triamide and triethyl phosphate) and reacting an aliphatic acyloxymethyl halide such as acetoxymethyl chloride or propionyloxymethyl bromide, a 1-lower alkoxycarbonyloxyethyl halide such as 1-methoxycarbonyloxyethyl chloride or 1-ethoxycarbonyloxyethyl iodide, a phthalidyl halide or a (2-oxo-5-methyl-1,3-dioxolen-4-yl)methyl halide with the reaction mixure.

While the reaction temperature and time vary depending on the starting material, the solvent and the kind of the reagents, the reaction is usually carried out at a temperature of from 0° C. to 100° C. for a period of from 0.5 to 10 hours.

Step 3 is a process for hydroxyamidation of the compound of formula (Ia) of the present invention. The compound of formula (Ib) of the present invention is produced by reacting the compound of formula (Ia) or a reactive derivative thereof with hydroxylamine.

In the case where the compound (Ia) per se is subjected to hydroxyamidation in the present step, the reaction is carried out in the presence of a condensation agent such as dicyclohexylcarbodiimide, 1-ethyl-3-(3- dimethylaminopropyl)carbodiimide or N,N'-carbonyldiimidazole.

Examples of the solvent employable here include halogenated hydrocarbons such as dichloromethane, chloroform, carbon tetrachloride and dichloroethane; ethers such as diethyl ether, diIsopropyl ether, tetrahydrofaran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; esters such as methyl acetate and ethyl acetate; and water or a mixture thereof.

The reaction may be carried out at a temperature of from −20° C. to 150° C., preferably from 0° C. to 100° C. The reaction time is usually for a period of from 10 minutes to 48 hours, preferably from 30 minutes to 12 hours.

In the case where the compound of formula (Ia) is converted into a reactive derivative first and, then, is subjected to hydroxyamidation, examples of the reactive derivative include acid halides, mixed acid anhydrides and activated esters.

The acid halides can be prepared by reacting the compound of formula (Ia) with a halogenating agent such as thionyl chloride or oxalyl chloride; the mixed acid anhydrides can be prepared by reacting the compound of formula (Ia) with an acid halide such as methyl chlorocarbonate or ethyl chlorocarbonate; and the activated esters can be prepared by reacting the compound of formula (Ia) with a hydroxy compound such as N-hydroxysuccinimide or N-hydroxyphthalimide in the presence of one of the condensation agent mentioned obove, and in each case reaction conditions usually employed in conventional organic synthetic chemistry are applied.

It is possible to prepare the compound of formula (Ib) by preparing a protected hydroxyamide using a protected hydroxylamine such as O-benzylhydroxylamine or O-(t-butyldimethylsilyl)hydroxylamine instead of hydroxylamine according to the present step and, then, by deprotecting it according to the method described in Step 2.

Step 4 is a process to prepare the compound of formula (5) by modifying the N atom in the sulfonamide moiety of the compound of formula (3).

a) In this step, if L of the compound of formula (4) is a hydroxyl group, the Mitsunobu reaction [D. L. Hughes, Org. React., 42, 335 (1992)] is applied.

The reagent employable in the Mitsunobu reaction is not particularly limited, provided that it can usually be used in the Mitsunobu reaction, and preferred examples nclude the combination of an azo compound such as a di-lower alkyl azodicarboxylate, e.g. diethyl azodicarboxylate or diisopropyl azodicarboxylate, or an azodicarbonyl, e.g. 1,1'-(azodicarbonyl)dipiperidine, and a phosphine such as a triarylphosphine, e.g. triphenylphosphine, or a tri-lower alkylphosphine such as tri-n-butylphosphine, the combination of the di-lower alkylazodicarboxylate and the triarylphosphine is more preferred, and the combination of diethyl azodicarboxylate and triphenylphosphine is most preferred.

The solvent employable here is not particularly limited, provided that it does not inhibit the reaction and dissolves the starting material to some extent, and preferred example include aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyronitrile; amides such as formamide, N,N-dimethylformamide, N,N-dimethylacetamide, N-methyl-2-pyrrolidone and hexamethylphosphoric triamide; sulfoxides such as dimethyl sulfoxide and sulfones such as sulfolane, of which the aromatic hydrocarbons and the ethers are preferred.

The reaction may be carried out at a temperature of from −20° C. to 150° C., preferably from 0° C. to 100° C.

While the reaction time varies mainly depending on the reaction temperature, the starting material, the reagent or the kind of the solvent used, it is usually for the period of from 10 minutes to 3 days, preferably from 30 minutes to 12 hours.

b) In the case where the group L of the compound of formula (4) is a leaving group, the reaction is carried out in a solvent in the presence or absence of a base.

Examples of the solvent employable here include alcohols such as methanol, ethanol, propanol and isopropanol; ethers such as diethyl ether, diisopropyl ether, tetrahydrofuran and dioxane; aprotic polar solvents such as N,N-dimethylformamide, N,N-dimethylacetamide and dimethyl sulfoxide; nitriles such as acetonitrile; esters such as methyl acetate and ethyl acetate; aromatic hydrocarbons such as benzene, toluene and xylene; and aliphatic hydrocarbons such as pentane, hexane and heptane.

Examples of the base employable here include alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]-7-undecene.

Step 5 is a process to prepare the compound of formula (Ic) of the present invention by removing the $G^1$ group of the compound of formula (5) and is carried out in a similar manner to the procedure described in Step 2.

Step 6 is a process to prepare the compound of formula (Id) of the present invention by hydroxyamidation of the compound of formula (Ic) of the present invention and is carried out in a similar manner to the procedure described in Step 3.

<Process B>

Process B is a process to prepare the compound of formula (1'), which is a compound of formula (1) in which $R^2$ is a group of formula —A—$R^6$ (in the formulae, A and $R^6$ have the same meanings as defined above), which is a starting material in Method A.

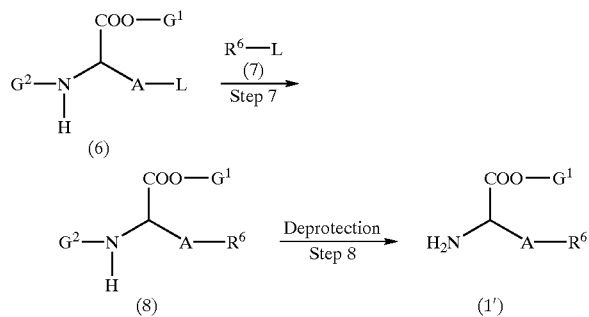

In the formulae, $R^6$, A, $G^1$ and L have the same meanings as defined above; and $G^2$ represents an amino protecting group.

The "amino protecting group" in the definition of $G^2$ means a protecting group which may be removed by a chemical process such as hydrogenolysis, hydrolysis, electrolysis and photolysis, and examples include the above-mentioned "aliphatic acyl groups", the above-mentioned "aromatic acyl groups", the above-mentioned "alkoxycarbonyl groups", the above-mentioned "alkenyloxycarbonyl groups", the above-mentioned "aralkyloxycarbonyl groups", the above-mentioned "silyl groups" and the above-mentioned "aralkyl groups", of which the "alkoxycarbonyl groups", the "alkenyloxycarbonyl groups" and the "aralkyloxycarbonyl groups" are preferred, and t-butoxycarbonyl, allyloxycarbonyl and benzyloxycarbonyl groups are more preferred.

Step 7 is a process to prepare the compound of formula (8) by reacting the compound of formula (6) with the compound of formula (7) and is carried out in a similar manner to procedures described in a) or b) of Step 4 above.

Step 8 is a process to prepare the compound of formula (1') by removing the $G^2$ group of the compound of formula (8).

The removal of the $G^2$ group, which may be varied depending on its kind, can be carried out according to methods generally known in the art, which are described below:

In the case where $G^2$ is a silyl group, it can be conventionally removed by treatment with a compound capable of producing a fluorine anion such as tetrabutylammonium fluoride.

The reaction solvent is not particularly limited, provided that it does not inhibit the reaction, and preferred examples include ethers such as tetrahydrofuran and dioxane.

The reaction temperature and time are not particularly limited and the reaction is usually carried out at room temperature for the period of from 10 to 18 hours.

In the case where $G^2$ is an aliphatic acyl group, an aromatic acyl group or an alkoxycarbonyl group, it can be removed by treatment with an acid or a base in the presence of an aqueous solvent.

The acid employable here is not particularly limited, provided that it is conventionally used and does not inhibit the reaction, and preferred examples include inorganic acids such as hydrochloric acid, sulfuric acid, phosphoric acid and hydrobromic acid, organic acids such as trifluoroacetic acid or Lewis acids such as B-bromocatecholborane (Lewis acids are more preferred and the B-bromocatecholborane is most preferred).

The base employable here is not particularly limited, provided that it does not affect other parts of the compounds, and preferred examples include metal alkoxides such as sodium methoxide, alkali metal carbonates such as sodium carbonate, potassium carbonate and lithium carbonate, alkali metal hydroxides such as sodium hydroxide, potassium hydroxide and lithium hydroxide and ammonias such as aqueous ammonia and conc. ammonia-methanol.

Incidentally, isomerization may occur in hydrolysis with a base.

The solvent employable here is not particularly limited, provided that it is usually used in hydrolysis reactions, and preferred examples include water; organic solvents such as alcohols, e.g. methanol, ethanol and n-propanol, and ethers, e.g. tetrahydrofuran and dioxane, and mixtures of these organic solvents and water.

While the reaction temperature and time vary depending on the starting material, the solvent, the acid or base used, etc. and are not particularly limited, the reaction is usually carried out at a temperature of from 0° C. to 150° C. for the period of from 1 to 10 hours to control any side reactions.

In the case where $G^2$ is an aralkyl group or an aralkyloxycarbonyl group, the removal method of $G^2$ is preferably achieved by bringing a compound into contact with a reducing agent in a solvent (preferably a catalytic reduction at a normal temperature in the presence of a catalyst) or by using an oxidizing agent.

The solvent employable in the removal by catalytic reduction is not particularly limited, provided that it does not affect the present reaction, and preferred examples include alcohols such as methanol, ethanol and isopropanol, ethers such as diethyl ether, tetrahydrofuran and dioxane, aromatic hydrocarbons such as toluene, benzene and xylene, aliphatic hydrocarbons such as hexane and cyclohexane, esters such as ethyl acetate and propyl acetate, aliphatic acids such as acetic acid and mixtures of these organic solvents and water.

The catalyst employable here is not particularly limited, provided that is conventionally used in catalytic reduction reactions, and preferred examples include palladium on carbon, palladium hydroxide, Raney nickel, platinum oxide, platinum black, rhodium-aluminum oxide, triphenylphosphine-rhodium chloride and palladium-barium sulfate.

The pressure is not particularly limited and the reaction is usually carried out at a temperature of from 1 to 10 atms.

While the reaction temperature and time vary depending on the starting material, the solvent and the kind of catalyst employed, the reaction is usually carried out at a temperature of from 0 to 100° C. for the period of from 5 minutes to 24 hours.

The solvent employable in the removal by oxidation is not particularly limited, provided that it does not affect the present reaction, and a hydrous organic solvent is preferred.

Preferred examples of such an organic solvent include ketones such as acetone, halogenated hydrocarbons such as methylene chloride, chloroform and carbon tetrachloride, nitriles such as acetonitrile, ethers such as diethyl ether, tetrahydrofuran and dioxane, amides such as N,N-dimethylformamide, N,N-dimethylacetamide and hexamethylphosphoric triamide and sulfoxides such as dimethyl sulfoxide.

The oxidizing agent employable here is not particularly limited, provided that it is used in oxidation, and preferred examples include potassium persulfate, sodium persulfate, cerium ammonium nitrate (CAN) and 2,3-dichloro-5,6-dicyano-p-benzoquinone (DDQ).

While the reaction temperature and time vary depending on the starting material, the kind of solvent and the catalyst, the reaction is usually carried out at a temperature of from 0° C. to 150° C. for the period of from 10 minutes to 24 hours.

In the case where $G^2$ is an alkenyloxycarbonyl group, the removal can usually be accomplished using conditions similar to those for the removal reaction in the case where the amino protecting group is an aliphatic acyl group, an aromatic acyl group or an alkoxycarbonyl group.

In the case where $G^2$ is an allyloxycarbonyl group, particularly, the removal can be carried out easily by using palladium and triphenylphosphine or nickel tetracarbonyl with less side reactions.

While the $G^1$ group may be removed in the present step, the carboxyl group can be protected again according to the following methods:

<Method 1>

The method 1 is to react the resulting carboxylic acid derivative with a compound of formula $G^1$-L' (wherein $G^1$ has the same meaning as defined above and L' represents a leaving group) in a solvent (the solvent employable here is not particularly limited, provided that it does not inhibit the reaction and dissolves the starting material to some extent, and preferred examples include aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; ethers such as diethyl ether, diisopropyl ether, tetrahydrofuran, dioxane, dimethoxyethane and diethyleneglycol dimethyl ether; ketones such as acetone, methyl ethyl ketone, methyl isobutyl ketone, isophorone and cyclohexanone; nitrites such as acetonitrile and isobutyronitrile; and amides such as formamide, N,N-dimethylformamide, N,N-dimethylacetamide, N-methyl-2-pyrrolidone, N-methylpyrrolidinone and hexamethylphosphoric triamide) in the presence of a base [the base employable here is not particularly limited, provided that it is used as a base in conventional reactions, and preferred examples include inorganic bases such as alkali metal carbonates, e.g. sodium carbonate, potassium carbonate and lithium carbonate; alkali metal hydrogencarbonates, e.g. sodium hydrogencarbonate, potassium hydrogencarbonate and lithium hydrogencarbonate; alkali metal hydrides, e.g. lithium hydride, sodium hydride and potassium hydride; alkali metal hydroxides such as sodium hydroxide, potassium hydroxide, barium hydroxide and lithium hydroxide; alkali metal fluorides, e.g. sodium fluoride and potassium fluoride; alkali metal alkoxides such as sodium methoxide, sodium ethoxide, potassium methoxide, potassium ethoxide, potassium t-butoxide and lithium methoxide; alkali metal mercaptans such as sodium methylmercaptan and sodium ethylmercaptan; organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene, 1,4-diazabicyclo[2.2.2]octane (DABCO) and 1,8-diazabicyclo [5.4.0]-7-undecene (DBU) and organic metal bases such as butyllithium, lithium diisopropylamide and lithium bis (trimethylsilyl)amide) usually at a temperature of from –20° C. to 150° C. (preferably from 0 to 100° C.) for a period of from 0.5 to 10 hours.

<Method 2>

The method 2 is to react the resulting carboxylic acid derivatives with a compound of formula $G^1$—OH (wherein $G^1$ has the same meaning as defined above) in a solvent in the presence or absence of a base with the following "condensation agent".

Examples of the condensation agent employable in the present reaction include:

(1) a combination of a phosphoric ester, such as diphenylphosphoryl azide or diethyl cyanophosphate, and a below-mentioned base;

(2) a carbodiimide, such as 1,3-dicyclohexylcarbodiimide, 1,3-diisopropylcarbodiimide or 1-ethyl-3-(3-dimethylaminopropyl)carbodiimide; a combination of the carbodiimides and a below-mentioned base; or a combination of the carbodiimide and an N-hydroxy compound, such as N-hydroxysuccinimide, 1-hydroxybenzotriazole or N-hydroxy-5-norbomene-2,3-dicarboxyimide;

(3) a combination of a disulfide, such as 2,2'-dipyridyl disulfide or 2,2'-dibenzothiazolyl disulfide, and a phosphine, such as triphenylphosphine or tributylphosphine;

(4) a carbonate, such as N,N'-disuccinimidyl carbonate, di-2-pyridyl carbonate or S,S'-bis(1-phenyl-1H-tetrazol-5-yl)dithiocarbonate;

(5) a phosphinic chloride, such as N,N'-bis(2-oxo-3-oxazolidinyl)phosphinic chloride;

(6) an oxalate, such as N,N'-disuccinimidyl oxalate, N,N'-diphthalimide oxalate, N,N'-bis(5-norbomene-2,3-dicarboxyimidyl)oxalate, 1,1'-bis(benzotriazolyl)-oxalate, 1,1'-bis(6-chlorobenzotriazolyl)oxalate or 1,1'-bis(6-trifluoromethylbenzotriazolyl)oxalate;

(7) a combination of the phosphine and an azodicarboxylic acid ester or an azodicarboxyamide, such as diethyl azodicarboxylate or 1,1'-(azodicarbonyl)-dipiperidine; a combination of the phosphines and a below-mentioned base;

(8) an N-lower alkyl-5-arylisoxazolium-3'-sulfonate, such as N-ethyl-5-phenylisoxazolium-3'-sulfonate;

(9) a diheteroaryldiselenide, such as di-2-pyridyldiselenide;

(10) an arylsulfonyltriazolide, such as p-nitrobenzenesulfonyltriazolide;

(11) a 2-halo-1-lower alkylpyridinium halaide, such as 2-chloro-1-methylpyridinium iodide;

(12) an imidazole, such as 1,1'-oxalyldiimidazole or N,N'-carbonyl-diimidazole;

(13) a 3-lower alkyl-2-halogen-benzothiazolium fluoroborate, such as 3-ethyl-2-chloro-benzothiazolium fluoroborate;

(14) a 3-lower alkyl-benzothiazole-2-selone, such as 3-methylbenzothiazole-2-selone;

(15) a phosphate, such as phenyldichlorophosphate or polyphosphate;

(16) a halosulfonyl isocyanate, such as chlorosulfonyl isocyanate;

(17) a halosilane, such as trimethylsilyl chloride or triethylsilyl chloride;

(18) a combination of a lower alkanesulfonyl halide, such as methanesulfonyl chloride, and a below-mentioned base;

(19) an N,N,N',N'-tetra-lower alkyl haloformamidium chloride, such as N,N,N',N'-tetramethylchloroformamidium chloride.

Of these, the carbodiimides or a combination of a phosphine and an azodicarboxylic ester or azodicarboxyamide is preferred.

The solvent employable here is not particularly limited, provided that it does not inhibit the reaction and dissolves the starting material to some extent, and preferred examples include aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethyleneglycol dimethyl ether; nitriles such as acetonitrile and isobutyronitrile; and amides such as formamide, N,N-dimethylformamide, N,N-dimethylacetamide, N-methyl-2-pyrrolidone, N-methylpyrrolidinone and hexamethylphosphoric triamide.

The base employable here is not particularly limited, provided that it is used as a base in conventional reactions, and preferred examples include organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline and N,N-diethylaniline.

Incidentally, 4-(N,N-dimethylamino)pyridine and 4-pyrrolidinopyridine can be used in a catalytic amount by combining it with other bases, and further a dehydrating agent such as molecular sieves, quaternary ammonium salts such as benzyltriethylammonium chloride and tetrabutylammonium chloride, crown ethers such as dibenzo-18-crown-6 and an acid scavenger such as 3,4-dihydro-2H-pyrid[1,2-a]pyrimidine-2-one can be also added thereto in order to effectively carry out the reaction.

The reaction is usually carried out at a temperature of from −20° C. to 100° C., preferably from 0° C. to 50° C.

The reaction time varies mainly depending on the reaction temperature, the starting material, the reagent and the kind of the solvent used, and is usually for a period of from 10 minutes to 3 days, preferably from 30 minutes to 1 day.

<Method 3>

In the case where the protecting group is a lower alkyl group, Method 3 is a method to react the resulting carboxylic acid derivatives with a corresponding alcohol, such as methanol, ethanol, propanol or butanol, in a solvent (the solvent employable here is not particularly limited, provided that it does not inhibit the reaction and dissolves the starting material to some extent, and preferred examples include alcohols identical to the reagent; aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; ethers such as diethyl ether, diisopropyl ether, tetrahydrofuran, dioxane, dimethoxyethane and diethyleneglycol dimethyl ether; ketones such as acetone, methyl ethyl ketone, methyl isobutyl ketone, isophorone and cyclohexanone; nitriles such as acetonitrile and isobutyronitrile; and amides such as formamide, N,N-dimethylformamide, N,N-dimethylacetamide, N-methyl-2-pyrrolidone, N-methylpyrrolidinone and hexamethylphosphoric triamide, of which the alcohols identical to the reagent are preferred) in the presence of an acid catalyst (the acid catalyst employable here is not particularly limited, provided that it is used as an acid catalyst in conventional reactions, and preferred examples include Bronsted acids such as inorganic acids, e.g. hydrogen chloride, hydrobromic acid, sulfuric acid, perchloric acid and phosphoric acid, and organic acids, e.g. acetic acid, formic acid, oxalic acid, methanesulfonic acid, paratoluenesulfonic acid, trifluoroacetic acid and trifluoromethanesulfonic acid, and Lewis acids, e.g. boron trichloride, boron trifluoride and boron tribromide, and acidic ion-exchange resins) at a temperature of from 0° C. to 150° C. (preferably from 50° C. to 100° C.) for a period of from 10 minutes to 24 hours (preferably from 30 minutes to 10 hours).

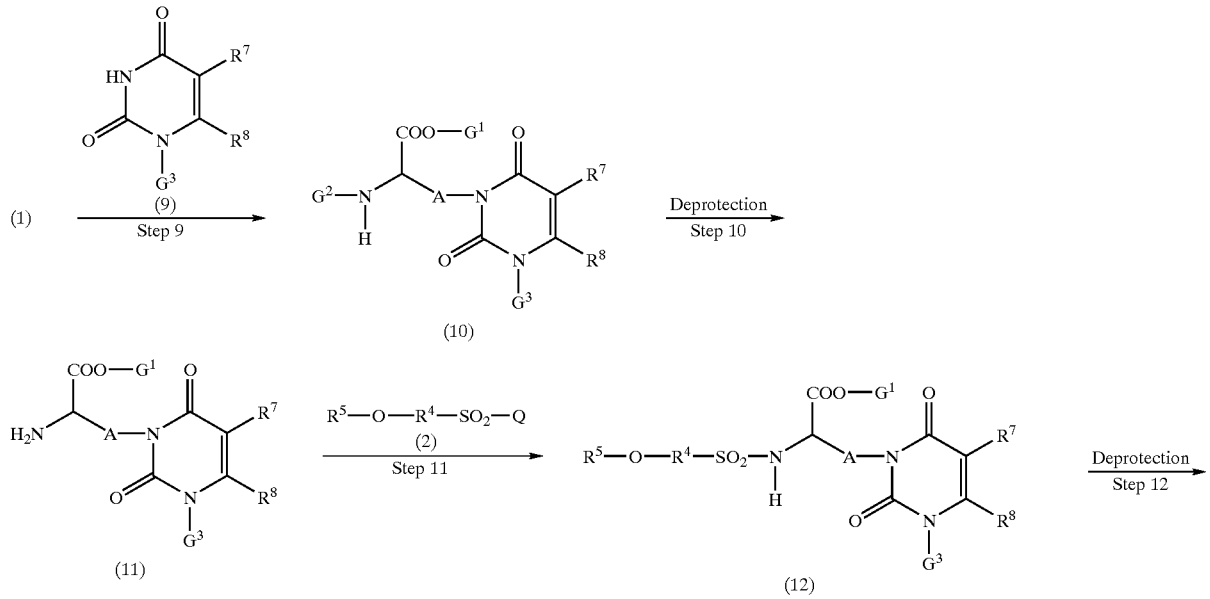

-continued

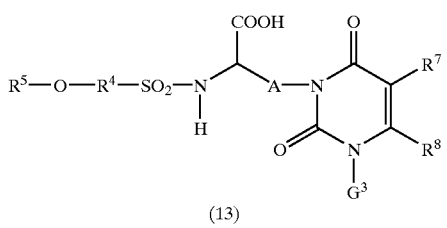

(13)

or

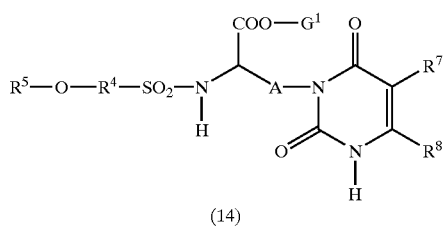

(14)

or

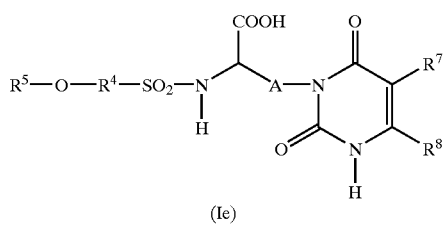

(Ie)

Hydroxyamidation | Step 13

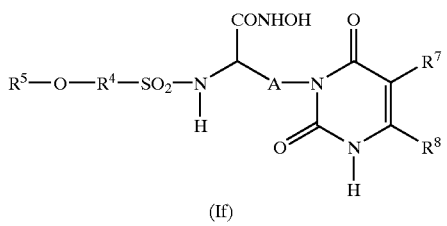

(If)

In the formulae, $R^4, R^5, R^7, R^8, A, G^1, G^2$ and Q have the same meanings as defined above; and $G^3$ represents an amide protecting group.

The "amide protecting group" in the definition of $G^3$ means a protecting group which may be removed by a chemical process such as hydrogenolysis, hydrolysis, electrolysis and photolysis, and preferred examples include lower alkoxy lower alkyl groups such as the above-mentioned "lower alkoxymethyl groups"; aralkyloxymethyl groups such as benzyloxymethyl; and 2-[tri(lower alkyl) silyl]ethoxy lower alkyl groups such as 2-(trimethylsilyl) ethoxymethyl, of which methoxymethyl, benzyloxymethyl and 2-(trimethylsilyl)ethoxymethyl groups.

Steps 9, 10, 11 and 13 in Method C are carried out in a similar manner to the procedures described in Steps 4, 8, 1 and 3 respectively.

Step 12 is a process to prepare the compound of formula (1e) of the present invention by removing the two protecting groups (the $G^1$ and $G^2$ groups) of the compound of formula (12), and is carried out in a similar manner to the procedure described in Steps 2 or 8. In the present invention, while the compound of formula (13) or (14), which is a compound of formula (12) in which one of the protecting groups is removed, may be produced, it can be converted into a compound of formula (Ie) by further carrying out a deprotection reaction in a similar manner to the procedure described above (Steps 12a and 12b).

<Method D>
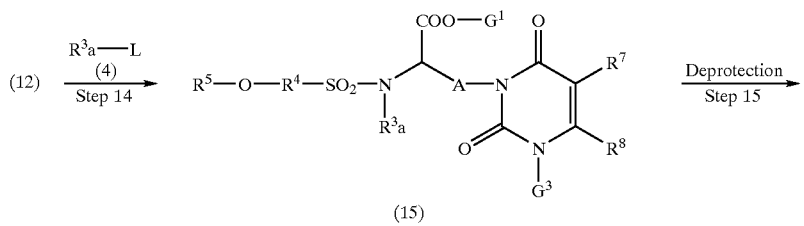
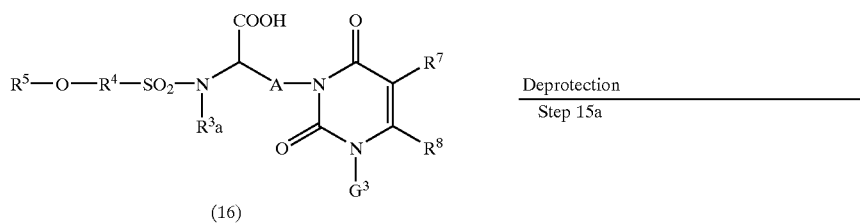
(16)
or
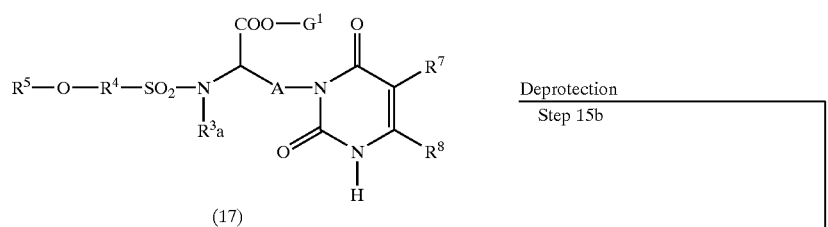
(17)
or
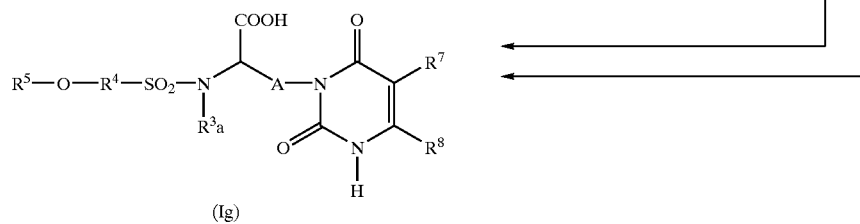
(Ig)
Hydroxyamidation | Step 16
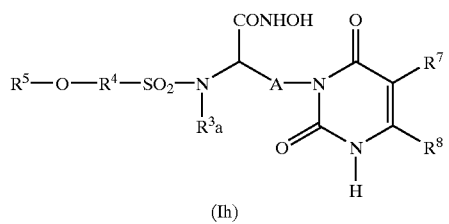
(Ih)

In the above formulae,

R$^3_a$, R$^4$, R$^5$, R$^7$, R$^8$, A, G$^1$, G$^3$ and L have the same meanings as defined above.

Steps 14 and 16 in Method D are carried out in a similar manner to the procedures described in Steps 4 and 3 in Method A respectively and Step 15 (15a and 15b) is carried out in a similar manner to the procedures described in Step 12 (12a and 12b).

examples include metal alkoxides such as sodium methoxide; alkali metal carbonates such as sodium carbonate, potassium carbonate and lithium carbonate; alkali metal hydroxides such as sodium hydroxide, potassium hydroxide, lithium hydroxide and barium hydroxide and ammonia such as aqueous ammonia and conc. ammonia-methanol.

The solvent employable here is not limited provided that it is usually used in hydrolysis reactions, and preferred examples include water; organic solvents such as alcohols, <Method E>

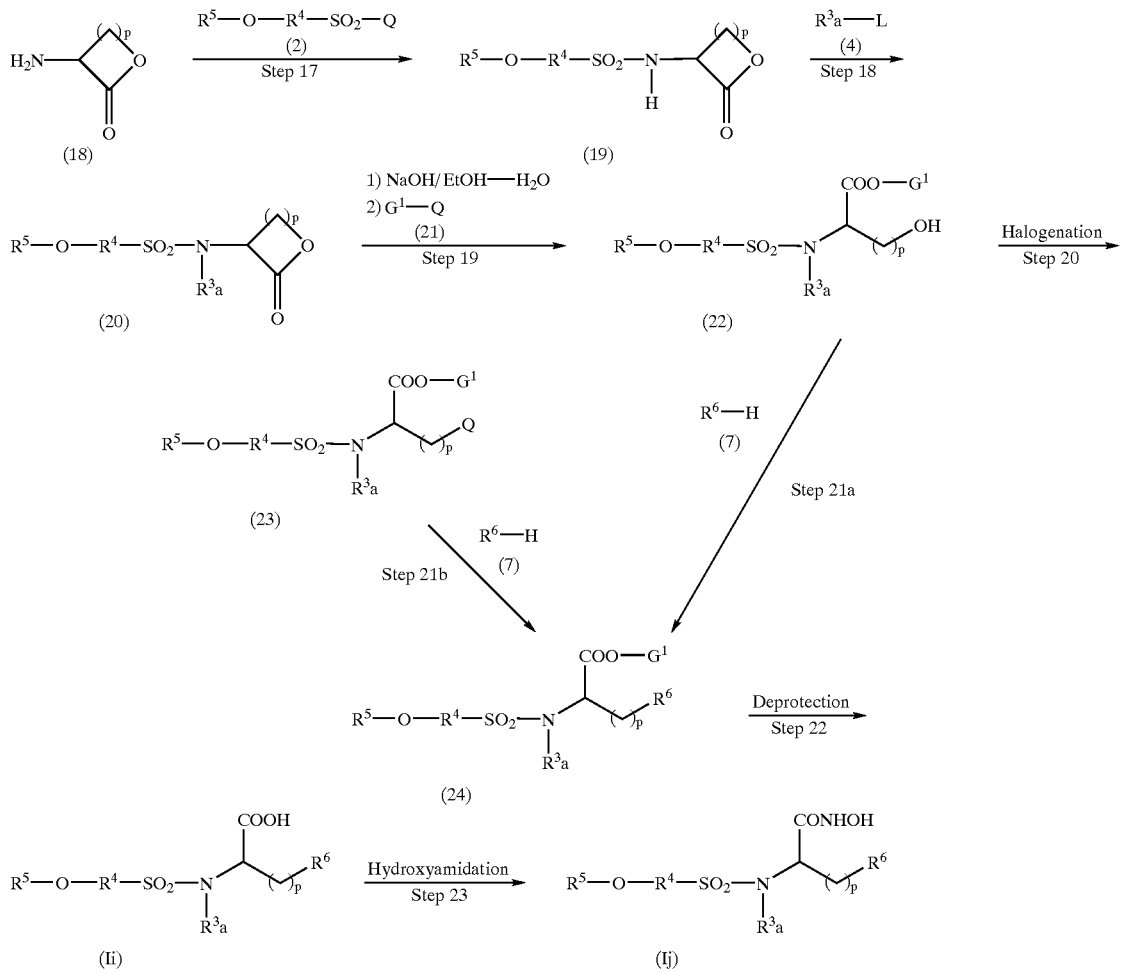

In the formulae,

R$^3$a, R$^4$, R$^5$, R$^6$, G$^1$, L and Q have the same meanings as defined above; and p is an integer of from 1 to 6, preferably from 2 to 4.

Steps 17, 18, 21a, 21b, 22 and 23 in Method E are carried out in a similar manner to the procedures described in Steps 1, 4, 4-a), 4-b), 2 and 3 respectively.

Step 19 is a process to prepare an ester derivative of formula (22) by hydrolizing the lactone compound of formula (20) followed by reacting the resulting compound with a halide compound of formula (21).

1) While the former hydrolysis reaction can be accomplished by a method generally used in organic synthetic chemistry, the method of treating the lactone compound of formula (20) with a base in a solvent is preferred.

The base employable here is not limited, provided that it does not affect other parts of the compound, and preferred e.g. methanol, ethanol and n-propanol, and ethers, e.g. tetrahydrofuran and dioxane, and mixtures of these organic solvents and water.

While the reaction temperature and time vary depending on the starting material, the solvent, the base used, etc. and are not particularly limited, the reaction is usually carried out at a temperature of from 0° C. to 150° C. for a period of from 1 to 10 hours to control any side reactions.

2) The latter protection reaction of the carboxyl group can be carried out in a similar manner to that described in Step 8. It is preferably carried out according to Method 1 described in Step 8.

Step 20 is a process to prepare the compound of formula (23) by converting the hydroxyl group of the compound of formula (22) into a halogen atom and, for example, a fluorination reaction with diethylamino sulfide trifluoride (DAST); a chlorination reaction with thionyl chloride, phosphorus trichloride, phosphorus pentachloride, phosphorus oxychloride or triphenylphosphine/carbon tetrachloride; a bromination reaction with hydrobromic acid, thionyl bromide, phosphorus tribromide or triphenylphosphine/carbon tetrabromide; or an iodination reaction with hydroiodic acid or phosphorus triiodide is carried out according to the method described in "W. J. Middleton [J. Org. Chem., 40, p. 574 (1975)]."

<Method F>

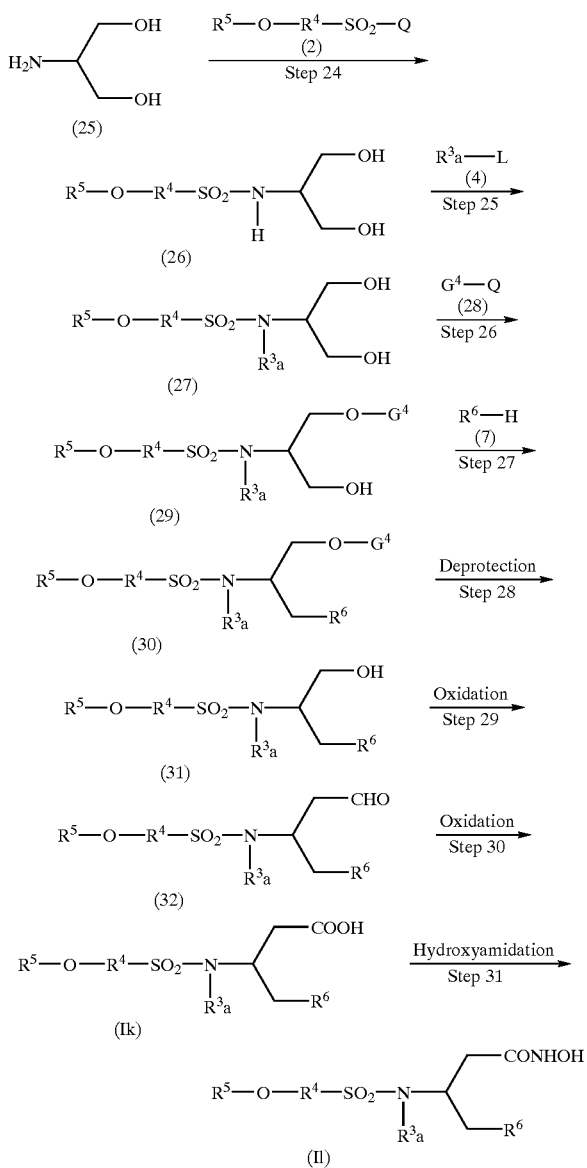

In the formulae, $R^3a$, $R^4$, $R^5$, $R^6$, L and Q have the same meanings as defined above; and $G^4$ represents a hydroxyl protecting group.

The "hydroxyl protecting group" in the definition of $G^4$ means a protecting group which may be removed by a chemical process such as hydrogenolysis, hydrolysis, electrolysis and photolysis, and preferred example include the above-mentioned "silyl groups", of which the above-mentioned "tri-lower alkylsilyl groups" are more preferred, and a trimethylsilyl, triethylsilyl, isopropyldimethylsilyl and t-butyldimethylsilyl groups are particularly preferred.

Step 24 is a process to prepare a compound of formula (26) by reacting the amino group of serinol (25) with the sulfonyl halide compound of formula (2) and is carried out in a similar manner to the procedure described in Step 1.

Step 25 is a process to prepare a compound of formula (27) by modifying the N atom in the sulfonamide moiety of the compound of formula (26) and is carried out in a similar manner to the procedure described in Step 4.

Step 26 is a process to prepare a compound of formula (29) by protecting one of two hydroxyl groups of the diol compound of formula (27) and is carried out, for example, by reacting it with a tri-lower alkylsilyl halide compound of formula (28). The reaction is carried out, for example, according to the process for the synthesis of silyl ethers described in "Protective Groups in Organic Synthesis, John Wiley & Sons, New York 1991."

Step 27 is a process to prepare a compound of formula (30) by reacting the compound of formula (29) with the compound of formula (7) and is carried out in a similar manner to the procedure described in Step 4-a).

Step 28 is a process to prepare a compound of formula (31) by removing the hydroxyl protecting group from the compound of formula (30) and is carried out, for example, according to the decomposition process of silyl ethers described in "Protective Groups in Organic Synthesis, John Wiley & Sons, New York 1991."

Step 29 is a process to prepare an aldehyde compound of formula (32) by oxidizing the hydroxyl group of the compound of formula (31) and is carried out, for example, by using chromic acid, manganese dioxide, dimethyl sulfoxide, etc. according to the processes described in "K. Omura, A. K. Sharma and D. Swem [J. Org. Chem., 41, p. 957 (1976)] and S. L. Huang, K. Omura and D. Swem [Tetrahedron, 34, p. 1651 (1978)]."

Step 30 is a process to prepare a compound of formula (Ik) of the present invention by oxidizing the aldehyde compound of formula (32) and is carried out by using permanganic acids, chromic acid, peroxides, oxygen, halogen, hypohalous acids, halous acids, halogen acids, nitric acid, etc. according to the processes described in "T. Kageyama, Y Ueno and M. Okawara [Synthesis, p. 815 (1983)] and C. D. Hurd, J. W. Garrett and E. N. Osborne [J. Am. Chem. Soc., 55, p. 1082 (1933)]."

Step 31 is a process to prepare a compound of formula (Il) of the present invention by hydroxyamidation of the compound of formula (Ik) of the present invention and is carried out in a similar manner to the procedure described in Step 3.

The starting materials, namely the compounds (1), (6), (18) and (25), and side-starting materials, namely the compounds (2), (4), (7), (9), (21) and (28), are known per se or can be obtained from known compounds by treatment according to known methods.

After completion of each reaction described above, the desired compound is isolated from the reaction mixture in a conventional manner.

For example, it is obtained by neutralizing the reaction mixture as needed, removing the insoluble matters by filtration, if any, adding organic solvents which are not miscible each other, such as water and ethyl acetate, washing with water or the like, separating the organic layer containing the desired compound, drying it over anhydrous magnesium sulfate or the like and then distilling off the solvent.

If necessary, the desired compound thus obtained can be isolated and purified by using a conventional method such as recrystallization or reprecipitation and chromatography in which a method ordinarily employed for the isolation and purification of an organic compound in combination as needed and eluting using a proper eluant. Examples of chromatography include adsorption column chromatography using a carrier such as silica gel, alumina or magnesium-silica gel type Florisil, chromatography using a synthetic adsorbent, for example, partition column chromatography using a carrier such as Sephadex LH-20 (product of Pharmacia), Amberlite XAD-11 (product of Rohm & Haas) or Diaion HP-20 (product of Mitsubishi Chemical), ion exchange chromatography or normal-phase-reverse-phase column chromatography (high-performance liquid chromatography) using a silica gel or alkylated silica gel.

Since the compounds of formula (I) of the present invention or pharmacologically acceptable salts, esters or other derivatives thereof exhibit excellent excellent MMP-13 inhibiting activity and an aglycanase inhibiting activity, it is effective as a medicament (particularly, an agent for the prevention or treatment of arthritis, such as osteoarthritis and chronic rheumatism, or a medicament for inhibiting metastasis, invasion or growth of cancer), and examples of the administration route include oral administration in the form of tablets, capsules, granules, powders or syrups and parenteral administration in the form of injections or suppositories. Such formulations can be prepared in a known manner by using carriers such as an excipient, lubricant, binder, disintegrator, stabilizer, corrigent or diluent.

Examples of the excipient include organic excipients, e.g., sugar derivatives such as lactose, sucrose, dextrose, mannitol and sorbitol; starch derivatives such as corn starch, potato starch, α-starch, dextrin and carboxymethyl starch; cellulose derivatives such as crystalline cellulose, low-substituted hydroxypropylcellulose, hydroxypropylmethylcellulose, carboxymethylcellulose, calcium carboxymethylcellulose and sodium internally-crosslinked carboxymethylcellulose; gum arabic; dextran; and pullulan; and inorganic excipients, e.g., silicate derivatives such as soft silicic acid anhydride, synthetic aluminum silicate and magnesium aluminometasilicate; phosphates such as calcium phosphate; carbonates such as calcium carbonate; and sulfates such as calcium sulfate.

Examples of the lubricant include stearic acid; metal salts of stearic acid such as calcium stearate and magnesium stearate; talc; colloidal silica; waxes such as bee gum and spermaceti; boric acid; adipic acid; sulfates such as sodium sulfate; glycol; fumaric acid; sodium benzoate; DL-leucine; sodium salts of an aliphatic acid; lauryl sulfates such as sodium lauryl sulfate and magnesium lauryl sulfate; silicic acid derivatives such as silicic acid anhydride and silicic acid hydrate; and starch derivatives exemplified above as the excipient.

Examples of the binders include polyvinylpyrrolidone, Macrogol and compounds similar to those exemplified above as the excipient.

Examples of the disintegrator include compounds similar to those exemplified above as the excipient and chemically modified starch or cellulose derivatives such as sodium cross carmellose, sodium carboxymethyl starch and crosslinked polyvinylpyrrolidone.

Examples of the stabilizer include paraoxybenzoate esters such as methylparaben and propylparaben; alcohols such as chlorobutanol, benzyl alcohol and phenylethyl alcohol; benzalkonium chloride; phenol derivatives such as phenol and cresol; thimerosal; dehydroacetic acid; and sorbic acid.

Examples of the corrigent include ordinarily-employed sweeteners, acidifiers and flavors.

The dose of the compound (I) or a pharmacologically acceptable salt, ester or derivative thereof according to the present invention will vary depending on the condition, age of the patient, or administration route. Orally, it is administered to an adult in an amount of 0.1 mg (preferably 1 mg) a day as a lower limit and 1000 mg (preferably 100 mg) a day as an upper limit. It is desired to be administered in one to several portions depending on the condition of the patient. Intravenously, it is administered to an adult in an amount of 0.01 mg (preferably 0.1 mg) a day as a lower limit and 100 mg (preferably 10 mg) a day as an upper limit. It is desired to be administered in one to several portions per day depending on the condition of the patient.

The present invention will hereinafter be described more specifically by examples, formulation examples and test examples. However the present invention is not limited to these.

EXAMPLES

Example 1

(±)-N-Methyl-N-(4-phenoxybenzenesulfonyl)-2-(2-phthalimidoethyl)-glycine (Compound No. 3-179)

(1) (±)-N-(tert-Butoxycarbonyl)-2-(phthalimidoethyl) glycine Allyl Ester

Diethyl azodicarboxylate (5.7 ml, 36.2 mmol, abbreviated as DEAD hereinafter) was added dropwise to a mixture of (±)-N-(tert-butoxycarbonyl)homoserine allyl ester (7.79 g, 30.0 mmol), phthalimide (4.41 g, 30 mmol), triphenylphosphine (9.45 g, 36.0 mmol) and tetrahydrofuiran (75 ml) at room temperature with stirring. This mixture was stirred for 1 hour. The solvent of the reaction mixture was evaporated under reduced pressure. The residue was purified by chromatography on a silica gel column using hexane/ethyl acetate=4/1 as the eluent to afford the desired compound (8.46 g, yield 73%) as a white powder.

$^1$H-Nuclear magnetic resonance spectrum (270 MHz, CDCl$_3$) δ ppm: 7.86–7.83 (2H, m), 7.74–7.70 (2H, m), 5.92–5.77 (1H, m), 5.31–5.19 (3H, m), 4.51–4.39 (3H, m), 3.80 (2H, t, J=7 Hz), 2.30–2.07 (2H, m), 1.44 (9H, s).

(2) (±)-N-(4-Phenoxybenzenesulfonyl)-2-(2-phthalimidoethyl)glycine Ally Ester a) Trifluoroacetic acid (14 ml) was added to a solution of (±)-N-(tert-butoxycarbonyl)-2-(2-phthalimidoethyl)glycine allyl ester (5.60 g, 14.4 mmol), the product of (1) above, in dichloromethane (30 ml) with ice-cooling. This mixture was stirred at room temperature for 2 hours. The solvent of the reaction mixture was evaporated under reduced pressure. Hydrochloric acid (6N) was added to the residue and the mixture was extracted with diethyl ether. The water layer was made basic with potassium carbonate and extracted with ethyl acetate. The organic layer was washed with water, dried over anhydrous magnesium sulfate and concentrated under reduced pressure. Hexane was added to the residue and the mixture was filtered to afford a white powder (3.77 g, yield 91%, de-tert-butoxycarbonylated product).

b) Triethylamine (4.5 ml, 32.4 mmol) was added to a solution of the white powder (3.71 g, 12.9 mmol), product of a) above, in dichloromethane.(40 ml). A solution of 4-phenoxybenzenesulfonyl chloride (3.64 g, 13.5 mmol) in dichloromethane (10 ml) was added dropwise to the solution with ice-cooling. This mixture was stirred at room temperature for 6 hours. The solvent of the reaction mixture was evaporated under reduced pressure. Hydrochloric acid (1N) was added to the residue in order to make it acidic. This was extracted with ethyl acetate. The organic layer was washed with water, dried over anhydrous magnesium sulfate and concentrated under reduced pressure. Diidopropyl ether was added to the residue and the mixture was filtered to afford the desired product (6.30 g, yield 94%) as a white powder.

¹H-Nuclear magnetic resonance spectrum (270 MHz, CDCl₃) δ ppm: 7.86–7.70 (6H, m), 7.40 (2H, t, J=7 Hz), 7.22 (1H, t, J=7 Hz), 7.07–6.98 (4H, m), 5.77–5.60 (1H, m), 5.49 (1H, d, J=9 Hz), 5.20–5.13 (2H, m), 4.36–4.22 (2H, m), 4.13–4.05 (1H, m), 3.97–3.86 (1H, m), 3.79–3.68 (1H, m), 2.20–2.13 (2H, m).

(3) (±)-N-Methyl-N-(4-phenoxybenzenesulfonyl)-2-(2-phthalimidoethyl)glycine Allyl Ester Methyl iodide (0.83 g, 5.8 mmol) and potassium carbonate (5.34 g, 38.4 mmol) were added to a solution of (±)-N-(4-phenoxybenzenesulfonyl)-2-(2-phthalimidoethyl) glycine allyl ester (2.00 g, 3.8 mmol), the product of (2) above, in N,N-dimethylformamide (20 ml). This mixture was stirred at room temperature for 1 hour. The insoluble material was removed by filtration. The filtrate was extracted with ethyl acetate and the organic layer was washed with water, dried over anhydrous magnesium sulfate and concentrated under reduced pressure. The residue was purified by chromatography on a silica gel column using hexane/ethyl acetate=3/1 as the eluant to afford the desired compound (1.90 g, yield 93%) as a colorless oil.

¹H-Nuclear magnetic resonance spectrum (270 MHz, CDCl₃) δ ppm: 7.87–7.70 (6H, m), 7.40 (2H, t, 7 Hz), 7.22 (1H, t, J=7 Hz), 7.08–6.98 (4H, m), 5.80–5.66 (1H, m), 5.28–5.19 (2H, m), 4.78 (1H, dd, J=9 Hz, 5 Hz), 4.49–4.37 (2H, m), 3.88–3.70 (2H, m), 2.93 (3H, s), 2.36–2.23 (1H, m), 2.10–1.96 (1H, m).

(4) (±)-N-Methyl-N-(4-phenoxybenzenesulfonyl)-2-(2-phthalimidoethyl)glycine

Water (1.75 ml), tetrakis(triphenylphosphine)palldium(0) (8.2 mg. 0.007 mmol) and pyrrolidine (0.45 ml, 5.3 mmol) were successively added to a solution of (±)-N-methyl-N-(4-phenoxybenzenesulfonyl)-2-(2-phthalimidoethyl)glycine allyl ester (1.88 g, 3.5 mmol), the product of (3) above, in dioxane (33 ml) and the mixture was stirred at room temperature for 4 hours. The reaction mixture was acidified with hydrochloric acid (1N) and extracted with ethyl acetate. The organic layer was washed with water, dried over anhydrous magnesium sulfate and concentrated under reduced pressure. The crystalline residue was washed with diethyl ether to give the title compound (1.64 g, yield 94%) as a white powder.

¹H-Nuclear magnetic resonance spectrum (270 MHz, CDCl₃-DMSO-d₆) δ ppm: 7.86–7.71 (6H, m), 7.44–7.36 (2H, m), 7.24–7.17 (1H, m), 7.80–6.97 (4H, m), 4.70 (1H, dd, J=10 Hz, 6 Hz), 3.88–3.71 (2H, m), 2.94 (3H, s), 2.38–2.24 (1H, m), 2.07–1.93 (1H, m).

Example 2

(±)-N-Hydroxy-Nα-methyl-Nα-(4-phenoxybenzenesulfonyl)-2-(2-phthalimidoethyl) glycinamnide (Compound No. 3-26)

N,N'-Carbonyldiimidazole (0.60 g, 3.7 mmol) was added to a solution of (±)-N-methyl-N-(4-phenoxybenzenesulfonyl)-2-(2-phthalimidoethyl)glycine (1.50 g, 3.0 mmol), the product of Example 1, in a mixture of dichloromethane (15 ml) and tetrahydrofuran (7.5 ml). The mixture was stirred at room temperature for 2 hours. The reaction mixture was added dropwise to a mixture of aqueous hydroxylamine [50% (wt.), 1.86 ml, 30.3 mmol], tetrahydrofuran (8 ml) and tert-butanol (4 ml) with ice-cooling with stirring and this was stirred for 3 hours. The reaction mixture was acidified with hydrochloric acid (1N) and extracted with ethyl acetate. The organic layer was washed with water, dried over anhydrous magnesium sulfate and concentrated under reduced pressure. The residue was purified by chromatography on a silica gel column using ethyl acetate as the eluant to give the title compound (0.95 g, yield 61%) as a pale yellow amorphous solid.

¹H-Nuclear magnetic resonance spectrum (400 MHz, CDCl₃) δ ppm: 9.38 (1H, br, s), 7.85–7.80 (2H, m), 7.77–7.71 (2H, m), 7.62–7.59 (2H, m), 7.45–7.40 (2H, m), 7.29–7.17 (2H, m), 7.09–7.06 (2H, m), 6.84–6.81 (2H, m), 4.33 (1H, dd, J=9 Hz, 5 Hz), 3.67–3.61 (1H, m), 3.50–3.43 (1H, m), 2.93 (3H, s), 2.38–2.27 (1H, m), 1.61–1.53 (1H, m).

Example 3

(±)-N-Methyl-N-(4-phenoxybenzenesulfonyl)-2-[2-(thiazolidin-2,4-dione-3-yl)ethyl]glycine (1) (±)-N-(tert-Butoxycarbonyl)-2-[2-(thiazolidin-2,4-dione-3-yl)ethyl]glycine Allyl Ester In a similar manner to that described in Example 1(1), a reaction was carried out using thiazolidin-2,4-dione instead of phthalimide to give the desired compound (yield 68%) as a colorless oil.

¹H-Nuclear magnetic resonance spectrum (270 MHz, CDCl₃) δ ppm: 5.98–5.84 (1H, m), 5.38–5.23 (3H, m), 4.63 (1H, dt, J=5 Hz, 1 Hz), 4.43–4.34 (1H, m), 3.94 (2H, s), 3.75 (2H, t, J=7 Hz), 2.24–1.98 (2H, m), 1.46 (9H, s).

(2) (±)-N-(4-Phenoxybenzenesulfonyl)-2-[2-(thiazolidin-2,4-dione-3-yl)ethyl]-glycine Allyl Ester In a similar manner to the procedures described in Example 1(2)-a and b, reactions were carried out using (±)-N-(tert-butoxycarbonyl)-2-[2-(thiazolidin-2,4-dione-3-yl)ethyl]glycine allyl ester, the product of (1) above, instead of (±)-N-(tert-butoxycarbonyl)-2-(2-phthalimdoethyl) glycine allyl ester to afford the desired compound (yield 43%) as a pale yellow oil.

¹H-Nuclear magnetic resonance spectrum (270 MHz, CDCl₃) δ ppm: 7.82–7.77 (2H, m), 7.41 (2H, t, J=7 Hz), 7.23 (1H, t, J=7 Hz), 7.08–6.99 (4H, m), 5.82–5.67 (1H, m), 5.44 (1H, d, J=10 Hz), 5.27–5.21 (2H, m), 4.43 (2H, d, J=5 Hz), 4.08–4.00 (1H, m), 3.95–3.82 (3H, m), 3.73–3.63 (1H, m), 2.14–2.06 (2H, m).

(3) (±)-N-Methyl-N-(4-phenoxybenzenesulfonyl)-2-[2-(thiazolidin(2,4-dione-3-yl)ethyl]glycine Allyl Ester In a similar manner to that described in Example 1(3), a reaction was carried out using (±)-N-(4-phenoxybenzenesulfonyl)-2-[2-(thiazolidin-2,4-dione-3-yl) ethyl]-glycine allyl ester, the product of (2) above, instead of (±)-N-(4-phenoxybenzenesulfonyl)-2-(2-phthalimidoethyl) glycine allyl ester to afford the desired compound (yield 88%) as a colorless amorphous solid.

¹H-Nuclear magnetic resonance spectrum (270 MHz, CDCl₃) δ ppm: 7.78–7.73 (2H, m), 7.42 (2H, t, J=8 Hz), 7.23 (1H, t, J=8 Hz), 7.08–6.99 (4H, m), 5.78–5.64 (1H, m), 5.37–5.19 (2H, m), 4.70 (1H, dd, J=10 Hz, 6 Hz), 4.48–4.36 (2H, m), 3.98 (2H, s), 3.83–3.67 (2H, m), 2.87 (3H, s), 2.29–2.17 (1H., m), 2.07–1.92 (1H, m).

(4) (±)-N-Methyl-N-(4-phenoxybenzenesulfonyl)-2-[2-(thiazolidin-2,4-dione-3-yl)ethyl]glycine In a similar manner to that described in Example 1(4), a reaction was carried out using (±)-N-methyl-N-(4-phenoxybenzenesulfonyl)-2-[2-(thiazolidin-2,4-dione-3-yl) ethyl]glycine allyl ester, the product of (3) above, instead of (±)-N-methyl-N-(4-phenoxybenzenesulfonyl)-2-(2-phthalimidoethyl)glycine allyl ester to give the title compound (quantitative yield) as a pale yellow amorphous solid.

¹H-Nuclear magnetic resonance spectrum (270 MHz, CDCl₃) δ ppm: 7.78–7.73 (2H, m), 7.45–7.37 (2H, m), 7.25–7.19 (1H, m), 7.08–6.99 (4H, m), 4.22 (1H, dd, J=10

Hz, 6 Hz), 3.96 (2H, s), 3.80–3.62 (2H, m), 2.86 (3H, s), 2.32–2.18 (1H, m), 2.03–1.88 (1H, m).

Example 4

(±)-N-Hydroxy-Nα-methyl-Nα-(4-phenoxybenzenesulfonyl)-2-[2-(thiazolidin-2,4-dione-3-yl)ethyl]glycinamide (Compound No. 5-44)

In a similar manner to that described in Example 2, a reaction was carried out using (±)-N-methyl-N-(4-phenoxybenzenesulfonyl)-2-[2-(thiazolidin-2,4-dione-3-yl)ethyl]glycine, product of Example 3 above, instead of (±)-N-methyl-N-(4-phenoxybenzenesulfonyl)-2-(2-phthalimidoethyl)glycine to give the title compound (yield 60%) as a colorless amorphous solid.

$^1$H-Nuclear magnetic resonance spectrum (400 MHz, CDCl$_3$) δ ppm: 9.17 (1H, br.s), 7.78–7.20 (2H, m), 7.48–7.39 (2H, m), 7.30–7.04 (6H, m), 4.33 (1H, dd, J=8 Hz, 6 Hz), 3.96 (1H, d, J=18 Hz), 3.94 (1H, d, J=18 Hz), 3.58–3.51 (1H, m), 3.45–3.38 (1H, m), 2.86 (3H, s), 2.30–2.21 (1H, m), 1.67–1.53 (1H, m).

Example 5

(±)-N-Methyl-N-(4-phenoxybenzenesulfonyl)-2-[2-(quinazolin-2,4-dione-3-yl)ethyl]glycine (Compound No. 1-178)

(1) (±)-2-[2-(1-Benzyloxymethylquinazolin-2,4-dione-3-yl)ethyl]-N-(tert-butoxycarbonyl)glycine Allyl Ester In a similar manner to that described in Example 1(1), a reaction was carried out using 1-benzyloxymethylquinazolin-2,4-dione instead of phthalimide to afford the desired compound (yield 76%) as a colorless oil.

$^1$H-Nuclear magnetic resonance spectrum (270 MHz, CDCl$_3$) δ ppm: 8.18 (1H, dd, J=8 Hz, 1 Hz), 7.67 (1H, dt, J=8 Hz, 1 Hz), 7.48 (1H, br.d, J=8 Hz), 7.31–7.25 (6H, m), 5.88–5.66 (3H, m), 5.53 (1H, br.d, J=9 Hz), 5.24 (1H, br.d, J=17 Hz), 5.16 (1H, br.d, J=10 Hz), 4.71 (2H, s), 4.49–4.42 (3H, m), 4.28–4.10 (2H, m), 2.24–2.17 (2H, m).

(2) (±)-2-[2-(1-Benzyloxymethylquinazolin-2,4-dione-3-yl)ethyl]-N-(4-phenoxybenzenesulfonyl)glycine Allyl Ester In a similar manner to the procedures described in Example 1(2)-a and b, reactions were carried out using (±)-2-[2-(1-benzyloxymethylquinazolin-2,4-dione-3-yl)ethyl]-N-(tert-butoxycarbonyl)glycine allyl ester, the product of (1) above, instead of (±)-N-(tert-butoxycarbonyl)-2-(2-phthalimidoethyl)glycine allyl ester to afford the desired compound (yield 88%) as a colorless oil.

$^1$H-Nuclear magnetic resonance spectrum (270 MHz, CDCl$_3$) δ ppm: 8.15 (1H, dd, J=8 Hz, 1 Hz), 7.82–7.77 (2H, m), 7.67 (1H, dt, J=8 Hz, 1 Hz), 7.48 (1H, br.d, J=8 Hz), 7.43–7.35 (2H, m), 7.32–7.18 (7H, m), 7.05–6.94 (4H, m), 5.90 (1H, d, J=9 Hz), 5.68–5.54 (3H, m), 5.15–5.08 (2H, m), 4.71 (2H, s), 4.35–4.03 (5H, m), 2.37–2.23 (1H, m), 2.18–2.05 (1H, m).

(3) (±)-2-[2-(1-Benzyloxymethylquinazolin-2,4-dione-3-yl)ethyl]-N-methyl-N-(4-phenoxybenzenesulfonyl)glycine Allyl Ester In a similar manner to that described in Example 1(3), a reaction was carried out using (±)-2-[2-(1-benzyloxymethylquinazolin-2,4-dione-3-yl)ethyl]-N-(4-phenoxybenzensulfonyl)glycine allyl ester, the product of (2) above, instead of (±)-N-(4-phenoxybenzenesulfonyl)-2-(2-phthalimidoethyl)glycine allyl ester to afford the desired compound (quantitative yield) as a pale yellow oil.

$^1$H-Nuclear magnetic resonance spectrum (270 MHz, CDCl$_3$) δ ppm: 8.16 (1H, dd, J=8 Hz, 1 Hz), 7.80–7.74 (2H, m), 7.67 (1H, dt, J=8 Hz, 1 Hz), 7.48 (1H, br.d, J=8 Hz), 7.43–7.36 (2H, m), 7.31–7.18 (7H, m), 7.08–6.97 (4H, m), 5.82–5.67 (3H, m), 5.28–5.18 (2H, m), 4.83 (1H, dd, J=11 Hz, 6 Hz), 4.70 (2H, s), 4.50–4.37 (2H, m), 4.22–4.04 (2H, m), 2.98 (3H, s), 2.33–2.20 (1H, m), 2.13–1.98 (1H, m).

(4) (±)-2-[2-(1-Benzyloxymethylquinazolin-2,4-dione-3-yl)ethyl]-N-methyl-N-(4-phenoxybenzenesulfonyl)glycine In a similar manner to that described in Example 1(4), a reaction was carried out using (±)-2-[2-(1-benzyloxymethylquinazolin-2,4-dione-3-yl)ethyl]-N-methyl-N-(4-phenoxybenzensulfonyl)glycine allyl ester, the product of (3) above, instead of (±)-N-methyl-N-(4-phenoxybenzenesulfonyl)-2-(2-phthalimidoethyl)glycine allyl ester to afford the desired compound (yield 99%) as a pale yellow amorphous solid.

$^1$H-Nuclear magnetic resonance spectrum (270 MHz, CDCl$_3$) δ ppm: 8.15 (1H, dd, J=8 Hz, 1 Hz), 7.78–7.72 (2H, m), 7.67 (1H, dt, J=8 Hz, 1 Hz), 7.47 (1H, br.d, J=8 Hz), 7.40–7.23 (8H, m), 7.16 (1H, br.t, J=8 Hz), 7.04–6.95 (4H, m), 5.69 (2H, br.s), 4.82 (1H, dd, J=10 Hz, 6 Hz), 4.68 (2H, s), 4.18–3.99 (2H, m), 3.70 (2H, s), 296 (3H, s), 2.35–2.22 (1H, m), 2.09–1.95 (1H, m).

(5) (±)-N-Methyl-N-(4-phenoxybenzenesulfonyl)-2-[2-(quinazolin-2,4-dione-3-yl)ethyl]glycine a) A solution of (±)-2-[2-(1-benzyloxymethylquinazolin-2,4-dione-3-yl)ethyl)]-N-methyl-N-(4-phenoxybenzenesulfonyl)glycine (1.89 g, 3.0 mmol), the product of (4) above, in tetrahydrofuran (30 ml) was added to a suspension of palladium hydroxide (20%, containing 50% water, 0.42 g, 0.30 mmol) in methanol (30 ml). The mixture was stirred vigorously under a hydrogen atmosphere at 50° C. for 2 hours. The reaction mixture was filtered and the filtrate was concentrated under reduced pressure to afford (±)-2-[2-(1-hydroxymethylquinazolin-2,4-dione-3-yl)ethyl]-N-methyl-N-(4-phenoxybenzenesulfonyl)glycine (1.62 g) as a colorless amorphous solid.

$^1$H-Nuclear magnetic resonance spectrum (270 MHz, CDCl$_3$) δ ppm: 8.15 (1H, dd, J=8 Hz, 1 Hz), 7.75–7.65 (3H, m), 7.45 (1H, br.d, J=8 Hz), 7.42–7.33 (2H, m), 7.29–7.16 (2H, m), 7.06–6.94 (4H, m), 5.68 (1H, d, J=11 Hz), 5.58 (1H, d, J=11 Hz), 4.79 (1H, dd, J=10 Hz, 6 Hz), 4.19–4.03 (2H, m), 2.91 (3H, s), 2.35–2.21 (1H, m), 2.07–1.92 (1H, m).

b) After addition of an aqueous solution of sodium hydroxide (1N, 15 ml) to a solution of the 1-hydroxymethyl compound, product of a) above, in tetrahydrofuran (30 ml), the mixture was stirred for 1 hour. The reaction mixture was neutralized with hydrochloric acid (6N) and extracted with ethyl acetate. The organic layer was washed with water, dried over anhydrous magnesium sulfate and concentrated under reduced pressure. The residual solid was washed with diethyl ether to give the title compound (1.33 g, yield 87%) as a white powder.

$^1$H-Nuclear magnetic resonance spectrum (270 MHz, CDCl$_3$-DMSO-d$_6$) δ ppm: 10.60 (1H, br.s), 8.06 (1H, br.d, J=8 Hz), 7.83–7.77 (2H, m), 7.55 (1H, dt, J=8 Hz, 1 Hz), 7.43–7.35 (2H, m), 7.23–7.14 (3H, m), 7.08–6.97 (4H, m), 4.76 (1H, dd, J=11 Hz, 6 Hz), 4.18–4.00 (2H, m), 2.98 (3H, s), 2.38–2.24 (1H, m), 2.12–1.96 (1H, m).

Example 6

(±)-N-Hydroxy-Nα-methyl-Nα-(4-phenoxybenzenesulfonyl)-2-[2-(quinazolin-2,4-dione-3-yl)ethyl]glycinamide (Compound No. 1-25)

In a similar manner to that described in Example 2, a reaction was carried out using (±)-N-methyl-N-(4- phenoxybenzenesulfonyl)-2-[2-(quinazolin-2,4-dione-3-yl) ethyl]glycine, the product of Example 5, instead of (±)-N-methyl-N-(4-phenoxybenzenesulfonyl)-2-(2-phthalimidoethyl)glycine to give the title compound (yield 93%) as a white powder.

Melting Point: 126–128° C. (decomposition); $^1$H-Nuclear magnetic resonance spectrum (400 MHz, DMSO-d$_6$) δ ppm: 11.45 (1H, s), 10.76 (1H, d, J=1 Hz), 8.95–8.94 (1H, m), 7.91 (1H, d, J=7 Hz), 7.79–7.76 (2H, m), 7.68–7.64 (1H, m), 7.47–7.41 (2H, m), 7.26–7.05 (7H, m), 4.32 (1H, dd, J=9 Hz, 6 Hz), 3.80–3.68 (2H, m), 2.95 (3H, s), 1.94–1.75 (2H, m).

Example 7

(±)-N-(4-Phenoxybenzenesulfonyl)-2-[2-(quinazolin-2,4-dione-3-yl)ethyl]glycine (Compound No. 1-177)

(1) (±)-2-[2-(1-Benzyloxymethylquinazolin-2,4-dione-3-yl) ethyl]-N-(4-phenoxy-benzenesulfonyl)glycine In a similar manner to that described in Example 1(4), a de-allylation reaction was carried out using (±)-2-[2-(1-benzyloxymethylquinazolin-2,4-dione-3-yl)ethyl]-N-(4-phenoxybenzensulfonyl)glycine allyl ester, product of Example 5(2), to afford the desired compound (quantitative yield) as a pale yellow amorphous solid.

$^1$H-Nuclear magnetic resonance spectrum (270 MHz, CDCl$_3$) δ ppm: 8.14 (1H, dd, J=8 Hz, 1 Hz), 7.80–7.74 (2H, m), 7.38 (1H, dt, J=8 Hz, 1 Hz), 7.48 (1H, br.d, J=8 Hz), 7.42–7.34 (2H, m), 7.31–7.17 (7H, m), 7.05–7.01 (2H, m), 6.98–6.93 (2H, m), 5.92 (1H, br.d, J=9 Hz), 5.68 (2H, br.s), 4.68 (2H, s), 4.24–4.02 (3H, m), 2.35–2.22 (1H, m), 2.16–2.04 (1H, m).

(2) (±)-N-(4-Phenoxybenzenesulfonyl)-2-[2-(quinazolin-2,4-dione-3-yl)ethyl]-glycine In a similar manner to the procedures described in Example 5(5)-a and b, a de-benzyloxymethylation reaction was carried out using (±)-2-[2-(1-benzyloxymethyl-quinazolin-2,4-dione-3-yl)ethyl]-N-(4-phenoxybenzenesulfonyl)glycine, the product of (1) above, to give the title compound (yield 89%) as a white powder.

$^1$H-Nuclear magnetic resonance spectrum (270 MHz, DMSO-d$_6$) δ ppm: 11.43 (1H, s), 8.19 (1H, br.d, J=9 Hz), 7.91 (1H, br.d, J=7 Hz), 7.80–7.75 (2H, m), 7.66 (1H, dt, J=7 Hz, 1 Hz), 7.49–7.42 (2H, m), 7.27–7.03 (7H, m), 4.02–3.77 (3H, m), 2.02–1.72 (2H, m).

Example 8

(±)-N-Hydroxy-Nα-(4-phenoxybenzenesulfonyl)-2-[2-(2-quinazolin-2,4-dione-3-yl)ethyl]glycinamide (Compound No. 1-9)

In a similar manner to that described in Example 2, a hydroxyamidation reaction was carried out using (±)-N-(4-phenoxybenzenesulfonyl)-2-[2-(quinazolin-2,4-dione-3-yl) ethyl]glycine to give the title compound (yield 73%) as a white powder.

Melting Point: 184–185° C. (decomposition); $^1$H-Nuclear magnetic resonance spectrum (400 MHz, DMSO-d$_6$) δ ppm: 11.42 (1H, s), 10.58(1H, d, J=2 Hz), 8.90 (1H, d, J=2 Hz), 8.10 (1H, d, J=9 Hz), 7.92–7.90 (1H, m), 7.80–7.75 (2H, m), 7.67–7.63 (1H, m), 7.47–7.40 (2H, m), 7.25–7.16 (3H, m), 7.11–7.04 (4H, m), 3.89–3.82 (1H, m), 3.78–3.67 (2H, m), 1.86–1.76 (1H, m), 1.69–1.60 (1H, m).

Example 9

(±)-N-(4-Methoxybenzensulfonyl)-2-[2-(pyrimidin-2,4-dione-3-yl)ethyl]glycine (1) (±)-2-[2-(1-Benzyloxymethylpyrimidin-2,4-dione-3-yl) ethyl]-N-(tert-butoxy-carbonyl)glycine Allyl Ester In a similar manner to that described in Example 1(1), a reaction was carried out using 1-benzyloxymethylpyrimidine-2,4-dione instead of phthalimide to afford the desired compound (yield 78%) as a colorless oil.

$^1$H-Nuclear magnetic resonance spectrum (270 MHz, CDCl$_3$) δ ppm: 7.36–7.30 (5H, m), 7.24 (1H, d, J=8 Hz), 5.96–5.82 (1H, m), 5.74 (1H, d, J=8 Hz), 5.50 (1H, br.d, J=9 Hz), 5.35–5.21 (4H, m), 4.64 (2H, s), 4.57 (2H, br.d, J=6 Hz), 4.48–4.37 (1H, m), 4.12–3.95 (2H, m), 2.17–2.09 (2H, m).

(2) (±)-2-[2-(1-Benzyloxymethylpyrimidin-2,4-dione-3-yl) ethyl]-N-(4-methoxy-benzenesulfonyl)glycine Allyl Ester In a similar manner to the procedures described in Example 1(2)-a and b, reactions were carried out using (±)-2-[2-(1-benzyloxymethylpyrimidin-2,4-dione-3-yl) ethyl]-N-(tert-butoxycarbonyl)glycine allyl ester, the product of (1) above, instead of (±)-N-(tert-butoxycarbonyl)-2-(2-phthalimidoethyl)glycine allyl ester and using 4-methoxybenzenesulfonyl chloride instead of 4-phenoxybenzenesulfonyl chloride to afford the desired compound (yield 93%) as a colorless oil.

$^1$H-Nuclear magnetic resonance spectrum (270 MHz, CDCl$_3$) δ ppm: 7.81–7.76 (2H, m), 7.36–7.30 (5H, m), 7.24 (1H, d, J=8 Hz), 6.95–6.89 (2H, m), 5.80–5.62 (3H, m), 5.23–5.14 (4H, m), 4.64 (2H, s), 4.39–4.27 (2H, m), 4.20–4.04 (2H, m), 3.97–3.87 (1H, m), 3.84 (3H, s), 2.25–1.98 (2H, m).

(3) (±)-2-[2-(1-Benzyloxymethylpyrimidin-2,4-dione-3-yl) ethyl]-N-(4-methoxybenzenesulfonyl)glycine In a similar manner to that described in Example 1(4), a de-allylation reaction was carried out using (±)-2-[2-(1-benzyloxymethylpyrimidin-2,4-dione-3-yl)ethyl]-N-(4-methoxybenzenesulfonyl)glycine allyl ester, product of (2) above, to afford the desired compound (yield 25%) as a colorless amorphous solid.

$^1$H-Nuclear magnetic resonance spectrum (270 MHz, CDCl$_3$) δ ppm: 7.81–7.76 (2H, m), 7.35–7.27 (6H, m), 6.96–6.91 (2H, m), 5.90 (1H, br.d, J=9 Hz), 5.76 (1H, d, J=8 Hz), 5.23 (2H, s), 4.63 (2H, s), 4.10–3.88 (3H, m), 3.84 (3H, s), 2.38–2.15 (1H, m), 2.08–1.97 (1H, m).

(4) (±)-N-(4-Methoxybenzensulfonyl)-2-[2-(pyrimidin-2,4-dione-3-yl)ethyl]glycine In a similar manner to the procedures described in Example 5(5)-a and b, reactions were carried out using (±)-2-[2-(1-benzyloxymethylpyrimidin-2,4-dione-3-yl) ethyl]-N-(4-methoxybenzenesulfonyl)glycine, the product of (3) above, to give the title compound (yield 89%) as a white powder.

$^1$H-Nuclear magnetic resonance spectrum (270 MHz, CDCl$_3$-DMSO-d$_6$) δ ppm: 10.47 (1H, br.d, J=6 Hz), 7.83–7.77 (2H, m), 7.13 (1H, dd, J=8 Hz, 6 Hz), 6.97–6.92 (2H, m), 6.05 (1H, br.d, J=9 Hz), 6.64 (1H, dd, J=8 Hz, 1 Hz), 4.14–3.88 (3H, m), 3.85 (3H, s), 2.23–1.97 (2H, m).

Example 10

(±)-N-Hydroxy-Nα-(4-methoxybenzenesulfonyl)-2-[2-(pyrimidin-2,4-dione-3-yl)ethyl]glycinamide (Compound No. 5-43)

In a similar manner to that described in Example 2, a hydroxyamidation reaction was carried out using (±)-N-(4-methoxybenzensulfonyl)-2-[2-(pyrimidin-2,4-dione-3-yl) ethyl]glycine to give the title compound (yield 59%) as a pale pink powder.

Melting Point: 112–115° C. (decomposition); $^1$H-Nuclear magnetic resonance spectrum (400 MHz, DMSO-d$_6$) δ ppm:

11.09 (1H, br.d, J=6 Hz), 10.53 (1H, br.s), 8.87 (1H, br.s), 7.93 (1H, d, J=9 Hz), 7.73–7.66 (2H, m), 7.40 (1H, dd, J=8 Hz, 6 Hz), 7.06–7.01 (2H, m), 5.55 (1H, dd, J=8 Hz, 1 Hz), 3.82 (3H, s), 3.75–3.54 (3H, m), 1.77–1.68 (1H, m), 1.58–1.49 (1H, m).

Example 11

(±)-N-(4-Methoxybenzenesulfonyl)-2-[2-(quinazolin-2,4-dione-3-yl)ethyl]glycine (Compound No. 1-168)

(1) (±)-N-(tert-Butoxycarbonyl)-2-[2-[1-(2-trimethylsilyl)ethoxyymethylquinazolin-2,4-dione-3-yl]ethyl]glycine Benzyl Ester In a similar manner to that described in Example 1(1), a reaction was carried out using (±)-N-(tert-butoxycarbonyl)homoserine benzyl ester, instead of (±)-N-(tert-butoxycarbonyl)homoserine allyl ester, and 1-(2-trimethylsilyl)ethoxymethyl-quinazolin-2,4-dione, instead of phthalimide, to afford the desired compound (yield 79%) as a colorless oil.

$^1$H-Nuclear magnetic resonance spectrum (270 MHz, CDCl$_3$) δ ppm: 8.17 (1H, dd, J=8 Hz, 1 Hz), 7.66 (1H, dt, J=8 Hz, 1 Hz), 7.43 (1H, br.d, J=8 Hz), 7.39–7.25 (6H, m), 5.55–5.51 (3H, m), 5.02 (1H, br.d, J=13 Hz), 4.96 (1H, br.d, J=13 Hz), 4.53–4.45 (1H, m), 4.30–4.12 (2H, m), 3.75–3.68 (2H, m), 2.26–2.17 (2H, m), 1.44 (9H, s), 0.98–0.91 (2H, m), −0.02 (9H, s).

(2) (±)-N-(4-Methoxybenzenesulfonyl)-2-[2-(quinazolin-2,4-dione-3-yl)ethyl]-glycine Benzyl Ester In a similar manner to the procedures described in Example 1(2)-a and b, reactions were carried out using (±)-N-(tert-butoxycarbonyl)-2-[2-[1-(2-trimethylsilyl)-ethoxymethylquinazolin-2,4-dione-3-yl]ethyl]glycine benzyl ester, the product of (1) above, instead of (±)-N-(tert-butoxycarbonyl)-2-(2-phthalimidoethyl)glycine allyl ester, and using 4-methoxybenzenesulfonyl chloride instead of 4-phenoxybenzenesulfonyl chloride to afford the desired compound (yield 27%) as a pale yellow powder.

$^1$H-Nuclear magnetic resonance spectrum (270 MHz, CDCl$_3$) δ ppm: 9.57 (1H, br.s), 8.07 (1H, br.d, J=8 Hz), 7.79–7.74 (2H, m), 7.61 (1H, dt, J=8 Hz, 1 Hz), 7.29–7.09 (7H, m), 6.88–6.83 (2H, m), 6.24 (1H, br.d, J=9 Hz), 4.85 (1H, d, J=13 Hz), 4.76 (1H, d, J=13 Hz), 4.32–4.02 (3H, m), 3.82 (3H, s), 2.46–2.05 (2H, m).

(3) (±)-N-(4-Methoxybenzenesulfonyl)-2-[2-(quinazolin-2,4-dione-3-yl)ethyl]-glycine In a similar manner to that described in Example 5(5)a, a de-benzylation reaction was carried out using (±)-N-(4-methoxybenzenesulfonyl)-2-[2-(quinazolin-2,4-dione-3-yl)ethyl]glycine benzyl ester, the product of (2) above, to give the title compound (yield 85%) as a white powder.

$^1$H-Nuclear magnetic resonance spectrun (400 MHz, DMSO-d$_6$) δ ppm: 12.69 (1H, br.s), 11.42 (1H, s), 8.05 (1H, br.d, J=9 Hz), 7.91 (1H, d, J=8 Hz), 7.72–7.63 (3H, m), 7.22–7.16 (2H, m), 7.05–7.01 (2H, m), 4.00–3.93 (1H, m), 3.87–3.74 (5H, m), 1.98–1.89 (1H, m), 1.82–1.73 (1H, m).

Example 12

(±)-N-Hydroxy-Nα-(4-methoxybenzenesulfonyl)-2-[2-(quinazolin-2,4-dione-3-yl)ethyl]glycinamide (Compound No. 1-2)

In a similar manner to that described in Example 2, a hydroxyamidation reaction was carried out using (±)-N-(4-methoxybenzenesulfonyl)-2-[2-(quinazolin-2,4-dione-3-yl)ethyl]glycine, the product of Example 11, to give the title compound (yield 83%) as a white powder.

Melting Point: 173–174° C. (decomposition); $^1$H-Nuclear magnetic resonance spectrum (400 MHz, DMSO-d$_6$) δ ppm: 11.41 (1H, br.s), 10.56 (1H, br.s), 8.87(1H, br.s), 7.96–7.90 (2H, m), 7.73–7.63 (3H, m), 7.22–7.15 (2H, m), 7.04–7.00 (2H, m), 3.90–3.65 (6H, m), 1.89–1.75 (1H, m), 1.68–1.59 (1H, m).

Example 13

(±)-N-Methyl-N-(4-phenoxybenzenesulfonyl)-2-[2-(pyrimidin-2,4-dione-3-yl)ethyl]glycine (1) (±)-2-[2-(1-Benzyloxymethylpyrimidin-2,4-dione-3-yl)ethyl]-N-(tert-butoxycarbonyl)glycine Benzyl Ester In a similar manner to that described in Example 1(1), a reaction was carried out using (±)-N-(tert-butoxycarbonyl)homoserine benzyl ester, instead of (±)-N-(tert-butoxycarbonyl)homoserine allyl ester, and using 1-benzyloxymethylpyrimidine-2,4-dione, instead of phthalimide, to afford the desired compound (yield 74%) as a pale yellow oil.

$^1$H-Nuclear magnetic resonance spectrum (270 MHz, CDCl$_3$) δ ppm: 7.47–7.30 (10H, m), 7.21 (1H, d, J=8 Hz), 5.70 (1H, d, J=8 Hz), 5.54 (1H, d, J=9 Hz), 5.19 (2H, s), 5.10 (2H, s), 4.63 (2H, s), 4.50–4.42 (1H, m), 4.08–3.97 (2H, m), 2.18–2.10 (2H, m), 1.44 (9H, s).

(2) (±)-2-[2-(1-Benzyloxymethylpyrimidin-2,4-dione-3-yl)ethyl]-N-(4-phenoxy-benzenesulfonyl)glycine Benzyl Ester In a similar manner to the procedures described in Example 1(2)-a and b, reactions were carried out using (±)-2-[2-(1-benzyloxymethylpyrimidin-2,4-dione-3-yl)ethyl]-N-(tert-butoxycarbonyl)glycine benzyl ester, the product of (1) above, instead of (±)-N-(tert-butoxycarbonyl)-2-(2-phthalimidoethyl)glycine allyl ester to afford the desired compound (yield 79%) as a pale yellow oil.

$^1$H-Nuclear magnetic resonance spectrum (270 MHz, CDCl$_3$) δ ppm: 7.79–7.73 (2H, m), 7.42–7.28 (10H, m), 7.24–7.17 (4H, m), 7.04–6.99 (2H, m), 6.94–6.89 (2H, m), 5.91 (1H, d, J=9 Hz), 5.69 (1H, d, J=8 Hz), 5.19 (2H, s), 4.93 (1H, d, J=12 Hz), 4.84 (1H, d, J=12 Hz), 4.63 (2H, s), 4.21–4.08 (2H, m), 3.98–3.89 (1H, m), 2.32–2.19 (1H, m), 2.12–2.00 (1H, m).

(3) (±)-2-[2-(1-Benzyloxymethylpyrimidin-2,4-dione-3-yl)ethyl]-N-methyl-N-(4-phenoxybenzenesulfonyl)glycine Benzyl Ester In a similar manner to that described in Example 1(3), a methylation reaction was carried out using (±)-2-[2-(1-benzyloxymethylpyrimidin-2,4-dione-3-yl)ethyl]-N-(4-phenoxybenzenesulfonyl)glycine benzyl ester, the product of (2) above, to afford the desired compound (yield 92%) as a colorless oil.

$^1$H-Nuclear magnetic resonance spectrum (270 MHz, CDCl$_3$) δ ppm: 7.74–7.68 (2H, m), 7.44–7.36 (2H, m), 7.35–7.28 (8H, m), 7.25–7.19 (4H, m), 7.06–7.01 (2H, m), 6.93–6.87 (2H, m), 5.74 (1H, d, J=8 Hz), 5.23 (2H, s), 5.02 (1H, d, J=12 Hz), 4.93 (1H, d, J=12 Hz), 4.82 (1H, dd, J=10 Hz, 5 Hz), 4.62 (2H, s), 4.16–3.96 (2H, m), 2.89 (3H, s), 2.28–2.15 (1H, m), 2.08–1.93 (1H, m).

(4) (±)-N-Methyl-N-(4-phenoxybenzenesulfonyl)-2-[2-(pyrimidin-2,4-dione-3-yl)ethyl]glycine In a similar manner to the procedures described in Example 5(5)-a and b, de-benzylation and de-hydroxymethylation reaction were carried out using (±)-2-[2-(1-benzyloxymethylpyrimidin-2,4-dione-3-yl)ethyl]-N-methyl-N-(4-phenoxybenzene-sulfonyl)glycine benzyl ester, the product of (3) above, to give the title compound (yield 85%) as a colorless amorphous solid.

$^1$H-Nuclear magnetic resonance spectrum (270 MHz, CDCl$_3$) δ ppm: 9.90–9.88 (1H, m), 7.77–7.12 (2H, m), 7.45–7.34 (2H, m), 7.23–7.17 (2H, m), 7.06–6.99 (4H, m), 5.76 (1H, d, J=8 Hz), 4.76 (1H, t, J=7 Hz), 3.96 (2H, t, J=7 Hz), 2.86 (3H, s), 2.34–2.09 (1H, m), 1.97–1.84 (1H, m).

Example 14

(±)-N-Hydroxy-Nα-methyl-Nα-(4-phenoxybenzenesulfonyl)-2-[2-(pyrimidin-2,4-dione-3-yl)ethyl]glycinamide (Compound No. 5-29)

In a similar manner to that described in Example 2, a hydroxyamidation reaction was carried out using (±)-N-methyl-N-(4-phenoxybenzenesulfonyl)-2-[2-(pyrimidin-2,4-dione-3-yl)ethyl]glycine, product of Example 13, to give the title compound (yield 87%) as a colorless amorphous solid.

$^1$H-Nuclear magnetic resonance spectrum (400 MHz, CDCl$_3$) δ ppm: 10.05 (1H, s), 10.04 (1H, s), 8.53 (1H, s), 7.70 (2H, d, J=9 Hz), 7.42–7.38 (2H, m), 7.25–7.19 (2H, m), 7.07–6.98 (4H, m), 5.73 (1H, d, J=10 Hz), 4.12 (1H, dd, J=14 Hz, 7 Hz), 3.80 (2H, t, J=6 Hz), 2.84 (3H, s), 2.30–2.22 (1H, m), 1.58–1.53 (1H, m).

Example 15

(±)-2-[2-(5-Methylpyrimidin-2,4-dione-3-yl)ethyl]-N-methyl-N-(4-phenoxybenzenesulfonyl)glycine (1) (±)-2-[2-(1-Benzyloxymethyl-5-methylpyrimidin-2,4-dione-3-yl)ethyl]-N-(tert-butoxycarbonyl)glycine Benzyl Ester In a similar manner to that described in Example 1(1), a reaction was carried out using (±)-N-(tert-butoxycarbonyl) homoserine benzyl ester, instead of (±)-N-(tert-butoxycarbonyl)homoserine allyl ester, and using 1-benzyloxymethyl-5-methyl-pyrimidine-2,4-dione, instead of phthalimide, to afford the desired compound (yield 51%) as a white powder.

$^1$H-Nuclear magnetic resonance spectrum (270 MHz, CDCl$_3$) δ ppm: 7.34–7.28 (10H, m), 7.06 (1H, s), 5.71 (1H, d, J=8 Hz), 5.20 (2H, s), 5.13 (1H, d, J=12 Hz), 5.08 (1H, d, J=12 Hz), 4.60 (2H, s), 4.18–4.07 (3H, m), 3.58–3.47 (1H, m), 2.19–2.09 (1H, m), 1.98–1.82 (4H, m), 1.55 (9H, s).

(2) (±)-2-[2-(1-Benzyloxymethyl-5-methylpyrimidin-2,4-dione-3-yl)ethyl]-N-(4-phenoxybenzenesulfonyl)glycine Benzyl Ester In a similar manner to the procedures described in Example 1(2)-a and b, reactions were carried out using (±)-2-[2-(1-benzyloxymethyl-5-methylpyrimidin-2,4-dione-3-yl)ethyl]-N-(tert-butoxycarbonyl)glycine benzyl ester, the product of (1) above, instead of (±)-N-(tert-butoxycarbonyl)-2-(2-phthalimidoethyl)glycine allyl ester to afford the desired compound (yield 64%) as a colorless amorphous solid.

$^1$H-Nuclear magnetic resonance spectrum (270 MHz, CDCl$_3$) δ ppm: 7.77 (2H, d, J=9 Hz), 7.39 (2H, t, J=8 Hz), 7.35–7.27 (8H, m), 7.22–7.15 (2H, m), 7.06–7.00 (3H, m), 6.92 (2H, dt, J=9 Hz, 3 Hz), 5.95 (1H, d, J=9 Hz), 5.18 (2H, s), 4.90 (1H, d, J=12 Hz), 4.84 (1H, d, J=12 Hz), 4.61 (2H, s), 4.22–4.08 (2H, m), 4.00–3.90 (1H, m), 2.32–2.20 (1H, m), 2.12–1.99 (1H, m), 1.86 (3H, s).

(3) (±)-2-[2-(1-Benzyloxymethyl-5-methylpyrimidin-2,4-dione-3-yl)ethyl]-N-methyl-N-(4-pbenoxybenzenesulfonyl) glycine Benzyl Ester In a similar manner to that described in Example 1(3), a methylation reaction was carried out using (±)-2-[2-(1-benzyloxymethyl-5-methylpyrimidin-2,4-dione-3-yl)ethyl]-N-(4-phenoxybenzenesulfonyl)glycine benzyl ester, the product of (2) above, to afford the desired compound (yield 94%) as a colorless oil.

$^1$H-Nuclear magnetic resonance spectrum (270 MHz, CDCl$_3$) δ ppm: 7.71 (2H, d, J=5 Hz), 7.43–7.24 (11H, m), 7.22–7.17 (2H, m), 7.06–7.02 (3H, m), 6.90 (2H, d, J=5 Hz), 5.23 (2H, s), 5.01 (1H, d, J=12 Hz), 4.96 (1H, d, J=12 Hz), 4.86–4.78 (1H, m), 4.61 (2H, s), 4.08–3.96 (2H, m), 2.86 (3H, s), 2.34–2.18 (1H, m), 2.12–2.00 (1H, m), 1.58 (3H, s).

(4) (±)-2-[2-(5-Methylpyrimidin-2,4-dione-3-yl)ethyl]-N-methyl-N-(4-phenoxy-benzenesulfonyl)glycine In a similar manner to the procedures described in Example 5(5)-a and b, de-benzylation and de-hydroxymethylation reactions were carried out using (±)-2-[2-(1-benzyloxymethyl-5-methylpyrimidin-2,4-dione-3-yl)ethyl]-N-methyl-N-(4-phenoxybenzenesulfonyl) glycine benzyl ester, the product of (3) above, to give the title compound (yield 39%) as a white powder.

$^1$H-Nuclear magnetic resonance spectrum (270 MHz, CDCl$_3$) δ ppm: 9.79 (1H, d, J=3 Hz), 7.74 (2H, d, J=5 Hz), 7.38 (2H, t, J=3 Hz), 7.31–7.22 (1H, m), 7.08–6.95 (5H, m), 4.78 (1H, t, J=9 Hz), 3.99 (2H, t, J=3 Hz), 3.82 (3H, s), 2.30–2.18 (1H, m), 2.10–1.95 (1H, m), 1.57 (3H, s).

Example 16

(±)-N-Hydroxy-2-[2-(5-methylpyrimidin-2,4-dione-3-yl)ethyl]-Nα-methyl-Nα-(4-phenoxybenzenesulfonyl)glycinamide (Compound No. 5-33)

In a similar manner to that described in Example 2, a hydroxyamidation reaction was carried out using (±)-2-[2-(5-methylpyrimidin-2,4-dione-3-yl)ethyl]-N-methyl-N-(4-phenoxybenzenesulfonyl)glycine, the product of Example 15, to give the title compound (yield 65%) as a white powder.

Melting Point: 166–167° C. (decomposition); $^1$H-Nuclear magnetic resonance spectrum (400 MHz, DMSO-d$_6$) δ ppm: 10.93 (1H, s), 10.73(1H, s), 8.94 (1H, s), 7.77 (2H, d, J=9 Hz), 7.45 (2H, t, J=8 Hz), 7.30 (1H, d, J=5 Hz), 7.25 (1H, t, J=7 Hz), 7.14–7.06 (4H, m), 4.27 (1H, dd, J=9 Hz, 6 Hz), 3.65–3.53 (2H, m), 2.92 (3H, s), 1.76–1.66 (5H, m).

Example 17

(±)-2-[2-(5,6-Dimethylpyrimidin-2,4-dione-3-yl) ethyl]-N-methyl-N-(4-phenoxybenzenesulfonyl) glycine (Compound No. 4-178)

(1) (±)-2-[2-(1-Benzyloxymethyl-5,6-dimethylpyrimidin-2,4-dione-3-yl)ethyl]-N-(tert-butoxycarbonyl)glycine Benzyl Ester In a similar manner to that described in Example 1(1), a reaction was carried out using (±)-N-(tert-butoxycarbonyl) homoserine benzyl ester, instead of (±)-N-(tert-butoxycarbonyl)homoserine allyl ester, and using 1-benzyloxymethyl-5-methyl-pyrimidine-2,4-dione, instead of phthalimide, to afford the desired compound (yield 69%) as a pale yellow oil.

$^1$H-Nuclear magnetic resonance spectrum (270 MHz, CDCl$_3$) δ ppm: 7.33–7.26 (10H, m), 5.56 (1H, d, J=9 Hz), 5.41 (2H, s), 5.08 (2H, s), 4.65 (2H, s), 4.48–4.41 (1H, m), 4.10–4.01 (2H, m), 2.31 (3H, s), 2.17–2.07 (2H, m), 1.91 (3H, s), 1.44 (9H, s).

(2) (±)-2-[2-(1-Benzyloxymethyl-5,6-dimethylpyrimidin-2,4-dione-3-yl)ethyl]-N-(4-phenoxybenzenesulfonyl)glycine Benzyl Ester In a similar manner to the procedures described in Example 1(2)-a and b, reactions were carried out using (±)-2-[2-(1-benzyloxymethyl-5,6-dimethylpyrimidin-2,4-dione-3-yl)ethyl]-N-(tert-butoxycarbonyl)glycine benzyl ester, the product of (1) above, instead of (±)-N-(tert-butoxycarbonyl)-2-(2-phthalimidoethyl)glycine allyl ester to afford the desired compound (yield 28%) as a pale yellow oil.

$^1$H-Nuclear magnetic resonance spectrum (270 MHz, CDCl$_3$) δ ppm: 7.79–7.74 (2H, m), 7.42–7.15 (13H, m), 7.04–6.99 (2H, m), 6.94–6.88 (2H, m), 6.02 (1H, d, J=10 Hz), 5.40 (2H, s), 4.91 (1H, d, J=12 Hz), 4.81 (1H, d, 12 Hz), 4.65 (2H, s), 4.19–4.08 (2H, m), 3.99–3.89 (1H, m), 2.33–2.14 (4H, m), 2.11–1.99 (1H, m), 1.90 (3H, s).

(3) (±)-2-[2-(1-Benzyloxymethyl-5,6-dimethylpyrimidin-2,4-dione-3-yl)ethyl]-N-methyl-N-(4-phenoxybenzenesulfonyl)glycine Benzyl Ester In a similar manner to that described in Example 1(3), a methylation reaction was carried out using (±)-2-[2-(1-benzyloxymethyl-5,6-dimethylpyrimidin-2,4-dione-3-yl)ethyl]-N-(4-phenoxybenzenesulfonyl)glycine benzyl ester, the product of (2) above, to afford the desired compound (quantitative yield) as a pale yellow oil.

$^1$H-Nuclear magnetic resonance spectrum (270 MHz, CDCl$_3$) δ ppm: 7.78–7.68 (2H, m), 7.43–7.19 (13H, m), 7.05–7.01 (2H, m), 6.93–6.87 (2H, m), 5.45 (2H, s), 5.01 (1H, d, J=12 Hz), 4.93 (1H, d, J=12 Hz), 4.82 (1H, dd, J=10 Hz, 5 Hz), 4.64 (2H, s), 4.14–3.93 (2H, m), 2.91 (3H, s), 2.33 (3H, s), 2.26–2.13 (1H, m), 2.07–1.94 (4H, m).

(4) (±)-2-[2-(5,6-Dimethylpyrimidin-2,4-dione-3-yl)ethyl]-N-methyl-N-(4-phenoxybenzenesulfonyl)glycine In a similar manner to the procedures described in Example 5(5)-a and b, de-benzylation and de-hydroxymethylation reactions were carried out using (±)-2-[2-(1-benzyloxymethyl-5,6-dimethylpyrimidin-2,4-dione-3-yl)ethyl]-N-methyl-N-(4-phenoxybenzenesulfonyl)glycine benzyl ester, the product of (3) above, to give the title compound (yield 62%) as a colorless amorphous solid.

$^1$H-Nuclear magnetic resonance spectrum (270 MHz, DMSO-d$_6$) δ ppm: 10.96 (1H, s), 7.81–7.76 (2H, m), 7.49–7.43 (2H, m), 7.28–7.22 (1H, m), 7.16–7.07 (4H, m), 4.46 (1H, dd, J=10 Hz, 6 Hz), 3.69 (2H, t, J=8 Hz), 2.82 (3H, s), 2.10–1.98 (4H, m), 1.76–1.66 (4H, m).

Example 18

(±)-2-[2-(5,6-Dimethylpyrimidin-2,4-dione-3-yl)ethyl]-N-hydroxy-Nα-methyl-Nα-(4-phenoxybenzenesulfonyl)glycinamide (Compound No. 4-25)

In a similar manner to that described in Example 2, a hydroxyamidation reaction was carried out using (±)-2-[2-(5,6-dimethylpyrimidin-2,4-dione-3-yl)ethyl]-N-methyl-N-(4-phenoxybenzenesulfonyl)glycine, the product of Example 17, to give the title compound (yield 81%) as a white powder.

Melting Point: 179–180° C.; $^1$H-Nuclear magnetic resonance spectrum (400 MHz, DMSO-d$_6$) δ ppm: 10.94 (1H, s), 10.73(1H, d, J=1 Hz), 8.94 (1H, d, J=2 Hz), 7.78–7.75 (2H, m), 7.47–7.42 (2H, m), 7.25 (1H, t, J=7 Hz), 7.14–7.08 (4H, m), 4.27 (1H, dd, J=9 Hz, 7 Hz), 3.64–3.52 (2H, m), 2.93 (3H, s), 2.05 (3H, s), 1.84–1.65 (5H, m).

Example 19

(±)-2-(2-Phthalimidoethyl)-N-[4-(pyridin-4-yl)oxybenzenesulfonyl]-glycine (1) (±)-N-(tert-Butoxycarbonyl)-2-(2-phthalimidoethyl)glycine Benzyl Ester In a similar manner to that described in Example 1(1), a reaction was carried out using (±)-N-(tert-butoxycarbonyl)homoserine benzyl ester instead of (±)-N-(tert-butoxycarbonyl)homoserine allyl ester to afford the desired compound (yield 58%) as a white powder.

$^1$H-Nuclear magnetic resonance spectrum (270 MHz, CDCl$_3$) δ ppm: 7.89–7.78 (2H, m), 7.74–7.68 (2H, m), 7.40–7.28 (5H, m), 5.31 1H, d, J=9 Hz), 5.07 (1H, d, J=12 Hz), 5.01 (1H, d, J=12 Hz), 4.51–4.33 (1H, br.s), 3.78 (2H, t, J=9 Hz), 2.30–2.18 (2H, m), 1.43 (9H, s).

(2) (±)-2-(2-Phthalimidoethyl)-N-[4-(pyridin-4-yl)oxybenzensulfonyl]glycine Benzyl Ester In a similar manner to the procedures described in Example 1(2)-a and b, reactions were carried out using (±)-N-(tert-butoxycarbonyl)-2-(2-phthalimidoethyl)glycine benzyl ester, instead of (±)-N-(tert-butoxycarbonyl)-2-(2-phthalimidoethyl)glycine allyl ester, and using 4-(pyridin-4-yl)oxybenzensulfonyl chloride, instead of 4-phenoxybenzenesulfonyl chloride, to afford the desired compound (yield 13%) as a white amorphous solid.

$^1$H-Nuclear magnetic resonance spectrum (270 MHz, CDCl$_3$) δ ppm: 8.52 (1H, d, J=4 Hz), 7.87–7.76 (4H, m), 7.74–7.65 (4H, m), 7.39–7.23 (5H, m), 7.23–7.14 (1H, m), 7.08 (1H, d, J=5 Hz), 6.88 (1H, d, J=3 Hz), 5.51 (1H, d, J=9 Hz), 4.84 (1H, d, J=12 Hz), 4.77 (1H, d, J=12 Hz), 3.98–3.82 (1H, m), 3.80–3.65 (1H, m), 2.25–2.10 (2H, m).

(3) (±)-2-(2-Phthalimidoethyl)-N-[4-(pyrdin-4-yl)oxybenzenesulfonyl]glycine

In a similar manner to that described in Example 5(5)-a, de-benzylation reaction was carried out using (±)-2-(2-phthalimidoethyl)-N-[4-(pyridin-4-yl)oxybenzensulfonyl]glycine benzyl ester, the product of (2) above, to give the title compound (yield 76%) as a brown amorphous solid.

$^1$H-Nuclear magnetic resonance spectrum (270 MHz, CDCl$_3$) δ ppm: 8.53 (1H, d, J=4 Hz), 7.87–7.75 (4H, m), 7.74–7.64 (4H, m), 7.22–7.11 (1H, m), 7.10 (1H, d, J=5 Hz), 6.90 (1H, d, J=4 Hz), 5.62 (1H, d, J=9 Hz), 4.15–4.04 (1H, m), 3.90–3.67 (2H, m), 2.26–2.13 (2H, m).

Example 20

(±)-N-Hydroxy-2-(2-phthalimidoethyl)-Nα-[4-(pyridin-4-yl)oxybenzensulfonyl]glycinamide (Compound No. 3-185)

In a similar manner to that described in Example 2, a hydroxyamidation reaction was carried out using (±)-2-(2-phthalimidoethyl)-N-[4-(pyridin-4-yl)oxybenzene-sulfonyl]glycine, the product of Example 19, to give the title compound (yield 6%) as a yellow amorphous solid.

$^1$H-Nuclear magnetic resonance spectrum (270 MHz, CDCl$_3$-DMSO-d$_6$) δ ppm: 8.55 (1H, d, J=4 Hz), 7.87–7.77 (4H, m), 7.73–7.60 (4H, m), 7.20–7.15 (1H, m), 7.04 (1H, d, J=5 Hz), 6.91 (1H, d, J=4 Hz), 5.55 (1H, d, J=9 Hz), 4.12–4.05 (1H, m), 3.89–3.72 (2H, m), 2.20–2.15 (2H, m).

Example 21

(±)-N-(4-Methoxybenzensulfonyl)-2-(2-phthalimidoethyl)glycine (Compound No. 3-169).

(1) (±)-N-(4-Methoxybenzensulfonyl)-2-(2-phthalimidoethyl)glycine Benzyl Ester

In a similar manner to the procedures described in Example 1(2)-a and b, reactions were carried out using (±)-N-(tert-butoxycarbonyl)-2-(2-phthalimidoethyl)glycine benzyl ester, the product of Example 19(1), instead of (±)-N-(tert-butoxycarbonyl)-2-(2-phthalimidoethyl)glycine allyl ester, and using 4-methoxybenzenesulfonyl chloride, instead of 4-phenoxybenzenesulfonyl chloride, to afford the desired compound (yield 61%) as a white powder.

¹H-Nuclear magnetic resonance spectrum (270 MHz, CDCl₃) δ ppm: 7.83–7.77 (2H, m), 7.73–7.67 (4H, m), 7.33–7.31 (3H, m), 7.16–7.13 (2H, m), 6.87 (2H, d, J=9 Hz), 5.51 (1H, d, J=9 Hz), 4.83 (1H, d, J=12 Hz), 4.76 (1H, d, J=12 Hz), 4.16–4.04 (1H, m), 3.96–3.83 (4H, m), 3.77–3.67 (1H, m), 2.15 (2H, dd, J=12 Hz, 8 Hz).

(2) (±)-N-(4-Methoxybenzenesulfonyl)-2-(2-phthalimidoethyl)glycine

In a similar manner to that described in Example 5(5)-a, a de-benzylation reaction was carried out using (±)-N-(4-methoxybenzensulfonyl)-2-(2-phthalimidoethyl)-glycine benzyl ester, the product of (1) above, to give the title compound (yield 75%) as a white powder.

Melting Point: 189–190° C.; ¹H-Nuclear magnetic resonance spectrum (270 MHz, CDCl₃) δ ppm: 7.84–7.82 (2H, m), 7.79 (2H, d, J=9 Hz), 7.73–7.69 (2H, m), 6.93 (2H, d, J=9 Hz), 5.56 (1H, d, J=8 Hz), 4.05–3.97 (1H, m), 3.93–3.68 (5H, m), 2.15 (2H, dd, J=12 Hz, 8 Hz).

Example 22

(±)-N-Hydroxy-Nα-(4-methoxybenzenesulfonyl)-2-(2-phthalimidoethyl)glycinamide (Compound No. 3-2)

In a similar manner to that described in Example 2, a hydroxyamidation reaction was carried out using (±)-N-(4-methoxybenzenesulfonyl)-2-(2-phthalimidoethyl)-glycine, the product of Example 21, to give the title compound (yield 34%) as a white powder.

Melting Point: 185–187° C. (decomposition); ¹H-Nuclear magnetic resonance spectrum (270 MHz, DMSO-d₆) δ ppm: 10.57 (1H, s), 8.88 (1H, s), 8.00 (1H, d, J=9 Hz), 7.84 (4H, m), 7.70 (2H, d, J=9 Hz), 7.02 (2H, d, J=9 Hz), 3.82 (3H, s), 3.68–3.65 (1H, m), 3.54–3.43 (2H, m), 1.92–1.80 (1H, m), 1.79–1.62 (1H, m).

Example 23

(±)-2-(2-Phthalimidoethyl)-N-(4-trifluoromethoxybenzensulfonyl)-glycine (1) (±)-2-(2-Phthalimidoethyl)-N-(4-trifluoromethoxybenzensulfonyl)glycine Benzyl Ester In a similar manner to the procedures described in Example 1(2)-a and b, reactions were carried out using (±)-N-(tert-butoxycarbonyl)-2-(2-phthalimidoethyl)glycine benzyl ester, the product of Example 19(1), instead of (±)-N-(tert-butoxycarbonyl)-2-(2-phthalimidoethyl)glycine allyl ester, and using 4-trifluoromethoxybenzenesulfonyl chloride, instead of 4-phenoxybenzenesulfonyl chloride, to afford the desired compound (yield 52%) as a yellow powder.

¹H-Nuclear magnetic resonance spectrum (270 MHz, CDCl₃) δ ppm: 7.88 (1H, s), 7.84 (1H, s), 7.83–7.81 (2H, m), 7.73–7.69 (2H, m), 7.43–7.31 (3H, m), 7.22 (1H, s), 7.19 (1H, s), 7.15 (2H, dd, J=7 Hz, 4 Hz), 5.65 (1H, d, J=9 Hz), 4.79 (1H, d, J=12 Hz), 4.72 (1H, d, J=12 Hz), 4.16–4.12 (1H, m), 3.93–3.85 (1H, m), 3.78–3.75 (1H, m), 2.25–2.16 (2H, m).

(2) (±)-2-(2-Phthalimidoethyl)-4-(4-trifluoromethoxybenzenesulfonyl)glycine

In a similar manner to that described in Example 5(5)-a, a de-benzylation reaction was carried out using (±)-2-(2-phthalimidoethyl)-4-(4-trifluoromethoxybenzene-sulfonyl) glycine benzyl ester, the product of Example 23(1), to give the title compound (yield 69%) as a yellow powder.

¹H-Nuclear magnetic resonance spectrum (270 MHz, CDCl₃) δ ppm: 7.87 (1H, s), 7.84 (1H, s), 7.83–7.80 (2H, m), 7.74–7.69 (2H, m), 7.18–7.11 (2H, m), 5.65 (1H, d, J=9 Hz), 4.00 (1H, d, J=9 Hz), 3.93–3.80 (1H, m), 3.78–3.65 (1H, m), 2.50 (2H, dd, J=12 Hz, 7 Hz).

Example 24

(±)-N-Hydroxy-2-(2-phthalimidoethyl)-Nα-(4-trifluoromethoxy-benzenesulfonyl)glycinamide (Compound No. 3-172)

In a similar manner to that described in Example 2, a hydroxyamidation reaction was carried out using (±)-2-(2-phthalimidoethyl)-N-(4-trifluoromethoxybenzene-sulfonyl) glycine, the product of Example 23, to give the title compound (yield 63%) as a white powder.

Melting Point: 153–155° C. (decomposition); ¹H-Nuclear magnetic resonance spectrum (270 MHz, DMSO-d₆) δ ppm: 10.62 (1H, s), 8.99–8.75 (1H, br.s), 8.43 (1H, d, J=9 Hz), 7.95–7.70 (6H, m), 7.52 (2H, d, J=9 Hz), 3.76 (1H, dd, J=10 Hz, 3 Hz), 3.60–3.42 (2H, m), 1.94–1.81 (1H, m), 1.75–1.66 (1H, m).

Example 25

(±)-N-(4-Phenoxybenzensulfonyl)-2-(2-phthalimidoethyl)glycine (Compound No. 3-178)

(1) (±)-N-(4-Phenoxybenzensulfonyl)-2-(2-phthalimidoethyl)glycine Benzyl Ester

In a similar manner to the procedures described in Example 1(2)-a and b, reactions were carried out using (±)-N-(tert-butoxycarbonyl)-2-(2-phthalimidoethyl)glycine benzyl ester, the product of Example 19(1), instead of (±)-N-(tert-butoxycarbonyl)-2-(2-phthalimidoethyl)glycine allyl ester, to afford the desired compound (yield 54%) as a pale yellow amorphous solid.

¹H-Nuclear magnetic resonance spectrum (270 MHz, CDCl₃) δ ppm: 7.88–7.67 (6H, m), 7.42–7.10 (8H, m), 7.02 (2H, d, J=6 Hz), 6.91 (2H, d, J=6 Hz), 5.52 (1H, d, J=9 Hz), 4.85 (1H, d, J=12 Hz), 4.80 (1H, d, J=12 Hz), 4.19–4.03 (1H, m), 3.99–3.81 (1H, m), 3.79–3.64 (1H, m), 2.25–2.10 (2H, m).

(2) (±)-N-(4-Phenoxybenzensulfonyl)-2-(2-phthalimidoethyl)glycine

In a similar manner to that described in Example 5(5)-a, a de-benzylation reaction was carried out using (±)-N-(4-phenoxybenzenesulfonyl)-2-(2-phthalimidoethyl)-glycine benzyl ester, the product of (1) above, to give the title compound (yield 67%) as a white amorphous solid.

¹H-Nuclear magnetic resonance spectrum (270 MHz, CDCl₃) δ ppm: 7.95–7.69 (6H, m), 7.50 (2H, t, J=4 Hz), 7.20 (1H, t, J=3 Hz), 7.13–6.98 (4H, m), 5.62 (1H, d, J=9 Hz), 4.15–4.02 (1H, m), 3.91–3.68 (2H, m), 2.19 (2H, dt, J=12 Hz, 8 Hz).

Example 26

(±)-N-Hydroxy-Nα-(4-phenoxybenzenesulfonyl)-2-(2-phthalimidoethyl)glycinamide (Compound No. 3-10)

In a similar manner to that described in Example 2, a hydroxyamidation reaction was carried out using (±)-N-(4-phenoxybenzenesulfonyl)-2-(2-phthalimidoethyl)-glycine, the product of Example 25, to give the title compound (yield 10%) as a white powder.

Melting Point: 91–96° C.; ¹H-Nuclear magnetic resonance spectrum (270 MHz, DMSO-d₆) δ ppm: 7.84(4H, s), 7.76 (2H, d, J=9 Hz), 7.44 (2H, t, J=8 Hz), 7.23 (1H, t, J=8

Hz), 7.13 (2H, d, J=9 Hz), 7.05 (2H, d, J=9 Hz), 3.68 (1H, t, J=7 Hz), 3.53–3.38 (2H, m), 1.89–1.83 (1H, m), 1.75–1.69 (1H, m).

Example 27

(±)-N-(4-Phenoxybenzenesulfonyl)-2-(2-phthalimidoethyl)-N-propargylglycine (Compound No. 3-180)

(1) (±)-N-(4-Phenoxybenzenesulfonyl)-2-(2-phthalimidoethyl)-N-propargylglycine Allyl Ester In a similar manner to that described in Example 1(3), a reaction was carried out using propargyl bromide instead of methyl iodide to afford the desired compound (yield 88%) as a pale yellow oil.

[1]H-Nuclear magnetic resonance spectrum (270 MHz, CDCl$_3$) δ ppm: 7.86–7.81 (4H, m), 7.74–7.70 (2H, m), 7.44–7.37 (2H, m), 7.25–7.20 (1H, m), 7.09–7.05 (2H, m), 7.01–6.97 (2H, m), 5.85–5.70 (1H, m), 5.30–5.20 (2H, m), 4.67 (1H, dd, J=9 Hz, 6 Hz), 4.52–4.45 (2H, m), 4.24–4.08 (2H, m), 3.94–3.72 (2H, m), 2.46–2.14 (3H, m).

(2) (±)-N-(4-Phenoxybenzenesulfonyl)-2-(2-phthalimidoethyl)-N-propargylglycine

In a similar manner to that described in Example 1(4), a reaction was carried out using (±)-N-(4-phenoxybenzenesulfonyl)-2-(2-phthalimidoethyl)-N-propargylglycine allyl ester, the product of (1) above, to give the title compound (yield 90%) as a colorless amorphous solid.

[1]H-Nuclear magnetic resonance spectrum (270 MHz, CDCl$_3$) δ ppm: 7.86–7.81 (4H, m), 7.74–7.71 (2H, m), 7.45–7.36 (2H, m), 7.23–7.18 (1H, m), 7.07–7.01 (2H, m), 6.99–6.94 (2H, m), 4.65 (1H, t, J=7 Hz), 4.32 (1H, dd, J=19 Hz, 2 Hz), 4.01 (1H, dd, J=19 Hz, 2 Hz), 3.90–3.67 (2H, m), 2.51–2.39 (1H, m), 2.29 (1H, t, J=2 Hz), 2.25–2.12 (1H, m).

Example 28

(±)-N-Hydroxy-Nα-(4-phenoxybenzenesulfonyl)-2-(2-phthalimidoethyl)-Nα-propargylglycinamide (Compound No. 3-90)

In a similar manner to that described in Example 2, a hydroxyamidation reaction was carried out using (±)-N-(4-phenoxybenzenesulfonyl)-2-(2-phthalimidoethyl)-N-propargylglycine, the product of Example 27, to give the title compound (yield 76%) as a white amorphous solid.

[1]H-Nuclear magnetic resonance spectrum (400 MHz, CDCl$_3$) δ ppm: 9.45 (1H, s), 7.84–7.80 (2H, m), 7.75–7.68 (4H, m), 7.49–7.41 (2H, m), 7.29–7.23 (1H, m), 7.06 (2H, d, J=8 Hz), 6.7 J=9 Hz), 4.37 (1H, dd, J=19 Hz, 2 Hz), 4.26 (1H, dd, J=19 Hz, 2 Hz), 4.21 (1H, dd, J=10 Hz, 5 Hz), 3.65–3.47 (2H, m), 2.54–2.45 (2H, m), 2.30 (1H, t, J=2 Hz), 1.83–1.75 (1H, m).

Example 29

(±)-N-[3-(4-Chlorophenyl)propyl]-N-(4-methoxybenzenesulfonyl)-2-(2-phthalimidoethyl) glycine (Compound No. 3-192)

(1) (±)-N-[3-(Chlorophenyl)propyl]-N-(4-methoxybenzenesulfonyl)-2-(2-phthalimidoethyl)glycine Benzyl Ester In a similar manner to that described in Example 1(3), a reaction was carried out using (±)-N-(4-methoxybenzensulfonyl)-2-(2-phthalimidoethyl)glycine benzyl ester, the product of Example 21(1), instead of (±)-N-(4-phenoxybenzensulfonyl)-2-(2-phthalimidoethyl) glycine allyl ester, and using 3-(4-chlorophenyl)propyl bromide, instead of methyl iodide, to afford the desired compound (yield 25%) as a white powder.

[1]H-Nuclear magnetic resonance spectrum (270 MHz, CDCl$_3$) δ ppm: 7.89–7.82 (2H, m), 7.77–7.68 (2H, m), 7.59 (2H, dt, J=8 Hz, 4 Hz), 7.36–7.28 (3H, m), 7.25–7.14 (4H, m), 7.06 (2H, dt, J=8 Hz, 3 Hz), 6.78 (2H, dt, J=9 Hz, 3 Hz), 4.97 (1H, d, J=12 Hz), 4.93 (1H, d, J=12 Hz), 4.72–4.62 (1H, m), 3.86–3.77 (4H, m), 3.26–3.11 (1H, m), 3.03–2.89 (1H, m), 2.51 (2H, dt, J=7 Hz, 3 Hz), 2.37–2.23 (1H, m), 2.15–1.92 (2H, m), 1.33–1.22 (2H, m).

(2) (±)-N-[3-(4-Chlorophenyl)propyl]-4-(4-methoxybenzenesulfonyl)-2-(2-phthalimidoethyl)glycine In a similar manner to that described in Example 5(5)-a, a de-benzylation reaction was carried out using (±)-N-[3-(4-chlorophenyl)propyl]-4-(4-methoxybenzene-sulfonyl)-2-(2-phthalimidoethyl)glycine benzyl ester, the product of (1) above, to give the title compound (yield 22%) as a white powder.

Melting Point: 140–142° C.; [1]H-Nuclear magnetic resonance spectrum (270 MHz, CDCl$_3$) δ ppm: 7.89–7.80 (2H, m), 7.79–7.71 (2H, m), 7.66 (2H, d, J=9 Hz), 7.22 (2H, d, J=8 Hz), 7.12 (2H, d, J=8 Hz), 6.86 (2H, d, J=9 Hz), 4.48 (1H, t, J=7 Hz), 3.81 (3H, s), 3.59 (2H, t, J=7 Hz), 3.47–3.09 (1H, m), 2.68–2.50 (2H, m), 2.40–2.22 (1H, m), 2.16–1.94 (2H, m), 1.92–1.80 (2H, m).

Example 30

(±)-Nα-[3-(4-Chlorophenyl)propyl]-N-hydroxy-Nα-(4-methoxy-benzenesulfonyl)-2-(2-phthalimidoethyl)glycinamide (Compound No. 3-7)

In a similar manner to that described in Example 2, a hydroxyamidation reaction was carried out using (±)-N-[3-(4-chlorophenyl)propyl]-4-(4-methoxybenzene-sulfonyl)-2-(2-phthalimidoethyl)glycine, the product of Example 29, to give the title compound (yield 42%) as a white powder.

Melting Point: 158–160° C. (Decomposition); [1]H-Nuclear magnetic resonance spectrum (400 MHz, DMSO-d$_6$) δ ppm: 10.71 (1H, s), 8.97 (1H, s), 7.90–7.82 (4H, m), 7.66 (2H, d, J=9 Hz), 7.31 (2H, d, J=8 Hz), 7.20 (2H, d, J=8 Hz), 7.02 (2H, d, J=9 Hz), 4.25 (1H, t, J=7 Hz), 3.83 (3H, s), 3.51–3.46 (2H, m), 3.23–3.04 (1H, m), 1.99–1.90 (3H, m), 1.84–1.70 (1H, m).

Example 31

(±)-N-(4-Methoxybenzenesulfonyl)-2-(2-phthalimidoethyl)-N-(pyridin-3-yl)methylglycine (Compound No. 3-191)

(1) (±)-N-(4-Methoxybenzenesulfonyl)-2-(2-phthalimidoethyl)-N-(pyridin-3-yl)methylglycine Benzyl Ester In a similar manner to that described in Example 1(3), a reaction was carried out using (±)-N-(4-methoxybenzensulfonyl)-2-(2-phthalimidoethyl)glycine benzyl ester, the product of Example 21(1), instead of (±)-N-(4-phenoxybenzensulfonyl)-2-(2-phthalimidoethyl) glycine allyl ester, and using (pyridin-3-yl)methyl chloride, instead of methyl iodide, to afford the desired compound (yield 51%) as a colorless oil.

[1]H-Nuclear magnetic resonance spectrum (270 MHz, CDCl$_3$) δ ppm: 8.44 (1H, d, J=5 Hz), 8.35 (1H, s), 7.86–7.78 (2H, m), 7.77–7.63 (6H, m), 7.42–7.30 (2H, m), 7.27–7.22 (2H, m), 7.16 (1H, dd, J=9 Hz, 5 Hz), 6.80 (2H, dt, J=9 Hz, 3 Hz), 4.90 (2H, dd, J=12 Hz, 8 Hz), 4.65 (1H, t, J=7 Hz), 4.50 (1H, d, J=12 Hz), 4.40 (1H, d, J=12 Hz), 3.82 (3H, s), 3.72–3.61 (2H, m), 2.38–2.22 (1H, m), 2.00–1.88 (1H, m).

(2) (±)-N-(4-Methoxybenzenesulfonyl)-2-(2-phthalimidoethyl)-N-(pyridin-3-yl)methylglycine In a similar manner to that described in Example 5(5)-a, a de-benzylation reaction was carried out using (±)-N-(4-methoxybenzenesulfonyl)-2-(2-phthalimidoethyl)-N-(pyridin-3-yl)methylglycine benzyl ester, the product of (1) above, to give the title compound (yield 31%) as a white amorphous solid.

$^1$H-Nuclear magnetic resonance spectrum (270 MHz, DMSO-$d_6$) δ ppm: 8.45 (1H, s), 8.40 (1H, d, J=4 Hz), 7.90–7.80 (4H, m), 7.76–7.65 (3H, m), 7.31–7.24 (1H, m), 7.03 (2H, d, J=9 Hz), 4.44 (1H, d, J=8 Hz), 4.40 (1H, d, J=8 Hz), 4.32 (1H, t, J=7 Hz), 3.83 (3H, s), 3.61–3.44 (2H, m), 2.34–2.21 (1H, m), 1.75–1.64 (1H, m).

Example 32

(±)-N-Hydroxy-Nα-(4-methoxybenzensulfonyl)-2-(phthalimidoethyl)-Nα-(pyridin-3-yl)methylglycinamide (Compound No. 3-8)

In a similar manner to that described in Example 2, a hydroxyamidation reaction was carried out using (±)-N-(4-methoxybenzenesulfonyl)-2-(2-phthalimidoethyl)-N-(pyridin-3-yl)methylglycine, the product of Example 31, to give the title compound (yield 35%) as a white powder.

Melting Point: 98–100° C.; $^1$H-Nuclear magnetic resonance spectrum (270 MHz, CDCl$_3$-DMSO-$d_6$) δ ppm: 8.50 (1H, s), 8.38 (1H, d, J=4 Hz), 7.90–7.85 (4H, m), 7.76–7.68 (3H, m), 7.31–7.26 (1H, m), 7.00 (2H, d, J=9 Hz), 4.39 (2H, dd, J=12 Hz, 6 Hz), 4.28 (1H, t, J=8 Hz), 3.80 (3H, s), 3.59–3.46 (2H, m), 2.30–2.25 (1H, m), 1.70–1.62 (1H, m).

Example 33

(±)-N-[3-(4-Chlorophenyl)propargyl]-N-(4-methoxybenzenesulfonyl)-2-(2-phthalimidoethyl)glycine (Compound No. 3-171)

(1) (±)-N-(4-Methoxybenzenesulfonyl)-2-(2-phthalimidoethyl)glycine Methyl Ester

After addition of trimethylsilyl chloride (0.65 g, 5.1 mmol) to a solution of (±)-N-(4-methoxybenzensulfonyl)-2-(2-phthalimidoethyl)glycine (1.08 g, 2.6 mmol), the product of Example 21, in a mixture of methanol (10 ml) and tetrahydrofuran (10 ml), the mixture was heated under reflux for 2 hours. The solvent of the reaction mixture was evaporated under reduced pressure. To the residue, a saturated aqueous solution of sodium hydrogencarbonate was added and this was extracted with ethyl acetate. The organic layer was washed with water, dried over anhydrous magnesium sulfate and concentrated under reduced pressure. Hexane was added to the residue for caking to afford the desired compound (yield 96%) as a white powder.

$^1$H-Nuclear magnetic resonance spectrum (270 MHz, CDCl$_3$) δ ppm: 7.92–7.74 (6H, m), 7.03–6.97 (2H, m), 5.50 (1H, br.d, J=9 Hz), 4.14–4.06 (1H, m), 4.00–3.89 (4H, m), 3.82–3.71 (1H, m), 3.47 (3H, s), 2.23–2.15 (2H, m).

(2) (±)-N-[3-(4-Chlorophenyl)propargyl]-N-(4-methoxybenzenesulfonyl)-2-(2-phthalimidoethyl)glycine Methyl Ester In a similar manner to that described in Example 1(3), a reaction was carried out using (±)-N-(4-methoxybenzenesulfonyl)-2-(2-phthalimidoethyl)glycine methyl ester, the product of (1) above, instead of (±)-N-(4-phenoxybenzensulfonyl)-2-(2-phthalimidoethyl)glycine allyl ester, and using 3-(4-chlorophenyl)propargyl bromide, instead of methyl iodide, to afford the desired compound (yield 97%) as a colorless amorphous solid.

$^1$H-Nuclear magnetic resonance spectrum (270 MHz, CDCl$_3$) δ ppm: 7.89–7.81 (4H, m), 7.75–7.68 (2H, m), 7.25–7.16 (4H, m), 6.94–6.88 (2H, m), 4.71 (1H, dd, J=9 Hz, 7 Hz), 4.44 (1H, d, J=18 Hz), 4.40 (1H, d, J=18 Hz), 3.84–3.78 (4H, m), 3.54 (3H, s), 2.50–2.37 (1H, m), 2.27–2.13 (1H, m).

(3) (±)-N-[3-(4-Chlorophenyl)propargyl]-N-(4-methoxybenzenesulfonyl)-2-(2-phthalimidoethyl)glycine After addition of 1N aqueous solution of sodium hydroxide (5 ml) to a solution of (±)-N-[3-(4-chlorophenyl)propargyl]-N-(4-methoxybenzenesulfonyl)-2-(2-phthalimidoethyl)glycine methyl ester (1.18 g, 2.0 mmol) in methanol (40 ml), the mixture was allowed to stand at room temperature overnight. The reaction mixture was concentrated under reduced pressure, hydrochloric acid (1N, 6 ml) was added to the resulting residue and the mixture was extracted with ethyl acetate. The organic layer was washed with water, dried over anhydrous magnesium sulfate and concentrated under reduced pressure. The residue was purified by chromatography on a silica gel column using dichloromethane/methanol=25/1 as the eluant to give the title compound (0.41 g, yield 35%) as a white powder.

Melting Point: 142–143° C.; $^1$H-Nuclear magnetic resonance spectrum (400 MHz, CDCl$_3$) δ ppm: 7.85–7.80 (4H, m), 7.74–7.70 (2H, m), 7.30–7.20 (4H, m), 6.89–6.85 (2H, m), 4.63 (1H, t, J=8 Hz), 4.44 (1H, d, J=18 Hz), 4.35 (1H, d, J=18 Hz), 3.86–3.68 (5H, m), (2.50–2.42 (1H, m), 2.19–2.10 (1H, m).

Example 34

(±)-Nα-[3-(4-Chlorophenyl)propargyl]-N-hydroxy-Nα-(4-methoxybenzensulfonyl)-2-(phthalimidoethyl)glycinamide (Compound No. 3-5)

In a similar manner to that described in Example 2, a hydroxyamidation reaction was carried out using (±)-N-[3-(4-chlorophenyl)propargyl]-N-(4-methoxybenzene-sulfonyl)-2-(2-phthalimidoethyl)glycine, the product of Example 33, to give the title compound (yield 62%) as a white powder.

Melting Point: 138–139° C.; $^1$H-Nuclear magnetic resonance spectrum (400 MHz, CDCl$_3$) δ ppm: 9.44 (1H, br.s), 7.86–7.70 (6H, m), 7.31–7.22 (4H, m), 6.65 (2H, d, J=9 Hz), 4.49 (2H, s), 4.30 (1H, dd, J=10 Hz, 5 Hz), 3.74 (3H, s), 3.65–3.58 (1H, m), 3.55–3.45 (1H, m), 2.59–2.50 (1H, m), 1.92–1.84 (1H, m).

Example 35

(±)-N-Methyl-N-(4-phenoxybenzenesulfonyl)-2-[3-(quinazolin-2,4-dione-3-yl)propyl]glycine (1) (±)-2-[3-(1-Benzyloxymethylquinazolin-2,4-dione-3-yl)propyl]-N-(tert-butoxycarbonyl)glycine Benzyl Ester In a similar manner to that described in Example 1(1), a reaction was carried out using (±)-N-(tert-butoxycarbonyl)-2-(3-hydroxypropyl)glycine benzyl ester, instead of (±)-N-(tert-butoxycarbonyl)homoserine allyl ester, and using 1-benzyloxyquinazolin-2,4-dione, instead of phthalimide, to afford the desired compound (yield 85%) as a colorless oil.

$^1$H-Nuclear magnetic resonance spectrum (270 MHz, CDCl$_3$) δ ppm: 8.17 (1H, dd, J=8 Hz, 1 Hz), 7.67 (1H, dt, J=8 Hz, 1 Hz), 7.47 (1H, br.d, J=8 Hz), 7.36–7.23 (11H, m), 5.69 (2H, s), 5.20–5.07 (3H, m), 4.68 (2H, s), 4.44–4.33 (1H, m), 4.05 (2H, br.t, J=7 Hz), 1.97–1.86 (1H, m), 1.81–1.64 (3H, m), 1.41 (9H, s).

(2) (±)-2-[3-(1-Benzyloxymethylquinazolin-2,4-dione-3-yl)propyl]-N-(4-phenoxybenzenesulfonyl)glycine Benzyl Ester In a similar manner to the procedures described in Example 1(2)-a and b, reactions were carried out using (±)-2-[3-(1-benzyloxymethylquinazolin-2,4-dione-3-yl)propyl]-N-(tert-butoxycarbonyl)glycine benzyl ester, the product of (1) above, instead of (±)-N-(tert-butoxycarbonyl)-2-(2-phthalimidoethyl)glycine allyl ester, to afford the desired compound (yield 92%) as a colorless amorphous solid.

$^1$H-Nuclear magnetic resonance spectrum (270 MHz, CDCl$_3$) δ ppm: 8.16 (1H, dd, J=8 Hz, 1 Hz), 7.78–7.63 (3H, m), 7.47 (1H, br.d, J=8 Hz), 7.42–7.16 (14H, m), 7.04–6.92 (4H, m), 5.68 (2H, s), 5.31 (1H, d, J=9 Hz), 4.93 (2H, s), 4.67 (2H, s), 4.10–3.98 (3H, m), 1.87–1.65 (4H, m).

(3) (±)-2-[3-(1-Benzyloxymethylquinazolin-2,4-dione-3-yl)propyl]-N-methyl-N-(4-phenoxybenzenesulfonyl)glycine Benzyl Ester In a similar manner to that described in Example 1(3), a reaction was carried out using (±)-2-[3-(1-benzyloxymethylquinazolin-2,4-dione-3-yl)propyl]-N-(4-phenoxy-benzenesulfonyl)glycine benzyl ester, the product of (2) above, instead of (±)-N-(4-phenoxybenzenesulfonyl)-2-(2-phthalimidoethyl)glycine allyl ester, to afford the desired compound (quantitative yield) as a colorless oil.

$^1$H-Nuclear magnetic resonance spectrum (270 MHz, CDCl$_3$) δ ppm: 8.18 (1H, dd, J=8 Hz, 1 Hz), 7.72–7.64 (3H, m), 7.48 (1H, br.d, J=8 Hz), 7.42–7.17 (14H, m), 7.02 (2H, br.d, J=9 Hz), 6.91–6.86 (2H, m), 5.70 (2H, s), 4.97 (1H, d, J=13 Hz), 4.90 (1H, d, J=13 Hz), 4.81–4.75 (1H, m), 4.68 (2H, s), 4.17–4.08 (2H, m), 2.81 (3H, s), 2.02–1.72 (4H, m).

(4) (±)-N-Methyl-N-(4-phenoxybenzenesulfonyl)-2-[3-(quinazolin-2,4-dione-3-yl)propyl]glycine In a similar manner to the procedures described in Example 5(5)-a and b, de-benzylation and de-hydroxymethylation reactions were carried out using (±)-2-[3-(1-benzyloxymethylquinazolin-2,4-dione-3-yl)propyl]-N-methyl-N-(4-phenoxy-benzenesulfonyl)glycine benzyl ester, the product of (3) above, to give the title compound (yield 80%) as a white powder.

$^1$H-Nuclear magnetic resonance spectrum (400 MHz, DMSO-d$_6$) δ ppm: 12.73 (1H, br.s), 11.43 (1H, s), 7.94–7.92 (1H, m), 7.78–7.74 (2H, m), 7.68–7.63 (1H, m), 7.47–7.43 (2H, m), 7.26–7.17 (3H, m), 7.10–7.04 (4H, m), 4.42 (1H, dd, J=10 Hz, 5 Hz), 3.96–3.85 (2H, m), 2.73 (3H, s), 1.84–1.75 (1H, m), 1.67–1.48 (3H, m).

Example 36

(±)-N-Hydroxy-Nα-methyl-Nα-(4-phenoxybenzensulfonyl)-2-[3-(quinazolin-2,4-dione-3-yl)propyl]glycinamide (Compound No. 1-26)

In a similar manner to that described in Example 2, a hydroxyamidation reaction was carried out using (±)-N-methyl-N-(4-phenoxybenzenesulfonyl)-2-[3-(quinazolin-2,4-dione-3-yl)propyl]glycine, the product of Example 35, to give the title compound (yield 97%) as a white powder.

Melting Point: 152–153° C. (decomposition); $^1$H-Nuclear magnetic resonance spectrum (400 MHz, CDCl$_3$) δ ppm: 11.44 (1H, s), 10.66 (1H, d, J=1 Hz), 8.89 (1H, d, J=1 Hz), 7.93 (1H, d, J=8 Hz), 7.77–7.73 (2H, m), 7.68–7.64 (1H, m), 7.47–7.43 (2H, m), 7.27–7.10 (5H, m), 7.07–7.04 (2H, m), 4.15 (1H, t, J=8 Hz), 3.92–3.80 (2H, m), 2.83 (3H, s), 1.67–1.59 (1H, m), 1.53–1.34 (3H, m).

Example 37

(±)-N-(4-Phenoxybenzenesulfonyl)-N-propargyl-2-[2-(quinazolin-2,4- dione-3-yl)ethyl]glycine (Compound No. 1-179)

(1) (±)-α-[N-(4-Phenoxybenzenesulfonyl)-N-propargylamino]-γ-butyrolactone

In a similar manner to that described in Example 1(3), a reaction was carried out using (±)-α-(4-phenoxybenzenesulfonylamino)-γ-butyrolactone, instead of (±)-N-(4-phenoxybenzensulfonyl)-2-(2-phthalimidoethyl)glycine allyl ester, and using propargyl bromide, instead of methyl iodide, to afford the desired compound (yield 89%) as a white powder.

$^1$H-Nuclear magnetic resonance spectrum (270 MHz, CDCl$_3$) δ ppm: 7.93–7.87 (2H, m), 7.45–7.38 (2H, m), 7.27–7.20 (1H, m), 7.10–7.02 (4H, m), (4H, m), 4.80 (1H, dd, J=11 Hz, 9 Hz), 4.50 (1H, dt, J=9 Hz, 2 Hz), 4.32–4.18 (2H, m), 3.91 (1H, dd, J=18 Hz, 3 Hz), 2.95–2.78 (1H, m), 2.66–2.54 (1H, m), 2.32 (1H, t, J=3 Hz).

(2) (±)-2-(2-Hydroxyethyl)-N-(4-phenoxybenzenesulfonyl)-N-propargylglycine Allyl Ester After addition of a solution of sodium hydroxide (1.05 g, 25.5 mmol) in water (7 ml) to a suspension of (±)-α-[N-(4-phenoxybenzenesulfonyl)-N-propargylamino]-γ-butyrolactone (8.42 g, 22.7 mmol) in ethanol (40 ml), the mixture was stirred at room temperature for 3 hours. The solvent of the reaction mixture was evaporated under reduced pressure. The residue, which was an amorphous solid, was dissolved in N,N-dimethylformamide (40 ml). After addition of allyl bromide (2.15 ml, 25.4 mmol) to the solution, the mixture was stirred at room temperature overnight. A saturated aqueous solution of ammonium chloride and water were added to the reaction mixture, and the mixture was extracted with ethyl acetate. The organic layer was washed with water, dried over anhydrous magnesium sulfate and concentrated under reduced pressure. The residue was purified by chyromatography on a silica gel column using hexane/ethyl acetate=3/1 as the eluant to give the desired compound (8.29 g, yield 85%) as a pale yellow oil.

(3) (±)-N-(4-Phenoxybenzenesulfonyl)-N-propargyl-2-[2-[1-(2-trimethylsilyl)-ethoxymethylquinazolin-2,4-dione-3-yl]ethyl]glycine Allyl Ester In a similar manner to that described in Example 1(1), a reaction was carried out using (±)-2-(2-hydroxyethyl)-N-(4-phenoxybenzenesulfonyl)-N-propargylglycine allyl ester, the product of (2) above, instead of (±)-N-(tert-butoxycarbonyl)homoserine allyl ester, and using 1-(2-trimethylsilyl)ethoxymethylquinazolin-2,4-dione, instead of phthalimide, to afford the desired compound (yield 23%) as a colorless oil.

$^1$H-Nuclear magnetic resonance spectrum (270 MHz, CDCl$_3$) δ ppm: 8.18 (1H, dd, J=8 Hz, 2 Hz), 7.89–7.83 (2H, m), 7.70–7.63 (1H, m), 7.46–7.37 (3H, m), 7.30–7.18 (2H, m), 7.08–6.96 (4H, m), 5.82–5.68 (1H, m), 5.59 (2H, s), 5.27–5.16 (2H, m), 4.75 (1H, dd, J=9 Hz, 7 Hz), 4.56–4.38 (2H, m), 4.33–4.10 (4H, m), 3.74–3.67 (2H, m), 2.45–2.32 (1H, m), 2.28–2.15 (2H, m), 0.98–0.91 (2H, m), −0.02 (9H, s).

(4) (±)-N-(4-Phenoxybenzenesulfonyl)-N-propargyl-2-[2-(quinazolin-2,4-dione-3-yl)ethyl]glycine Allyl Ester In a similar manner to that described in Example 1(2)-a, a reaction effecting removal of the protecting group at the 1-position of the quinazoline ring was carried out using (±)-N-(4-phenoxybenzenesulfonyl)-N-propargyl-2-[2-[1-(2-trimethylsilyl)-ethoxymethylquinazolin-2,4-dione-3-yl]ethyl]glycine allyl ester, the product of (3) above, to afford the desired compound (yield 90%) as a colorless amorphous solid.

(5) (±)-N-(4-Phenoxybenzenesulfonyl)-N-propargyl-2-[2-(quinazolin-2,4-dione-3-yl)ethyl]glycine In a similar manner to that described in Example 33(3), a hydrolysis reaction of an ester was carried out using (±)-N-(4-phenoxybenzenesulfonyl)-N-propargyl-2-[2-(quinazolin-2,4-dione-3-yl)ethyl]glycine allyl ester to give the title compound (yield 97%) as a white powder.

Melting Point: 194–195° C.; $^1$H-Nuclear magnetic resonance spectrum (400 MHz, DMSO-$d_6$) δ ppm: 12.97 (1H, br.s), 11.46 (1H, s), 7.91 (1H, d, J=7 Hz), 7.82–7.79 (2H, m), 7.65 (1H, t, J=7 Hz), 7.48–7.44 (2H, m), 7.28–7.18 (3H, m), 7.11 (2H, d, J=8 Hz), 7.03–6.99 (2H, m), 4.46 (1H, t, J=7 Hz), 4.19 (1H, dd, J=19 Hz, 2 Hz), 4.07–3.86 (3H, m), 3.17 (1H, t, J=2 Hz), 2.33–2.22 (1H, m), 1.98–1.89 (1H, m).

Example 38

(±)-N-Hydroxy-Nα-(4-phenoxybenzensulfonyl)-Nα-propargyl-2-[2-(quinazolin-2,4-dione-3-yl)ethyl]glycinamide (Compound No. 1-89)

In a similar manner to that described in Example 2, a hydroxyamidation reaction was carried out using (±)-N-(4-phenoxybenzenesulfonyl)-N-propargyl-2-[2-(quinazolin-2,4-dione-3-yl)ethyl]glycine, the product of Example 37, to give the title compound (yield 89%) as a white powder.

Melting Point: 161–162° C. (decomposition); $^1$H-Nuclear magnetic resonance spectrum (400 MHz, DMSO-$d_6$) δ ppm: 11.45 (1H, s), 10.76(1H, s), 9.08 (1H, br.s), 7.91 (1H, d, J=8 Hz), 7.89–7.84 (2H, m), 7.68–7.64 (1H, m), 7.48–7.43 (2H, m), 7.28–7.12 (5H, m), 7.07–7.02 (2H, m), 4.47 (1H, dd, J=19 Hz, 2 Hz), 4.30–4.20 (2H, m), 3.87–3.73 (2H, m), 3.09 (1H, t, J=2 Hz), 2.15–2.06 (1H, m), 1.99–1.82 (1H, m).

Example 39

(±)-2-[2-(5-Fluoropyrimidin-2,4-dione-3-yl)ethyl]-N-methyl-N-(4-phenoxybenzenesulfonyl)glycine (1) (±)-2-[2-(1-Benzyloxymethyl-5-fluoropyrimidin-2,4-dione-3-yl)ethyl]-N-(tert-butoxycarbonyl)glycine Benzyl Ester In a similar manner to that described in Example 1(1), a reaction was carried out using (±)-N-(tert-butoxycarbonyl)homoserine benzyl ester, instead of (±)-N-(tert-butoxycarbonyl)homoserine allyl ester, and using 1-benzyloxymethyl-5-fluoro-pyrimidin-2,4-dione instead of phthalimide, to afford the desired compound (yield 54%) as a pale yellow oil.

$^1$H-Nuclear magnetic resonance spectrum (270 MHz, CDCl$_3$) δ ppm: 7.77 (2H, d, J=9 Hz), 7.44–7.27 (3H, m), 7.22–7.19 (2H, m), 7.04 (2H, d, J=8 Hz), 6.94 (2H, d, J=9 Hz), 5.74 (1H, d, J=9 Hz), 5.21 (2H, s), 4.94 (1H, d, J=12 Hz), 4.89 (1H, d, J=12 Hz), 4.64 (2H, s), 4.18–4.15 (2H, m), 4.05–3.92 (1H, m), 2.25–2.06 (2H, m).

(2) (±)-2-[2-(1-Benzyloxymethyl-5-fluoropyrimidin-2,4-dione-3-yl)ethyl]-N-(4-phenoxybenzenesulfonyl)glycine Benzyl Ester In a similar manner to the procedures described in Example 1(2)-a and b, reactions were carried out using (±)-2-[2-(1-benzyloxymethyl-5-fluoropyrimidin-2,4-dione-3-yl)ethyl]-N-(tert-butoxycarbonyl)glycine benzyl ester, the product of (1) above, instead of (±)-N-(tert-butoxycarbonyl)-2-(2-phthalimidoethyl)glycine allyl ester, to afford the desired compound (yield 65%) as a pale yellow amorphous solid.

$^1$H-Nuclear magnetic resonance spectrum (270 MHz, CDCl$_3$) δ ppm: 7.70 (2H, d, J=9 Hz), 7.43–7.29 (12H, m), 7.24–7.18 (2H, m), 7.04 (2H, d, J=8 Hs), 6.89 (2H, d, J=9 Hz), 5.95 (1H, d, J=9 Hz), 5.22 (2H, s), 5.00 (1H, d, J=12 Hz), 4.94 (1H, d, J=12 Hz), 4.63 (2H, s), 4.23–4.05 (2H, m), 4.00–3.86 (1H, m), 2.32–2.16 (1H, m), 2.12–2.00 (1H, m).

(3) (±)-2-[2-(1-Benzyloxymethyl-5-fluoropyrimidin-2,4-dione-3-yl)ethyl]-N-methyl-N-(4-phenoxybenzenesulfonyl)glycine Benzyl Ester In a similar manner to that described in Example 1(3), a reaction was carried out using (±)-2-[2-(1-benzyloxymethyl-5-fluoropyrimidin-2,4-dione-3-yl)ethyl]-N-(4-phenoxybenzenesulfonyl)glycine benzyl ester, the product of (2) above, instead of (±)-N-(4-phenoxybenzensulfonyl)-2-(2-phthalimidoethyl)glycine allyl ester, to afford the desired compound (yield 91%) as a pale yellow amorphous solid.

$^1$H-Nuclear magnetic resonance spectrum (270 MHz, CDCl$_3$) δ ppm: 7.70 (2H, d, J=9 Hz), 7.43–7.29 (12H, m), 7.22–7.18 (2H, m), 7.04 (2H, d, J=8 Hz), 6.90 (2H, d, J=9 Hz), 5.23 (2H, s), 5.00 (1H, d, J=12 Hz), 4.94 (1H, d, J=12 Hz), 4.85–4.79 (1H, m), 4.63 (2H, m), 4.11–3.98 (2H, m), 2.87 (3H, s), 2.27–2.13 (1H, m).

(4) (±)-2-[2-(5-Fluoropyrimidin-2,4-dione-3-yl)ethyl]-N-methyl-N-(4-phenoxy-benzenesulfonyl)glycine In a similar manner to the procedures described in Example 5(5)-a and b, de-benzylation and de-hydroxymethylation reactions were carried out using (±)-2-[2-(1-benzyloxymethyl-5-fluoropyrimidin-2,4-dione-3-yl)ethyl]-N-methyl-N-(4-phenoxybenzenesulfonyl)glycine benzyl ester, the product of (3) above, to give the title compound (yield 78%) as a white amorphous solid.

$^1$H-Nuclear magnetic resonance spectrum (270 MHz, CDCl$_3$) δ ppm: 9.80 (1H, d, J=6 Hz), 7.75 (2H, d, J=9 Hz), 7.39 (2H, t, J=8 Hz), 7.31–7.17 (2H, m), 7.06–6.99 (3H, m), 4.79 (1H, t, J=8 Hz), 3.99 (2H, t, J=7 Hz), 2.83 (3H, s), 2.34–2.24 (1H, m), 2.01–1.88 (1H, m).

Example 40

(±)-2-[2-(5-Fluoropyrimidin-2,4-dione-3-yl)ethyl]-N-hydroxy-Nα-methyl-Nα-(4-phenoxybenzensulfonyl)glycinamide (Compound No. 5-31)

In a similar manner to that described in Example 2, a hydroxyamidation reaction was carried out using (±)-2-[2-(5-fluoropyrimidin-2,4-dione-3-yl)ethyl]-N-methyl-N-(4-phenoxybenzenesulfonyl)glycine, the product of Example 39, to give the title compound (yield 41%) as a pale pink amorphous solid.

$^1$H-Nuclear magnetic resonance spectrum (270 MHz, DMSO-$d_6$) δ ppm: 7.80 (3H, dd, J=12 Hz, 8 Hz), 7.46 (2H, t, J=8 Hz), 7.25 (1H, t, J=7 Hz), 7.15–7.05 (4H, m), 4.28 (1H, dd, J=9 Hz, 6 Hz), 3.66–3.51 (2H, m), 2.91 (3H, s), 1.94–1.71 (2H, m).

Example 41

(±)-N-Methyl-N-(4-phenoxybenzenesulfonyl)-2-[2-(thieno[3,2-d]pyrimidin-2,4-dione-3-yl)ethyl]glycine (1) (±)-α-[N-Methyl-N-(4-phenoxybenzenesulfonyl)amino]-γ-butyrolactone In a similar manner to that described in Example 1(3), a reaction was carried out using (±)-α-(4-phenoxybenzenesulfonylamino)-γ-butyrolactone, instead of (±)-N-(4-phenoxybenzensulfonyl)-2-(2-phthalimidoethyl)glycine, to afford the desired compound (yield 98%) as a white powder.

$^1$H-Nuclear magnetic resonance spectrum (270 MHz, CDCl$_3$) δ ppm: 7.87–7.82 (2H, m), 7.45–7.36 (2H, m), 7.26–7.19 (1H, m), 7.10 (4H, m), 5.01 (1H, dd, J=12 Hz, 9 Hz), 4.43 (1H, dt, J=9 Hz, 2 Hz), 4.36 (1H, ddd, J=11 Hz, 9 Hz, 6 Hz), 2.78 (3H, s), 2.55–2.29 (2H, m).

(2) (±)-2-(2-Hydroxyethyl)-N-methyl-N-(4-phenoxybenzenesulfonyl)glycine Allyl Ester In a similar manner to that described in Example 37(2), a reaction was carried out using (±)-α-[N-methyl-N-(4-phenoxybenzenesulfonyl)amino]-γ-butyrolactone, instead of (±)-α-[N-(4-phenoxybenzenesulfonyl)-N-propargylamino]-γ-butyrolactone, to afford the desired compound (yield 97%) as a pale yellow oil.

$^1$H-Nuclear magnetic resonance spectrum (270 MHz, CDCl$_3$) δ ppm: 7.81–7.75 (2H, m), 7.45–7.38 (2H, m), 7.25–7.19 (1H, m), 7.09–6.99 (4H, m), 5.87–5.72 (1H, m), 5.25–5.17 (2H, m), 4.83 (1H, dd, J=9 Hz, 5 Hz), 4.48–4.35 (2H, m), 3.83–3.72 (2H, m), 2.84 (3H, s), 2.42 (1H, br.t, J=7 Hz), 2.25–2.12 (1H, m), 1.92–1.79 (1H, m).

(3) (±)-N-Methyl-N-(4-phenoxybenzenesulfonyl)-2-[2-[1-(2-trimethylsilyl)ethoxy-methylthieno[3,2-d]pyrimidin-2,4-dione-3-yl]ethyl]glycine Allyl Ester In a similar manner to that described in Example 1(1), a reaction was carried out using (±)-2-(2-hydroxyethyl)-N-methyl-N-(4-phenoxybenzenesulfonyl)glycine allyl ester, the product of (2) above, instead of (±)-N-(tert-butoxycarbonyl)homoserine allyl ester, and using 1-(2-trimethylsilyl)ethoxymethylthieno[3,2-d]pyrimidine-2,4-dione, instead of phthalimide, to afford the desired compound (yield 81%) as a colorless oil.

$^1$H-Nuclear magnetic resonance spectrum (270 MHz, CDCl$_3$) δ ppm: 7.80–7.74 (2H, m), 7.74 (1H, d, J=5 Hz), 7.44–7.36 (2H, m), 7.23–7.18 (1H, m), 7.11–6.98 (5H, m), 5.81–5.66 (1H, m), 5.48 (2H, s), 5.26–5.17 (2H, m), 4.82 (1H, dd, J=10 Hz, 5 Hz), 4.49–4.36 (2H, m), 4.21–4.04 (2H, m), 3.70–3.63 (2H, m), 2.97 (3H, s), 2.33–2.20 (1H, m), 2.14–1.99 (1H, m), 0.96–0.90 (2H, m), −0.02 (9H, s).

(4) (±)-N-Methyl-N-(4-phenoxybenzenesulfonyl)-2-[2-(thieno[3,2-d]pyrimidin-2,4-dione-3-yl)ethyl]glycine In a similar manner to the procedures described in Example 37(4) and (5), deprotection and hydrolysis of ester reactions were successively carried out using (±)-N-methyl-N-(4-phenoxybenzenesulfonyl)-2-[2-[1-(2-trimethylsilyl)ethoxymethyl-thieno[3,2-d]pyrimidin-2,4-dione-3-yl]ethyl]glycine allyl ester to give the title compound (yield 88%) as a white powder.

Melting Point: 218–219° C.;

$^1$H-Nuclear magnetic resonance spectrum (400 MHz, DMSO-d$_6$) δ ppm: 12.90 (1H, br.s), 11.91 (1H, s), 8.07 (1H, d, J=5 Hz), 7.81–7.76 (2H, m), 7.48–7.43 (2H, m), 7.29–7.23 (1H, m), 7.15–7.04 (4H, m), 6.93 (1H, d, J=5 Hz), 4.50 (1H, dd, J=10 Hz, 6 Hz), 3.86–3.75 (2H, m), 2.83 (3H, s), 2.17–2.07 (1H, m), 1.82–1.72 (1H, m).

Example 42

(±)-N-Hydroxy-Nα-methyl-Nα-(4-phenoxybenzensulfonyl)-2-[2-(thieno[3,2-d]pyrimidin-2,4-dione-3-yl)ethyl]glycinamide (Compound No. 5-23)

In a similar manner to that described in Example 2, a hydroxyamidation reaction was carried out using (±)-N-methyl-N-(4-phenoxybenzenesulfonyl)-2-[2-(thieno[3,2-d]pyrimidin-2,4-dione-3-yl)ethyl]glycine, the product of Example 41, to give the title compound (yield 92%) as a white powder.

Melting Point: 186–187° C. (decomposition); $^1$H-Nuclear magnetic resonance spectrum (400 MHz, DMSO-d$_6$) δ ppm: 11.89 (1H, s), 10.75(1H, s), 8.95 (1H, br.s), 8.07 (1H, d, J=5 Hz), 7.79–7.76 (2H, m), 7.47–7.42 (2H, m), 7.26–7.22 (1H, m), 7.14–7.07 (4H, m), 6.92 (1H, d, J=5 Hz), 4.31 (1H, dd, J=9 Hz, 7 Hz), 3.75–3.60 (2H, m), 2.94 (3H, s), 1.91–1.72 (2H, m).

Example 43

(±)-2-[2-(3,7-Dimethylxanthin-1-yl)ethyl]-N-methyl-N-(4-phenoxy-benzenesulfonyl)glycine (1) (±)-2-(2-Bromoethyl)-N-methyl-N-(4-phenoxybenzenesulfonyl)glycine Allyl Ester After triphenylphosphine (4.72 g, 18.0 mmol) was added to a solution of (±)-2-(2-hydroxyethyl)-N-methyl-N-(4-phenoxybenzenesulfonyl)glycine allyl ester (6.08 g, 15.0 mmol), the product of Example 41(2), in tetrahydrofuran (45 ml), a solution of carbon tetrabromide (5.97 g, 18.0 mmol) in tetrahydrofuran (20 ml) was added over 20 minutes to the solution with ice-cooling and with stirring. The mixture was stirred at room temperature for 1 hour. To the reaction mixture, water was added and this was extracted with ethyl acetate. The organic layer was washed with water, dried over anhydrous magnesium sulfate and concentrated under reduced pressure. The residue was purified by chromatography on a silica gel column using hexane/ethyl acetate=5/1 as the eluant to afford the desired compound (6.05 g, yield 86%) as a colorless oil.

$^1$H-Nuclear magnetic resonance spectrum (270 MHz, CDCl$_3$) δ ppm: 7.81–7.76 (2H, m), 7.45–7.38 (2H, m), 7.25–7.19 (1H, m), 7.09–6.99 (4H, m), 5.82–5.68 (1H, m), 5.29–5.21 (2H, m), 4.85 (1H, dd, J=10 Hz, 5 Hz), 4.53–4.40 (2H, m), 3.52–3.35 (2H, m), 2.82 (3H, s), 2.51–2.38 (1H, m), 2.30–2.16 (1H, m).

(2) (±)-2-[2-(3,7-Dimethylxanthin-1-yl)ethyl]-N-methyl-N-(4-phenoxybenzene-sulfonyl)glycine Allyl Ester After addition of 3,7-dimethylxanthin (1.10 g, 6.1 mmol) to a suspension of sodium hydride (60%, 0.24 g, 6.0 mmol) in N,N-dimethylformamide (20 ml), the mixture was stirred at 50° C. for 2 hours. After cooling it to room temperature, a solution of (±)-2-(2-bromoethyl)-N-methyl-N-(4-phenoxybenzenesulfonyl)glycine allyl ester (2.34 g, 5.0 mmol) in N,N-dimethylformamide (10 ml) was added to the reaction mixture. This was heated at 80° C. for 2 hours. After cooling it to room temperature, a saturated aqueous solution of ammonium chloride was added and then this was extracted with ethyl acetate. The organic layer was washed with water, dried over anhydrous magnesium sulfate and concentrated under reduced pressure. The residue was purified by chromatography on a silica gel column using hexane/ethyl acetate 3/1 as the eluant to afford the desired compound (0.86 g, yield 30%) as a colorless amorphous solid.

Melting Point: 207–209° C.; $^1$H-Nuclear magnetic resonance spectrum (270 MHz, CDCl$_3$) δ ppm: 7.80–7.74 (2H, m), 7.51 (1H, s), 7.43–7.36 (2H, m), 7.24–7.18 (1H, m), 7.07–6.97 (4H, m), 5.82–5.67 (1H, m), 5.28–5.18 (2H, m), 4.82 (1H, dd, J=11 Hz, 6 Hz), 4.49–4.37 (2H, m), 4.18–4.01 (2H, m), 3.98 (3H, s), 3.57 (3H, s), 2.97 (3H, s), 2.31–2.18 (1H, m), 2.12–1.98 (1H, m).

(3) (±)-2-[2-(3,7-Dimethylxanthin-1-yl)ethyl]-N-methyl-N-(4-phenoxybenzene-sulfonyl)glycine In a similar manner to that described in Example 33(3), hydrolysis of the ester group was carried out using (±)-2-[2-(3,7-dimethylxanthin-1-yl)ethyl]-N-methyl-N-(4-phenoxybenzenesulfonyl)glycine allyl ester, the product of (2) above, to give the title compound (yield 96%) as a white powder.

$^1$H-Nuclear magnetic resonance spectrum (270 MHz, CDCl$_3$-DMSD-d$_6$) δ ppm: 12.89 (1H, br.s), 8.02 (1H, s), 7.81–7.75 (2H, m), 7.48–7.42 (2H, m), 7.27–7.23 (1H, m), 7.13–7.06 (4H, m), 4.50 (1H, dd, J=10 Hz, 6 Hz), 3.87–3.75 (5H, m), 3.41 (3H, s), 2.84 (3H, s), 2.13–2.05 (1H, m), 1.82–1.72 (1H, m).

Example 44

(±)-2-[2-(3,7-Dimethylxanthin-1-yl)ethyl]-N-hydroxy-Nα-methyl-Nα-(4-phenoxybenzensulfonyl) glycinamide (Compound No. 5-27)

In a similar manner to that described in Example 2, a hydroxyamidation reaction was carried out using (±)-2-[2-(3,7-dimethylxanthin-1-yl)ethyl]-N-methyl-N-(4-phenoxybenzenesulfonyl)glycine, product of Example 43, to give the title compound (yield 87%) as a white powder.

Melting Point: 117–119° C. (decomposition);

$^1$H-Nuclear magnetic resonance spectrum (400 MHz, DMSO-$d_6$) δ ppm: 10.76 (1H, s), 8.94 (1H, s), 8.02 (1H, s), 7.80–7.76 (2H, m), 7.46–7.41 (2H, m), 7.27–7.23 (1H, m), 7.14–7.07 (4H, m), 4.30 (1H, dd, J=9 Hz, 6 Hz), 3.86 (3H, s), 3.76–3.64 (2H, m), 3.40 (3H, s), 2.94 (3H, s), 1.88–1.72 (2H, m).

Example 45

(±)-N-Methyl-2-[2-(1-methylquinazolin-2,4-dione-3-yl)ethyl]-N-(4-phenoxybenzenesulfonyl)glycine (1) (±)-N-Methyl-2-[2-(1-methylquinazolin-2,4-dione-3-yl]ethyl)-N-(4-phenoxybenzenesulfonyl)glycine Allyl Ester In a similar manner to that described in Example 1(1), a reaction was carried out using (±)-2-(2-hydroxyethyl)-N-methyl-N-(4-phenoxybenzenesulfonyl)glycine allyl ester, the product of Example 41(2), instead of (±)-N-(tert-butoxycarbonyl)homoserine allyl ester, and using 1-methylquinazoline-2,4-dione, instead of phthalimide, to afford the desired compound (yield 72%) as a white powder.

$^1$H-Nuclear magnetic resonance spectrum (270 MHz, CDCl$_3$) δ ppm: 8.22–8.19 (1H, m), 7.79–7.66 (3H, m), 7.43–7.36 (2H, m), 7.29–7.18 (3H, m), 7.07–6.99 (4H, m), 5.81–5.67 (1H, m), 5.27–5.18 (2H, m), 4.83 (1H, dd, J=10 Hz, 5 Hz), 4.47–4.37 (2H, m), 4.24–4.06 (2H, m), 3.60 (3H, s), 2.99 (3H, s), 2.35–2.22 (1H, m), 2.15–2.00 (1H, m).

(2) (±)-N-Methyl-2-[2-(1-methylquinazolin-2,4-dione-3-yl)ethyl]-N-(4-phenoxy-benzenesulfonyl)glycine In a similar manner to that described in Example 33(3), hydrolysis of the ester group was carried out using (±)-N-methyl-2-[2-(]-methylquinazolin-2,4dione-3-yl)ethyl]-N-(4-phenoxybenzenesulfonyl)glycine allyl ester, the product of (1) above, to give the title compound (yield 74%) as a colorless amorphous solid.

$^1$H-Nuclear magnetic resonance spectrum (270 MHz, CDCl$_3$) δ ppm: 8.22–8.18 (1H, m), 7.78–7.67 (3H, m), 7.40–7.34 (2H, m), 7.30–7.15 (3H, m), 7.05–6.96 (4H, m), 4.80 (1H, dd, J=10 Hz, 6 Hz), 4.21–4.02 (2H, m), 3.59 (3H, s), 2.98 (3H, s), 2.37–2.24 (1H, m), 2.11–1.97 (1H, m).

Example 46

(±)-N-Hydroxy-Nα-methyl-2-[2-(1-methylquinazolin-2,4-dione-3-yl)ethyl]-Nα-(4-phenoxybenzensulfonyl)glycinamide (Compound No. 5-15)

In a similar manner to that described in Example 2, a hydroxyamidation reaction was carried out using (±)-N-methyl-2-[2-(1-methylquinazolin-2,4-dione-3-yl)ethyl]-N-(4-phenoxybenzenesulfonyl)glycine, the product of Example 45, to give the title compound (yield 76%) as a white powder.

Melting Point: 184–185° C. (decomposition); $^1$H-Nuclear magnetic resonance spectrum (400 MHz, DMSO-$d_6$) δ ppm: 10.77 (1H, s), 8.95 (1H, s), 8.04 (1H, dd, J=8 Hz, 1 Hz), 7.80–7.76 (3H, m), 7.46–7.41 (3H, m), 7.31 (1H, t, J=8 Hz), 7.27–7.23 (1H, m), 7.14–7.06 (4H, m), 4.33 (1H, dd, J=9 Hz, 6 Hz), 3.85–3.74 (2H, m), 3.51 (3H, s), 2.95 (3H, s), 1.94–1.75 (2H, m).

Example 47

(±)-N-Methyl-2-[7-(1-methylxanthin-1-yl)ethyl]-N-(4-phenoxy-benzenesulfonyl)glycine (1) (±)-N-Methyl-2-[2-[7-methyl-3-(2-trimethylsilyl)ethoxymethylxanthin-1-yl]ethyl]-N-(4-phenoxybenzenesulfonyl)glycine Allyl Ester In a similar manner to that described in Example 43(2), a reaction was carried out using 7-methyl-3-(2-trimethylsilyl)ethoxymethylxanthine, instead of 3,7-dimethylxanthine, to afford the desired compound (yield 51%) as a colorless oil.

$^1$H-Nuclear magnetic resonance spectrum (270 MHz, CDCl$_3$) δ ppm: 7.80–7.74 (2H, m), 7.51 (1H, s), 7.43–7.36 (2H, m), 7.25–7.18 (1H, m), 7.08–6.98 (4H, m), 5.81–5.67 (1H, m), 5.53 (2H, s), 5.26–5.17 (2H, m), 4.81 (1H, dd, J=10 Hz, 5 Hz), 4.49–4.46 (2H, m), 4.17 4.02 (2H, m), 3.98 (3H, s), 3.75–3.68 (2H, m), 2.96 (3H, s), 2.30–2.17 (1H, m), 2.12–1.98 (1H, m), 1.01–0.97 (2H, m), –0.02 (9H, s).

(2) (±)-N-Methyl-2-[2-(7-methylxanthin-1-yl)ethyl]-N-(4-phenoxybenzene-sulfonyl)glycine In a similar manner to the procedures described in Example 37(4) and (5), deprotection and ester hydrolysis reactions were carried out using (±)-N-methyl-2-[2-[7-methyl-3-(2-trimethylsilyl)ethoxymethylxanthin-1-yl]ethyl]-N-(4-phenoxybenzenesulfonyl)glycine allyl ester, product of (1) above, to give the title compound (yield 92%) as a white powder.

$^1$H-Nuclear magnetic resonance spectrum (400 MHz, DMSO-$d_6$) δ ppm: 12.90 (1H, br.s), 11.89 (1H, s), 7.93 (1H, s), 7.81–7.76 (2H, m), 7.48–7.43 (2H, m), 7.28–7.23 (1H, m), 7.13–7.03 (4H, m), 4.49 (1H, dd, J=10 Hz, 6 Hz), 3.84 (3H, s), 3.80–3.72 (2H, m), 2.84 (3H, s), 2.13–2.04 (1H, m), 1.80–1.70 (1H, m).

Example 48

(±)-N-Hydroxy-Nα-methyl-2-[2-(7-methylxanthin-1-yl)ethyl]-Nα-(4-phenoxybenzensulfonyl) glycinamide (Compound No. 5-25)

In a similar manner to that described in Example 2, a hydroxyamidation reaction was carried out using (±)-N-methyl-2-[2-(7-methylxanthin-1-yl)ethyl]-N-(4-phenoxy-benzenesulfonyl)glycine, the product of Example 47, to give the title compound (yield 78%) as a white powder.

Melting Point: 194–195° C. (decomposition); $^1$H-Nuclear magnetic resonance spectrum (400 MHz, DMSO-$d_6$) δ ppm: 11.89 (1H, s), 10.75 (1H, d, J=1 Hz), 8.94 (1H, d, J=1 Hz), 7.93 (1H, s), 7.82–7.76 (2H, m), 7.47–7.41 (2H, m), 7.26–7.22 (1H, m), 7.13–7.07 (4H, m), 4.30 (1H, dd, J=9 Hz, 6 Hz), 3.83 (3H, s), 3.71–3.59 (3H, m), 2.94 (3H, s), 1.88–1.70 (2H, m).

Example 49

(±)-Nα-[3-(4-Chlorophenyl)propargyl]-N-hydroxy-Nα-(4-methoxybenzenesulfonyl)valinamide (Compound No. 6-25)

(1) (±)-N-(4-Methoxybenzenesulfonyl)valine Methyl Ester

In a similar manner to that in Example 1(2)-b, a reaction was carried out using (±)-valine methyl ester and 4-methoxybenzenesulfonyl chloride to afford the desired compound (yield 90%) as a white powder.

$^1$H-Nuclear magnetic resonance spectrum (270 MHz, CDCl$_3$) δ ppm: 7.79–7.32 (2H, m), 6.98–6.93 (2H, m), 5.05 (1H, d, J=10 Hz), 3.86 (3H, s), 3.71 (1H, dd, J=10 Hz, 5 Hz), 3.48 (3H, s), 2.08–1.96 (1H, m), 0.95 (3H, d, J=7 Hz), 0.87 (3H, d, J=7 Hz).

(2) (±)-N-[3-(4-Chlorophenyl)propargyl]-N-(4-methoxybenzenesulfonyl)valine Methyl Ester In a similar manner to that described in Example 1(3), a reaction was carried out using (±)-N-(4-methoxybenzenesulfonyl)valine methyl ester, the product of (1) above, and 3-(4-chlorophenyl)propargyl bromide to afford the desired compound (yield 84%) as a white powder.

$^1$H-Nuclear magnetic resonance spectrum (270 MHz, CDCl$_3$) δ ppm: 7.88–7.83 (2H, m), 7.27–7.23 (2H, m), 7.18–7.12 (2H, m), 6.92–6.86 (2H, m), 4.59 (1H, d, J=19 Hz), 4.32 (1H, d, J=19 Hz), 4.15 (1H, d, J=11 Hz), 3.80 (3H, s), 3.51 (3H, s), 2.32–1.75 (1H, m), 1.05 (3H, d, J=7 Hz), 0.95 (3H, d, J=7 Hz).

(3) (±)-N-[3-(4-Chlorophenyl)propargyl]-N-(4-methoxybenzenesulfonyl)valine

In a similar manner to that described in Example 33(3), an ester hydrolysis reaction was carried out using (±)-N-[3-(4-chlorophenyl)propargyl]-N-(4-methoxybenzene-sulfonyl) valine methyl ester, the product of (2) above, to afford the desired compound (yield 36%) as a colorless oil.

$^1$H-Nuclear magnetic resonance spectrum (270 MHz, CDCl$_3$) δ ppm: 7.88–7.83 (2H, m), 7.27–7.21 (2H, m), 7.18–7.15 (2H, m), 6.90–6.86 (2H, m), 4.49 (1H, d, J=19 Hz), 4.41 (1H, d, J=19 Hz), 4.13 (1H, d, J=10 Hz), 3.80 (3H, s), 2.28–1.76 (1H, m), 0.99 (3H, d, J=7 Hz), 0.97 (3H, d, J=7 Hz).

(4) (±)-Nα-[3-(4-Chlorophenyl)propargyl]-N-hydroxy-Nα-(4-methoxybenzene-sulfonyl)valinamide In a similar manner to that described in Example 2, a hydroxyamidation reaction was carried out using (±)-N-[3-(4-chlorophenyl)propargyl]-N-(4-methoxybenzene-sulfonyl)valine, the product of (3) above, to afford the title compound (yield 84%) as a white powder.

Melting Point: 153–154° C.; $^1$H-Nuclear magnetic resonance spectrum (400 MHz, CDCl$_3$) δ ppm: 9.00 (1H, s), 7.85 (2H, d, J=9 Hz), 7.57 (1H, br.s), 7.27–7.26 (2H, m), 7.25–7.19 (2H, m), 6.90 (2H, d, J=9 Hz), 4.55 (1H, d, J=19 Hz), 4.50 (1H, d, J=19 Hz), 3.81 (3H, s), 3.69 (1H, d, J=11 Hz), 2.41–2.32 (1H, m), 0.89 (3H, d, J=6 Hz), 0.71 (3H, d, J=6 Hz).

Example 50

(±)-Nα-[3-(4-Chlorophenyl)propargyl]-N-hydroxy-Nα-(4-phenoxybenzenesulfonyl)valinamide (Compound No. 6-26)

In a similar manner to the procedures described in Example 49(1), (2), (3) and (4), the reactions were carried out using (±)-valine methyl ester and 4-phenoxybenzenesulfonyl chloride as starting materials to give the title compound (total yield through the 4 steps 9%) as a pale yellow amorphous solid.

$^1$H-Nuclear magnetic resonance spectrum (400 MHz, CDCl$_3$) δ ppm: 8.97 (1H, s), 7.87 (2H, d, J=9 Hz), 7.74 (1H, br.s), 7.38 (2H, t, J=8 Hz), 7.26–7.18 (5H, m), 6.97–6.95 (4H, m), 4.57 (1H, d, J=19 Hz), 4.52 (1H, d, J=19 Hz), 3.71 (1H, d, J=11 Hz), 2.44–2.31 (1H, m), 0.91 (3H, d, J=6 Hz), 0.76 (3H, d, J=6 Hz).

Example 51

(±)-N-Hydroxy-Nα-(4-phenoxybenzenesulfonyl)-Nα-propargyl valinamide (Compound No. 6-4)

In a similar manner to that described in Example 49(1), a reaction was carried out using 4-phenoxybenzenesulfonyl chloride, instead of 4-methoxybenzenesulfonyl chloride. Using the product and propargyl bromide, instead of 3-(4-chlorophenyl)-propargyl bromide, a reaction was carried out in a similar manner to that described in Example 49(2). Further, reactions were carried out using the resulting product, in a similar manner to the procedures described in Example 49(3) and (4) to give the title compound (total yield through the 4 steps 24%) as a pale yellow amorphous solid.

$^1$H-Nuclear magnetic resonance spectrum (400 MHz, CDCl$_3$) δ ppm: 8.99 (1H, s), 7.85 (2H, d, J=9 Hz), 7.45–7.39 (2H, m), 7.25–7.21 (1H, m), 7.07–7.03 (4H, m), 4.37 (1H, dd, J=19 Hz, 2 Hz), 4.30 (1H, dd, J=19 Hz, 2 Hz), 3.60 (1H, d, J=11 Hz), 2.36–2.27 (1H, m), 2.22 (1H, t, J=2 Hz), 0.88 (3H, d, J=7 Hz), 0.69 (3H, d, J=7 Hz).

Example 52

(±)-Nα-[3-(4-Chlorophenyl)propargyl]-N-hydroxy-Nα-(4-methoxybenzenesulfonyl)alanine (Compound No. 6-27)

In a similar manner to the procedures described in Example 49(1), (2), (3) and (4), reactions were carried out using (±)-alanine methyl ester and 4-phenoxybenzene-sulfonyl chloride as starting materials to give the title compound (total yield through the 4 steps 58%) as a pale yellow amorphous solid.

$^1$H-Nuclear magnetic resonance spectrum (400 MHz, CDCl$_3$) δ ppm: 9.32 (1H, s), 7.85–7.82 (2H, m), 7.33–7.20 (4H, m), 6.95–6.91 (2H, m), 4.5 (1H, q, J=7 Hz), 4.33 (2H, s), 3.82 (3H, s), 1.32 (3H, d, J=7 Hz).

Example 53

(±)-N-Methyl-N-(4-phenoxybenzenesulfonyl)-2-[2-(pteridin-2,4-dione-3-yl)ethyl]glycine In a similar manner to that described in Example 41(3), a reaction was carried out using 1-(2-trimethtylsilyl) ethoxymethylpteridin-2,4-dione, instead of 1-(2-trimethyl-silyl)ethoxymethylthieno[3,2-d]pyrimidine-2,4-dione, and then, using the resulting allyl ester derivative, deprotection and ester hydrolysis reactions were carried out in a similar manner to that described in Example 41(4) to give the title compound (total yield 53%) as a yellow powder.

$^1$H-Nuclear magnetic resonance spectrum (270 MHz, DMSO-d$_6$) δ ppm: 12.25 (1H, s), 8.67 (1H, d, J=2 Hz), 8.56 (1H, d, J=2 Hz), 7.81 (2H, d, J=9 Hz), 7.46 (2H, t, J=8 Hz), 7.25 (1H, t, J=8 Hz), 7.14–7.05 (4H, m), 4.53 (1H, dd, J=10 Hz, 5 Hz), 3.92–3.80 (2H, m), 2.86 (3H, s), 2.23–2.12 (1H, m), 1.93–1.79 (1H, m).

Example 54

(±)-N-Hydroxy-Nα-methyl-Nα-(4-phenoxybenzenesulfonyl)-2-[2-(pteridin-2,4-dione-3-yl)ethyl]glycinamide (Compound No. 5-21)

In a similar manner to that described in Example 2, a hydroxyamidation reaction was carried out using (±)-N-methyl-N-(4-phenoxybenzenesulfonyl)-2-[2-(pteridin-2,4-dione-3-yl)ethyl]glycine to give the title compound (yield 54%) as a white powder.

$^1$H-Nuclear magnetic resonance spectrum (400 MHz, DMSO-d$_6$) δ ppm: 12.23 (1H, s), 10.77 (1H, s), 8.96 (1H, t, J=1 Hz), 8.67 (1H, d, J=2 Hz), 8.56 (1H, d, J=2 Hz), 7.81–7.78 (2H, m), 7.48–7.43 (2H, m), 7.25 (1H, t, J=7 Hz), 7.16–7.09 (4H, m), 4.33 (1H, t, J=7 Hz), 3.78–3.72 (2H, m), 2.96 (3H, s), 1.95–1.80 (2H, m).

Example 55

(±)-N-[3-(4-Chlorophenyl)propargyl]-N-(4-phenoxybenzenesulfonyl)-2-(phthalimidoethyl)glycine In a similar manner to the procedures described in Example 27(1) and (2), reactions were carried out using 3-(4-chlorophenyl)propargyl bromide, instead of propargyl bromide, to give the title compound (yield 88%) as a pale yellow amorphous solid.

$^1$H-Nuclear magnetic resonance spectrum (270 MHz, CDCl$_3$) δ ppm: 7.87–7.78 (4H, m), 7.74–7.68 (2H, m), 7.42–7.34 (2H, m), 7.26–7.17 (5H, m), 7.01–6.96 (2H, m), 6.94–6.89 (2H, m), 4.67 (1H, t, J=7 Hz), 4.46 (1H, d, J=19 Hz), 4.35 (1H, d, J=19 Hz), 3.78 (2H, t, J=7 Hz), 2.52–2.39 (1H, m), 2.23–2.09 (1H, m).

Example 56

(±)-Nα-[3-(4-Chlorophenyl)propargyl]-N-hydroxy-Nα-(4-phenoxybenzenesulfonyl)-2-(phthalimidoethyl)glycinamide (Compound No. 3-136)

In a similar manner to that described in Example 2, a hydroxyamidation reaction was carried out using (±)-N-[3-(4-chlorophenyl)propargyl]-N-(4-phenoxybenzenesulfonyl)-2-(2-phthalimidoethyl)glycine, the product of Example 55, to give the title compound (yield 61%) as a pale yellow amorphous solid.

$^1$H-Nuclear magnetic resonance spectrum (400 MHz, CDCl$_3$) δ ppm: 9.42 (1H, br.s), 7.84–7.80 (2H, m), 7.75–7.67 (4H, m), 7.44–7.39 (2H, m), 7.27–7.20 (6H, m), 7.00–6.98 (2H, m), 6.63 (2H, d, J=9 Hz), 4.52 (1H, d, J=19 Hz), 4.50 (1H, d, J=19 Hz), 4.29 (1H, dd, J=10 Hz, 5 Hz), 3.70–3.64 (1H, m), 3.58–3.50 (1H, m), 2.60–2.51 (1H, m), 1.90–1.81 (1H, m).

Example 57

(±)-N-(4-Phenoxybenzenesulfonyl)-N-(3-phenylpropargyl)-2-(2-phthalimidoethyl)glycine In a similar manner to the procedures described in Example 27(1) and (2), reactions were carried out using 3-phenylpropargyl bromide, instead of propargyl bromide, to give the title compound (yield 90%) as a pale yellow amorphous solid.

$^1$H-Nuclear magnetic resonance spectrum (270 MHz, CDCl$_3$) δ ppm: 7.89–7.79 (4H, m), 7.74–7.68 (2H, m), 7.40–7.16 (8H, m), 7.00–6.88 (4H, m), 4.75 (1H, t, J=8 Hz), 4.46 (1H, d, J=19 Hz), 4.37 (1H, d, J=19 Hz), 3.87 (1H, t, J=7 Hz), 2.49–2.37 (1H, m), 2.23–2.09 (1H, m).

Example 58

(±)-N-Hydroxy-Nα-(4-phenoxybenzenesulfonyl)-Nα-(3-phenylpropargyl)-2-(2-phthalimidoethyl)glycinamide (Compound No. 3-122)

In a similar manner to that described in Example 2, a hydroxyamidation reaction was carried out using (±)-N-(4-phenoxybenzenesulfonyl)-N-(3-phenylpropargyl)-2-(2-phthalimidoethyl)glycine, the product of Example 57, to give the title compound (yield 87%) as a pale yellow amorphous solid.

$^1$H-Nuclear magnetic resonance spectrum (400 MHz, CDCl$_3$) δ ppm: 9.42 (1H, br.s), 7.83–7.79 (2H, m), 7.74–7.69 (4H, m) 7.48–7.21 (9H, m), 7.00–6.96 (2H, m), 6.62 (2H, d, J=9 Hz), 4.55 (1H, d, J=19 Hz), 4.49 (1H, d, J=19 Hz), 4.31 (1H, dd, J=10 Hz, 5 Hz), 3.71–3.65 (1H, m), 3.59–3.52 (1H, m), 2.62–2.53 (1H, m), 1.91–1.83 (1H, m).

Example 59

(±)-N-(2-Butynyl)-N-(4-phenoxybenzenesulfonyl)-2-(2-phthalimido-ethyl)glycine

In a similar manner to the procedures described in Example 27(1) and (2), reactions were carried out using 1-methanesulfonyloxy-2-butyne, instead of propargyl bromide, to give the title compound (yield 63%) as a pale yellow amorphous solid.

$^1$H-Nuclear magnetic resonance spectrum (270 MHz, CDCl$_3$) δ ppm: 7.87–7.79 (4H, m), 7.75–7.68 (2H, m), 7.44–7.36 (2H, m), 7.23–7.17 (1H, m), 7.07–7.03 (2H, m), 6.98–6.93 (2H, m), 4.62 (1H, t, J=8 Hz), 4.21 (1H, dq, J=19 Hz, 3 Hz), 4.06 (1H, dq, J=19 Hz, 3 Hz), 3.88–3.66 (2H, m), 2.51–2.38 (1H, m), 2.23–2.07 (1H, m), 1.72 (3H, t, J=3 Hz).

Example 60

(±)-Nα-(2-Butynyl)-N-hydroxy-Nα-(4-phenoxybenzenesulfonyl)-2-(2-phthalimidoethyl)glycinamide (Compound No. 3-106)

In a similar manner to that described in Example 2, a hydroxyamidation reaction was carried out using (±)-N-(2-butynyl)-N-(4-phenoxybenzenesulfonyl)-2-(2-phthalimidoethyl)glycine, the product of Example 59, to give the title compound (yield 86%) as a pale yellow amorphous solid.

$^1$H-Nuclear magnetic resonance spectrum (400 MHz, CDCl$_3$) δ ppm: 9.36 (1H, br.s), 7.84–7.79 (2H, m), 7.74–7.68 (4H, m), 7.45–7.40 (2H, m), 7.30–7.22 (2H, m), 7.05 (2H, d, J=8 Hz), 6.75 (2H, d, J=9 Hz), 4.28–4.12 (3H, m), 3.63–3.48 (2H, m), 2.52–2.44 (1H, m), 1.83–1.75 (4H, m).

Example 61

(±)-2-[2-(1,1-Dioxo-1,2-benzisothiazol-3-one-2-yl)ethyl[-N-methyl-N-(4-phenoxybenzenesulfonyl)glycine (Compound No. 2-178)

In a similar manner to that described in Example 43 (2), a reaction was carried out using 1,1-dioxo-1,2-benzisothiazol-3-one, instead of 3,7-dimethylxanthine and, further, a deallylation reaction was carried out using the resulting allyl ester derivative in a similar manner to that described in Example 1(4) to give the title compound (total yield 62%) as a white powder.

$^1$H-Nuclear magnetic resonance spectrum (400 MHz, DMSO-d$_6$) δ ppm: 13.00 (1H, br.s), 8.32 (1H, d, J=7 Hz), 8.11–7.99 (3H, m), 7.81–7.78 (2H), m), 7.48–7.43 (2H, m), 7.27–7.23 (1H, m), m 7.13–7.05 (4H, m), 4.65 (1H, dd, J=9 Hz), 3.82–3.75 (1H, m), 3.66–3.57 (1H, m), 2.80 (3H, s), 2.38–2.29 (1H, m), 2.00–1.90 (1H, m).

Example 62

(±)-2-[2-[2-(1,1-Dioxo-1,2-benzisothiazol-3-one-2-yl)ethyl]-N-hydroxy-Nα-methyl-Nα-(4-phenoxybenzenesulfonyl)glycinamide (Compound No. 2-25)

In a similar manner to that described in Example 2, a hydroxyamidation reaction was carried out using (±)-2-[2-

(1,1-dioxo-1,2-benzisothiazol-3-one-2-yl)ethyl]-N-methyl-N-(4-phenoxybenzenesulfonyl)glycine to give the title compound (yield 65%) as a colorless amorphous solid.

$^1$H-Nuclear magnetic resonance spectrum (400 MHz, CDCl$_3$) δ ppm: 9.23(1H, br.s), 8.02 (1H, d, J=7 Hz), 7.95–7.82 (3H, m), 7.68–7.65 (2H, m), 7.44–7.39 (3H, m), 7.24 (1H, t, J=Hz), 7.10–7.07 (2H, m), 6.85–6.82 (2H, m), 4.51 (1H, dd, J=9 Hz, 6 Hz), 3.78–3.71 (1H, m), 3.61–3.54 (1H, m), 2.91 (3H, s), 2.48–2.39 (1H, m), 1.83–1.61 (1H, m).

Example 63

(±)-N-Methyl-2-[2-(6-methylpyrimidin-2,4-dione-3-yl)ethyl]-N-(4-phenoxybenzenesulfonyl)glycine In a similar manner to that described in Example 41(3), a reaction was carried out using 6-methyl-1-(2-trimethylsilyl)ethoxymethylpyrimidin-2,4-dione, instead of 1-(2-trimethylsilyl)ethoxymethylthieno[3,2-d]pyrimidin-2,4-dione, and then deprotection and ester hydrolysis reactions were carried out using the resulting allyl ester derivative in a similar manner to that described in Example 41(4) to give the title compound (total yield 19%) as a white powder.

$^1$H-Nuclear magnetic resonance spectrum (270 MHz, DMSO-d$_6$) δ ppm: 11.14 (1H, s), 7.79 (2H, d, J=9 Hz), 7.46 (2H, t, J=8 Hz), 7.25 (1H, t, J=8 Hz), 7.13–7.07 (4H, m), 5.46 (1H, s), 4.46 (1H, dd, J=10 Hz, 6 Hz), 3.70–3.65 (2H, m), 2.81 (3H, s), 2.12–2.00 (1H, m), 1.79–1.66 (1H, m).

Example 64

(±)-N-Hydroxy-Nα-methyl-2-[2-(6-methylpyrimidin-2,4-dione-3-yl)ethyl]-Nα-(4-phenoxybenzenesulfonyl)glycinamide (Compound No. 5-39)

In a similar manner to that described in Example 2, a hydroxyamidation reaction was carried out using (±)-N-methyl-2-[2-(6-methylpyrimidin-2,4-dione-3-yl)ethyl]-N-(4-phenoxybenzenesulfonyl)glycine, the product of Example 63, to give the title compound (yield 73%) as a white amorphous solid.

$^1$H-Nuclear magnetic resonance spectrum (400 MHz, CDCl$_3$) δ ppm: 7.76 (1H, br.s), 7.68 (2H, d, J=9 Hz), 7.39 (2H, t, J=8 Hz), 7.21 (1H, t, J=8 Hz), 7.08–7.05 (2H, m), 6.98 (2H, d, J=9 Hz), 5.49 (1H, s), 4.48 (1H, dd, J=8 Hz, 6 Hz), 3.79–3.75 (2H, m), 2.88 (3H, s), 2.30–2.23 (1H, m), 2.09 (3H, s), 1.66–1.61 (1H, m).

Example 65

(±)-N-Methyl-N-(4-phenoxybenzenesulfonyl)-2-[2-(5-trifluoromethyl-pyrimidin-2,4-dione-3-yl)ethyl]glycine In a similar manner to that described in Example 41(3), a reaction was carried out using 5-trifluoromethyl-1-(2-trimethylsilyl)ethoxymethylpyrimidin-2,4-dione, instead of 1-(2-trimethylsilyl)ethoxymethylthieno[3,2-d]pyrimidine-2,4-dione, and then deprotection and ester hydrolysis reactions were carried out using the resulting allyl ester derivative in a similar manner to that described in Example 41(4) to give the title compound (total yield 27%) as a white powder.

$^1$H-Nuclear magnetic resonance spectrum (270 MHz, DMSO-d$_6$) δ ppm: 8.09 (1H, s), 7.79 (2H, d, J=9 Hz), 7.49–7.43 (2H, m), 7.28–7.22 (1H, m), 7.13–7.07 (4H, m), 4.48 (1H, dd, J=10 Hz, 5 Hz), 3.79–3.67 (2H, m), 2.81 (3H, s), 2.15–1.99 (1H, m), 1.84–1.70 (1H, m).

Example 66

(±)-N-Hydroxy-Nα-methyl-Nα-(4-phenoxybenzenesulfonyl)-2-[2-(5-trifluoromethylpyrimidin-2,4-dione-3-yl)ethyl]glycinamide (Compound No. 5-37)

In a similar manner to that described in Example 2, a hydroxyamidation reaction was carried out using (±)-N-methyl-N-(4-phenoxybenzenesulfonyl)-2-[2-(5-trifluoromethylpyrimidin-2,4-dione-3-yl)ethyl]glycine, the product of Example 65, to give the title compound (yield 39%) as a pale yellow amorphous solid.

$^1$H-Nuclear magnetic resonance spectrum (400 MHz, CDCl$_3$) δ ppm: 10.51 (1H, br.s), 9.89 (1H, br.s), 8.41 (1H, br.s), 7.69 (2H, d, J=9 Hz), 7.40–7.36 (2H, m), 7.20 (1H, t, J=7 Hz), 7.05–7.00 (4H, m), 4.56 (1H, br.s), 3.82–3.75 (2H, m), 2.81 (3H, s), 2.25–2.23 (1H, m), 1.79–1.78 (1H, m).

Example 67

(±)-N-Methyl-N-(4-phenoxybenzenesulfonyl)-2-(2-phthalimido-methyl)glycine (1) N-(4-Phenoxybenzenesulfonyl)serinol After triethylamine (10.12 g, 100 mmol) was added dropwise to a solution of serinol (3.64 g, 40 mmol) in a mixture of dioxane (100 ml) and water (200 ml), the mixture was stirred at room temperature for 30 minutes. To the reaction mixture, a solution of 4-phenoxybenzenesulfonyl chloride (10.75 g, 40 mmol) in dioxane (100 ml) was added dropwise and this was stirred for 3 hours. Most of the solvent was evaporated under reduced pressure and the residue was extracted with ethyl acetate. The organic layer was washed with water, dried over anhydrous magnesium sulfate and concentrated under reduced pressure to afford the desired compound (10.62 g, yield 82%) as a white powder.

$^1$H-Nuclear magnetic resonance spectrum (400 MHz, CDCl$_3$-DMSO-d$_6$) δ ppm: 7.84 (2H, d, J=8 Hz), 7.41 (2H, t, J=8 Hz), 7.22 (2H, t, J=7 Hz), 7.09–7.01 (4H, m), 6.69 (1H, d, J=7 Hz), 4.10–4.06 (1H, m), 3.63–3.45 (4H, m).

(2) N-Methyl-N-(4-phenoxybenzenesulfonyl)serinol

After potassium carbonate (45.39 g, 328.4 mmol) was added to a solution of N-(4-phenoxybenzenesulfonyl)serinol (10.62 g, 32.84 mmol), the product of (1) above, in N,N-dimethylformamide (250 ml), methyl iodide (5.12 g, 36.12 mmol) was added dropwise to the mixture. After stirring it at room temperature for 2 hours, the same amount of methyl iodide was further added to this mixture and stirred for 1 hour. The solvent of the reaction mixture was evaporated under reduced pressure, ice-water was added to the resulting residue and this was extracted with ethyl acetate. The organic layer was washed with water, dried over anhydrous magnesium sulfate and concentrated under reduced pressure to afford the desired compound (8.32 g, yield 75%) as a white powder.

$^1$H-Nuclear magnetic resonance spectrum (400 MHz, CDCl$_3$-DMSO-d$_6$) δ ppm: 7.81 (2H, d, J=8 Hz), 7.41 (2H, t, J=8 Hz), 7.22 (1H, t, J=7 Hz), 7.08–7.00 (4H, m), 4.06–3.97 (1H, m), 3.70–3.56 (4H, m), 2.86 (3H, s).

(3) (±)-O-(tert-Butyldimethylsilyl)-N-methyl-N-(4-phenoxybenzenesulfonyl)serinol A solution of tert-butyldimethylsilyl chloride (3.53 g, 23.43 mmol) in N,N-dimethylformamide (50 ml) was added dropwise to a solution of N-methyl-N-(4-phenoxybenzenesulfonyl)serinol (8.32 g, 24.66 mmol), which is the product of Example 67(2), and imidazole (4.13 g, 61.65 mmol) in N,N-dimethylformamide (200 ml) at room temperature with stirring. The mixture was further stirred for 2 hours. The solvent of the reaction mixture was evaporated under reduced pressure. To the residue, water was added and this was extracted with ethyl acetate. The organic layer was washed with water, dried over anhydrous magnesium sulfate and concentrated under reduced pressure. The residue was purified by chromatography on a silica gel column using hexane/ethyl acetate=2/1 as the eluant to afford the desired compound (4.15 g, yield 38%) as a colorless oil.

$^1$H-Nuclear magnetic resonance spectrum (270 MHz, CDCl$_3$) δ ppm: 7.78 (2H, d, J=9 Hz), 7.44–7.38 (2H, m), 7.25–7.19 (1H, m), 7.07–6.99 (4H, m), 4.01 –3.96 (1H, m), 3.74–3.69 (2H, m), 3.66 (2H, d, J=6 Hz), 2.88 (3H, s), 0.84 (9H, s), 0.02 (6H, s).

(4) (±)-1-(tert-Butyldimethylsilyloxymethyl)-N-methyl-N-(4-phenoxybenzene-sulfonyl)-2-phthalimidoethylamine In a similar manner to that described in Example 1(1), a reaction was carried out using (±)-O-(tert-butyldimethylsilyl)-N-methyl-N-(4-phenoxybenzenesulfonyl)-serinol, the product of (3) above, instead of (±)-N-(tert-butoxycarbonyl)homoserine allyl ester, to afford the desired compound (yield 93%) as a white powder.

$^1$H-Nuclear magnetic resonance spectrum (270 MHz, CDCl$_3$) δ ppm: 7.82–7.77 (2H, m), 7.73–7.69 (2H, m), 7.59 (2H, d, J=8 Hz), 7.39 (2H, t, J=8 Hz), 7.20 (1H, t, J=7 Hz), 6.98 (2H, d, J=8 Hz), 6.74 (2H, d, J=8 Hz), 4.37–4.31 (1H, m), 4.02–3.93 (1H, m), 3.72–3.63 (3H, m), 2.97 (3H, s), 0.88 (9H, s), 0.04 (3H, s), 0.02 (3H, s).

(5) (±)-1-Hydroxymethyl-N-methyl-N-(4-phenoxybenzenesulfonyl)-2-phthalimidoethylamine After addition of 1M solution of tetrabutylanimonium fluoride (19.11 ml, 19.11 mmol) in tetrahydrofuran to a solution of (±)-1-(tert-butyldimethylsilyloxymethyl)-N-methyl-N-(4-phenoxybenzenesulfonyl)-2-phthalimidoethylamine (7.40 g, 12.74 mmol), the product of (4) above, in tetrahydrofuran (50 ml), the mixture was stirred at room temperature for 1 hour. The solvent of the reaction mixture was evaporated under reduced pressure. To the resulting residue, water was added and this was extracted with ethyl acetate. The organic layer was washed with water, dried over anhydrous magnesium sulfate and concentrated under reduced pressure. The residue was purified by chromatography on a silica gel column using hexane/ethyl acetate=2/1 as the eluant to afford the desired compound (1.70 g, yield 29%) as a white powder.

$^1$H-Nuclear magnetic resonance spectrum (270 MHz, CDCl$_3$) δ ppm: 7.84–7.78 (2H, m), 7.75–7.70 (2H, m), 7.65 (2H, d, J=9 Hz), 7.39 (2H, t, J=9 Hz), 7.21 (2H, t, J=8 Hz), 7.00 (2H, d, J=8 Hz), 6.78 (2H, d, J=9 Hz), 4.41–4.31 (1H, m), 3.48–3.62 (4H, m), 2.98 (3H, s).

(6) (±)-1-Formyl-N-methyl-N-(4-phenoxybenzenesulfonyl)-2-phthalimido-ethylamine

Oxalyl cloride (0.51 g, 4.00 mmol) and dimethyl sulfoxide (0.63 g, 8.01 mmol) were dissolved in dichloromethane (10 ml) and the solution was cooled to −78° C. To the solution, a solution of (±)-1-hydroxymethyl-N-methyl-N-(4-phenoxybenzene-sulfonyl)-2-phthalimidoethylamine (1.70 g, 3.64 mmol), the product of (5) above, in dichloromethane (25 ml) was added dropwise with stirring and this was stirred for 30 minutes. Triethylamine (1.84 g, 18.2 mmol) was added dropwise to the mixture and this was stirred at room temperature for 2 hours. To the reaction mixture, ice-water was added and then this was extracted with dichloromethane. The organic layer was washed with water, dried over anhydrous magnesium sulfate and concentrated under reduced pressure to afford the desired compound (1.58 g, yield 93%) as a white amorphous solid.

$^1$H-Nuclear magnetic resonance spectrum (400 MHz, CDCl$_3$) δ ppm: 9.57 (1H, s), 7.83–7.80 (2H, m), 7.76–7.72 (2H, m), 7.62 (2H, d, J=9 Hz), 7.40 (2H, t, J=8 Hz), 7.24–7.20 (1H, m), 7.00 (2H, d, J=8 Hz), 6.76 (2H, d, J=9 Hz), 5.00–4.96 (1H, m), 4.08–3.95 (2H, m), 2.98 (3H, s).

(7) (±)-N-Methyl-N-(4-phenoxybenzenesulfonyl)-2-(2-phthalimidomethyl)glycine

An aqueous solution (10 ml) of sodium chlorite (0.92 g, 10.2 mmol) and sodium dihydrogenphosphate dehydrate (1.06 g, 6.80 mmol) was added to a solution of 2-methyl-2-butene (0.95 g, 13.6 mmol) and (±)-1-formyl-N-methyl-N-(4-phenoxybenzenesulfonyl)-2-phthalimidoethylamine (1.58 g, 3.40 mmol), which is the product of (6) above, in a mixture of tert-butanol (12 ml) and N,N-dimethylacetamide (5 ml). The mixture was stirred at room temperature for 2 hours. To the reaction mixture, ice-water was added and then this was extracted with ethyl acetate. The organic layer was washed with water, dried over anhydrous magnesium sulfate and concentrated under reduced pressure. The residue was purified by chromatography on a silica gel column using dichloromethane/methanol=10/1 as the eluant to afford the title compound (0.60 g, yield 34%) as a white amorphous solid.

$^1$H-Nuclear magnetic resonance spectrum (400 MHz, CDCl$_3$) δ ppm: 7.94–7.83 (2H, m), 7.80–7.71 (2H, m), 7.69–7.59 (2H, m), 7.41–7.37 (2H, m), 7.25–7.20 (1H, m), 7.01 (2H, d, J=7 Hz), 6.83–6.77 (2H, m), 5.18–5.12 (1H, m), 4.21–4.02 (2H, m), 2.94 (3H, s).

Example 68

(±)-N-Hydroxy-Nα-methyl-Nα-(4-phenoxybenzenesulfonyl)-2-(2-phthalimidomethyl) glycinamide (Compound No. 3-25)

In a similar manner to that described in Example 2, a hydroxyamidation reaction was carried out using (±)-N-methyl-N-(4-phenoxybenzenesulfonyl)-2-(2-phthalimidomethyl)glycine, the product of Example 67, to give the title compound (yield 81%) as a white amorphous solid.

$^1$H-Nuclear magnetic resonance spectrum (400 MHz, DMSO-d$_6$) δ ppm: 11.06 (1H, s), 9.08 (1H, s), 7.86 (4H, s), 7.66 (2H, d, J=9 Hz), 7.46 (2H, t, J=8 Hz), 7.26 (1H, t, J=8 Hz), 7.10 (2H, d, J=8 Hz), 6.87 (2H, d, J=9 Hz), 4.67–4.63 (1H, m), 4.05–3.98 (1H, m), 3.63–3.58 (1H, m), 2.88 (3H,s).

Example 69

N-Methyl-N-(4-phenoxybenzenesulfonyl)-2(S)-(2-phthalimidoethyl)-glycine (Compound No. 3-179)

In a similar manner to the procedures described in Example 1, reactions were carried out using optically active N-(tert-butoxycarbonyl)homoserine allyl ester, instead of (±)-N-(tert-butoxycarbonyl)homoserine allyl ester, to give the title compound (total yield 49%) as a white powder.

Melting Point: 155–156° C.

$^1$H-Nuclear magnetic resonance spectrum (400 MHz, CDCl$_3$) δ ppm: 7.87–7.82 (2H, m), 7.77–7.70 (4H, m), 7.42–7.36 (2H, m), 7.23–7.19 (1H, m), 7.06–6.96 (4H, m), 4.76 (1H, dd, J=10 Hz, 6 Hz), 3.82–3.67 (2H, m), 2.93 (3H, s), 2.36–2.27 (1H, m), 2.05–1.94 (1H, m). HPLC analysis: retention time 36.8 minutes.

<Experimental Conditions>
column: CHIRALCEL OJ-R (product of Daicel Chem. Ind. Ltd
inside diameter: 0.46 cm,
length: 15 cm, grain size: 5 μm
eluant: acetonitrile/triethylamine-phosphate buffer solution (0.2%(v/v), pH 2.2)=2/3
flow rate: 1.0 ml/minute
temperature: 30° C.
detection: UV 254 nm Example 70

N-Hydroxy-Nα-methyl-Nα-(4-phenoxybenzenesulfonyl)-2(S)-(2-phthalimidoethyl)glycinamide (Compound No. 3-26)

In a similar manner to that described in Example 2, a hydroxyamidation reaction was carried out using N-methyl-N-(4-phenoxybenzenesulfonyl)-2(S)-(2-phthalimidomethyl)glycine, the product of Example 69, to give the title compound (yield 90%) as a colorless amorphous solid.

$^1$H-Nuclear magnetic resonance spectrum (400 MHz, CDCl$_3$) δ ppm: 9.37 (1H, br.s), 7.84–7.80 (2H, m), 7.75–7.70 (2H, m), 7.60 (2H, d, J=9 Hz), 7.45–7.22 (4H, m), 7.09–7.07 (2H, m), 6.82 (2H, d, J=9 Hz), 4.33 (1H, dd, J=9 Hz, 5 Hz), 3.70–3.61 (1H, m), 3.51–3.43 (1H, m), 2.93 (3H, s), 2.38–2.29 (1H, m), 1.61–1.52 (1H, m). HPLC analysis: retention time 42.6 minutes.
<Experimental Conditions>
column: CHIRALCEL OJ-R (product of Daicel Chem. Ind. Ltd
inside diameter: 0.46 cm,
length: 15 cm, grain size: 5 μm
eluant: acetonitrile/triethylamine-phosphate buffer solution (0.2%(v/v), pH 2.2)=3/7
flow rate: 1.0 ml/minute
temperature: 40° C.
detection: UV 254 nm Example 71

N-Methyl-N-(4-phenoxybenzensulfonyl)-2(R)-(2-phthalimidoethyl)-glycine (Compound No. 3-179)

In a similar manner to that described in Example 69, reactions were carried out using N-(tert-butoxycarbonyl)-D-homoserine allyl ester, instead of N-(tert-butoxycarbonyl)-L-homoserine allyl ester, to give the title compound as a white powder.

Melting Point: 155–157° C.;

$^1$H-Nuclear magnetic resonance spectrum (400 MHz, CDCl$_3$) δ ppm: 7.87–7.82 (2H, m), 7.77–7.70 (2H, m), 7.42–7.37 (2H, m), 7.22–7.19 (1H, m), 7.06–6.96 (4H, m), 4.76 (1H, dd, J=10 Hz, 6 Hz), 3.82–3.67 (2H, m), 2.93 (3H, s), 2.36–2.27 (1H, m), 2.05–1.94 (1H, m). HPLC analysis: retention time 34.2 minutes.
<Experimental Conditions>
Same as Example 69.

Example 72

N-Hydroxy-Nα-methyl-Nα-(4-phenoxybenzensulfonyl)-2(R)-(2-phthalimidoethyl)glycinamide (Compound No. 3-26)

In a similar manner to that described in Example 2, hydroxyamidation reaction was carried out using N-methyl-N-(4-phenoxybenzensulfonyl)-2(R)-(2-phthalimido-ethyl)glycine, the product of Example 71, to give the title compound (yield 93%) as a colorless amorphous solid.

$^1$H-Nuclear magnetic resonance spectrum (400 MHz, CDCl$_3$) δ ppm: 9.36 (1H, br.s), 7.84–7.80 (2H, m), 7.75–7.70 (2H, m), 7.62–7.59 (2H, m), 7.45–7.40 (2H, m), 7.26–7.23 (2H, m), 7.08 (2H, d, J=8 Hz), 6.83 (1H, d, J=9 Hz), 4.33 (1H, dd, J=9 Hz, 5 Hz), 3.67–3.61 (1H, m), 3.51–3.43 (1H, m), 2.93 (3H, s), 2.92–2.38 (1H, m), 1.60–1.52 (1H, m). HPLC analysis: retention time 39.0 minutes.
<Experimental Conditions>: Same as Example 70.

Example 73

(±)-2-[2-(6,7-Dihydro-5H-cyclopenta[d]pyrimidin-2,4-dione-3-yl)ethyl]-N-methyl-N-(4-phenoxybenzenesulfonyl)glycine In a similar manner to that described in Example 41(3), a reaction was carried out using 1-(2-trimethylsilyl)ethoxymethyl-6,7-dihydro-5H-cyclopenta[d]pyrimidine-2,4-dione, instead of 1-(2-trimethylsilyl)ethoxymethylthieno[3,2-d]pyrimidine-2,4-dione, followed by deprotection and ester hydrolysis reactions on the resulting product according to Example 41(4) to give the title compound (total yield 23%) as a white powder.

$^1$H-Nuclear magnetic resonance spectrum (270 MHz, DMSO-d$_6$) δ ppm: 11.38 (1H, s), 7.78 (2H, d, J=9 Hz), 7.49–7.43 (2H, m), 7.25 (1H, t, J=8 Hz), 7.13–7.07 (4H, m), 4.47 (1H, dd, J=10 Hz, 6 Hz), 3.69 (2H, t, J=8 Hz), 2.83 (3H, s), 2.69–2.64 (2H, m), 2.58–2.47 (2H, m), 2.10–1.91 (3H, m), 1.76–1.62 (1H, m).

Example 74

(±)-2-[2-(6,7-Dihydro-5H-cyclopenta[d]pyrimidin-2,4-dione-3-yl)ethyl]-N-hydroxy-Nα-methyl-Nα-(4-phenoxybenzenesulfonyl)glycinamide (Compound No. 5-68)

In a similar manner to that described in Example 2, a hydroxyamidation reaction was carried out using (±)-2-[2-(6,7-dihydro-5H-cyclopenta[d]pyrimidin-2,4-dione-3-yl)-ethyl]-N-methyl-N-(4-phenoxybenzenesulfonyl)glycine, the product of Example 73, to give the title compound (yield 49%) as a white powder.

Melting Point: 207–209° C. (decomposition); $^1$H-Nuclear magnetic resonance spectrum (400 MHz, DMSO-d$_6$) δ ppm: 11.40 (1H, s), 10.73(1H, s), 8.95 (1H, d, J=3 Hz), 7.79–7.75 (2H, m), 7.48–7.43 (2H, m), 7.25 (1H, t, J=7 Hz), 7.14–7.08 (4H, m), 4.27 (1H, dd, J=9 Hz, 7 Hz), 3.63–3.51 (2H, m), 2.92 (3H, s), 2.66 (2H, t, J=7 Hz), 2.51–2.48 (2H, m), 1.99–1.92 (2H, m), 1.84–1.74 (1H, m), 1.73–1.63 (1H, m).

Example 75

(±)-N-[4-(4-Chlorophenoxy)benzensulfonyl]-N-methyl-2-(2-phthalimidoethyl)glycine In a similar manner to that described in Example 1(2)-b, a reaction was carried out using 4-(4-chlorophenoxy)benzenesulfonyl chloride, instead of 4-phenoxybenzensulfonyl chloride, followed by methylation of the product according to Example 1(3), and then by de-allylation of the product according to Example 1(4) to give the title compound (total yield 71%) as a pale yellow powder.

Melting Point: 166–167° C.; $^1$H-Nuclear magnetic resonance spectrum (270 MHz, CDCl$_3$) δ ppm: 7.87–7.82 (2H, m), 7.80–7.70 (4H, m), 7.38–7.33 (2H, m), 7.03–6.96 (4H, m), 4.76 (1H, dd, J=10 Hz, 6 Hz), 3.84–3.64 (2H, m), 2.92 (3H, s), 2.48–2.35 (1H, m), 2.06–1.92 (1H, m).

Example 76

(±)-Nα-[4-(4-Chlorophenoxy)benzensulfonyl]-N-hydroxy-Nα-methyl-2-(2-phthalimidoethyl)glycinamide (Compound No. 3-181)

In a similar manner to that described in Example 2, hydroxyamidation was carried out using (±)-N-[4-(4-chlorophenoxy)benzensulfonyl]-N-methyl-2-(2-phthalimido-ethyl)glycine, the product of Example 75, to give the title compound (yield 90%) as a white powder.

Melting Point: 90–93° C.; $^1$H-Nuclear magnetic resonance spectrum (400 MHz, CDCl$_3$) δ ppm: 9.34 (1H, br.s), 7.85–7.80 (2H, m), 7.77–7.72 (2H, m), 7.62 (2H, d, J=9 Hz), 7.42–7.23 (3H, m), 7.04–7.00 (2H, m), 6.86–6.82 (2H, m), 4.33 (1H, dd, J=9 Hz, 5 Hz), 3.68–3.62 (1H, m), 3.50–3.43 (1H, m), 2.93 (3H, s), 2.37–2.28 (1H, m), 1.61–1.53 (1H, m).

Example 77

(±)-N-Ethyl-N-(4-phenoxybenzenesulfonyl)-2-(2-phthalimidoethyl)-glycine

In a similar manner to that described in Example 1(3), a reaction was carried out using ethyl iodide, instead of methyl iodide, followed by a de-allylation reaction according to Example 1(4) to give the title compound (yield 92%) as a pale yellow amorphous solid.

$^1$H-Nuclear magnetic resonance spectrum (270 MHz, CDCl$_3$) δ ppm: 7.88–7.81 (2H, m), 7.79–7.69 (4H, m), 7.43–7.35 (2H, m), 7.23–7.17 (1H, m), 7.06–7.02 (2H, m), 6.97–6.92 (2H, m), 4.57 (1H, dd, J=8 Hz, 6 Hz), 3.84–3.67 (2H, m)3.50–3.37 (1H, m), 3.33–3.20 (1H, m), 2.44–2.31 (1H, m), 2.03–1.90 (1H, m), 1.33 (3H, t, J=7 Hz).

Example 78

(±)-Nα-Ethyl-N-hydroxy-Nα-(4-phenoxybenzenesulfonyl)-2-(phthalimidoethyl)glycinamide In a similar manner to that described in Example 2, a hydroxyamidation reaction was carried out using (±)-N-ethyl-N-(4-phenoxybenzenesulfonyl)-2-(2-phthalimidoethyl)glycine, the product of Example 77, to give the title compound (yield 88%) as a colorless amorphous solid.

$^1$H-Nuclear magnetic resonance spectrum (400 MHz, CDCl$_3$) δ ppm: 9.49 (1H, br.s), 7.84–7.78 (2H, m), 7.74–7.70 (2H, m), 7.60 (2H, d, J=9 Hz), 7.44–7.40 (2H, m), 7.31–7.22 (2H, m), 7.06 (2H, d, J=8 Hz), 6.76 (2H, d, J=9 Hz), 4.17 (1H, dd, J=9 Hz, 5 Hz), 3.56–3.32 (4H, m), 2.45–2.36 (1H, m), 1.67–1.55 (1H, m), 1.26 (3H, t, J=7 Hz).

Example 79

(±)-N-(4-Phenoxybenzenesulfonyl)-2-(2-phthalimidoethyl)-N-propylglycine

In a similar manner to that described in Example 1(3), a reaction was carried out using propyl iodide, instead of methyl iodide, followed by a de-allylation reaction of the product according to Example 1(4) to give the title compound (yield 86%) as a pale yellow amorphous solid.

$^1$H-Nuclear magnetic resonance spectrum (270 MHz, CDCl$_3$) δ ppm: 7.86–7.71 (2H, m), 7.76–7.69 (4H, m), 7.44–7.36 (2H, m), 7.26–7.18 (1H, m), 7.07–7.03 (2H, m), 6.94–6.89 (2H, m), 4.49 (1H, t, J=7 Hz), 3.76–3.65 (2H, m), 3.32–3.09 (2H, m), 2.43–2.31 (1H, m), 1.97–1.66 (3H, m), 0.89 (3H, t, J=8 Hz).

Example 80

(±)-N-Hydroxy-Nα-(4-phenoxybenzenesulfonyl)-2-(2-phthalimidoethyl)-Nα-propylglycinamide (Compound No. 3-58)

In a similar manner to that described in Example 2, a hydroxyamidation reaction was carried out using (±)-N-(4-phenoxybenzenesulfonyl)-2-(2-phthalimidoethyl)-N-propylglycine, the product of Example 79, to give the title compound (yield 96%) as a colorless amorphous solid.

$^1$H-Nuclear magnetic resonance spectrum (400 MHz, CDCl$_3$) δ ppm: 9.49 (1H, br.s), 7.84–7.80 (2H, m), 7.74–7.70 (2H, m), 7.61–7.57 (2H, m), 7.45–7.40 (2H, m), 7.26–7.20 (2H, m), 7.06 (2H, d, J=8 Hz), 6.75–6.72 (2H, m), 4.16 (1H, dd, J=10 Hz, 5 Hz), 3.55–3.32 (3H, m), 3.23–3.16 (1H, m), 2.44–2.36 (1H, m), 1.75–1.50 (3H, m), 0.88 (3H, t, J=7 Hz).

Example 81

(±)-2-[2-(2,3-Dimethylmaleimido)ethyl]-N-methyl-N-(4-phenoxybenzenesulfonyl)glycine In a similar manner to that described in Example 41(3), a reaction was carried out using 2,3-dimethyhnaleimide, instead of 1-(2-trimethylsilyl)ethoxymethylthieno[3,2-d]pyrimidine-2,4-dione, followed by deprotection and ester hydrolysis reactions on the resulted allyl ester compound according to Example 41(4) to give the title compound (total yield 29%) as a pale yellow amorphous solid.

$^1$H-Nuclear magnetic resonance spectrum (270 MHz, CDCl$_3$) δ ppm: 7.77–7.73 (2H, m), 7.46–7.37 (2H, m), 7.21 (1H, t, J=7 Hz), 7.07–6.99 (4H, m), 4.69 (1H, dd, J=10 Hz, 6 Hz), 4.65–4.42 (2H, m), 2.88 (3H, s), 2.27–2.17 (1H, m), 2.03–1.83 (7H, m).

Example 82

(±)-2-[2-(2,3-Dimethylmaleimido)ethyl]-N-hydroxy-Nα-methyl-Nα-(4-phenoxybenzenesulfonyl)glycinamide (Compound No. 5-17)

In a similar manner to that described in Example 2, a hydroxyamidation reaction was carried out using (±)-2-[2-(2,3-dimethylmaleimido)ethyl]-N-methyl-N-(4-phenoxybenzenesulfonyl)glycine, the product of Example 81, to give the title compound (yield 73%) as a pale yellow amorphous solid.

$^1$H-Nuclear magnetic resonance spectrum (400 MHz, CDCl$_3$) δ ppm: 9.41 (1H, br.s), 7.68 (2H, d, J=9 Hz), 7.44–7.39 (2H, m), 7.23 (1H, t, J=7 Hz), 7.09–7.06 (2H, m), 7.02–6.98 (2H, m), 4.29 (1H, dd, J=9 Hz, 6 Hz), 3.48–3.42 (1H, m), 3.27–3.20 (1H, m), 2.90 (3H, s), 2.25–2.17 (1H, m), 1.96 (6H, s), 1.60–1.51 (1H, m).

The following compounds (Examples 83 to 88) were obtained according to Example 81 or 82 above.

Example 83

(±)-2-[2-(4,5-Dichlorophthalimido)ethyl]-N-methyl-N-(4-phenoxy-benzenesulfonyl)glycine a white powder (total yield 14%); $^1$H-Nuclear magnetic resonance spectrum (270 MHz, DMSO-d$_6$) δ ppm: 8.08 (2H, s), 7.83 (2H, d, J=9 Hz), 7.47–7.41 (2H, m), 7.23 (1H, t, J=7 Hz), 7.12–7.08 (2H, m), 7.02–6.98 (2H, m), 4.21 (1H, dd, J=9 Hz, 6 Hz), 3.63–3.44 (2H, m), 2.76 (3H, s), 2.31–2.16 (1H, m), 1.73–1.56 (1H, m).

Example 84

(±)-2-[2-(4,5-Dichlorophthalimido)ethyl]-N-hydroxy-Nα-methyl-Nα-(4-phenoxybenzenesulfonyl)glycinamide (Compound No. 5-74)

a white powder (yield 64%); Melting Point: 155–156° C.; $^1$H-Nuclear magnetic resonance spectrum (400 MHz, DMSO-$d_6$) δ ppm: 10.73 (1H, d, J=1 Hz), 8.96 (1H, d, J=1 Hz), 8.17 (2H, s), 7.79–7.75 (2H, m), 7.49–7.44 (2H, m), 7.26 (1H, t, J=7 Hz), 7.19–7.14 (2H, m), 7.10–7.07 (2H, m), 4.30–4.26 (1H, m), 3.52–3.40 (2H, m), 2.88 (3H, s), 2.00–1.93 (1H, m), 1.86–1.78 (1H, m).

Example 85

(±)-N-Methyl-2-[2-(4-methylphthalimido)ethyl]-N-(4-phenoxybenzenesulfonyl)glycine a white powder (total yield 53%); $^1$H-Nuclear magnetic resonance spectrum (270 MHz, CDCl$_3$) δ ppm: 7.77–7.70 (3H, m), 7.63 (1H, s), 7.50 (1H, d, J=8 Hz), 7.42–7.35 (1H, m), 7.22–7.17 (2H, m), 7.06–7.03 (2H, m), 7.00–6.95 (2H, m), 4.75 (1H, dd, J=10 Hz, 6 Hz), 3.82–3.62 (2H, m), 2.92 (3H, s), 2.51 (3H, s), 2.36–2.23 (1H, m), 2.04–1.92 (1H, m).

Example 86

(±)-N-Hydroxy-Nα-methyl-2-[2-(4-methylphthalimido)ethyl]-Nα-(4-phenoxybenzenesulfonyl)glycinamide (Compound No. 5-76)

a white powder (yield 83%); Melting Point: 157–158° C.; $^1$H-Nuclear magnetic resonance spectrum (400 MHz, CDCl$_3$) δ ppm: 9.41 (1H, s), 7.68 (1H, d, J=8 Hz), 7.60–7.58 (3H, m), 7.54–7.49 (1H, m), 7.46–7.40 (2H, m), 7.26–7.22 (1H, m), 7.09–7.06 (2H, m), 6.82 (2H, d, J=9 Hz), 4.32 (1H, dd, J=10 Hz, 5 Hz), 3.65–3.59 (1H, m), 3.48–3.41 (1H, m), 2.92 (3H, s), 2.50 (3H, s), 2.35–2.27 (1H, m), 1.58–1.49 (1H, m).

Example 87

(±)-N-methyl-N-(4-phenoxybenzenesulfonyl)-2-[2-(3,4-pyridine-dicarboxyimido)ethyl]glycine a white powder (total yield 35%); $^1$H-Nuclear magnetic resonance spectrum (270 MHz, DMSO-$d_6$) δ ppm: 9.11–9.09 (2H, m), 7.90–7.87 (1H, m), 7.81–7.77 (2H, m), 7.49–7.43 (2H, m), 7.25 (1H, t, J=7 Hz), 7.14–7.06 (4H, m), 4.52 (1H, dd, J=9 Hz, 6 Hz), 3.71–3.50 (2H, m), 2.81 (3H, s), 2.31–2.17 (1H, m), 1.94–1.80 (1H, m).

Example 88

(±)-N-Hydroxy-Nα-methyl-Nα-(4-phenoxybenzenesulfonyl)-2-[2-(3,4-pyridinedicarboxyimido)ethyl]glycinamide (Compound No. 5-5)

a white powder (yield 95%); Melting Point: 99–101° C.; $^1$H-Nuclear magnetic resonance spectrum (400 MHz, DMSO-$d_6$) δ ppm: 10.74 (1H, d, J=2 Hz), 9.11–9.09 (2H, m), 8.97–8.96 (1H, m), 7.89–7.88 (1H, m), 7.79–7.76 (2H, m), 7.49–7.44 (2H, m), 7.26 (1H, t, J=7 Hz), 7.17–7.15 (2H, m), 7.12–7.06 (2H, m), 4.31–4.27 (1H, m), 3.55–3.44 (2H, m), 2.89 (3H, s), 2.03–1.96 (1H, m), 1.94–1.82 (1H, m).

Example 89

(±)-2-[2-(6,7-Dimethoxyquinazolin-2,4-dione-3-yl)ethyl]-N-methyl-N-(4-phenoxybenzenesulfonyl)glycine In a similar manner to that described in Example 41(3), a reaction was carried out using 6,7-dimethoxy-1-(2-trimethylsilyl)ethoxymethylquinazoline-2,4-dione, instead of 1-(2-trimethylsilyl)ethoxymethylthieno[3,2-d]pyrimidine-2,4-dione, followed by deprotection and ester hydrolysis reactions on the resulting allyl ester compound according to Example 41(4) to give the title compound (total yield 53%) as a white powder.

$^1$H-Nuclear magnetic resonance spectrum (270 MHz, DMSO-$d_6$) δ ppm: 11.24 (1H, s), 7.79–7.75 (2H, m), 7.48–7.42 (2H, m), 7.29–7.21 (2H, m), 7.12–7.04 (4H, m), 6.69 (1H, s), 4.51 (1H, dd, J=9 Hz, 6 Hz), 3.86–3.80 (5H, m), 3.78 (3H, s), 2.85 (3H, s), 2.20–2.07 (1H, m), 1.83–1.69 (1H, m).

Example 90

(±)-2-[2-(6,7-Dimethoxyquinazolin-2,4-dione-3-yl)ethyl]-N-hydroxy-Nα-methyl-Nα-(4-phenoxybenzenesulfonyl)glycinamide (Compound No. 5-19)

In a similar manner to that described in Example 2, a hydroxyamidation reaction was carried out using (±)-2-[2-(6,7-dimethoxyquinazolin-2,4-dione-3-yl)ethyl]-N-methyl-N-(4-phenoxybenzenesulfonyl)glycine, the product of Example 89, to give the title compound (yield 60%) as a white powder.

Melting Point: 146–148° C.p; $^1$H-Nuclear magnetic resonance spectrum (400 MHz, DMSO-$d_6$) δ ppm: 11.26 (1H, s), 10.75 (1H, s), 8.95 (1H, s), 7.79–7.76 (2H, m), 7.46–7.41 (2H, m), 7.28 (1H, s), 7.24 (1H, t, J=7 Hz), 7.13–7.07 (4H, m), 6.68 (1H, s), 4.32 (1H, dd, J=9 Hz, 7 Hz), 3.83 (3H, s), 3.77 (3H, s), 3.74–3.67 (2H, m), 2.95 (3H, s), 1.93–1.83 (1H, m), 1.81–1.74 (1H, m).

Example 91

(±)-N-[4-(4-Fluorophenoxy)benzensulfonyl]-N-methyl-2-(2-phthalimidoethyl)glycine In a similar manner to that described in Example 1(2)-b, a reaction was carried out using 4-(4-fluorophenoxy)benzenesulfonyl chloride, instead of 4-phenoxybenzenesulfonyl chloride, followed by methylation of the product according to Example 1(3) and then by de-allylation of the product according to Example 1(4) to give the title compound (total yield 82%) as a white powder.

$^1$H-Nuclear magnetic resonance spectrum (270 MHz, CDCl$_3$) δ ppm: 7.88–7.82 (2H, m), 7.78–7.72 (4H, m), 7.12–6.93 (6H, m), 4.76 (1H, dd, J=9 Hz, 6 Hz), 3.84–3.61 (2H, m), 2.92 (3H, s), 2.38–2.25 (1H, m), 2.05–1.90 (1H, m).

Example 92

(±)-Nα-[4-(4-Fluorophenoxy)benzensulfonyl]-N-hydroxy-Nα-methyl-2-(2-phthalimidoethyl)glycinamide (Compound No. 3-182)

In a similar manner to that described in Example 2, a hydroxyamidation reaction was carried out using (±)-N-[4-

(4-fluorophenoxy)benzensulfonyl]-N-methyl-2-(2-phthalimidoethyl)glycine to give the title compound (yield 93%) as a white powder.

Melting Point: 100–101° C.; $^1$H-Nuclear magnetic resonance spectrum (270 MHz, CDCl$_3$) δ ppm: 9.38 (1H, br.s), 7.87–7.72 (4H, m), 7.64–7.58 (2H, m), 7.23 (1H, br.s), 7.16–7.03 (4H, m), 6.82 (2H, d, J=8 Hz), 4.33 (1H, dd, J=10 Hz, 5 Hz), 3.70–3.60 (1H, m), 3.52–3.41 (1H, m), 3.92 (3H, s), 2.40–2.26 (1H, m), 1.65–1.53 (1H, m).

Example 93

(±)-2-[2-(6-Chloropyrimidin-2,4-dione-3-yl)ethyl]-N-methyl-N-(4-phenoxybenzenesulfonyl)glycine In a similar manner to that described in Example 41(3), a reaction was carried out using 6-chloro-1-(2-timethylsilyl)ethoxymethylpyrimidine-2,4-dione, instead of 1-(2-trimethylsilyl)ethoxymethylthieno[3,2-d]pyrimidine-2,4-dione, followed by deprotection and ester hydrolysis reactions on the resulting allyl ester compound according to Example 41(4) to give the title compound (total yield 70%) as a white powder.

$^1$H-Nuclear magnetic resonance spectrum (270 MHz, DMSO-d$_6$) δ ppm: 12.41 (1H, br.s), 7.78 (2H, d, J=7 Hz), 7.47 (2H, m), 7.26 (1H, m), 7.12 (4H, m), 5.89 (1H, s), 4.47 (1H, dd, J=9 Hz, 5 Hz), 3.70 (2H, br.t, J=6 Hz), 2.82 (3H, s), 2.08 (1H, m), 1.76 (1H, m).

Example 94

(±)-2-[2-(6-Chloropyrimidin-2,4-dione-3-yl)ethyl]-N-hydroxy-Nα-methyl-Nα-(4-phenoxybenzenesulfonyl)glycinamide (Compound No. 5-84)

In a similar manner to that described in Example 2, a hydroxyamidation reaction was carried out using (±)-2-[2-(6-chloropyrimidin-2,4-dione-3-yl)ethyl]-N-methyl-N-(4-phenoxybenzenesulfonyl)glycine, the product of Example 93, to give the title compound (yield 68%) as a white powder.

Melting Point: 144–145° C. (decomposition); H-Nuclear magnetic resonance spectrum (400 MHz, DMSO-d$_6$) δ ppm: 12.46 (1H, br.s), 10.73 (1H, s), 8.93 (1H, s), 7.77 (2H, dd, J=9 Hz, 2 Hz), 7.46 (2H, m), 7.26 (1H, t, J=8 Hz), 7.13 (2H, d, J=8 Hz), 7.09 (2H, d, J=9 Hz), 5.87 (1H, s), 4.28 (1H, dd, J=9 Hz, 7 Hz), 3.57 (2H, m), 2.91 (3H, s), 1.81 (1H, m), 1.73 (1H, m).

Example 95

(±)-N-Methyl-N-(4-phenoxybenzenesulfonyl)-2-[2-(6-trifluoromethyl-pyrimidin-2,4-dione-3-yl)ethyl] glycine In a similar manner to that described in Example 41(3), a reaction was carried out using 6-trifluoromethyl-1-(2-trimethylsilyl)ethoxymethylpyrimidine-2,4-dione, instead of 1-(2-trimethylsilyl)ethoxymethylthieno[3,2-d] pyrimidine-2,4-dione, followed by deprotection and ester hydrolysis reactions of the resulted allyl ester compound according to Example 41(4) to give the title compound (total yield 71%) as a white powder.

$^1$H-Nuclear magnetic resonance spectrum (270 MHz, DMSO-d$_6$) δ ppm: 7.82–7.77 (2H, m), 7.43–7.36 (2H, m), 7.24–7.18 (1H, m), 7.08–6.98 (4H, m), 6.02 (1H, s), 4.71 (1H, dd, J=11 Hz, 6 Hz), 4.04–3.88 (2H, m), 2.93 (3H, s), 2.32–2.19 (1H, m), 2.06–1.91 (1H, m).

Example 96

(±)-N-Hydroxy-Nα-methyl-Nα-(4-phenoxybenzenesulfonyl)-2-[2-(6-trifluoromethylpyrimidin-2,4-dione-3-yl)ethyl] glycinamide (Compound No. 5-88)

In a similar manner to that described in Example 2, a hydroxyamidation reaction was carried out using (±)-N-methyl-N-(4-phenoxybenzenesulfonyl)-2-[2-(6-trifluoromethylpyrimidin-2,4-dione-3-yl)ethyl]glycine, the product of Example 95, to give the title compound (yield 95%) as a white powder.

Melting Point: 179–180° C. (decomposition); $^1$H-Nuclear magnetic resonance spectrum (400 MHz, DMSO-d$_6$) δ ppm: 12.45 (1H, br.s), 10.75 (1H, br.s), 8.95 (1H, br.s), 7.81–7.76 (2H, m), 7.48–7.43 (2H, m), 7.28–7.24 (1H, m), 7.15–7.05 (4H, m), 6.21 (1H, s), 4.28 (1H, dd, J=9 Hz, 7 Hz), 3.70–3.56 (2H, m), 2.91 (3H, s), 1.88–1.72 (2H, m).

Example 97

2(R)-[2-(6-Chloropyrimidin-2,4-dione-3-yl)ethyl]-N-hydroxy-Nα-methyl-Nα-(4-phenoxybenzenesulfonyl)glycinamide (Compound No. 5-84)

In a similar manner to the procedures described in Examples 93 and 94, reactions were carried out using D-homoserine as a starting material to give the title compound as a white powder. The $^1$H-Nuclear magnetic resonance spectrum of the product was the same as that of the compound of Example 94, which is a racemate of the product. HPLC analysis: retention time 8.9 minutes.

<Experimental Condition>
column: CHIRALCEL OD-RH (product of Daicel Chem. Ind. Ltd)
inside diameter: 0.46 cm,
length: 15 cm, grain size 5 μm
eluant: acetonitrile/triethylamine-phosphate buffer solution (0.2%(v/v), pH 2.2)=55/45
flow rate: 0.5 ml/minute
temperature: 20° C.
detection: UV 254 nm

Example 98

2(S)-[2-(6-Chloropyrimidin-2,4-dione-3-yl)ethyl]-N-hydroxy-Nα-methyl-Nα-(4phenoxybenzenesulfonyl) glycinamide (Compound No. 5-84)

In a similar manner to the procedures described in Example 97, reactions were carried out using L-homoserine as a starting material to give the title compound as a white powder. The $^1$H-Nuclear magnetic resonance spectrum of the product was same as that of the compound of Example 94, which is a racemate of the product. HPLC analysis: retention time 12.1 minutes.

<Experimental Condition>
Same as Example 97.

Example 99

N-Hydroxy-Nα-methyl-Nα-(4-phenoxybenzenesulfonyl)-2(R)-[2-(6-trifluoromethylpyrimidin-2,4-dione-3-yl)ethyl] glycinamide (Compound No. 5-88)

In a similar manner to the procedures described in Examples 95 and 96, reactions were carried out using D-homoserine as a starting material to give the title compound as a white amorphous solid. The $^1$H-Nuclear magnetic resonance spectrum of the product was same as that of the compound of Example 96, which is a racemate of the product. HPLC analysis: retention time 10.3 minutes.
<Experimental Condition>
Same as Example 97.

Example 100

N-Hydroxy-Nα-methyl-Nα-(4-phenoxybenzenesulfonyl)-2(S)-[2-(6-trifluoromethylpyrimidin-2,4-dione-3-yl)ethyl]glycinamide (Compound No. 5-88)

In a similar manner to the procedures described in Example 99, reactions were carried out using L-homoserine as a starting material to give the title compound as a white amorphous solid. The $^1$H-Nuclear magnetic resonance spectrum of the product was same as that of the compound of Example 96, which is a racemate of the product. HPLC analysis: retention time 13.2 minutes.
<Experimental Condition>
Same as Example 97.

The following compounds of Examples 101 to 145 were prepared in a similar manner to that selected appropriately from the methods described in Examples 1 to 100.

Example 101

(±)-Hydroxy-Nα-(4-phenoxybenzenesulfonyl)-Nα-propargyl-2-[2-(pyrimidin-2,4-dione-3-yl)ethyl]glycinamide (Compound No. 5-30)

In similar manners to the procedures described in Examples 14 and 28, the title compound was prepared.

a white amorphous solid; $^1$H-Nuclear magnetic resonance spectrum (400 MHz, DMSO-d$_6$) δ ppm: 11.14 (1H, s), 10.69 (1H, s), 9.07 (1H, s), 7.82 (2H, d, J=9 Hz), 7.51–7.37 (3H, m), 7.25 (1H, t, J=8 Hz), 7.14 (2H, d, J=9 Hz), 7.06 (2H, d, J=9 Hz), 5.55 (1H, d, J=7 Hz), 4.45–4.40 (1H, m), 4.29–4.11 (2H, m), 3.71–3.53 (2H, m), 3.08 (1H, s), 2.10–1.93 (1H, m), 1.81–1.69 (1H, m).

Example 102

(±)-Hydroxy-Nα-methyl-2-[2-(2,3-naphthalenedicarboxyimido)ethyl]-Nα-(4-phenoxybenzenesulfonyl)glycinamide (Compound No. 5-1)

The title compound was prepared in a similar manner to that described in Example 2.

white powder; Melting Point: 192–194° C.; $^1$H-Nuclear magnetic resonance spectrum (400 MHz, DMSO-d$_6$) δ ppm: 10.76 (1H, t, J=1 Hz), 8.97 (1H, t, J=2 Hz), 8.50 (2H, s), 8.29–8.25 (2H, m), 7.80–7.77 (4H, m), 7.48–7.43 (2H, m), 7.25 (1H, t, J=7 Hz), 7.18–7.03 (4H, m), 4.33 (1H, t, J=7 Hz), 3.57–3.45 (2H, m), 2.91 (3H, s), 2.07–1.98 (1H, m), 1.94–1.78 (1H, m).

Example 103

(±)-Hydroxy-Nα-(4-phenoxybenzenesulfonyl)-Nα-propargyl-2-[2-(pteridin-2,4-dione-3-yl)ethyl]glycinamide (Compound No. 5-22)

The title compound was prepared in similar manners to the procedures described in Examples 28 and 54.

pale yellow powder; Melting Point: 101–104° C.; $^1$H-Nuclear magnetic resonance spectrum (400 MHz, DMSO-d$_6$) δ ppm: 12.22 (1H, br.s), 10.76 (1H, d, J=2 Hz), 9.08 (1H, t, J=2 Hz), 8.67 (1H, d, J=2 Hz), 8.55 (1H, d, J=2 Hz), 7.91–7.83 (2H, m), 7.48–7.44 (2H, m), 7.27–7.24 (1H, m), 7.17–7.06 (4H, m), 4.49 (1H, dd, J=19 Hz, 2 Hz), 4.32–4.20 (2H, m), 3.87–3.74 (2H, m), 3.09 (1H, t, J=2 Hz), 2.14–2.05 (1H, m), 1.99–1.89 (1H, m).

Example 104

(±)-2-[2-(5,6-Dimethylpyrimidin-2,4-dione-3-yl)ethyl]-N-hydroxy-Nα-(4-phenoxybenzenesulfonyl)-Nα-propargylglycinamide (Compound No. 4-89)

The title compound was prepared in similar manners to the procedures described in Examples 18 and 28.

white powder; Melting Point: 180–181° C. (Decomposition); $^1$H-Nuclear magnetic resonance spectrum (270 MHz, CDCl$_3$-DMSO-d$_6$) δ ppm: 8.82–8.77 (1H, br.s), 7.77 (2H, d, J=9 Hz), 7.40 (2H, t, J=9 Hz), 7.22 (1H, t, J=8 Hz), 7.17 (2H, d, J=9 Hz), 6.95 (2H, d, J=9 Hz), 5.54 (1H, d, J=8 Hz), 4.35–4.32 (1H, m), 4.29–4.22 (2H, m), 3.83–3.75 (2H, m), 2.56 (3H, s), 2.10 (3H, s), 2.08–1.7 (2H, m).

Example 105

(±)-N-Hydroxy-Nα-methyl-Nα-(4-phenoxybenzenesulfonyl)-2-[2-(6-phenylpyrimidin-2,4-dione-3-yl)ethyl]glycinamide (Compound No. 5-90)

The title compound was prepared in similar manners to the procedures described in Examples 2 and 64.

white powder; Melting Point: 179–181° C. (Decomposition); $^1$H-Nuclear magnetic resonance spectrum (400 MHz, DMSO-d$_6$) δ ppm: 11.44 (1H, br.s), 10.75 (1H, br.s), 8.96 (1H, br.s), 7.81–7.72 (4H, m), 7.57–7.42 (5H, m), 7.62–7.22 (1H, m), 7.14–7.06 (4H, m), 5.95 (1H, d, J=2 Hz), 4.32 (1H, dd, J=9 Hz, 7 Hz), 3.70–3.59 (2H, m), 2.94 (3H, s), 1.92–1.72 (2H, m).

Example 106

(±)-2-[2-(6-Ethylpyrimidin-2,4-dione-3-yl)ethyl]-N-hydroxy-Nα-methyl-Nα-(4-phenoxybenzenesulfonyl)glycinamide (Compound No. 5-86)

The title compound was prepared in similar manners to the procedures described in Examples 2 and 64.

white powder; Melting Point: 177–179° C. (Decomposition); $^1$H-Nuclear magnetic resonance spectrum (400 MHz, DMSO-d$_6$) δ ppm: 11.13 (1H, s), 10.73 (1H, s), 8.95 (1H, s), 7.77 (2H, dt, J=9 Hz, 3 Hz), 7.45 (2H, t, J=8 Hz), 7.25 (1H, t, J=8 Hz), 7.14–7.08 (4H, m), 5.45 (1H, s), 4.27 (1H, dd, J=9 Hz, 7 Hz), 3.63–3.47 (2H, m), 2.92 (3H, s), 2.32 (2H, q, J=7 Hz), 1.85–1.76 (1H, m), 1.74–1.64 (1H, m), 1.10 (3H, t, J=7 Hz).

Example 107

(±)-Nα-[4-(3-Chlorophenoxy)benzenesulfonyl]-N-hydroxy-Nα-methyl-2-(2-phthalimidoethyl)glycinamide (Compound No. 3-183)

The title compound was prepared in a similar manner to that described in Example 2.

white powder; Melting Point: 81–84° C.; $^1$H-Nuclear magnetic resonance spectrum (400 MHz, CDCl$_3$) δ ppm: 9.41 (1H, br.s), 7.85–7.81 (2H, m), 7.76–7.72 (2H, m), 7.66–7.63 (2H, m), 7.37–7.21 (2H, m), 7.10 (1H, t, J=2 Hz), 6.98–6.96 (1H, m), 6.90–6.86 (2H, m), 4.34 (1H, dd, J=9 Hz, 5 Hz), 3.68–3.62 (1H, m), 3.50–3.42 (1H, m), 2.94 (3H, s), 2.38–2.29 (1H, m), 1.62–1.54 (1H, m).

Example 108

(±)-2-[2-(5-Fluoropyrimidin-2,4-dione-3-yl)ethyl]-N-hydroxy-Nα-(4-phenoxybenzenesulfonyl)-Nα-propargylglycinamide (Compound No. 5-32)

The title compound was prepared in similar manners to the procedures described in Examples 28 and 40.

pale brown amorphous solid; $^1$H-Nuclear magnetic resonance spectrum (400 MHz, DMSO-d$_6$) δ ppm: 11.11 (1H, s), 10.75 (1H, s), 9.08 (1H, s), 7.88–7.79 (3H, m), 7.47 (2H, dd, J=9 Hz, 7 Hz), 7.26 (1H, t, J=7 Hz), 7.15 (2H, d, J=9 Hz), 7.08 (2H, d, J=9 Hz), 4.50–4.42 (1H, m), 4.24–4.18 (2H, m), 3.76–3.61 (2H, m), 3.20 (1H, s), 2.09–2.00 (1H, m), 1.85–1.76 (1H, m).

Example 109

(±)-N-Hydroxy-Nα-(4-phenoxybenzenesulfonyl)-Nα-propargyl-2-[2-(5-trifluoromethylpyrimidin-2,4-dione-3-yl)ethyl]glycinamide (Compound No. 5-38)

The title compound was prepared in similar manners to the procedures described in Examples 28 and 66.

pale brown powder; Melting Point: 170–171° C. (Decomposition); $^1$H-Nuclear magnetic resonance spectrum (270 MHz, DMSO-d$_6$) δ ppm: 11.07 (1H, s), 10.66 (1H, s), 9.11 (1H, s), 7.88–7.77 (3H, m), 7.44 (2H, dd, J=9 Hz, 7 Hz), 7.27 (1H, t, J=7 Hz), 7.16 (2H, d, J=9 Hz), 7.08 (2H, d, J=9 Hz), 4.94–4.49 (1H, m), 4.22–4.13 (2H, m), 3.77–3.62 (2H, m), 3.18 (1H, s), 2.09–1.91 (1H, m), 1.88–1.77 (1H, m).

Example 110

(±)-2-[2-(1,1-Dioxo-1,2-benzisothiazol-3-one-2-yl)ethyl]-N-hydroxy-Nα-(4-phenoxybenzenesulfonyl)-Nα-propargylglycinamide (Compound No. 2-89)

The title compound was prepared in similar manners to the procedures described in Examples 28 and 62.

yellow amorphous solid; $^1$H-Nuclear magnetic resonance spectrum (400 MHz, CDCl$_3$) δ ppm: 9.31 (1H, s), 8.02 (1H, d, J=7 Hz), 7.94–7.81 (3H, m), 7.76 (2H, d, J=9 Hz), 7.70–7.65 (1H, m), 7.49–7.46 (1H, m), 7.41 (2H, t, J=8 Hz), 7.23 (1H, t, J=7 Hz), 7.08 (2H, d, J=8 Hz), 6.75 (2H, d, J=8 Hz), 4.44–4.36 (2H, m), 4.40–4.10 (1H, m), 3.74–3.59 (2H, m), 2.60–2.51 (1H, m), 2.10–1.99 (1H, m).

Example 111

(±)-Nα-[4-(3-Fluorophenoxy)benzenesulfonyl]-N-hydroxy-Nα-methyl-2-(2-phthalimidoethyl)glycinamide (Compound No. 3-184)

The title compound was prepared in a similar manner to that described in Example 2.

pale yellow amorphous solid; $^1$H-Nuclear magnetic resonance spectrum (400 MHz, CDCl$_3$) δ ppm: 9.42 (1H, br.s), 7.84–7.61 (6H, m), 7.42–7.34 (2H, m), 6.97–6.80 (4H, m), 4.3 (1H, dd, J=9 Hz, 5 Hz), 3.68–3.62 (1H, m), 3.50–3.42 (1H, m), 2.94 (3H, s), 2.38–2.29 (1H, m), 1.63–1.54 (1H, m).

Example 112

(±)-N-Hydroxy-Nα-methyl-2-[2-(5-methylthieno[2,3-d]pyrimidin-2,4-dione-3-yl)ethyl]-Nα-(4-phenoxybenzenesulfonyl)glycinamide (Compound No. 5-92)

The title compound was prepared in a similar manner to that described in Example 2.

white powder; Melting Point: 142–144° C. (Decomposition); $^1$H-Nuclear magnetic resonance spectrum (400 MHz, DMDO-d$_6$) δ ppm: 12.17 (1H, s), 10.76 (1H, s), 9.40 (1H, s), 7.78 (2H, d, J=7 Hz), 7.44 (2H, t, J=8 Hz), 7.25 (1H, t, J=7 Hz), 7.13–7.07 (4H, m), 6.69 (1H, s), 4.33–4.29 (1H, m), 3.68–3.56 (2H, m), 2.94 (3H, s), 2.34 (3H, s), 1.85–1.71 (2H, m).

Example 113

(±)-N-Hydroxy-Nα-methyl-Nα-(4-phenoxybenzenesulfonyl)-2-[2-(pyrido[2,3-d]pyrimidin-2,4-dione-3-yl)ethyl]glycinamide (Compound No. 5-93)

The title compound was prepared in similar manners to the procedures described in Examples 2 and 6.

white powder; Melting Point: 125–126° C. (Decomposition); $^1$H-Nuclear magnetic resonance spectrum (400 MHz, DMDO-d$_6$) δ ppm: 11.99 (1H, br.s), 10.76 (1H, br.s), 8.95 (1H, t, J=2 Hz), 8.62 (1H, dd, J=5 Hz, 2 Hz), 8.29 (1H, dd, J=8 Hz, 2 Hz), 7.80–7.77 (2H, m), 7.47–7.42 (2H, m), 7.29–7.23 (2H, m), 7.14–7.07 (4H, m), 4.32 (1H, dd, J=9 Hz, 7 Hz), 3.79–3.67 (2H, m), 2.95 (3H, s), 1.90–1.81 (2H, m).

Example 114

(±)-N-Hydroxy-Nα-methyl-Nα-(4-phenoxybenzenesulfonyl)-2-[2-(thieno[3,4-d]pyrimidin-2,4-dione-3-yl)ethyl]glycinamide (Compound No. 5-94)

The title compound was prepared in a similar manner to that described in Example 2.

white powder; Melting Point: 135–137° C. (Decomposition); $^1$H-Nuclear magnetic resonance spectrum (270 MHz, DMDO-d$_6$) δ ppm: 11.98 (1H, s), 10.70 (1H, s), 9.35 (1H, s), 8.28 (1H, d, J=3 Hz), 7.80 (2H, d, J=9 Hz), 7.44 (2H, t, J=8 Hz), 7.26 (1H, t, J=8 Hz), 7.14–6.98 (4H, m), 6.89 (1H, d, J=3 Hz), 4.20–4.11 (1H, m), 3.66–3.50 (2H, m), 2.92 (3H, s), 2.00–1.93 (1H, m), 1.90–1.75 (1H, m).

Example 115

(±)-N-Hydroxy-Nα-methyl-2-[2-(7-methylthieno[3,2-d]pyrimidin-2,4-dione-3-yl)ethyl]-Nα-(4-phenoxybenzenesulfonyl)glycinamide (Compound No. 5-95)

The title compound was prepared in similar manners to the procedures described in Examples 2 and 42.

white powder; Melting Point: 170–171° C. (Decomposition); $^1$H-Nuclear magnetic resonance spectrum (270 MHz, DMDO-d$_6$) δ ppm: 12.10 (1H, s), 10.69 (1H, s), 9.21 (1H, s), 7.80 (2H, dt, J=9 Hz), 7.43 (2H, t, J=8 Hz), 7.26 (1H, t, J=8 Hz), 7.16–7.00 (5H, m), 4.21–4.08 (1H, m), 3.60–3.43 (2H, m), 2.91 (3H, s), 2.40 (3H, s), 1.98–1.65 (2H, m).

Example 116

(±)-2-[2-(5-Fluoro-6-methylpyrimidin-2,4-dione-3-yl)ethyl]-N-hydroxy-Nα-methyl-Nα-(4-phenoxybenzenesulfonyl)glycinamide (Compound No. 5-96)

The title compound was prepared in similar manners to the procedures described in Examples 2 and 18.

white powder; Melting Point: 196–198° C. (Decomposition); $^1$H-Nuclear magnetic resonance spectrum (400 MHz, DMDO-d$_6$) δ ppm: 11.16 (1H, s), 10.73 (1H, s), 8.94 (1H, s), 7.77 (2H, dt, J=9 Hz, 2 Hz), 7.46 (2H, t, J=8 Hz), 7.26 (1H, t, J=7 Hz), 7.14 (2H, d, J=8 Hz), 7.10 (2H, dt, J=9 Hz, 2 Hz), 4.28 (1H, dd, J=9 Hz, 7 Hz), 3.62–3.55 (2H, m), 2.91 (3H, s), 2.08 (3H, d, J=3 Hz), 1.87–168 (2H, m).

Example 117

(±)-N-Hydroxy-Nα-methyl-2-[2-(1-methylimidazolidin-2,4-dione-3-yl)ethyl]-Nα-(4-phenoxybenzenesulfonyl)glycinamide (Compound No. 5-97)

The title compound was prepared in similar manners to the procedures described in Examples 2 and 4.

white amorphous solid; $^1$H-Nuclear magnetic resonance spectrum (400 MHz, DMDO-d$_6$) δ ppm: 10.70 (1H, s), 8.98 (1H, s), 7.77 (2H, d, J=9 Hz), 7.47 (2H, t, J=8 Hz), 7.26 (1H, t, J=8 Hz), 7.16 (2H, d, J=8 Hz), 7.10 (2H, d, J=9 Hz), 4.22 (1H, t, J=8 Hz), 3.92 (2H, s), 3.25–3.14 (2H, m), 2.87 (3H, s), 2.84 (3H, s), 1.91–1.80 (1H, m), 1.71–1.62 (1H, m).

Example 118

(±)-N-Hydroxy-2-[2-(imidazolidin-2,4-dione-3-yl)ethyl]-Nα-methyl-Nα-(4-phenoxybenzenesulfonyl)glycinamide (Compound No. 5-50)

The title compound was prepared in similar manners to the procedures described in Examples 2 and 4.

white powder; Melting Point: 146–147° C.; $^1$H-Nuclear magnetic resonance spectrum (400 MHz, DMDO-d$_6$) δ ppm: 10.71 (1H, s), 8.97 (1H, s), 8.06 (1H, s), 7.77 (2H, dt, J=9 Hz, 3 Hz), 7.47 (2H, t, J=8 Hz), 7.26 (1H, t, J=7 Hz), 7.15 (2H, d, J=8 Hz), 7.10 (2H, dt, J=8 Hz, 3 Hz), 4.24 (1H, t, J=8 Hz), 3.88 (2H, s), 3.24–3.11 (2H, m), 2.87 (3H, s), 1.89–1.80 (1H, m), 1.75–1.64 (1H, m).

Example 119

(±)-N-Hydroxy-Nα-methyl-Nα-(4-phenoxybenzenesulfonyl)-2-[2-(1,5,5-trimethylimidazolidin-2,4-dione-3-yl)ethyl]glycinamide (Compound No. 5-54)

The title compound was prepared in similar manners to the procedures described in Examples 2 and 4.

white powder; $^1$H-Nuclear magnetic resonance spectrum (400 MHz, DMDO-d$_6$) δ ppm: 10.72 (1H, s), 8.97 (1H, br.s), 7.77 (2H, dt, J=9 Hz, 3 Hz), 7.47 (2H, t, J=7 Hz), 7.26 (1H, t, J=7 Hz), 7.16 (2H, d, J=7 Hz), 7.10 (2H, dt, J=9 Hz, 3 Hz), 4.24 (1H, t, J=8 Hs), 3.28–3.15 (2H, m), 2.86 (3H, s), 2.78 (3H, s), 1.92–1.83 (1H, m), 1.74–1.65 (1H, m).

Example 120

(±)-N-Hydroxy-Nα-methyl-Nα-[(4-pyridin-4-yl)oxybenzene-sulfonyl]-2-[2-(thieno[3,2-d]pyrimidin-2,4-dione-3-yl)ethyl]glycinamide (Compound No. 5-98)

The title compound was prepared in similar manners to the procedures described in Examples 2, 20 and 42.

white powder; Melting Point: 167–168° C. (Decomposition); $^1$H-Nuclear magnetic resonance spectrum (400 MHz, DMDO-d$_6$) δ ppm: 11.90 (1H, br.s), 10.74 (1H, br.s), 8.97 (1H, br.s), 8.50 (2H, d, J=6 Hz), 8.07 (1H, d, J=5 Hz), 7.89–7.86 (2H, m), 7.35–7.32 (2H, m), 7.05 (2H, dd, J=5 Hz, 1 Hz), 6.93 (1H, d, J=5 Hz), 4.30 (1H, dd, J=9 Hz, 6 Hz), 3.75–3.58 (2H, m), 3.00 (3H, s), 1.93–1.73 (2H, m).

Example 121

(±)-2-[2-(6-Chloro-1-methylpyrimidin-2,4-dione-3-yl)ethyl]-N-hydroxy-Nα-methyl-Nα-(4-phenoxybenzenesulfonyl)glycinamide (Compound No. 7-212)

The title compound was prepared in similar manners to the procedures described in Examples 2 and 46.

white powder; Melting Point: 90–93° C.; $^1$H-Nuclear magnetic resonance spectrum (400 MHz, DMDO-d$_6$) δ ppm: 10.74 (1H, br.s), 8.95 (1H, br.s), 7.80–7.75 (2H, m), 7.48–7.44 (2H, m), 7.28–7.24 (1H, m), 7.15–7.06 (4H, m), 6.07 (1H, s), 4.27 (1H, dd, J=9 Hz, 7 Hz), 3.70–3.55 (2H, m), 3.42 (3H, s), 2.91 (3H, s), 1.86–1.68 (2H, m).

Example 122

(±)-2-[2-(6-Chloro-1-methylpyrimidin-2,4-dione-3-yl)ethyl]-N-methyl-N-(4-phenoxybenzenesulfonyl)glycine (Compound No. 7-222)

The title compound was prepared in similar manners to the procedures described in Examples 2 and 45.

white powder; Melting Point: 115–117° C.; $^1$H-Nuclear magnetic resonance spectrum (400 MHz, DMDO-d$_6$) δ ppm: 7.78–7.74 (2H, m), 7.42–7.37 (2H, m), 7.23–7.19 (1H, m), 7.06–6.99 (4H, m), 5.93 (1H, s), 4.74 (1H, dd, J=10 Hz, 6 Hz), 4.02–3.89 (2H, m), 3.55 (3H, s), 2.92 (3H, s), 2.28–2.20 (1H, m), 2.05–1.94 (1H, m).

Example 123

(±)-Nα-[4-(4-Chlorophenoxy)benzenesulfonyl]-2-[2-(6-chloropyrimidin-2,4-dione-3-yl)ethyl]-N-hydroxy-Nα-methylglycinamide (Compound No. 7-181)

The title compound was prepared in similar manners to the procedures described in Examples 2 and 94.

white powder; Melting Point: 171–173° C. (Decomposition); $^1$H-Nuclear magnetic resonance spectrum (400 MHz, DMDO-d$_6$) δ ppm: 12.38 (1H, br.s), 10.72 (1H, s), 7.78 (2H, dt, J=9 Hz, 3 Hz), 7.50 (2H, dt, J=9 Hz, 4 Hz), 7.17 (2H, dt, J=9 Hz, 4 Hz), 7.14–7.12 (2H, m), 5.90 (1H, s), 4.27 (1H, dd, J=9 Hz, 6 Hz), 3.63–3.51 (2H, m), 2.91 (3H, s), 1.86–1.75 (1H, m), 1.75–1.69 (1H, m).

Example 124

(±)-2-[2-(6-Chloropyrimidin-2,4-dione-3-yl)ethyl]-Nα-[4-(4-fluorophenoxy)benzenesulfonyl]-N-hydroxy-Nα-methylglycinamide (Compound No. 7-182)

The title compound was prepared in similar manners to the procedures described in Examples 2 and 94.

white powder; Melting Point: 190–191 CC (Decomposition); $^1$H-Nuclear magnetic resonance spectrum (400 MHz, DMDO-d$_6$) δ ppm: 12.38 (1H, s), 10.72 (1H, s), 7.76 (2H, dt, J=9 Hz, 3 Hz), 7.32–7.26 (2H, m), 7.23–7.18 (2H, m), 7.08 (2H, dt, J=9 Hz, 3 Hz), 5.89 (1H, s), 4.27 (1H, dd, J=9 Hz, 7 Hz), 3.63–3.54 (2H, m), 2.90 (3H, s), 1.86–1.79 (1H, m), 1.77–1.67 (1H, m).

Example 125

(±)-Nα-[4-(4-Chlorophenoxy)benzenesulfonyl]-N-hydroxy-Nα-methyl-2-[2-(6-trifluoromethylpyrimidin-2,4-dione-3-yl)ethyl]glycinamide (Compound No. 8-181)

The title compound was prepared in similar manners to the procedures described in Examples 2 and 96.

white powder; Melting Point: 173–174° C. (Decomposition); $^1$H-Nuclear magnetic resonance spectrum (400 MHz, DMDO-$d_6$) δ ppm: 12.40 (1H, br.s), 10.74 (1H, br.s), 8.94 (1H, br.s), 7.80–7.77 (2H, m), 7.51–7.47 (2H, m), 7.19–7.11 (4H, m), 6.20 (1H, s), 4.28 (1H, dd, J=8 Hz, 7 Hz), 3.67–3.56 (2H, m), 2.92 (3H, s), 1.88–1.71 (2H, m).

Example 126

(±)-Nα-[4-(4-Fluorophenoxy)benzenesulfonyl]-N-hydroxy-Nα-methyl-2-[2-(6-trifluoromethylpyrimidin-2,4-dione-3-yl)ethyl]glycinamide (Compound No. 8-182)

The title compound was prepared in similar manners to the procedures described in Examples 2 and 96.

white powder; Melting Point: 163–164° C. (Decomposition); $^1$H-Nuclear magnetic resonance spectrum (400 MHz, DMDO-$d_6$) δ ppm: 12.40 (1H, br.s), 10.74 (1H, br.s), 8.95 (1H, br.s), 7.79–7.75 (2H, m), 7.33–7.26 (2H, m), 7.24–7.17 (2H, m), 7.11–7.05 (2H, m), 6.21 (1H, s), 4.28 (1H, dd, J=9 Hz, 7 Hz), 3.70–3.57 (2H, m), 2.90 (3H, s), 1.88–1.71 (2H, m).

Example 127

(±)-Nα-[4-(3-Chlorophenoxy)benzenesulfonyl]-N-hydroxy-Nα-methyl-2-[2-(6-trifluoromethylpyrimidin-2,4-dione-3-yl)ethyl]glycinamide (Compound No. 8-194)

The title compound was prepared in similar manners to the procedures described in Examples 2 and 96.

white powder; Melting Point: 168–169° C. (Decomposition); $^1$H-Nuclear magnetic resonance spectrum (400 MHz, DMDO-$d_6$) δ ppm: 12.41 (1H, br.s), 10.74 (1H, br.s), 8.96 (1H, br.s), 7.82–7.79 (2H, m), 7.47 (1H, t, J=8 Hz), 7.31 (1H, dd, J=8 Hz, 2 Hz), 7.24 (1H, t, J=2 Hz), 7.18–7.07 (3H, m), 6.21 (1H, s), 4.28 (1H, dd, J=8 Hz, 6 Hz), 3.67–3.55 (2H, m), 2.93 (3H, s), 1.88–1.72 (2H, m).

Example 128

(±)-Nα-[4-(3-Chlorophenoxy)benzenesulfonyl]-2-[2-(6-chloro-pyrimidin-2,4-dione-3-yl)ethyl]-N-hydroxy-Nα-methylglycinamide (Compound No. 7-194)

The title compound was prepared in similar manners to the procedures described in Examples 2 and 94.

white powder; Melting Point: 168–170° C. (Decomposition); $^1$H-Nuclear magnetic resonance spectrum (400 MHz, DMDO-$d_6$) δ ppm: 12.41–12.35 (1H, br.s), 10.73 (1H, s), 8.95 (1H, s), 7.79 (2H, dt, J=9 Hz, 3 Hz), 7.47 (1H, t, J=8 Hz), 7.31 (1H, dd, J=8 Hz, 2 Hz), 7.25 (1H, t, J=2 Hz), 7.16 (2H, dt, J=9 Hz, 3 Hz), 7.11 (1H, dd, J=8 Hz, 2 Hz), 5.89 (1H, s), 4.26 (11H, dd, J=9 Hz, 7 Hz), 3.66–3.50 (2H, m), 2.92 (3H, s), 1.86–1.68 (2H, m).

Example 129

(±)-2-[2-(6-Chloropyrimidin-2,4-dione-3-yl)ethyl]-Nα-ethyl-N-hydroxy-Nα-(4-phenoxybenzenesulfonyl)glycinamide (Compound No. 7-42)

The title compound was prepared in similar manners to the procedures described in Examples 78 and 94.

pale pink amorphous solid; $^1$H-Nuclear magnetic resonance spectrum (400 MHz, DMDO-$d_6$) δ ppm: 12.38 (1H, br.s), 10.67 (1H, s), 8.98 (1H, s), 7.81 (2H, d, J=9 Hz), 7.46 (2H, t, J=8 Hz), 7.26 (1H, t, J=7 Hz), 7.14 (2H, d, J=8 Hz), 7.08 (2H, d, J=9 Hz), 5.88 (1H, s), 4.21 (1H, t, J=8 Hz), 3.69–3.61 (1H, m), 3.59–3.52 (2H, m), 3.24 (1H, dq, J=15 Hz, 7 Hz), 1.90–1.82 (1H, m), 1.77–1.68 (1H, m), 1.20 (3H, t, J=7 Hz).

Example 130

(±)-2-[2-(6-Chloropyrimidin-2,4-dione-3-yl)ethyl]-Nα-[4-(3-fluorophenoxy)benzenesulfonyl]-N-hydroxy-Nα-methylglycinamide (Compound No. 7-196)

The title compound was prepared in similar manners to the procedures described in Examples 2 and 94.

pale yellow powder; Melting Point: 147–148° C.; $^1$H-Nuclear magnetic resonance spectrum (400 MHz, DMDO-$d_6$) δ ppm: 12.40–12.36 (1H, br.s), 10.74 (1H, s), 8.94 (1H, s), 7.78 (2H, d, J=9 Hz), 7.51–7.45 (1H, m), 7.16 (2H, d, J=9 Hz), 7.11–7.01 (2H, m), 6.97 (1H, d, J=8 Hz), 5.76 (1H, s), 4.25 (1H, t, J-8 Hz), 3.68–3.43 (2H, m), 2.93 (3H, s), 1.87–1.65 (2H, m).

Example 131

(±)-2-[2-(6-Chloropyrimidin-2,4-dione-3-yl)ethyl]-N-hydroxy-Nα-methyl-Nα-[4-(pyridin-4-yl)oxybenzenesulfonyl]glycinamide (Compound No. 7-26)

The title compound was prepared in similar manners to the procedures described in Examples 2, 20 and 94.

pale brown powder; Melting Point: 163–165° C. (Decomposition); $^1$H-Nuclear magnetic resonance spectrum (400. MHz, DMDO-$d_6$) δ ppm: 12.43 (1H, br.s), 10.72 (1H, s), 8.96 (1H, s), 8.52 (2H, br.s), 7.86 (2H, d, J=9 Hz), 7.34 (2H, d, J=9 Hz), 7.06 (2H, d, J=5 Hz), 5.89 (1H, s), 4.26 (1H, dd, J=9 Hz, 6 Hz), 3.62–3.50 (2H, m), 2.96 (3H, s), 1.87–1.70 (2H, m).

Example 132

(±)-Nα-[4-(3-Fluorophenoxy)benzenesulfonyl]-N-hydroxy-Nα-methyl-2-[2-(6-trifluoromethylpyrimidin-2,4-dione-3-yl)ethyl]glycinamide (Compound No. 8-196)

The title compound was prepared in similar manners to the procedures described in Examples 2 and 96.

white powder; Melting Point: 168–169° C. (Decomposition); $^1$H-Nuclear magnetic resonance spectrum (400 MHz, DMDO-$d_6$) δ ppm: 12.41 (1H, br.s), 10.74 (1H, br.s), 8.96 (1H, br.s), 7.82–7.79 (2H, m), 7.47 (1H, dd, J=15 Hz, 8 Hz), 7.19–7.16 (2H, m), 7.15–7.03 (2H, m), 6.97 (1H, dd, J=8 Hz, 2 Hz), 6.21 (1H, s), 4.28 (1H, dd, J=9 Hz, 7 Hz), 3.68–3.51 (2H, m), 2.93 (3H, s), 1.91–1.71 (2H, m).

Example 133

(±)-N-Hydroxy-Nα-methyl-Nα-[4-(pyridin4-yl)oxybenzenesulfonyl]-2-[2-(6-trifluoromethylpyrimidin-2,4-dione-3-yl)ethyl]glycinamide (Compound No. 8-26)

The title compound was prepared in similar manners to the procedures described in Examples 2, 20 and 96.

white powder; Melting Point: 116–118° C. (Decomposition); ¹H-Nuclear magnetic resonance spectrum (400 MHz, DMDO-d₆) δ ppm: 10.77 (1H, br.s), 8.97 (1H, br.s), 8.52–8.50 (2H, m), 7.87–7.83 (2H, m), 7.34–7.32 (2H, m), 7.06–7.04 (2H, m), 5.99 (1H, s), 4.25 (1H, dd, J=9 Hz, 7 Hz), 3.64–3.51 (2H, m), 2.98 (3H, s), 1.87–1.68 (2H, m).

Example 134

(±)-2-[2-(6-Chloropyrimidin-2,4-dione-3-yl)ethyl]-N-hydroxy-Nα-propyl-Nα-(4-phenoxybenzenesulfonyl)glycinamide (Compound No. 7-58)

The title compound was prepared in similar manners to the procedures described in Examples 80 and 94.

pale pink amorphous solid; ¹H-Nuclear magnetic resonance spectrum (400 MHz, DMDO-d₆) δ ppm: 12.38 (1H, br.s), 10.65 (1H, s), 8.98 (1H, s), 7.81 (2H, d, J=9 Hz), 7.46 (2H, t, J=8 Hz), 7.15 (1H, t, J=7 Hz), 7.14 (2H, d, J=7 Hz), 7.08 (2H, d, J=9 Hz), 5.88 (1H, s), 4.19 (1H, t, J=8 Hz), 3.65–3.54 (2H, m), 3.41 (1H, dt, J=16 Hz, 8 Hz), 3.08 (1H, dt, J=16 Hz, 8 Hz), 1.90–1.82 (1H, m), 1.74–1.60 (3H, m), 0.78 (3H, t, J=7 Hz).

Example 135

(±)-Nα-Ethyl-N-hydroxy-Nα-(4-phenoxybenzenesulfonyl)-2-[2-(6-trifluoromethylpyrimidin-2,4-dione-3-yl)ethyl]glycinamide (Compound No. 8-42)

The title compound was prepared in similar manners to the prodcedures described in Examples 78 and 96.

pale pink amorphous solid; ¹H-Nuclear magnetic resonance spectrum (400 MHz, DMDO-d₆) δ ppm: 12.39 (1H, br.s), 10.69 (1H, br.s), 8.99 (1H, br.s), 7.83–7.78 (2H, m), 7.48–7.43 (2H, m), 7.27–7.23 (1H, m), 7.15–7.05 (4H, m), 6.20 (1H, s), 4.23 (1H, t, J=7 Hz), 3.74–3.53 (3H, m), 3.40–3.32 (1H, m), 1.94–1.72 (2H, m), 1.20 (3H, t, J=7 Hz).

Example 136

(±)-N-Hydroxy-Nα-(4-phenoxybenzenesulfonyl)-Nα-propyl-2-[2-(6-trifluoromethylpyrimidin-2,4-dione-3-yl)ethyl]glycinamide (Compound No. 8-58)

The title compound was prepared in similar manners to the procedures described in Examples 80 and 96.

pale pink amorphous solid; ¹H-Nuclear magnetic resonance spectrum (400 MHz, DMDO-d₆) δ ppm: 12.39 (1H, br.s), 10.66 (1H, br.s), 8.98 (1H, br.s), 7.84–7.78 (2H, m), 748–7.43 (2H, m), 7.27–7.24 (1H, m), 7.15–7.05 (4H, m), 6.20 (1H, s), 4.21 (1H, t, J=8 Hz), 3.72–3.56 (2H, m), 3.47–3.33 (1H, m), 3.15–3.05 (1H, m), 1.94–1.85 (1H, m), 1.80–1.61 (3H, m), 0.78 (3H, t, J=7 Hz).

Example 137

(±)-N-Hydroxy-Nα-methyl-2-[2-(1-methyl-6-trifluoromethyl-pyrimidin-2,4-dione-3-yl)ethyl]-Nα-(4-phenoxybenzenesulfonyl)glycinamide (Compound No. 8-212)

The title compound was prepared in similar manners to the procedures described in Examples 2 and 46.

white amorphous solid; ¹H-Nuclear magnetic resonance spectrum (400 MHz, DMDO-df) δ ppm: 9.36 (1H, br.s), 7.73 (2H, d, J=9 Hz), 7.44–7.38 (2H, m), 7.30–7.21 (1H, m), 7.09–6.99 (4H, m), 6.66 (1H, br.s), 6.23 (1H, s), 4.39 (1H, t, J=7 Hz), 3.86–3.67 (2H, m), 3.50 (3H, s), 2.93 (3H, s), 2.33–2.24 (1H, m), 1.83–1.73 (1H, m).

Example 138

(±)-2-[2-(5-Chloropyrimidin-2,4-dione-3-yl)ethyl]-N-hydroxy-Nα-methyl-Nα-(4-phenoxybenzenesulfonyl)glycinamide (Compound No. 5-35)

The title compound was prepared in similar manners to the procedures described in Examples 2 and 40.

pink amorphous solid; ¹H-Nuclear magnetic resonance spectrum (400 MHz, DMDO-d₆) δ ppm: 11.56 (1H, br.d, J=6 Hz), 10.73 (1H, br.s), 8.95 (1H, br.s), 7.90 (1H, d, J=5 Hz), 7.79–7.76 (2H, m), 7.48–7.43 (2H, m), 7.25 (1H, t, J=7 Hz), 7.15–7.07 (4H, m), 4.28 dd, J=9 Hz, 7 Hz), 3.70–3.57 (2H, m), 2.91 (3H, s), 1.87–1.69 (2H, m).

Example 139

Nα-[4-(3-Chlorophenoxy)benzenesulfonyl]-N-hydroxy-Nα-methyl-2(R)-[2-(quinazolin-2,4-dione-3-yl)ethyl]glycinamide (Compound No. 1-182)

The title compound was prepared in similar manners to the procedures described in Examples 2, 6 and 72.

white powder; Melting Point: 137–140° C. (Decomposition); ¹H-Nuclear magnetic resonance spectrum (400 MHz, DMDO-d₆) δ ppm: 11.45 (1H, br.s), 10.76 (1H, br.s), 8.95 (1H, br.s), 7.93–7.91 (1H, m), 7.82–7.79 (2H, m), 7.67–7.63 (1H, m), 7.48–7.43 (1H, m), 7.31–7.06 (7H, m), 4.32 (1H, dd, J=9 Hz, 6 Hz), 3.82–3.67 (2H, m), 2.97 (3H, s), 1.94–1.76 (2H, m).

Example 140

Nα-[4-(3-Chlorophenoxy)benzenesulfonyl]-N-hydroxy-Nα-methyl-2(R)-[2-(thieno[3,2-d]pyrimidin-2,4-dione-3-yl)ethyl]glycinamide (Compound No. 5-99)

The title compound was prepared in similar manners to the procedures described in Examples 2, 42 and 72.

white powder; Melting Point: 192–194° C. (Decomposition); ¹H-Nuclear magnetic resonance spectrum (400 MHz, DMDO-d₆) δ ppm: 11.88 (1H, br.s), 10.74 (1H, t, J=2 Hz), 8.94 (1H, t, J=2 Hz), 8.07 (1H, d, J=5 Hz), 7.81–7.79 (2H, m), 7.48–7.43 (1H, m), 7.30 (1H, d, J=8 Hz), 7.24 (1H, dd, J=4 Hz, 2 Hz), 7.17–7.07 (3H, m), 6.92 (1H, d, J=5 Hz), 4.30 (1H, dd, J=9 Hz, 6 Hz), 3.75–3.59(2H, m), 2.95 (3H, s), 1.92–1.72 (2H, m).

Example 141

Nα-[4-(3-Chlorophenoxy)benzenesulfonyl]-N-hydroxy-Nα-methyl-2(R)-(2-phthalimidoethyl)glycinamide (Compound No. 3-183)

The title compound was prepared in similar manners to the procedures described in Examples 2, and 72.

a white amorphous solid; The ¹H-Nuclear magnetic resonance spectrum of the product was same as that shown in Example 107. HPLC analysis: retention time: 22.0 minutes.

<Experimental Condition>
column: CHIRALCEL OJ-R (product of Daicel Chem. Ind. Ltd)
inside diameter: 0.46 cm,
length: 15 cm, grain size 5 μm
eluant: acetonitrile/triethylamine-phosphate buffer solution (0.2%(v/v), pH 2.2)=35/65
flow rate: 0.5 ml/minute
temperature: 40° C.
detection: UV 254 nm Example 142

(±)-2-(1,1-Dimethyl-2-phthalimidoethyl)-N-hydroxy-Nα-methyl-Nα-(4-phenoxybenzenesulfonyl)glycinamide (Compound No. 3-32)

In a similar manner to that described in Example 1(2)-b, a 4-phenoxybenzylsulfonylation reaction was carried out using (±)-2-(1,1-dimethyl-2-phthalimidoethyl)-glycine benzyl ester as a starting material, followed by a N-methylation reaction according to Example 1(3), by a de-benzylation reaction according to Example 5(5)-a and then by a hydroxyamidation reaction according to Example 2 to give the title compound as a white powder.

Melting Point: 189–190° C.; $^1$H-Nuclear magnetic resonance spectrum (400 MHz, DMDO-d$_6$) δ ppm: 10.79 (1H, s), 9.03 (1H, s), 7.90–7.84 (4H, m), 7.50–7.46 (2H, m), 7.29–7.25 (1H, m), 7.19–7.16 (2H, m), 7.11 (2H, dt, J=9 Hz, 3 Hz), 4.19 (1H, s), 3.87 (1H, d, J=14 Hz), 3.51 (1H, d, J=14 Hz), 3.00 (3H, s), 1.01 (3H, s), 0.94 (3H, s).

Example 143

(±)-Nα-Cyclopropyl-N-hydroxy-Nα-(4-phenoxybenzenesulfonyl)-2-(2-phthalimidoethyl) glycinamide (Compound No. 3-193)

In a similar manner to the procedures described in Example 37(2), cyclization and allyl esterification reactions were carried out using (±)-α-[N-cyclopropyl-N-(4-phenoxybenzenesulfonyl)amino]-γ-butyrolactone as a starting material, followed by a phthalimidation according to Example 1(1), by de-allylation according to 1(4) and then by hydroxyamidation according to Example 2 to give the title compound as a white amorphous solid.

$^1$H-Nuclear magnetic resonance spectrum (400 MHz, DMDO-d$_6$) δ ppm: 10.59 (1H, s), 8.97 (1H, br.s), 7.87–7.79 (4H, m), 7.47 (2H, t, J=8 Hz), 7.27 (1H, t, J=8 Hz), 7.15 (2H, d, J=9 Hz), 7.05 (2H, dt, J=9 Hz, 3 Hz), 4.33 (1H, t, J=7 Hz), 3.54–3.45 (1H, m), 3.43–3.35 (1H, m), 2.29–2.24 (1H, m), 2.20–2.11 (1H, m), 1.93–1.83 (1H, m), 1.11–0.99 (1H, m), 0.89–0.83 (1H, m), 0.75–0.68 (1H, m), 0.63–0.58 (1H, m).

Example 144

(±)-2-[2-(6-Acetylpyrimidin-2,4-dione-3-yl)ethyl]-N-hydroxy-Nα-methyl-Nα-(4-phenoxybenzensulfonyl)glycinamide (Compound No. 9-153)

The title compound was prepared in a similar manner to the procedures described in Example 94.

white powder; Melting Point: 167–169° C.; $^1$H-Nuclear magnetic resonance spectrum (270 MHz, CDCl$_3$-DMDO-d$_6$) δ ppm: 9.92 (1H, br.s), 9.38 (1H, br.s), 8.31 (1H, br.s), 7.77–7.72 (2H, m), 7.45–7.37 (2H, m), 7.25–7.19 (1H, m), 7.08–6.98 (4H, m), 6.30 (1H, d, J=2 Hz), 4.93 (1H, t, J=8 Hz), 3.87–3.73 (2H, m), 2.96 (3H, s), 2.52 (3H, s), 2.27–2.11 (1H, m).

Example 145

(±)-2-[2-(6-Ethoxycarbonylpyrimidin-2,4-dione-3-yl)ethyl]-N-hydroxy-Nα-methyl-Nα-(4-phenoxybenzenesulfonyl)glycinamide (Compound No. 9-10)

The title compound was prepared in a similar manner to the procedures described in Example 94.

white powder; Melting Point: 159–160° C.; $^1$H-Nuclear magnetic resonance spectrum (270 MHz, CDCl$_3$) δ ppm 9.50 (1H, br.s), 8.99 (1H, br.s), 7.73–7.68 (2H, m), 7.45–7.38 (2H, m), 7.26–7.19 (1H, m), 7.09–6.99 (4H, m), 4.47–4.39 (3H, m), 3.87–3.71 (2H, m), 2.90 (3H, s), 2.37–2.23 (1H, m), 1.78–1.63 (1H, m), 1.39 (3H, t, 7 Hz).

REFERENCE EXAMPLE

Reference Example 1

N-(tert-Butoxycarbonyl)homoserine Benzyl Ester

A solution of di-tert-butylcarbonate (36.40 g, 166.8 mmol) in dioxane (100 ml) was added to a solution of (±)-α-amino-γ-butyrolactone hydrobromide (25.28 g, 138.9 mmol) in a mixture of dioxane/water=1/1 (200 ml). 20 minutes were spent in adding dropwise a solution of sodium hydroxide (12,58 g, 321.1 mmol) in water (100 ml) to the mixture with ice-cooling and with stirring. This mixture was stirred for 30 minutes with ice-cooling and then at room temperature for 3 hours. The reaction mixture was concentrated under reduced pressure. Water (300 ml) was added to the residue and the mixture was acidified by citric acid (25 g) and extracted with ethyl acetate. The organic layer was washed with water, dried over anhydrous magnesium sulfate and concentrated under reduced pressure. The residue was dissolved in ethanol (200 ml), and a solution of sodium hydroxide (5.44 g, 138.9 mmol) in water (33 ml) was added to the solution with ice-cooling. After this mixture was allowed to stand at room temperature overnight, it was concentrated under reduced pressure. The resulting residue was dissolved in N,N-dimethylformamide (150 ml), benzyl bromide (16.5 ml, 138.7 mmol) was added to the solution, the mixture was stirred at room temperature overnight, and then it was concentrated under reduced pressure. To the residue, a saturated aqueous solution of ammonium chloride was added and this was extracted with ethyl acetate. The organic layer was washed with water, dried over anhydrous magnesium sulfate and concentrated under reduced pressure to give the title compound (39.75 g, yield 93%) as a pale yellow oil.

$^1$H-Nuclear magnetic resonance spectrum (270 MHz, CDCl$_3$) δ ppm: 7.41–7.31 (5H, m), 5.40 (1H, br.d, J=8 Hz), 5.19 (2H, s), 4.58–4.48 (1H, m), 3.77–3.58 (2H, m), 3.12 (1H, br.s), 2.23–2.11 (1H, m), 1.73–1.58 (1H, m), 1.45 (9H, s).

Reference Example 2

(±)-N-(tert-Butoxycarbonyl)homoserine Allyl Ester

In a similar manner to the procedures described in Reference Example 1, reactions were carried out using allyl bromide, instead of benzyl bromide, to give the title compound (yield 89%) as a colorless oil.

$^1$H-Nuclear magnetic resonance spectrum (270 MHz, CDCl$_3$) δ ppm: 5.91 (1H, ddd, J=17 Hz, 12 Hz, 6 Hz), 5.40–5.25 (3H, m), 4.67 (2H, d, J=6 Hz), 4.57–4.48 (1H, m), 3.79–3.63 (2H, m), 3.17 (1H, br.s), 2.24–2.12 (1H, m), 1.69–1.59 (1H, m), 1.45 (9H, s).

Reference Example 3

1-Benzyloxymethylpyrimidine-2,4-dione

After N,O-bis(trimethylsilyl)acetoamide (18.5 ml, 74.8 mmol) was added dropwise to a suspension of pyrimidine-2,4-dione (3.36 g, 30.0 mmol) in dichloromethane (90 ml) at room temperature, the mixture was stirred for 2 hours. Tetra-n-butyl ammonium iodide (1.12 g, 3.0 mmol) was added to the reaction mixture, and benzyloxymethyl chloride (4.4 ml, 31.7 mmol) was further added to it. This mixture was stirred at room temperature for 3 hours. The reaction mixture was neutralized with water and a saturated aqueous solution of sodium hydrogencarbonate, and it was extracted with ethyl acetate. The organic layer was washed with a 10% aqueous solution of sodium thiosulfate and with water successively, dried over anhydrous magnesium sulfate and concentrated under reduced pressure. The solid residue was washed with diisopropyl ether and collected by filtration to give the title compound (6.00 g, yield 86%) as a white powder.

$^1$H-Nuclear magnetic resonance spectrum (270 MHz, CDCl$_3$) δ ppm: 8.50 (1H, br.s), 7.36–7.28 (6H, m), 5.74 (1H, dd, J=7 Hz, 2 Hz), 5.23 (2H, s), 4.62 (2H, s).

Reference Example 4

1-Benzyloxymethylquinazoline-2,4-dione

In a similar manner to the procedures described in Reference Example 3, reactions were carried out using quinazoline-2,4-dione, instead of pyrimidine-2,4-dione, to give the title compound (yield 82%) as a white solid.

$^1$H-Nuclear magnetic resonance spectrum (270 MHz, DMSO-d$_6$) δ ppm: 11.63 (1H, s), 8.00 (1H, dd, J=8 Hz, 2 Hz), 7.77 (1H, dt, J=8 Hz, 2 Hz), 7.52 (1H, d, J=8 Hz), 7.33–7.26 (6H, m), 5.61 (2H, s), 4.62 (2H, s).

Reference Example 5

1-(2-Trimethylsilyl)ethoxymethylquinazoline-2,4-dione

In a similar manner to the procedures described in Reference Example 3, reactions were carried out using quinazoline-2,4-dione, instead of pyrimidine-2,4-dione, and using 2-(trimethylsilyl)ethoxymethyl chloride, instead of benzyloxymethyl chloride, to give the title compound (yield 87%) as a white powder.

$^1$H-Nuclear magnetic resonance spectrum (270 MHz, CDCl$_3$) δ ppm: 8.65 (1H, br.s), 8.23 (1H, dd, J=8 Hz, 2 Hz), 7.72 (1H, dt, J=8 Hz, 2 Hz), 7.51 (1H, d, J=8 Hz), 7.32 (1H, t, J=8 Hz), 5.60 (2H, s), 3.74 (2H, t, J=8 Hz), 0.97 (2H, t, J=8 Hz), −0.02 (9H, s).

Reference Example 6

1-Benzyloxymethyl-5-methylpyrimidine-2,4-dione

In a similar manner to the procedures described in Reference Example 3, reactions were carried out using 5-methylpyrimidine-2,4-dione, instead of pyrimidine-2,4-dione, to give the title compound (yield 98%) as a yellow powder.

$^1$H-Nuclear magnetic resonance spectrum (270 MHz, CDCl$_3$) δ ppm: 8.78 (1H, br.s), 7.33 (5H, s), 7.11 (1H, s), 5.21 (2H, s), 4.62 (2H, s), 1.19 (3H, s).

Reference Example 7

1-Benzyloxymethyl-5,6-dimethylpyrimidine-2,4-dione

In a similar manner to the procedures described in Reference Example 3, reactions were carried out using 5,6-dimethylpyrimidine-2,4-dione, instead of pyrimidine-2,4-dione, to give the title compound (yield 78%) as a white powder.

$^1$H-Nuclear magnetic resonance spectrum (270 MHz, CDCl$_3$) δ ppm: 8.46 (1H, s), 7.38–7.26 (5H, m), 5.44 (2H, s), 4.65 (2H, s), 2.35 (3H, s), 1.94 (3H, s).

Reference Example 8

1-Benzyloxymethyl-5-fluoropyrimidine-2,4-dione

In a similar manner to the procedures described in Reference Example 3, reactions were carried out using 5-fluoropyrimidine-2,4-dione, instead of pyrimidine-2,4-dione, to give the title compound (yield 87%) as a white powder.

$^1$H-Nuclear magnetic resonance spectrum (270 MHz, CDCl$_3$-DMSO-d$_6$) δ ppm: 11.60–11.52 (1H, br.s), 7.47 (1H, d, J=6 Hz), 7.39–7.27 (5H, m), 5.20 (2H, s), 4.62 (2H, s).

Reference Example 9

(±)-α-(4-Phenoxybenzensulfonylamino)-γ-butyrolactone

Triethylamine (20.0 ml, 143.9 mmol) was added to a suspension of α-amino-γ-butyrolactone hydrobromide (7.28 g, 40.0 mmol) in dichloromethane (80 ml), and then 20 minutes were spent in adding dropwise a solution of 4-phenoxybenzenesulfonyl chloride (11.0 g, 40.9 mmol) in dichloromethane (40 ml) to the mixture with ice-cooling. After this mixture was stirred at room temperature for 2 hours, the solvent of the reaction mixture was evaporated under reduced pressure. The residue was acidified with water and hydrochloric acid (1N), and then extracted with ethyl acetate. The organic layer was washed with water, dried over anhydrous magnesium sulfate and concentrated under reduced pressure. The residue was purified by chromatography on a silica gel column using hexane/ethyl acetate=2/1 as the eluant to give the title compound (8.74 g, yield 73%) as a white powder.

$^1$H-Nuclear magnetic resonance spectrum (270 MHz, CDCl$_3$) δ ppm: 7.88–7.82 (2H, m), 7.46–7.39 (2H, m), 7.26–7.21 (1H, m), 7.10–7.03 (4H, m), 5.18 (1H, br.d, J=3 Hz), 4.45 (1H, t, J=9 Hz), 4.21 (1H, ddd, J=12 Hz, 9 Hz, 6 Hz), 3.93 (1H, ddd, J=12 Hz, 8 Hz, 3 Hz), 2.80–2.70 (1H, m), 2.37–2.22 (1H, m).

Reference Example 10

1-(2-Trimethylsilyl)ethoxymethylthieno[3,2-d]pyrimidine-2,4-dione

In a similar manner to the procedures described in Reference Example 3, reactions were carried out using thieno[3,2-d]pyrimidine-2,4-dione, instead of pyrimidine-2,4-dione, and using 2-(trimethylsilyl)ethoxymethyl chloride, instead of benzyloxymethyl chloride, to give the title compound (yield 87%) as a pale yellow powder.

$^1$H-Nuclear magnetic resonance spectrum (270 MHz, CDCl$_3$) δ ppm: 8.62 (1H, br.s), 7.78 (1H, d, J=6 Hz), 7.13 (1H, d, J=6 Hz), 5.46 (2H, s), 3.67 (2H, t, J=8 Hz), 0.93 (2H, t, J=8 Hz), −0.02 (9H, s).

Reference Example 11

7-Methyl-3-(2-trimethylsilyl)ethoxymethylxanthine

In a similar manner to the procedures described in Reference Example 3, reactions were carried out using 7-methylxanthine, instead of pyrimidine-2,4-dione, and using 2-(trimethylsilyl)ethoxymethyl chloride, instead of benzyloxymethyl chloride, to give the title compound (yield 69%) as a pale yellow powder.

$^1$H-Nuclear magnetic resonance spectrum (270 MHz, CDCl$_3$) δ ppm: 8.09 (1H, br.s), 7.55 (1H, s), 5.51 (2H, s), 3.97 (3H, s), 3.75–3.69 (2H, m), 1.01–0.95 (2H, m), −0.02 (9H, s).

Reference Example 12

1-(2-Trimethylsilyl)ethoxymethylpteridin-2,4-dione

In a similar manner to the procedures described in Reference Example 3, reactions were carried out using pteridin-2,4-dione, instead of pyrimidine-2,4-dione, and using 2-(trimethylsilyl)ethoxymethyl chloride, instead of benzyloxymethyl chloride, to give the title compound (yield 53%) as a yellow powder.

$^1$H-Nuclear magnetic resonance spectrum (270 MHz, CDCl$_3$) δ ppm: 9.01 (1H, br.s), 8.71 (1H, d, J=2 Hz), 8.66 (1H, d, J=2 Hz), 5.77 (2H, s), 3.80–3.74 (2H, m), 1.02–0.96 (2H, m), 0.01 (9H, s).

Reference Example 13

6-Methyl-1-(2-trimethylsilyl)ethoxymethylpyrimidine-2,4-dione

In a similar manner to the procedures described in Reference Example 3, reactions were carried out using 6-methylpyrimidine-2,4-dione, instead of pyrimidine-2,4-dione, and using 2-(trimethylsilyl)ethoxymethyl chloride, instead of benzyloxymethyl chloride, to give the title compound (yield 56%) as a white powder.

$^1$H-Nuclear magnetic resonance spectrum (270 MHz, CDCl$_3$) δ ppm: 8.70 (1H, br.s), 5.58 (1H, s), 5.28 (2H, s), 3.68–3.62 (2H, m), 2.34 (3H, s), 0.96–0.87 (2H, m), −0.01 (9H, s).

Reference Example 14

5-Trifluoromethyl-1-(2-trimethylsilyl)ethoxymethyl-pyrimidine-2,4-dione

In a similar manner to the procedures described in Reference Example 3, reactions were carried out using 5-trifluoromethylpyrimidine-2,4-dione, instead of pyrimidine-2,4-dione, and using 2-(trimethylsilyl)ethoxymethyl chloride, instead of benzyloxymethyl chloride, to give the title compound (yield 76%) as a white powder.

$^1$H-Nuclear magnetic resonance spectrum (270 MHz, CDCl$_3$) δ ppm: 8.48 (1H, br.s), 7.81 (1H, s), 5.17 (2H, s), 3.66–3.60 (2H, m), 0.98–0.92 (2H, m), −0.03 (9H, s).

Reference Example 15

1-(2-Trimethylsilyl)ethoxymethyl-6,7-dihydro-5H-cyclopenta[d]pyrimidine-2,4-dione In a similar manner to the procedures described in Reference Example 3, reactions were carried out using 6,7-dihydro-5H-cyclopenta[d]pyrimidine-2,4-dione, instead of pyrimidine-2,4-dione, and using 2-(trimethylsilyl)ethoxymethyl chloride, instead of benzyloxymethyl chloride, to give the title compound (yield 71%) as a pale yellow powder.

$^1$H-Nuclear magnetic resonance sperrun (270 MHz, CDCl$_3$) δ ppm: 8.38 (1H, br.s), 5.17 (2H, s), 3.67–3.60 (2H, m), 2.97–2.91 (2H, m), 2.76–2.69 (2H, m), 2.18–2.07 (2H, m), 0.96–0.89 (2H, m), 0.01(9H, s).

Reference Example 16

6,7-Dimethoxy-1-(2-trimethylsilyl)ethoxymethyl-quinazoline-2,4-dione

In a similar manner to the procedures described in Reference Example 3, reactions were carried out using 6,7-dimethoxyquinazoline-2,4-dione, instead of pyrimidine-2,4-dione, and using 2-(trimethylsilyl)ethoxymethyl chloride, instead of benzyloxymethyl chloride, to give the title compound (yield 93%) as a white powder.

$^1$H-Nuclear magnetic resonance spectrum (270 MHz, DNSO-d$_6$) δ ppm: 11.52 (1H, s), 7.48 (1H, s), 7.03 (1H, s), 5.62 (2H, s), 4.00 (3H, s), 3.92 (3H, s), 3.73 (2H, t, J=8 Hz), 0.98 (2H, t, J=8 Hz), 0.04 (9H, s).

Reference Example 17

6-Chloro-1-(2-trimethylsilyl)ethoxymethylpyrimidine-2,4-dione

In a similar manner to the procedures described in Reference Example 3, reactions were carried out using 6-chloropyrimidine-2,4-dione, instead of pyrimidine-2,4-dione, and using 2-(trimethylsilyl)ethoxymethyl chloride, instead of benzyloxymethyl chloride, to give the title compound (yield 71%) as a white powder.

$^1$H-Nuclear magnetic resonance spectrum (400 MHz, CDCl$_3$) δ ppm: 9.10 (1H, br.s), 5.93 (1H, s), 5.45 (2H, s), 3.68 (2H, t, J=8 Hz), 0.96 (2H, t, J=8 Hz), 0.01 (9H, s).

Reference Example 18

6-Trifluoromethyl-1-(2-trimethylsilyl)ethoxymethyl-pyrimidine-2,4dione

In a similar manner to the procedures described in Reference Example 3, reactions were carried out using 6-trifluoromethylpyrimidine-2,4-dione, instead of pyrimidine-2,4-dione, and using 2-(trimethylsilyl)ethoxymethyl chloride, instead of benzyloxymethyl chloride, to give the title compound (yield 48%) as a colorless oil. $^1$H-Nuclear magnetic resonance spectrum (270 MHz, CDCl$_3$) δ ppm: 8.84 (1H, br.s), 6.24 (1H, d, J=2 Hz), 5.32 (2H, s), 3.73–3.68 (2H, m), 0.97–0.90 (2H, m), 0.01 (9H, s).

Reference Example 19

6-Phenyl-1-(2-trimethylsilyl)ethoxymethylpyrimidine-2,4-dione

The title compound was prepared in a similar manner to the procedures described in Reference Example 5.

white powder; $^1$H-Nuclear magnetic resonance spectrum (270 MHz, CDCl$_3$) δ ppm: 8.28 (1H, br.s), 7.55–7.45 (5H, m), 5.66 (1H, d, J=2 Hz), 5.00 (2H, s), 3.61–3.55 (2H, m), 0.94–0.87 (2H, m), −0.01 (9H, s).

Reference Example 20

6-Ethyl-1-(2-trimethylsilyl)ethoxymethylpyrimidine-2,4-dione

The title compound was prepared in a similar manner to the procedures described in Reference Example 5.

white powder; ¹H-Nuclear magnetic resonance spectrum (270 MHz, CDCl₃) δ ppm: 8.80–8.74 (1H, br.s), 5.60 (1H, s), 5.29 (2H, s), 3.64 (2H, t, J=8 Hz), 2.67 (2H, q, J=7 Hz), 1.22 (3H, t, J=7 Hz), 0.90 (2H, t, J=8 Hz), 0.01 (9H, s).

Reference Example 21

5-Methyl-1-(2-trimethylsilyl)ethoxymethylthieno[2,3-d]pyrimidine-2,4-dione

The title compound was prepared in a similar manner to the procedures described in Reference Example 5.

white powder; ¹H-Nuclear magnetic resonance spectrum (270 MHz, CDCl₃) δ ppm: 8.46 (1H, br.s), 6.54 (1H, d, J=1 Hz), 5.43 (2H, s), 3.71–3.65 (2H, m), 2.51 (3H, d, J=1 Hz), 1.00–0.94 (2H, m), 0.01 (9H, s).

Reference Example 22

1-(2-Trimethylsilyl)ethoxymethylpyrido[2,3-d]pyrimidine-2,4-dione

The title compound was prepared in a similar manner to the procedures described in Reference Example 5.

white powder; ¹H-Nuclear magnetic resonance spectrum (270 MHz, CDCl₃) δ ppm: 8.96 (1H, br.s), 8.73 (1H, dd, J=5 Hz, 2 Hz), 8.47 (1H, dd, J=8 Hz, 2 Hz), 7.37 (1H, dd, J=8 Hz, 5 Hz), 5.80 (2H, s), 3.81–3.74 (2H, m), 1.03–0.96 (2H, m), −0.02 (9H, s).

Reference Example 23

1-(2-Trimethylsilyl)ethoxymethylthieno[3,4-d]pyrimidine-2,4-dione

The title compound was prepared in a similar manner to the procedures described in Reference Example 5.

white powder; ¹H-Nuclear magnetic resonance spectrum (270 MHz, CDCl₃) δ ppm: 8.30 (1H, d, J=3 Hz), 8.10 (1H, br.s), 6.96 (1H, d, J=3 Hz), 5.46 (2H, s), 3.72–3.65 (2H, m), 1.01–0.94 (2H, m), −0.02 (9H, s).

Reference Example 24

7-Methyl-1-(2-trimethylsilyl)ethoxymethylthieno[3,2-d]pyrimidine-2,4-dione

The title compound was prepared in a similar manner to the procedures described in Reference Example 5.

white powder; ¹H-Nuclear magnetic resonance spectrum (270 MHz, CDCl₃) δ ppm: 8.71 (1H, br.s), 7.42 (1H, s), 5.62 (2H, br.s), 3.79–3.73 (3H, m), 2.60 (3H, s), 101–0.95 (2H, m), −0.02 (9H, s).

Reference Example 25

5-Fluoro-6-methyl-1-(2-trimethylsilyl)ethoxymethyl-pyrimidine-2,4-dione

The title compound was prepared in a similar manner to the procedures described in Reference Example 5.

white powder; ¹H-Nuclear magnetic resonance spectrum (270 MHz, CDCl₃) δ ppm: 8.34–8.21 (1H, br.s), 5.29 (2H, s), 3.66 (2H, t), 2.38 (3H, d, J=4 Hz), 0.94 (2H, t, J=8 Hz), 0.01 (9H, s).

Reference Example 26

5-Chloro-1-(2-trimethylsilyl)ethoxymethylpyrimidine-2,4-dione

The title compound was prepared in a similar manner to the procedures described in Reference Example 5.

white powder; ¹H-Nuclear magnetic resonance spectrum (270 MHz, CDCl₃) δ ppm: 8.48 (1H, br.s), 7.54 (1H, s), 5.14 (2H, s), 3.67–3.60 (2H, m), 0.99–0.92 (2H, m), 0.03 (9H, s).

Reference Example 27

6-Acetyl-1-(2-trimethylsilyl)ethoxymethylpyrimidine-2,4-dione

The title compound was prepared in a similar manner to the procedures described in Reference Example 5.

white powder; ¹H-Nuclear magnetic resonance spectrun (270 MHz, CDCl₃) δ ppm: 8.49 (1H, br.s), 5.90 (1H, d, J=2 Hz), 5.35 (2H, s), 3.53–3.47 (2H, m), 2.51 (3H, s), 0.91–0.85 (2H, m), 0.00 (9H, s).

Reference Example 28

6-Ethoxycarbonyl-1-(2-trimethylsilyl)ethoxymethyl-pyrimidine-2,4-dione

The title compound was prepared in a similar manner to the procedures described in Reference Example 5.

colorless oil; ¹H-Nuclear magnetic resonance spectrum (270 MHz, CDCl₃) δ ppm: 8.72 (1H, br.s), 6.11 (1H, d, J=2 Hz), 5.52 (2H, s), 4.39 (2H, q, J=7 Hz), 3.55–3.48 (2H, m), 1.38 (3H, t, J=7 Hz), 0.91–0.85 (2H, m), −0.01 (9H, s).

Reference Example 29

1-Methyl-6-trifluoromethylpyrimidine-2,4-dione

A solution of pyrimidine-2,4-dione (158 mg, 0.88 mmol) in anhydrous tetrahydrofuran (1 ml) was added dropwise to a suspension of potassium tert-butoxide (99 mg, 0.88 mmol) in tetrahydrofaran (2 ml) with ice-cooling, and the mixture was stirred at room temperature for 1 hour. Methyl trifloromethanesulfonate (100 μl, 0.88 mmol) was added dropwise to the reaction mixture with ice-cooling. This mixture was stirred at the same temperature for 12 hours. The reaction mixture was poured into 1N hydrochloric acid, and then this was extracted with ethyl acetate. The organic layer was dried over anhydrous sodium sulfate and concentrated under reduced pressure. The residue was purified by chromatography on a silica gel column using hexane/ethyl acetate=8/2 as the eluant to give the title compound (105 mg, yield 62%) as a white powder.

¹H-Nuclear magnetic resonance spectrum (270 MHz, CDCl₃) δ ppm: 8.58 (1H, br.s), 6.21 (1H, br.s), 3.50 (3H, q, J=1 Hz).

Reference Example 30

(±)-2-(1,1-Dimethyl-2-phthalimidoethyl)glycine Benzyl Ester Hydrochloride

After potassium phthalimide (3.71 g, 21.1 mmol) was added to a solution of DL-pantolactone (2.61 g, 20.1 mmol) in N,N-dimethylformamide (40 ml), the mixture was stirred at 150° C. for 16 hours. After cooling the reaction mixture to room temperature, benzyl bromide (2.6 ml, 21.9 mmol) and potassium carbonate (3.0 g, 21.6 mmol) were further added to it and this was stirred for 2 hours. To the reaction mixture, water was added and then this was extracted with ethyl acetate. The organic layer was washed with water, dried over anhydrous magnesium sulfate and concentrated under reduced pressure. The residue was purified by chromatography on a silica gel column using hexane/ethyl acetate=3/1 as the eluant to give (±)-2-hydroxy-3,3- dimethylphthalimidobutanoic acid benzyl ester (3.27 g, yield 42%) as a colorless oil.

2.00 g (5.44 mmol) of the product were dissolved in dichloromethane (7.5 ml), and pyridine (554 µl, 6.85 mmol) was added to it. After the mixture was cooled to −78° C., trifluoromethanesulfonic acid anhydride (962 µl, 5.72 mmol) was added and this was stirred at −78° C. for 20 minutes and then stirred at room temperature for 1 hour.

The reaction mixture was concentrated under reduced pressure and diethyl ether was added to the residue. The insoluble material was removed by filtration and the filtrate was concentrated under reduced pressure. The resulting residue was dissolved in N,N-dimethylformamide (30 ml) and sodium azide (707 mg, 10.9 mmol) was added to the solution. After the mixture was stirred at 50° C. for 4 hours, water was added to the reaction mixture and then this was extracted with ethyl acetate. The organic layer was washed with water, dried over anhydrous magnesium sulfate and concentrated under reduced pressure to afford (±)-2-azido-3,3-dimethyl-4-phthalimidobutanoic acid benzyl ester as a pale yellow oil (this product was used in the next reaction without further purification).

$^1$H-Nuclear magnetic resonance spectrum (400 MHz, CDCl$_3$) δ ppm: 7.89–7.85 (2H, m), 7.78–7.73 (2H, m), 7.41–7.33 (5H, m), 5.25 (2H, s), 4.00 (1H, s), 3.81 (1H, d, J=15 Hz), 3.65 (1H, d, J=15 Hz), 1.07 (3H, s), 0.97 (3H, s).

The thus obtained azide compound (whole amount) was dissolved in methanol (22 ml), a solution of hydrogen chloride in dioxane (4N, 1.63 ml, 6.53 mmol) was added to the solution, platinum oxide (38 mg, 0.17 mmol) was added to the mixture, and this was stirred under a hydrogen atmosphere at room temperature for 10 hours. The reaction mixture was filtered and the filtrate was concentrated under reduced pressure to give the title compound (620 mg, yield 28%) as a white powder. Mass spectrum (EI) m/z: 366 [M$^+$].

Reference Example 31

(±)-α-[N-Cyclopropyl-N-(4-phenoxybenzenesulfonyl)-amino]-γ-butyrolactone

After potassium carbonate (18.24 g, 132.0 mmol) was added to a solution of cyclopropylamine (5.50 ml, 80.0 mmol) and (±)-α-bromo-γ-butyrolactone (3.32 ml, 42.0 mmol) in acetonitrile (80 ml), the mixture was stirred at room temperature for 8 hours. To the reaction mixture, water was added and then this was extracted with ethyl acetate. The organic layer was washed with water, dried over anhydrous sodium sulfate and concentrated under reduced pressure. The residue was purified by chromatography on a silica gel column using hexane/ethyl acetate=1/1 as the eluant to give (±)-α-cyclopropylamino-γ-butyrolactone (4.10 g, yield 73%) as a yellow oil.

$^1$H-Nuclear magnetic resonance spectrum (400 MHz, CDCl$_3$) δ ppm: 4.41 (1H, dd, J=16 Hz, 10 Hz), 4.27–4.18 (1H, m), 3.69 (1H, t, J=9 Hz), 2.60–2.52 (1H, m), 2.29–2.24 (1H, m), 0.51–0.46 (2H, m), 0.44–0.36 (2H, m).

4.10 g (29.0 mmol) of the product was dissolved in dichloromethane (60 ml), 4-phenoxybenzensulfonyl chloride (9.35 g, 34.8 mmol) and triethylamine (5.04 ml, 36.3 mmol) were added to the solution, and the mixture was stirred at room temperature for 60 hours. To the reaction mixture, 1N hydrochloric acid was added and then this was extracted with ethyl acetate. The organic layer was washed with water, dried over anhydrous sodium sulfate and concentrated under reduced pressure. The residue was purified by chromatography on a silica gel column using hexane/ethyl acetate=4/1 as the eluant to give the title compound (8.54 g, yield 79%) as a white powder.

$^1$H-Nuclear magnetic resonance spectrum (400 MHz, CDCl$_3$) δ ppm: 7.97 (2H, dt, J=9 Hz, 3 Hz), 7.41 (2H, t, J=8 Hz), 7.25 (1H, t, J=8 Hz), 7.09 (2H, d, J=8 Hz), 7.05 (2H, dt, J=9 Hz, 3 Hz), 4.80 (1H, dd, J=13 Hz, 11 Hz), 4.52 (1H, t, J=9 Hz), 4.29 (1H, dd, J=16 Hz, 9 Hz), 2.78–2.67 (1H, m), 2.58–2.51 (1H, m), 2.48–2.41 (1H, m), 0.83–0.76 (1H, m), 0.74–0.69 (2H, m), 0.69–0.62 (1H, m).

FORMULATION EXAMPLE

Formulation Example 1: Powder 5 g of the compound of Example 72, 895 g of lactose and 100 g of cornstarch were mixed in a blender to obtain a powder.

Formulation Example 2: Granules

After mixing 5 g of the compound of Example 72, 865 g of lactose and 100 g of low-substituted hydroxypropylcellulose, 300 g of a 10% aqueous solution of hydroxypropylcellulose were added, followed by kneading. This mixture was formed into granules using an extrusion granulating machine, followed by drying to obtain granules.

Formulation Example 3: Tablets

After mixing 5 g of the compound of Example 72, 90 g of lactose, 34 g of cornstarch, 20 g of crystaline cellulose and 1 g of magnesium stearate in a blender, the mixture was formed into tablets with a tableting machine to obtain tablets.

TEST EXAMPLE

Test Example 1: MMP-13 Inhibition Test (in vitro)

MMP-13 exists in chondrocytes and chondrosarcoma cells, and the DNA sequence corresponding to the amino acid sequence of its precursor (proMMP-13) has been reported by Freije et al. (Freije, J. M. P., et al., J. Biol. Chem., vol. 269, 16766–16773, 1994). Therefore, proMMP-13 can be expressed by acquiring cDNA of proMMP-13 from chondrocytes and chondrosarcoma cells in accordance with conventional methods, by incorporating this into an ordinarily used vector, and by introducing this vector into suitable cells to transform the cells.

An MMP-13 inhibition test can be conducted by, for example, treating recombinant proMMP-13 obtained in the above manner with p-aminophenyl-mercuric(II) acetate (APMA) to convert proMMP-13 to active MMP-13, and then using this as enzyme to measure MMP-13 activity in the presence or absence of a test compound using a fluorescent substrate.

(1) Expression of Recombinant proMMP-13 mRNA was isolated from human chondrosarcoma HCS-2/8, which is a chondrosarcoma cell line established by Takigawa et al. (Jpn. J. Cancer. Res., vol. 85, 364–371, 1994), in accordance with conventional methods, and cDNA of proMMP-13 was acquired by reverse transcription polymerase chain reaction (RT-PCR). 5'-gctgagctcatgcatccaggggtcctggctgcc-3' (Sequence No. 1 of the Sequence listing) and 5'-cgataccattaccccaaatgctcttcagga-3' (Sequence No. 2 of the Sequence listing), which contain the restriction enzyme cleavage site sacI or KpnI (portions indicated by underlining) were used for primers. The amplified cDNA was incorporated into expression vector pcDL- SRα296 (provided by Dr. Yutaka Takebe of the National Institute of Health) by coupling at the sites of restriction enzyme cleavage sites sacI and KpnI (Takara Shuzo Co., Ltd.) (the resulting vector is referred to as "pSRα-proMMP-13"). Simultaneously, the amplified cDNA was also incorporated in pUC19 (Takara Shuzo Co., Ltd.) and the amplified cDNA nucleotide sequence was confirmed to be identical to the reported sequence (Freije, J. M. P., et al., J. Biol. Chem., vol. 269, 16766–16773, 1994). pSRα-proMMP-13 gene was introduced into COS-1 cells grown in Dulbecco's Modified Eagle Medium (DMEM) containing 10% fetal bovine serum by electroporation (Current Protocols in Molecular Biology, 9.3.1, CURRENT PROTOCOLS). After 12 hours, the medium was replaced with DMEM which does not contain fetal bovine serum, followed by culturing for 48 hours to express proMMP-13. The resulting culture supernatant was then used as the proMMP-13 fraction.

(2) Measurement of MMP-13 Activity

The proMMP fraction obtained in (1) was treated for 1 hour at 37° C. with 1 mM APMA (Sigma) to be converted to active MMP-13, which was then used as an enzyme solution. In addition, 7-methoxycoumarin-4-yl(MOCAc)-Pro-Leu-Gly-Leu-2,4-dinitrophenyl(DPa)-Ala-Arg-NH$_2$ (Peptide) was used for the substrate.

This enzyme solution and substrate (20 µM) were added to 50 mM Tris-HCl buffer (pH 7.5) containing 0.15 M sodium chloride, 10 mM calcium chloride, 0.05% Brij 35 and 0.02% sodium azide to bring the final volume to 0.1 ml, followed by reacting for 1 hour at 37° C. After stopping the reaction by adding 0.1 ml of 3% acetic acid, enzyme activity was determined by measuring with a fluorophotometer (Labsystems Fluoroskan II) at an excitation wavelength of 330 nm and emission wavelength of 390 nm.

Inhibition rate was determined according to enzyme activity in the presence and absence of the test compound followed by calculation of the 50% inhibitory concentration ($IC_{50}$).

TABLE 10

| Test Compound | $IC_{50}$ (nM) |
| --- | --- |
| Compound of Example 42 | 0.47 |
| Compound of Example 139 | 0.43 |
| Compound of Example 140 | 0.32 |

As shown in Table 10 above, the compounds of the present invention exhibited excellent MMP-13 inhibitory activity.

Test Example 2: Aglycanase Inhibition Test (in vitro)

An aglycanase inhibition test can be conducted by, for example, measuring aglycanase activity in the presence or absence of a test compound according to the method of Nagase et al. (H. Nagase and J. F. Woessner, Analytical Biochemistry, vol. 107, 385–392, 1980).

The enzyme used for measurement of aglycanase activity can be extracted from mammalian cartilage tissue itself or from its cultured medium. Extraction is performed by combining various types of chromatography, and the activity of aglycanase in the purification process can be detected by adding substrate (aglycan) to an eluted fraction and testing whether or not the substrate is cleaved. Whether or not the substrate is cleaved can be determined by performing imnunoblotting for the reaction liquid using an antibody that binds to the epitope, CNLeNIEGE, that is produced by cleavage of aglycan (substrate) by aglycanase (enzyme). It should be noted that antibody that binds to CNLeNIEGE can be prepared according to the method of Sandy et al. (J. D. Sandy et al., Journal of Biological Chemistry, vol. 270, 2550–2556, 1995).

(1) Preparation of Aglycanase

Bovine nasal septum cartilage was cultured for 7 days at 37° C. in the presence of 1 µm retinoic acid in DMEM [containing 20 mM N-2-hydroxyethyl-piperazine-N'-2-ethane sulfonic acid (HEPES), 0.005% bovine serum albumin (BSA), 5 µg/ml insulin-transferrin sodium selenite media supplement, 1% penicillin and 1% streptomycin] while changing the medium once a day. The culture liquid collected from day 3 to day 7 was subjected to chromatography [carrier: Q-sepharose (Pharmacia), mobile phase: 20 mM Tris-HCl buffer (pH 7.2) containing 5 mM calcium chloride] and the fraction that passed through the column was collected. This was then subjected to additional chromatography [carrier: Zn-chelating sepharose (Pharmacia), mobile phase: Tris-HCl buffer (pH 7.2) containing 5 mM calcium chloride and 0.5 M sodium chloride], followed by elution using imidazole as the mobile phase. The fraction of the resulting eluted fractions that was confirmed to have aglycanase activity was collected. Moreover, this was subjected to additional chromatography [carrier: LCA-agarose (Honen Corporation), mobile phase: 20 mM aqueous solution of 2-(N-morpholino)ethanesulfonic acid (pH 6.5) containing 5 mM calcium chloride and 0.25 M sodium chloride], followed by elution using 2-methylmannopyranoside as the mobile phase. The fraction of the resulting eluted fractions that was confirmed to have aglycanase activity was collected, and this fraction was used as the enzyme liquid for measurement of aglycanase activity.

Separate from the above, antibody that binds with CNLeNIEGE was prepared according to the method of Sandy et al. (J. D. Sandy et al., Journal of Biological Chemistry, vol. 270, 2550–2556, 1995), and this antibody was used in immunoblotting to detect aglycanase activity in the above-mentioned purification process of the aglycanase. Immunoblotting was performed in accordance with conventional methods.

(2) Measurement of Aglycanase Activity

Measurement of activity was performed using a modification of the protease activity measurement method that uses polyacrylamide particles of Nagase et al. (H. Nagase and J. F. Woessner, Analytical Biochemistry, vol. 107, 385–392, 1980).

The aglycan used for the substrate was isolated from bovine nasal septum cartilage in accordance with cesium chloride sedimentation equilibrium centrifugation (New Biochemical Experimentation Course, 3, Saccharides II, 4–7, Tokyo Kagaku Dojin Publishing, 1991). By using this aglycan, polyacrylamide particles containing aglycan were prepared in accordance with the method of Nagase et al. (H. Nagase and J. F. Woessner, Analytical Biochemistry, vol. 107, 385–392, 1980). Namely, aglycan (dry weight: 480 mg) was first added to 28 ml of liquid A [1 M Tris-HCl buffer (pH 8.5) containing 0.2% N,N,N',N'-tetramethylethylenediamine (TEMED)] and the mixture was stirred at 4° C. for 1 hour. Next, 8 ml of liquid B (aqueous solution containing 3 g of acrylamide and 61 mg of bis-acrylamide in 10 ml) and 12 ml of liquid C (aqueous solution containing 0.112 g of ammonium persulfate in 20 ml) were added to this suspension, followed by stirring and allowing to stand for about one hour at room temperature. The polymerized gel was sliced into thin sections, followed by homogenizing in cold water to form the gel into particles. After washing these particles with water, the particles were dehydrated using acetone and then air-dried to evaporate the acetone. The resulting powder was passed through a sieve (mesh size: 420 μm) to remove the large particles.

The enzyme liquid obtained in (1) and the test compound were pipetted into a 96-well plate, and further a suspension I [50 mM Tris-HCl buffer (pH 7.2) containing 5 mM calcium chloride and 0.25 M sodium chloride), in which the above aglycan-containing polyacrylamide particles were suspended so that the final concentration of the above aglycan-containing polyacrylamide particles was 10 mg/ml] was added to make the amount of each reaction liquid to be 100 μl. After allowing to react at 37° C. for 2.5 hours, the reaction was stopped by adding 20 μl of 100 mM ethylenediamine tetraacetic acid to the reaction liquid. This reaction liquid was then centrifuged (at 4° C. and 2500 rpm for 10 minutes), 10 μl of supernatant were transferred to a different 96-well plate, and 190 μl of 1,9-dimethylmethylene blue solution were added, followed immediately by measurement of optical absorbance at 525 nm. Using the resulting measured values as indicators of aglycanase activity, inhibition rates were determined from aglycanase activity in the presence and absence of the test compounds, followed by calculation of 50% inhibitory concentration ($IC_{50}$).

TABLE 11

| Test Compound | $IC_{50}$ (nM) |
|---|---|
| Compound of Example 6 | 7.0 |
| Compound of Example 18 | 7.6 |
| Compound of Example 42 | 5.4 |
| Compound of Example 72 | 4.9 |
| Compound of Example 141 | 2.9 |
| Compound of Example 139 | 3.7 |
| Compound of Example 140 | 2.2 |

As shown in Table 11, the compounds of the present invention demonstrated excellent aglycanase inhibitory action.

Test Example 3: Test for Inhibiting Cartilage Tissue Decomposition (in vitro)

A test for inhibiting cartilage tissue decomposition can be performed by investigating the action that inhibits decomposition of proteoglycan and collagen, which are the two main components of cartilage tissue, and the cartilage tissue used in the test can be prepared according to, for example, the method of Ellis et al. (Ellis, A. J. et al., BBRC, 201, 94, 1994).

The amount of decomposition of proteoglycan can be determined by measuring the amount of glycosaminoglycan formed by decomposition of proteoglycan, while the amount of collagen decomposition can be determined by measuring the amount of hydroxyproline formed by decomposition of collagen.

(1) Preparation of Cartilage Tissue

Bovine nasal septum cartilage was sampled according to the method of Ellis et al. (Ellis, A. J. et al., BBRC, 201, 94, 1994), followed by immersing this in ice-cooled Leibovitz's L-15 medium (Gibco BRL) containing 500 μg/ml of gentamycin and 100 μg/ml of chloromycetin to remove connective tissue and other tissue and to obtain cartilage only. The following procedure was performed on a clean bench. The resulting cartilage was sliced in sections having a thickness of 2 mm to prepare cartilage pieces (2 mm×2 mm). After washing these twice with Hank's Balanced Salt Solution (HBSS), the cartilage pieces were cultured in a 24-well plate. At this time, 600 μl of medium I [DMEM medium containing 25 mM HEPES, 0.05% BSA, 2 mM glutamine, 100 μg/ml of streptomycin, 100 μ/ml of penicillin and 2.5 μg/ml of amphotericin] and three pieces of cartilage were added to each well, and then this was cultured at 37° C. for 24 hours. The resulting culture was used in the following test.

(2) Proteoglycan Decomposition Inhibitory Action a) Proteoglycan Decomposition Reaction The cartilage pieces obtained in (1) were cultured at 37° C. for 7 days in 600 μl of medium I and in the presence of 1 μM retinoic acid. At this time, dimethyl sulfoxide or a dimethyl sulfoxide solution of the test compound was added simultaneous to the addition of retinoic acid at 1/1000 volume of the medium. After culturing, the medium was collected and the amount of glycosaminoglycan in the medium was measured as an indicator of the amount of decomposition of proteoglycan.

b) Measurement of Glycosaminoglycan

Measurement of glycosaminoglycan was performed according to the dimethylmethylene blue pigment bonding method. Namely, 250 μl of pigment reagent (aqueous solution containing 16 mg of 1,9-dimethylmethylene blue, 3.04 g of glycine, 2.37 g of sodium chloride and 95 ml of 0.1 M hydrogen chloride in 1 liter, pH 3.0) was added to 10 μl of collected medium, followed immediately by measurement of optical absorbance at 525 nm to determine the amount of proteoglycan. At this time, chondroitin sulfate A (Sigma, 5 to 180 μg/ml) (from porcine rib cartilage) was used as the reference sample.

The proteoglycan decomposition inhibitory action of the test compound was determined from the ratio of the amount of proteoglycan of the test compound addition group to the amount of proteoglycan of the dimethyl sulfoxide addition group.

(3) Collagen Decomposition Inhibitory Action (a) Collagen Decomposition Reaction The cartilage pieces obtained in (1) were cultured at 37° C. for 7 days in 600 μl of medium I and in the presence of 10 ng/ml of Interleukin-1α (IL-1α, Genzyme) and 50 ng/ml of Oncostatin M (Genzyme). At this time, dimethyl sulfoxide or a dimethyl sulfoxide solution of the test compound was added simultaneously with addition of IL-1α and Oncostatin M at 1/1000 volume of the medium. After the culturing, the culture liquid was collected and culturing was repeated three times under the same conditions (for a total of 4 weeks of culturing). All of the collected culture liquids were combined and the amount of hydroxyproline in the culture liquid was measured as an indicator of the amount of decomposition of collagen.

b) Measurement of Hydroxyproline

100 μl of culture liquid collected in (3)-a) above was transferred to a round-bottom screw-top centrifuge tube, followed by the addition of 100 μl of 12 N hydrochloric acid and by hydrolyzing at 105° C. for 16 hours (Heating Block HF-61, Yamato Science, Ltd.). 100 μl of this reaction liquid was then transferred to a disposable glass tube and dried with a centrifugal evaporator. 500 μl of a mixture of isopropanol and water (1:1) was added to this disposable glass tube to dissolve the dry solid. Moreover, 250 μl of Chloramine-T reagent [consisting of a mixture of 0.141 g of Chloramine-T (p-toluenesulfonylchloramine, Sigma), 2 ml of water, 3 ml of methyl cellosolve and acetate-citrate buffer (said acetate-citrate buffer comprising an aqueous solution containing 7.5 g of citric acid monohydrate, 6 ml of glacial acetic acid, and 60 g of sodium acetate trihydrate in 500 ml, pH 6.0)] were added, followed by stirring and allowing to stand at room temperature for 20 minutes. Moreover, after adding 250 µl of 3.15 M perchloric acid, stirring and allowing to stand at room temperature for 5 minutes, 250 µl of 20% dimethylaminobenzaldehyde (Sigma) in methyl cellosolve solution was added, stirred and allowed to react at 60° C. for 20 minutes. Next, the reaction liquid was cooled to room temperature for 5 minutes and transferred to a microplate in a portion of 200 µl, followed by measurement of optical absorbance at 557 nm.

Separate from the above, L-hydroxyproline (Sigma) was dissolved in an isopropanol-water (1:1) mixture and 500 µl of the resulting solution was transferred to a disposable glass tube to prepare a standard line. (At this time, the solution was prepared so that the amount of L-hydroxyproline in the tube was within the range of 0.05 µg to 2 µg). 250 µl of the above Chloramine-T reagent was added to this solution after which the procedure was performed in the same manner as above to prepare the standard line by measuring optical absorbance at 557 nm.

The collagen decomposition inhibitory action of the test compound was determined from the ratio of the amount of hydroxyproline of the test compound addition group to the amount of hydroxyproline of the dimethyl sulfoxide addition group.

In this test, the compounds of the present invention demonstrated excellent cartilage tissue decomposition inhibitory activity.

Test Example 4: MMP-13 Inhibition Test of Orally Administered Test Compound (ex vivo)

An MMP-13 inhibition test was conducted according to the procedures described in Test Example 1 above on a solution obtained by removing the protein from blood sampled at fixed times after oral administration of test compound as an indicator of oral absorptivity and hemodynamics.

Namely, the test compound was suspended in 0.5% tragacanth and the suspension was administered orally at 5 ml/kg to rats (Wister-Imnamichi: age 5 to 6 weeks) which had been fasted overnight. Blood was collected from the caudal vein in the presence of heparin at fixed time (1, 2 or 4 hours) after administration. This blood was transferred to an Eppendorf tube and centrifuged at 12,000 rpm for 3 minutes. The plasma was transferred to a different tube, followed by the addition of an equal volume of acetonitrile and by allowing to stand undisturbed at 4° C. for 10 minutes. This was then centrifuged at 12,000 rpm for 3 minutes, followed by collection of the supernatant. This supernatant was concentrated and dried with a centrifugal evaporator after which a small amount of dimethyl sulfoxide was added to dissolve. MMP-13 activity was then measured according to the part (2) of the above Test Example 1 in the presence of the resulting solution.

The same procedure was performed on blood sampled from the caudal vein of animals to which no drug was administered, and this was used as the control.

Inhibition rate was calculated from the MMP-13 activities of the control and drug administration groups.

In this test, the compounds of the present invention demonstrated excellent oral absorptivity and hemodynamics.

Test Example 5: Naturally-occurring Osteoarthritis (OA) Inhibition Test (in vivo)

This test can be conducted according to the method of Bendele et al. (Bendele, A. M. and Hulman, J. F., Arthritis and Rheumatism, vol. 31, 561–563, 1998).

(1) Preparation of a Naturally-occurring Model of OA and Drug Administration

Six-weeks-old male guinea pigs purchased from Japan Charles River were given free access to food and water and two animals were raised in each cage. After continuing to raise the animals until age of 6 months, the animals were divided into three groups (of six animals each) so that the mean body weights of each group were nearly equal.

One group was immediately put to euthanasia, followed by excision of the knee joins, which were then used for pathologic tissue study. One of the remaining two groups was designated as the drug administration group and the other as a control group. Animals of the control group were given ordinary guinea pig solid laboratory diet, while animals of the drug administration group were given guinea pig solid laboratory diet containing the test compound. The animals were raised under these conditions until age of 12 months. Next, all of the animals were killed euthanasically, the knee joints were excised and used for pathologic tissue study.

(2) Pathologic Tissue Study

After removing soft tissue including the tendons of the patella, while leaving the joint capsule, the left and right knee joints were immersed for 24 hours in a 10% formalin/phosphate buffer solution (PBS), followed by decalcifying for 2 weeks using the Surgi Path Decalcifier I (Surgi Path Medical Industries). The knee joints were divided into anterior and posterior portions and additionally decalcified for one or two days.

After embedding the thus obtained joint tissue in paraffin, thin sections for hematoxylin-eosin staining (thickness: 6 µm) and toluidine staining (thickness: 8 µm) were prepared from the joint tissue. Sections were also prepared every 150 to 200 µm to allow observation of the entire joint surface (total of 6 sections). The left and right joints of all animals in each group were observed from the viewpoint of pathological tissues in a blind test and assigned an OA onset score based on the following standards.

A score of 0 was given when changes in the medial tibeal plateau and femoral condoyl were observed in the absence of lesions. A score of 1 was given when chondrocyte disturbances, decreases or other small foci were observed in the surface layer of the joint cartilage and decreased toluidine blue staining and splitting of the surface layer were observed in the matrix. A score of 2 was given when foci similar to "1" were observed in the upper layer of the cartilage intermediate layer as well. A score of 3 was given when foci generally covered the cartilage surface layer and had also spread to the lower layer of the intermediate layer. A score of 4 was given when definite disturbances (disappearance of chondrocytes and proteoglycan) had reached the deep layer but had not reached the tidemark. A score of 5 was given when disturbances covered the entire cartilage and had reached the tidemark.

The total score of the left and right knee joints was averaged for each group, and inhibition rate was calculated for the drug administration group versus the control group.

In this test, the compounds of the present invention demonstrated excellent inhibitory action on the onset of OA.

It should be noted that inhibitory action on osteoarthritis can also be evaluated by preparing an arthritis animal model according to the method of Colombo et al. (Colombo et al. Arthritis and Rheumatism, vol. 26, No. 7 (July 1983), 875–886), by administering the compound of the present invention to those animals, and by performing evaluation according to the method of Toshiyuki Kikuchi et al. (Toshiyuki Kikuchi et al., Osteoarthritis and Cartilage (1996) 4, 99–110).

The compounds of the present invention strongly inhibit both MMP-13 and aglycanase, and are, therefore, useful as a preventive or therapeutic agent for arthritis (and particularly osteoarthritis), and as a medicament for inhibiting the metastasis, invasion or growth of cancer (and particularly breast cancer). The present invention provides a method for inhibiting MMP-13 and/or aglycanase in a warm blooded animal (and particularly a human) in need thereof by administering an effective amount of a compound of the present invention to inhibit said MMP-13 and/or aglycanase. Accordingly, the method of the present invention inhibits pathological changes associated with the presence of elevated levels of MMP-13 and/or aglycanase. The present invention provides a method to prevent (or inhibit) or treat arthritis or osteoarthritis. The method may also be used to inhibit MMP-13 and thereby inhibit the metastasis, invasion or growth of cancer (and particularly breast cancer) in a patient in need thereof.

$R^6$ represents a group of the following formula (II):

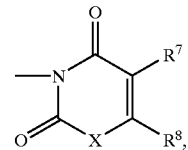

(II)

wherein
X represents a group of formula —N($R^{10}$)—,
$R^7$ and $R^8$ are the same or different from each other and each is selected from the group consisting of hydrogen atoms, lower alkyl groups defined below, carboxyl groups, one group from Substituent group α defined below, lower alkyl groups defined below substituted with at least one group from Substituent group α

What is claimed is:

1. A compound of the following formula (I) or a pharmacologically acceptable salt thereof:

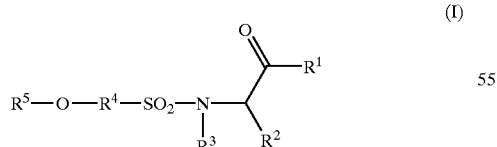

(I)

wherein:

$R^1$ represents hydroxyamino groups;

$R^2$ is a group of the formula —A—$R^6$, wherein

A represents lower alkylene groups defined below, and defined below, lower alkoxy groups defined below substituted with at least one group from Substituent group α defined below, lower alkylthio groups defined below substituted with at least one group from Substituent group α defined below, lower alkylsulfinyl groups defined below substituted with at least one group from Substituent group α defined below and lower alkylsulfonyl groups defined below substituted with at least one group from Substituent group α defined below, or $R^7$ and $R^8$ together with the carbon atoms to which they are attached form a moiety selected from the group consisting of non-aromatic hydrocarbon rings defined below which are unsubstituted, non-aromatic heterocyclic rings defined below which are unsubstituted, non-aromatic hydrocarbon rings defined below substituted with at least one group selected from the group consisting of Substituent group α defined below and Substituent group β defined below, non-aromatic heterocyclic rings defined below substituted with at least one group selected from the group consisting of Substituent group α defined below and Substituent group β defined below, aryl rings defined below which are unsubstituted, heteroaryl rings defined below which are unsubstituted, aryl rings defined below substituted with at least one group selected from the group consisting of Substituent group α defined below and Substituent group β defined below and heteroaryl rings defined below substituted with at least one group selected from the group consisting of Substituent group α defined below and Substituent group β defined below, and $R^{10}$ is selected from the group consisting of hydrogen atoms and lower alkyl groups defined below;

$R^3$ is selected from the group consisting of methyl, ethyl, propyl, cyclopropyl, allyl, 2-butenyl, propargyl, 2-butynyl, benzyl, 2-phenylethyl, 3-phenylpropyl, 3-(4-chlorophenyl)propyl, 3-phenylpropargyl and 3-(4-chlorophenyl)propargyl-groups;

$R^4$ represents an unsubstituted arylene group or an arylene group substituted with at least one group selected from the group consisting of Substituent group α defined below and Substituent group β defined below; and $R^5$ represents a substituent selected from the group consisting of aryl groups defined below which are unsubstituted, heteroaryl groups defined below which are unsubstituted, aryl groups defined below substituted with at least one group selected from the group consisting of Substituent group α defined below and Substituent group β defined below, and heteroaryl groups defined below substituted with at least one group selected from the group consisting of Substituent group α defined below and Substituent group β defined below;

Substituent group α is selected from the group consisting of halogen atoms, cycloalkyl groups having from 3 to 7 carbon atoms, lower alkoxy groups defined below, halogeno lower alkoxy groups defined below, lower alkanoyl groups defined below, lower alkylthio groups defined below, halogeno lower alkylthio groups defined below, lower alkylsulfinyl groups defined below, lower alkylsulfonyl groups defined below, amino groups, mono-lower alkylamino groups defined below, di-(lower alkyl)amino groups defined below, cyano groups, nitro groups, aryl groups defined below which are unsubstituted, heteroaryl groups defined below which are unsubstituted, aryloxy groups defined below which are unsubstituted, heteroaryloxy groups defined below which are unsubstituted, arylthio groups defined below which are unsubstituted, heteroarylthio groups defined below which are unsubstituted, aryl groups defined below substituted with at least one group from Substituent group γ defined below, heteroaryl groups defined below substituted with at least one group from Substituent group γ defined below, aryloxy groups defined below substituted with at least one group from Substituent group γ defined below, heteroaryloxy groups defined below substituted with at least one group from Substituent group γ defined below, arylthio groups defined below substituted with at least one group from Substituent group γ defined below and heteroarylthio groups defined below substituted with at least one group from Substituent group γ defined below;

Substituent group β is selected from the group consisting of lower alkyl groups defined below and halogeno lower alkyl groups defined below; and Substituent group γ is selected from the group consisting of halogen atoms, lower alkyl groups defined below, halogeno lower alkyl groups defined below, lower alkoxy groups defined below, halogeno lower alkoxy groups defined below, lower alkylthio groups defined below, halogeno lower alkylthio groups defined below, nitrogroups and cyano groups;

the lower alkyl group in the definition of $R^5$, $R^7$, $R^8$ and $R^{10}$, Substituent group β and Substituent group γ and the lower alkyl moiety of the lower alkyl group substituted with at least one group from Substituent group α in the definition of $R^5$, $R^7$ and $R^8$ is a straight or branched chain alkyl group having from 1 to 6 carbon atoms;

the lower alkylene group in the definition of A above is a straight or branched alkylene group having from 1 to 6 carbon atoms;

the lower alkoxy group in the definition of Substituent group α and Substituent group γ above and the lower alkoxy moiety of the lower alkoxy group substituted with at least one group from Substituent group α in the definition of $R^7$ and $R^8$ above is a group in which an oxygen atom is attached to the lower alkyl group defined above;

the lower alkylthio group in the definition of Substituent group α and Substituent group γ above and the alkylthio moiety of the lower alkylthio group substituted with at least one group from Substituent group α in the definition of $R^7$ and $R^8$ above is a group in which a sulfur atom is attached to the lower alkyl group defined above;

the lower alkylsulfinyl group in the definition of Substituent group α above and the lower alkylsulfinyl moiety of the lower alkylsulfinyl group substituted with at least one group from Substituent group α in the definition of $R^7$ and $R^8$ above is a group in which a sulfinyl moiety of the formula —SO— is attached to the lower alkyl group defined above;

the lower alkylsulfonyl group in the definition of Substituent group α above and the lower alkylsulfonyl moiety of the lower alkylsulfonyl group substituted with at least one group from Substituent group α in the definition of $R^7$ and $R^8$ above is a group in which a sulfonyl moiety of the formula —$SO_2$— is attached to the lower alkyl group defined above;

the non-aromatic hydrocarbon ring which is formed by $R^7$ and $R^8$, together with the carbon atoms to which they are attached, and the non-aromatic hydrocarbon ring moiety of the non-aromatic hydrocarbon ring substituted with at least one group selected from the group consisting of Substituent group α and Substituent group β, which is formed by $R^7$ and $R^8$, together with the carbon atoms to which they are attached, is each a saturated or unsaturated hydrocarbon ring having from 3 to 7 carbon atoms;

the non-aromatic heterocyclic ring which is formed by $R^7$ and $R^8$, together with the carbon atoms to which they are attached, and the non-aromatic heterocyclic ring moiety of the non-aromatic heterocyclic ring substituted with at least one group selected from the group consisting of Substituent group α and Substituent group β, which is formed by $R^7$ and $R^8$, together with the carbon atoms to which they are attached, is each a 5- to 7-membered saturated or partially saturated heterocyclic ring containing from 1 to 3 sulfur atoms, oxygen atoms and/or nitrogen atoms;

the aryl ring which is formed by $R^7$ and $R^8$, together with the carbon atoms to which they are attached and the aryl ring moiety of the aryl ring substituted with at least one group selected from the group consisting of Substituent group α and Substituent group β, which is formed by $R^7$ and $R^8$, together with the carbon atoms to which they are attached, is an aromatic hydrocarbon ring having from 6 to 10 carbon atoms, said ring optionally being fused with a cycloalkyl group having from 3 to 10 carbon atoms;

the heteroaryl ring which is formed by $R^7$ and $R^8$, together with the carbon atoms to which they are attached and the heteroaryl ring moiety of the heteroaryl ring substituted with at least one group selected from the group consisting of Substituent group α and Substituent group β, which is formed by $R^7$ and $R^8$, together with the carbon atoms to which they are attached is a 5- to 7-membered aromatic heterocyclic ring containing from 1 to 3 sulfur atoms, oxygen atoms and/or nitrogen atoms, said ring optionally being be fused with another cyclic group;

the arylene group and the arylene moiety of the arylene group substituted with at least one group selected from the group consisting of Substituent group α and Substituent group β in the definition of $R^4$ above is a divalent aromatic hydrocarbon ring having from 6 to 10 carbon atoms, said group optionally being fused with a cycloalkyl group having from 3 to 10 carbon atoms;

the aryl group in the definition of $R^5$ and Substituent group α above, the aryl moiety of the aryl group substituted with at least one group selected from Substituent group α and Substituent group β in the definition of $R^5$ above and the aryl moiety of the aryl group substituted with at least one group from Substituent group γ in the definition of Substituent group α above is a monovalent aromatic hydrocarbon ring having from 6 to 10 carbon atoms, said group optionally being fused with a cycloalkyl group having from 3 to 10 carbon atoms;

the heteroaryl group in the definition of $R^5$ and Substituent group α above, the heteroaryl moiety of the heteroaryl group substituted with at least one group selected from the group consisting of Substituent group α and Substituent group β in the definition of $R^5$ above, and the heteroaryl moiety of the heteroaryl group substituted with at least one group from Substituent group γ in the definition of Substituent group α above is a monovalent 5- to 7-membered aromatic heterocyclic group containing from 1 to 3 sulfur atoms, oxygen atoms and/or nitrogen atoms, said group optionally being fused with another cyclic group;

the halogeno lower alkoxy group in the definition of Substituent group α and Substituent group γ above is a group in which a halogeno lower alkyl group defined below is attached to an oxygen atom;

the lower alkanoyl group in the definition of Substituent group α above is a formyl group or a group in which a carbonyl group is attached to the lower alkyl group defined above;

the halogeno lower alkylthio group in the definition of Substituent group α and Substituent group γ above represents a group in which a halogeno lower alkyl group defined below is attached to a sulfur atom;

the mono-lower alkylamino group in the definition of Substituent group α above is a group in which one hydrogen atom of a —NH$_2$ group is substituted with the lower alkyl group defined above;

the di(lower alkyl)amino group in the definition of Substituent group α above is a group in which the two hydrogen atoms of a —NH$_2$ group are substituted with the above lower alkyl group, the two alkyl groups being the same or different;

the aryloxy group and the aryloxy moiety of the aryloxy group substituted with at least one group from Substituent group γ in the definition of Substituent group α above is a group in which the aryl group defined above is attached to an oxygen atom;

the heteroaryloxy group and the heteroaryloxy moiety of the heteroaryloxy group substituted with at least one group from Substituent group γ in the definition of the Substituent group α above is a group in which the heteroaryl group defined above is attached to an oxygen atom;

the arylthio group and the arylthio moiety of the arylthio group substituted with at least one group from Substituent group γ in the definition of Substituent group α above is a group in which the aryl group defined above is attached to a sulfur atom;

the heteroarylthio group and the heteroarylthio moiety of the heteroarylthio group substituted with at least one group selected from Substituent group γ in the definition of Substituent group α above is a group in which the heteroaryl group defined above is attached to a sulfur atom; and the halogeno lower alkyl group in the definition of Substituent group β and Substituent group γ above is a group in which a lower alkyl group defined above is substituted with at least one halogen atom.

2. The compound or a pharmacologically acceptable salt thereof according to claim 1, in which A represents alkylene groups having from 1 to 4 carbon atoms.

3. The compound or a pharmacologically acceptable salt thereof according to claim 1, in which A is selected from the group consisting of methylene, ethylene, 1,1-dimethylethylene, trimethylene and tetramethylene groups.

4. The compound or a pharmacologically acceptable salt thereof according to claim 1, in which A is selected from the group consisting of methylene, ethylene and trimethylene groups.

5. The compound or a pharmacologically acceptable salt thereof according to claim 3, wherein $R^6$ is selected from the group consisting of:

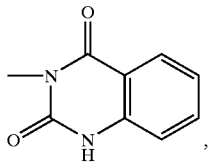 , 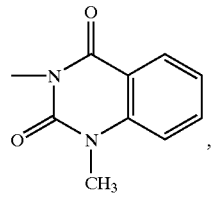 ,

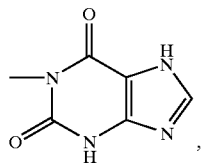 , 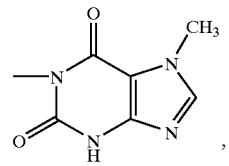 ,

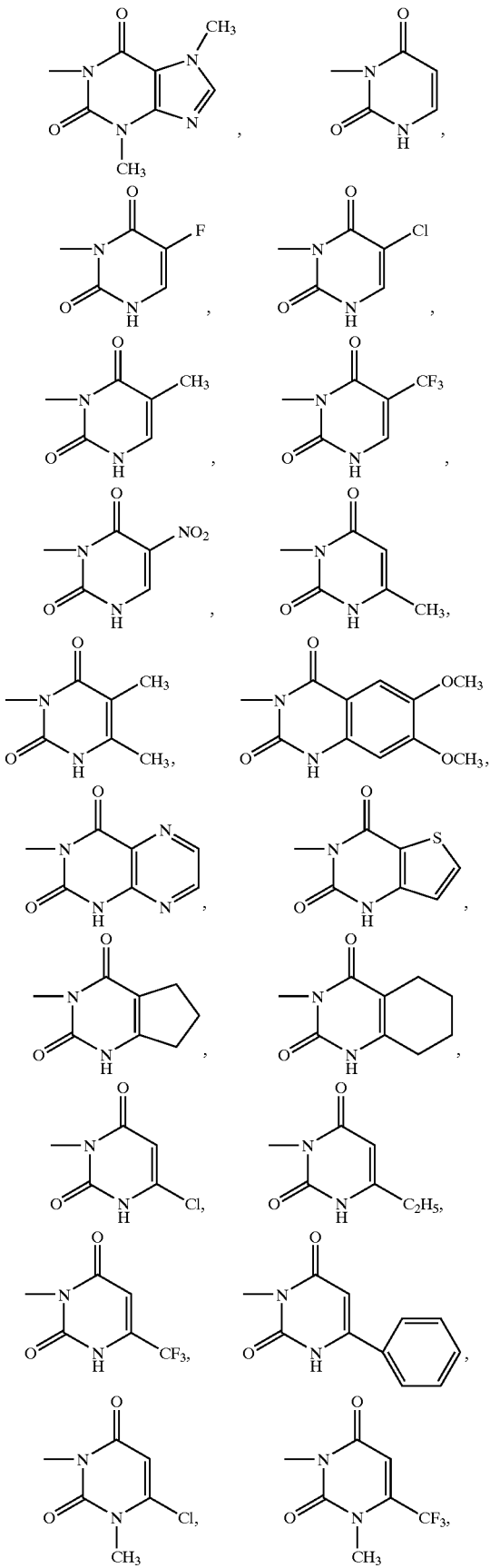
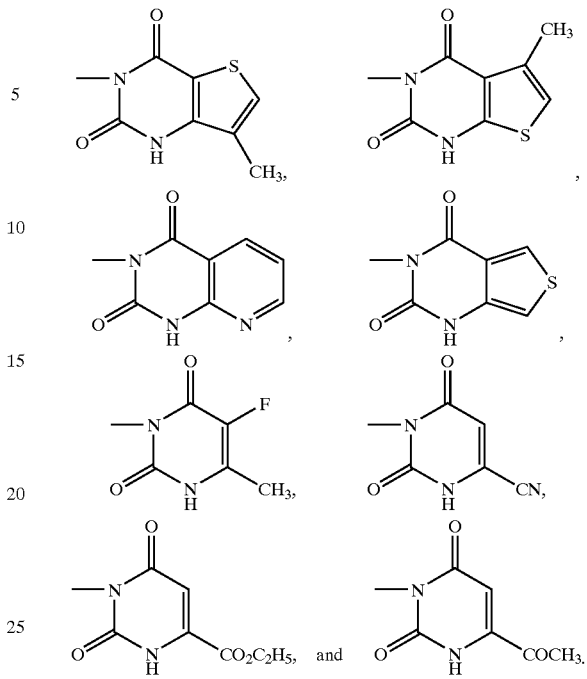

6. The compound or a pharmacologically acceptable salt thereof according to claim 1, in which $R^4$ is selected from the group consisting of phenylene and naphthylene.

7. The compound or a pharmacologically acceptable salt thereof according to claim 1, in which $R^4$ is a p-phenylene group.

8. The compound or a pharmacologically acceptable salt thereof according to claim 1, in which $R^5$ is selected from the group consisting of phenyl, 3-fluorophenyl, 4-fluorophenyl, 3-chlorophenyl, 4-chlorophenyl, 3-methylphenyl, 4-methylphenyl, 3-methoxyphenyl, 4-methoxyphenyl, 3-cyanophenyl, 4-cyanophenyl, 2,4-difluorophenyl, 2,4-dichlorophenyl, 3,4-difluorophenyl, 3-pyridyl, 4-pyridyl, 2-thienyl and 3-thienyl groups.

9. The compound or a pharmacologically acceptable salt thereof according to claim 1, in which $R^7$ and $R^8$ are the same or different from each other and each is selected from the group consisting of hydrogen atoms, nitro groups, amino groups, cyano groups, carboxyl groups, halogen atoms, mono-lower alkylamino groups, di(lower alkyl)amino groups, aryl groups, heteroaryl groups, unsubstituted lower alkyl groups, lower alkanoyl groups, lower alkyl groups substituted with at least one group from Substituent group α, lower alkoxy groups substituted with at least one group from Substituent group α, lower alkylthio groups substituted with at least one group from Substituent group α, lower alkylsulfinyl groups substituted with at least one group from Substituent group α and lower alkylsulfonyl groups substituted with at least one group from Substituent group α, all as defined in claim 1, or $R^7$ and $R^8$ form, together with the carbon atoms to which they are attached, a substituent selected from the group consisting of unsubstituted non-aromatic hydrocarbon rings, unsubstituted non-aromatic heterocyclic rings, nonaromatic hydrocarbon rings substituted with at least one group selected from the group consisting of Substituent group α and Substituent group β, non-aromatic heterocyclic rings substituted with at least one group selected from the group consisting of Substituent group α and Substituent group β, unsubstituted aryl rings, unsubstituted heteroaryl rings, aryl rings substituted with at least one group selected from the group consisting of Substituent group α and Substituent group β and heteroaryl rings substituted with at least one group selected from the group consisting of Substituent group α and Substituent group β, all as defined in claim 1.

10. The compound or a pharmacologically acceptable salt thereof according to claim 1, in which $R^7$ and $R^8$ are the same or different from each other and each is selected from the group consisting of hydrogen atoms, nitro groups, cyano groups, carboxyl groups, halogen atoms, aryl groups, heteroaryl groups, unsubstituted lower alkyl groups, lower alkanoyl groups and lower alkyl groups substituted with at least one group from Substituent group α, all as defined in claim 1, or $R^7$ and $R^8$ form, together with the carbon atoms to which they are attached, a substituent selected from the group consisting of unsubstituted non-aromatic hydrocarbon rings, unsubstituted non-aromatic heterocyclic rings, non-aromatic hydrocarbon rings substituted with at least one group selected from the group consisting of Substituent group α and Substituent group β, non-aromatic heterocyclic rings substituted with at least one group selected from the group consisting of Substituent group α and Substituent group β, unsubstituted aryl rings, unsubstituted heteroaryl rings, aryl rings substituted with at least one group selected from the group consisting of Substituent group α and Substituent group β and heteroaryl rings substituted with at least one group selected from the group consisting of Substituent group α and Substituent group β, all as defined in claim 1.

11. The compound or a pharmacologically acceptable salt thereof according to claim 1, in which:

A represents alkylene groups having from 1 to 4 carbon atoms;

$R^4$ is selected from the group consisting of phenylene and naphthylene;

$R^7$ and $R^8$ are the same or different from each other and each is selected from the group consisting of hydrogen atoms, nitro groups, amino groups, cyano groups, carboxyl groups, halogen atoms, mono-lower alkylamino groups, di(lower alkyl)amino groups, aryl groups, heteroaryl groups, unsubstituted lower alkyl groups, lower alkanoyl groups, lower alkyl groups substituted with at least one group from Substituent group α, lower alkoxy groups substituted with at least one group from Substituent group α, lower alkylthio groups substituted with at least one group from Substituent group α, lower alkylsulfinyl groups substituted with at least one group from Substituent group α and lower alkylsulfonyl groups substituted with at least one group from Substituent group α, all as defined in claim 1, or $R^7$ and $R^8$ form, together with the carbon atoms to which they are attached, a substituent selected from the group consisting of unsubstituted non-aromatic hydrocarbon rings, unsubstituted non-aromatic heterocyclic rings, non-aromatic hydrocarbon rings substituted with at least one group selected from the group consisting of Substituent group α and Substituent group β, non-aromatic heterocyclic rings substituted with at least one group selected from the group consisting of Substituent group α and Substituent group β, unsubstituted aryl rings, unsubstituted heteroaryl rings, aryl rings substituted with at least one group selected from the group consisting of Substituent group α and Substituent group β and heteroaryl rings substituted with at least one group selected from the group consisting of Substituent group α and Substituent group β, all as defined in claim 1.

12. The compound or a pharmacologically acceptable salt thereof according to claim 1, in which:

A is selected from the group consisting of methylene, ethylene, 1,1-dimethylethylene, trimethylene and tetramethylene;

X is $-N(R^{10})-$;

$R^4$ is selected from the group consisting of phenylene and naphthylene groups;

$R^7$ and $R^8$ are the same or different from each other and each is selected from the group consisting of hydrogen atoms, nitro groups, amino groups, cyano groups, carboxyl groups, halogen atoms, mono-lower alkylamino groups, di(lower alkyl)amino groups, aryl groups, heteroaryl groups, unsubstituted lower alkyl groups, lower alkanoyl groups, lower alkyl groups substituted with at least one group from Substituent group α, lower alkoxy groups substituted with at least one group selected from Substituent group α, lower alkylthio groups substituted with at least one group from Substituent group α, lower alkylsulfinyl groups substituted with at least one group from Substituent group α and lower alkylsulfonyl groups substituted with at least one group from Substituent group α, all as defined in claim 1, or $R^7$ and $R^8$ form, together with the carbon atoms to which they are attached, a substituent selected from the group consisting of unsubstituted non-aromatic hydrocarbon rings, unsubstituted non-aromatic heterocyclic rings, non-aromatic hydrocarbon rings substituted with at least one group selected from the group consisting of Substituent group α and Substituent group β, non-aromatic heterocyclic rings substituted with at least one group selected from the group consisting of Substituent group α and Substituent group β, unsubstituted aryl rings, unsubstituted heteroaryl rings, aryl rings substituted with at least one group selected from the group consisting of Substituent group α and Substituent group β and heteroaryl rings substituted with at least one group selected from Substituent group α and Substituent group β, all as defined in claim 1.

13. The compound or a pharmacologically acceptable salt thereof according to claim 1, in which:

A is selected from the group consisting of methylene, ethylene and trimethylene groups;

X is $-N(R^{10})-$;

$R^4$ is a p-phenylene group;

$R^5$ is selected from the group consisting of phenyl, 3-fluorophenyl, 4-fluorophenyl, 3-chlorophenyl, 4-chlorophenyl, 3-methylphenyl, 4-methylphenyl, 3-methyoxyphenyl, 4-methoxyphenyl, 3-cyanophenyl, 4-cyanophenyl, 2,4-difluorophenyl, 2,4-dichlorophenyl, 3,4-difluorophenyl, 3,4-dichlorophenyl, 3-pyridyl, 4-pyridyl, 2-thienyl and 3-thienyl groups; and $R^7$ and $R^8$ are the same or different from each other and each is selected from the group consisting of hydrogen atoms, nitro groups, cyano groups, carboxyl groups, halogen atoms, aryl groups, heteroaryl groups, unsubstiuted lower alkyl groups, lower alkanoyl groups and lower alkyl groups substituted with at least one group from Substituent group α, all as defined in claim 1, or $R^7$ and $R^8$ form, together with the carbon atoms to which they are attached, a substituent selected from the group consisting of unsubstituted non-aromatic hydrocarbon rings, unsubstituted non-aromatic heterocyclic rings, nonaromatic hydrocarbon rings substituted with at least one group selected from the group consisting of Substituent group α and Substituent group β, non-aromatic heterocyclic rings substituted with at least one group selected from the group consisting of Substituent group α and Substituent group β, unsubstituted aryl rings, unsubstituted heteroaryl rings, aryl rings substituted with at least one group selected from the group consisting of Substituent group α and Substituent group β and heteroaryl rings substituted with at least one group selected from the group consisting of Substituent group α and Substituent group β, all as defined in claim 1.

14. The compound according to claim 1, wherein the compound is selected from the group consisting of (±)-N-hydroxy-Nα-methyl-Nα-(4-phenoxybenzenesulfonyl)-2-[2-(quinazolin-2,4-dione-3-yl)ethyl]glycinamide, (±)-2-[2-(5-fluoropyrimidin-2,4-dione-3-yl)ethyl]-N-hydroxy-Nα-methyl-Nα-(4-phenoxybenzenesulfonyl) glycinamide, (±)-N-hydroxy-Nα-methyl-Nα-(4-phenoxybenzenesulfonyl)-2-[2-(thieno[3,2-d]pyrimidin-2,4-dione-3-yl)ethyl]glycinamide, (±)-N-hydroxy-Nα-methyl-2-[2-(7-methylxanthin-1-yl)ethyl]-Nα-(4-phenoxybenzenesulfonyl)glycinamide, (±)-N-hydroxy-Nα-methyl-Nα-(4-phenoxybenzenesulfonyl)-2-[2-pteridin-2,4-dione-3-yl)ethyl]glycinamide, (±)-N-hydroxy-Nα-methyl-2-[2-(6-methylpyrimidin-2,4-dione-3-yl)ethyl]-Nα-(4-phenoxybenzenesulfonyl) glycinamide, (±)-N-hydroxy-Nα-methyl-Nα-(4-phenoxybenzenesulfonyl)-2-[2-(5-trifluoromethylpyrimidin-2,4-dione-3-yl)ethyl]glycinamide, (±)-2-[2-(6-chloropyrimidin-2,4-dione-3-yl)ethyl]-N-hydroxy-Nα-methyl-Nα-(4-phenoxybenzenesulfonyl) glycinamide, (±)-N-hydroxy-Nα-methyl-Nα-(4-phenoxybenzenesulfonyl)-2-[2-(6-trifluoromethylpyrimidin-2,4-dione-3-yl)ethyl] glycinamide, (±)-N-hydroxy-Nα-methyl-Nα-(4-(pyridin-4-yl (oxybenzenesulfonyl]-2-[2-thieno-[3,2-d]pyrimidin-2,4-dione-3-yl(ethyl]glycinamide, (±)-2-[2-(6-chloro-1-methylpyrimidin-2,4-dione-3-yl)ethyl]-N-hydroxy-Nα-methyl-Nα-(4-phenoxybenzenesulfonyl)glycinamide, ±-Nα-[4-(4-(chlorophenoxy)benzenesulfonyl]-2-[2-(6-chloropyrimidin-2,4-dione-3-yl)ethyl]-N-hydroxy-Nα-methylglycinamide, (±)-2-[2-(6-chloropyrimidin-2,4-dione-3-yl)ethyl-Nα-[4-(4-fluorophenoxy)benzenesulfonyl]-N-hydroxy-Nα-methylglycinamide, (±)-Nα-[4-(4-(chlorophenoxy)benzenesulfonyl]-N-hydroxy-Nα-methyl-2-[2-(6-trifluoromethylpyrimidin-2,4-dione-3-yl)ethyl] glycinamide, (±)-Nα-[4-(4-fluorophenoxy)benzenesulfonyl]-N-hydroxy-Nα-methyl-2-[2-(6-trifluoromethylpyrimidin-2,4-dione-3-yl)ethyl] glycinamide, (±)-Nα-[4-(3-chlorophenoxy)benzenesulfonyl]-N-hydroxy-Nα-methyl-2-[2-(6-trifluoromethylpyrimidin-2,4-dione-3-yl)ethyl] glycinamide, (±)-Nα-[4-(3-chlorophenoxy)benzenesulfonyl]-2-[2-(6-chloropyrimidin-2,4-dione-3-yl)ethyl]-N-hydroxy-Nα-methylglycinamide, (±)-2-[2-(6-chloropyrimidin-2,4-dione-3-yl)ethyl]-Nα-ethyl-N-hydroxy-Nα-(4-phenoxybenzenesulfonyl) glycinamide, (±)-2-[2-(6-chloropyrimidin-2,4-dione-3-yl)ethyl]-Nα-[4-)3-fluorophenoxy)-benzenesulfonyl]-N-hydroxy-Nα-methylglycinaide, (±)-2-[2-(6-chloropyrimidin-2,4-dione-3-yl)ethyl]-N-hydroxy-Nα-methyl-Nα-[4-(pyridin-4-yl)oxybenzenesulfonyl]glycinamide, (±)-Nα-[4-(3-fluorophenoxy)benzenesulfonyl]-N-hydroxy-Nα-methyl-2-[2-(6-trifluoromethylpyrimidin-2,4-dione-3-yl)ethyl] glycinamide, (±)-N-hydroxy-Nα-methyl-Nα-[4-(pyridin-4-yl)oxybenzenesulfonyl]-2-[2-(6-trifluoromethylpyrimidin-2,4-dione-3-yl)ethyl] glycinamide, (±)-Nα-ethyl-N-hydroxy-Nα-(4-phenoxybenzenesulfonyl)-2-[2-(6-trifluoromethylpyrimidin-2,4-dione-3-yl)ethyl] glycinamide, (±)-N-hydroxy-Nα-methyl-2-[2-(1-methyl-6-trifluoromethylpyrimidin-2,4-dione-3-yl)ethyl]-Nα-(4-phenoxybenzenesulfonyl)glycinamide, (±)-2-[2-(5-chloropyrimidin-2,4-dione-3-yl)ethyl]-N-hydroxy-Nα-methyl-Nα-[4-phenoxybenzenesulfonyl) glycinamide, Nα-[4-(3-chlorophenoxy)benzenesulfonyl]-N-hydroxy-Nα-methyl-2-[2-quinazolin-2,4-dione-3-yl)ethyl] glycinamide, and Nα-[4-(3-chlorophenoxy)benzenesulfonyl]-N-hydroxy-Nα-methyl-2-[2-(thieno[3,2-d]pyrimidin-2,4-dione-3-yl)ethyl]glycinamide, or a pharmaceutically acceptable salt or ester thereof, said ester being an ester of a hydroxy group or an ester of a carboxyl group.

15. The compound of claim 1 which is (±)-N-Hydroxy-Nα-methyl-Nα-(4-phenoxybenzenesulfonyl)-2-[2-(quinazolin-2,4-dione-3-yl)ethyl]glycinamide or a pharmacologically acceptable salt thereof.

16. The compound of claim 1 which is (±)-2-[2-(5,6-Dimethylpyrimidin-2,4-dione-3-yl)ethyl]-N-hydroxy-Nα-methyl-Nα-(4-phenoxybenzenesulfonyl)glycinamide or a pharmacologically acceptable salt thereof.

17. The compound of claim 1 which is (±)-2-[2-(5-Fluoropyrimidin-2,4-dione-3-yl)ethyl]-N-hydroxy-Nα-methyl-Nα-(4-phenoxybenzensulfonyl)glycinamide or a pharmacologically acceptable salt thereof.

18. The compound of claim 1 which is (±)-N-Hydroxy-Nα-methyl-Nα-(4-phenoxybenzensulfonyl)-2-[2-(thieno[3,2-d]pyrimidin-2,4-dione-3-yl)ethyl]glycinamide or a pharmacologically acceptable salt thereof.

19. The compound of claim 1 which is (±)-N-Hydroxy-Nα-methyl-Nα-(4-phenoxybenzenesulfonyl)-2-[2-(pteridin-2,4-dione-3-yl)ethyl]glycinamide or a pharmacologically acceptable salt thereof.

20. The compound of claim 1 which is (±)-N-Hydroxy-Nα-methyl-2-[2-(6-methylpyrimidin-2,4-dione-3-yl)ethyl]-Nα-(4-phenoxybenzenesulfonyl)glycinamide or a pharmacologically acceptable salt thereof.

21. The compound of claim 1 which is (±)-N-Hydroxy-Nα-methyl-Nα-(4-phenoxybenzenesulfonyl)-2-[2-(5-trifluoromethylpyrimidin-2,4-dione-3-yl)ethyl]glycinamide or a pharmacologically acceptable salt thereof.

22. The compound of claim 1 which is (±)-2-[2-(6-Chloropyrimidin-2,4-dione-3-yl)ethyl]-N-hydroxy-Nα-methyl-Nα-(4-phenoxybenzenesulfonyl)glycinamide or a pharmacologically acceptable salt thereof.

23. The compound of claim 1 which is (±)-N-Hydroxy-Nα-methyl-Nα-(4-phenoxybenzenesulfonyl)-2-[2-(6-trifluoromethylpyrimidin-2,4-dione-3-yl)ethyl]glycinamide or a pharmacologically acceptable salt thereof.

24. The compound of claim 1 which is (±)-2-[2-(6-chloro-1-methylpyrimidin-2,4-dione-3-yl)ethyl]-N-hydroxy-Nα-methyl-Nα-(4-phenoxybenzenesulfonyl)glycinamide or a pharmacologically acceptable salt thereof.

25. The compound of claim 1 which is (±)-Nα-[4-(4-Chlorophenoxy) benzenesulfonyl]-2-[2-(6-chloropyrimidin-2,4-dione-3-yl)ethyl]-N-hydroxy-Nα-methylglycinamide or a pharmacologically acceptable salt thereof.

26. The compound of claim 1 which is (±)-2-[2-(6-Chloropyrimidin-2,4-dione-3-yl)ethyl]-Nα-[4-(4-fluorophenoxy)benzenesulfonyl]-N-hydroxy-Nα-methylglycinamide or a pharmacologically acceptable salt thereof.

27. The compound of claim 1 which is (±)-Nα-[4-(4-Chlorophenoxy) benzenesulfonyl]-N-hydroxy-Nα-methyl-2-[2-(6-trifluoromethylpyrimidin-2,4-dione-3-yl)ethyl] glycinamide or a pharmacologically acceptable salt thereof.

28. The compound of claim 1 which is (±)-Nα-[4-(4-Fluorophenoxy) benzenesulfonyl]-N-hydroxy-Nα-methyl-2-[2-(6-trifluoromethylpyrimidin-2,4-dione-3-yl)ethyl] glycinamide or a pharmacologically acceptable salt thereof.

29. The compound of claim 1 which is (±)-Nα-[4-(3-Chlorophenoxy) benzenesulfonyl]-N-hydroxy-Nα-methyl-2-[2-(6-trifluoromethylpyrimidin-2,4-dione-3-yl)ethyl] glycinamide or a pharmacologically acceptable salt thereof.

30. The compound of claim 1 which is (±)-Nα-[4-(3-Chlorophenoxy) benzenesulfonyl]-2-[2-(6-chloropyrimidin-2,4-dione-3-yl)ethyl]-N-hydroxy-Nα-methylglycinamide or a pharmacologically acceptable salt thereof.

31. The compound of claim 1 which is (±)-2-[2-(6-Chloropyrimidin-2,4-dione-3-yl)ethyl]-Nα-ethyl-N-hydroxy-Nα-(4-phenoxybenzenesulfonyl)glycinamide or a pharmacologically acceptable salt thereof.

32. The compound of claim 1 which is (±)-2-[2-(6-Chloropyrimidin-2,4-dione-3-yl)ethyl]-Nα-[4-(3-fluorophenoxy)benzenesulfonyl]-N-hydroxy-Nα-methylglycinamide or a pharmacologically acceptable salt thereof.

33. The compound of claim 1 which is (±)-2-[2-(6-Chloropyrimidin-2,4-dione-3-yl)ethyl]-N-hydroxy-Nα-methyl-Nα-[4-(pyridin-4-yl)oxybenzenesulfonyl] glycinamide or a pharmacologically acceptable salt thereof.

34. The compound of claim 1 which is (±)-Nα-[4-(3-Fluorophenoxy) benzenesulfonyl]-N-hydroxy-Nα-methyl-2-[2-(6-trifluoromethylpyrimidin-2,4-dione-3-yl)ethyl] glycinamide or a pharmacologically acceptable salt thereof.

35. The compound of claim 1 which is (±)-N-Hydroxy-Nα-methyl-Nα-[4-(pyridin-4-yl)oxybenzenesulfonyl]-2-[2-(6-trifluoromethylpyrimidin-2,4-dione-3-yl)ethyl] glycinamide or a pharmacologically acceptable salt thereof.

36. The compound of claim 1 which is (±)-Nα-Ethyl-N-hydroxy-Nα-(4-phenoxybenzenesulfonyl)-2-[2-(6-trifluoromethylpyrimidin-2,4-dione-3-yl)ethyl]glycinamide or a pharmacologically acceptable salt thereof.

37. The compound of claim 1 which is (±)-N-Hydroxy-Nα-methyl-2-[2-(1-methyl-6-trifluoromethylpyrimidin-2,4-dione-3-yl)ethyl]-Nα-(4-phenoxybenzenesulfonyl) glycinamide or a pharmacologically acceptable salt thereof.

38. The compound of claim 1 which is (±)-2-[2-(5-Chloropyrimidin-2,4-dione-3-yl)ethyl]-N-hydroxy-Nα-methyl-Nα-(4-phenoxybenzenesulfonyl)glycinamide or a pharmacologically acceptable salt thereof.

39. The compound of claim 1 which is Nα-[4-(3-Chlorophenoxy)benzenesulfonyl]-N-hydroxy-Nα-methyl-2 (R)-[2-(quinazolin-2,4-dione-3-yl)ethyl]glycinamide or a pharmacologically acceptable salt thereof.

40. The compound of claim 1 which is Nα-[4-(3-Chlorophenoxy)benzenesulfonyl]-N-hydroxy-Nα-methyl-2 (R)-[2-(thieno[3,2-d]pyrimidin-2,4-dione-3-yl)ethyl] glycinamide or a pharmacologically acceptable salt thereof.

41. The compound or a pharmacologically acceptable salt thereof according to claim 1, wherein $R^5$ is phenyl.

42. The compound or a pharmacologically acceptable salt thereof according to claim 1, wherein $R^5$ is pyridine.

43. A pharmaceutical composition comprising an effective amount of a pharmacologically active compound together with a pharmaceutically acceptable carrier therefor, wherein said pharmacologically active compound is a compound of formula (I) or a pharmacologically acceptable salt or ester thereof according to claim 1.

44. A pharmaceutical composition comprising an effective amount of a pharmacologically active compound together with a pharmaceutically acceptable carrier therefor, wherein said pharmacologically active compound is a compound of formula (I) or a pharmacologically acceptable salt or ester thereof according to claim 14.

* * * * *